United States Patent
Lape et al.

(10) Patent No.: US 12,410,418 B2
(45) Date of Patent: Sep. 9, 2025

(54) OPTIMIZED ENGINEERED MEGANUCLEASES HAVING SPECIFICITY FOR A RECOGNITION SEQUENCE IN THE HEPATITIS B VIRUS GENOME

(71) Applicant: Precision BioSciences, Inc., Durham, NC (US)

(72) Inventors: Janel Lape, Wake Forest, NC (US); James Jefferson Smith, Morrisville, NC (US)

(73) Assignee: Precision BioSciences, Inc., Durham, NC (US)

( * ) Notice: Subject to any disclaimer, the term of this patent is extended or adjusted under 35 U.S.C. 154(b) by 482 days.

(21) Appl. No.: 17/782,610

(22) PCT Filed: Dec. 4, 2020

(86) PCT No.: PCT/US2020/063479
§ 371 (c)(1),
(2) Date: Jun. 3, 2022

(87) PCT Pub. No.: WO2021/113765
PCT Pub. Date: Jun. 10, 2021

(65) Prior Publication Data
US 2023/0031465 A1 Feb. 2, 2023

Related U.S. Application Data

(60) Provisional application No. 62/944,862, filed on Dec. 6, 2019.

(51) Int. Cl.
| | |
|---|---|
| *C12N 9/22* | (2006.01) |
| *A61P 31/20* | (2006.01) |
| *C12N 15/10* | (2006.01) |
| *C12N 15/90* | (2006.01) |

(52) U.S. Cl.
CPC ............. *C12N 9/22* (2013.01); *A61P 31/20* (2018.01); *C12N 15/102* (2013.01); *C12N 15/90* (2013.01); *C12N 2730/10121* (2013.01)

(58) Field of Classification Search
CPC ........ C12N 9/22; C12N 15/102; C12N 15/90; C12N 2730/10121; A61P 31/20
See application file for complete search history.

(56) References Cited

U.S. PATENT DOCUMENTS

| | | |
|---|---|---|
| 4,873,192 A | 10/1989 | Kunkel |
| 6,015,832 A | 1/2000 | Baker, Jr. et al. |
| 6,506,803 B1 | 1/2003 | Baker, Jr. et al. |
| 6,559,189 B2 | 5/2003 | Baker, Jr. et al. |
| 6,635,676 B2 | 10/2003 | Baker, Jr. et al. |
| 7,074,596 B2 | 7/2006 | Darzynkiewicz et al. |
| 7,672,016 B2 | 3/2010 | Kaneko et al. |
| 8,021,867 B2 | 9/2011 | Smith et al. |
| 8,278,036 B2 | 10/2012 | Kariko et al. |
| 8,445,251 B2 | 5/2013 | Smith et al. |
| 8,513,184 B2 | 8/2013 | Appleby et al. |
| 8,722,054 B2 | 5/2014 | Apelian et al. |
| 9,181,288 B2 | 11/2015 | Hartman et al. |
| 9,186,337 B2 | 11/2015 | Baker et al. |
| 9,340,777 B2 | 5/2016 | Smith et al. |
| 9,434,931 B2 | 9/2016 | Smith et al. |
| 9,670,205 B2 | 6/2017 | Aktoudianakis et al. |
| 9,884,866 B2 | 2/2018 | Feguson et al. |
| 10,041,053 B2 | 8/2018 | Smith et al. |
| 10,662,416 B2 | 5/2020 | Jantz et al. |
| 10,851,358 B2 | 12/2020 | Jantz et al. |
| 11,142,750 B2 | 10/2021 | Smith et al. |
| 11,274,285 B2 | 3/2022 | Jantz et al. |
| 2002/0045667 A1 | 4/2002 | Baker, Jr. et al. |
| 2004/0043041 A1 | 3/2004 | Baker, Jr. et al. |
| 2008/0234251 A1 | 9/2008 | Doherty et al. |
| 2008/0306050 A1 | 12/2008 | Doherty et al. |
| 2009/0047249 A1 | 2/2009 | Graupe et al. |
| 2010/0015178 A1 | 1/2010 | Combs et al. |
| 2010/0029585 A1 | 2/2010 | Howbert et al. |
| 2010/0143301 A1 | 6/2010 | Desai et al. |
| 2011/0092485 A1 | 4/2011 | Howbert et al. |

(Continued)

FOREIGN PATENT DOCUMENTS

| | | |
|---|---|---|
| JP | 2009-511085 A | 3/2009 |
| JP | 2011-501971 A | 1/2011 |

(Continued)

OTHER PUBLICATIONS

Invitation to Pay Additional Fees for Application No. PCT/US2017/056638 mailed Jan. 31, 2018.
International Search Report and Written Opinion for Application No. PCT/US2017/056638 mailed Apr. 9, 2018.
International Preliminary Report on Patentability for Application No. PCT/US2017/056638 mailed Apr. 25, 2019.
International Search Report and Written Opinion for Application No. PCT/US2019/027203 mailed Jul. 16, 2019.
International Preliminary Report on Patentability for Application No. PCT/US2019/027203 mailed Oct. 22, 2020.
International Search Report and Written Opinion for Application No. PCT/US2020/063479 mailed Mar. 8, 2021.

(Continued)

*Primary Examiner* — Li N Komatsu
(74) *Attorney, Agent, or Firm* — Womble Bond Dickinson (US) LLP

(57) ABSTRACT

The present invention encompasses engineered nucleases which recognize and cleave a recognition sequence within a Hepatitis B virus (HBV) genome. The engineered meganucleases can exhibit at least one optimized characteristic, such as enhanced specificity and/or efficiency of indel formation, when compared to previously described HBV meganucleases. Further, the invention encompasses pharmaceutical compositions comprising engineered meganuclease proteins, nucleic acids encoding engineered meganucleases, and the use of such compositions for treating HBV infections or hepatocellular carcinoma.

12 Claims, 21 Drawing Sheets
Specification includes a Sequence Listing.

(56) References Cited

U.S. PATENT DOCUMENTS

| | | |
|---|---|---|
| 2011/0098248 A1 | 4/2011 | Halcomb et al. |
| 2011/0118235 A1 | 5/2011 | Howbert et al. |
| 2012/0082658 A1 | 4/2012 | Hershberg |
| 2012/0171191 A1 | 7/2012 | Choulika et al. |
| 2012/0219615 A1 | 8/2012 | Hershberg et al. |
| 2013/0079327 A1 | 3/2013 | Yamamoto et al. |
| 2013/0217880 A1 | 8/2013 | Yamamoto et al. |
| 2013/0251673 A1 | 9/2013 | Hartman et al. |
| 2013/0267517 A1 | 10/2013 | Guo et al. |
| 2013/0344029 A1 | 12/2013 | Aciro et al. |
| 2013/0344030 A1 | 12/2013 | Steadman et al. |
| 2014/0030221 A1 | 1/2014 | Aciro et al. |
| 2014/0045849 A1 | 2/2014 | McGowan et al. |
| 2014/0066432 A1 | 3/2014 | Howbert et al. |
| 2014/0073642 A1 | 3/2014 | McGowan et al. |
| 2014/0088085 A1 | 3/2014 | Burgess et al. |
| 2014/0171432 A1 | 6/2014 | Kanouni et al. |
| 2014/0178337 A1 | 6/2014 | Hartman et al. |
| 2014/0179005 A1 | 6/2014 | Jantz et al. |
| 2014/0194469 A1 | 7/2014 | Nie et al. |
| 2014/0213591 A1 | 7/2014 | Chen et al. |
| 2014/0275084 A1 | 9/2014 | Kanouni et al. |
| 2014/0275092 A1 | 9/2014 | Albrecht et al. |
| 2014/0275167 A1 | 9/2014 | Hartman |
| 2014/0330015 A1 | 11/2014 | Yamamoto et al. |
| 2014/0343032 A1 | 11/2014 | Guo et al. |
| 2014/0350031 A1 | 11/2014 | McGowan et al. |
| 2014/0371195 A1 | 12/2014 | Labelle et al. |
| 2014/0371214 A1 | 12/2014 | Labelle et al. |
| 2015/0031687 A1 | 1/2015 | Guo et al. |
| 2015/0132258 A1 | 5/2015 | Hartman |
| 2015/0197533 A1 | 7/2015 | Hartman et al. |
| 2015/0210682 A1 | 7/2015 | Han et al. |
| 2015/0225355 A1 | 8/2015 | Hartman |
| 2015/0252057 A1 | 9/2015 | Guo et al. |
| 2015/0259324 A1 | 9/2015 | Hartman et al. |
| 2015/0274652 A1 | 10/2015 | Hartman |
| 2015/0315159 A1 | 11/2015 | Hartman |
| 2015/0368670 A1 | 12/2015 | Quake et al. |
| 2016/0039808 A1 | 2/2016 | Kanouni et al. |
| 2016/0102096 A1 | 4/2016 | Boesen et al. |
| 2016/0122344 A1 | 5/2016 | Han et al. |
| 2016/0137652 A1 | 5/2016 | Beck et al. |
| 2016/0176899 A1 | 6/2016 | Schwitter et al. |
| 2016/0220586 A1 | 8/2016 | Andre et al. |
| 2016/0237090 A1 | 8/2016 | Hu et al. |
| 2016/0289229 A1 | 10/2016 | Aktoudianakis et al. |
| 2017/0044206 A1 | 2/2017 | Altman et al. |
| 2017/0121328 A1 | 5/2017 | Hartman et al. |
| 2017/0121329 A1 | 5/2017 | Hartman et al. |
| 2017/0158724 A1 | 6/2017 | Adams et al. |
| 2017/0334882 A1 | 11/2017 | Hartman et al. |
| 2017/0334898 A9 | 11/2017 | Guo et al. |
| 2018/0030053 A1 | 2/2018 | Fu et al. |
| 2018/0065929 A1 | 3/2018 | Vandyck et al. |
| 2018/0065938 A1 | 3/2018 | Chin et al. |
| 2018/0086755 A1 | 3/2018 | Chin et al. |
| 2019/0017075 A1 | 1/2019 | Bartsevich et al. |
| 2019/0142973 A1 | 5/2019 | Jantz et al. |
| 2019/0284543 A1 | 9/2019 | Jantz et al. |
| 2019/0338263 A1* | 11/2019 | Smith ............... C12N 9/22 |
| 2021/0180038 A1 | 6/2021 | Jantz et al. |
| 2022/0056427 A1 | 2/2022 | Jantz et al. |
| 2022/0243187 A1 | 8/2022 | Jantz et al. |

FOREIGN PATENT DOCUMENTS

| | | |
|---|---|---|
| JP | 6811857 B2 | 1/2021 |
| WO | 93/13120 A1 | 7/1993 |
| WO | WO 2002/012514 A2 | 2/2002 |
| WO | WO 2007/047859 A2 | 4/2007 |
| WO | WO 2008/005555 A1 | 1/2008 |
| WO | WO 2009/001159 A1 | 12/2008 |
| WO | WO 2009/059195 A2 | 5/2009 |
| WO | WO 2009/086558 A1 | 7/2009 |
| WO | WO 2010/136841 A2 | 12/2010 |
| WO | WO 2011/161699 A2 | 12/2011 |
| WO | WO 2012/167192 A2 | 12/2012 |
| WO | WO 2012/168944 A1 | 12/2012 |
| WO | WO 2013/096744 A1 | 6/2013 |
| WO | WO 2013/132317 A1 | 9/2013 |
| WO | WO 2013/144129 A1 | 10/2013 |
| WO | WO 2013/144704 A1 | 10/2013 |
| WO | WO 2013/159109 A1 | 10/2013 |
| WO | WO 2013/173223 A1 | 11/2013 |
| WO | WO 2014/023813 A1 | 2/2014 |
| WO | WO 2014/033167 A1 | 3/2014 |
| WO | WO 2014/033170 A1 | 3/2014 |
| WO | WO 2014/033176 A1 | 3/2014 |
| WO | WO 2014/037480 A1 | 3/2014 |
| WO | WO 2014/056953 A1 | 4/2014 |
| WO | WO 2014/076221 A1 | 5/2014 |
| WO | WO 2014/128189 A1 | 8/2014 |
| WO | WO 2014/131847 A1 | 9/2014 |
| WO | WO 2014/151634 A1 | 9/2014 |
| WO | WO 2014/161888 A1 | 10/2014 |
| WO | WO 2014/164708 A1 | 10/2014 |
| WO | WO 2014/179760 A1 | 11/2014 |
| WO | WO 2014/184350 A1 | 11/2014 |
| WO | WO 2014/184365 A1 | 11/2014 |
| WO | WO 2015/011281 A1 | 1/2015 |
| WO | WO 2015/014815 A1 | 2/2015 |
| WO | WO 2015/019284 A2 | 2/2015 |
| WO | WO 2015/023958 A1 | 2/2015 |
| WO | WO 2015/033299 A1 | 3/2015 |
| WO | WO 2015/033301 A1 | 3/2015 |
| WO | WO 2015/033303 A1 | 3/2015 |
| WO | WO 2015/034820 A1 | 3/2015 |
| WO | WO 2015/036927 A1 | 3/2015 |
| WO | WO 2015/044900 A1 | 4/2015 |
| WO | WO 2015/057655 A1 | 4/2015 |
| WO | WO 2015/057659 A1 | 4/2015 |
| WO | WO 2015/059212 A1 | 4/2015 |
| WO | WO 2015/088045 A1 | 6/2015 |
| WO | WO 2015/095780 A1 | 6/2015 |
| WO | WO 2015/118057 A1 | 8/2015 |
| WO | WO 2015/119944 A1 | 8/2015 |
| WO | WO 2015/134605 A1 | 9/2015 |
| WO | WO 2015/160641 A2 | 10/2015 |
| WO | WO 2015/162075 A1 | 10/2015 |
| WO | WO 2015/168269 A1 | 11/2015 |
| WO | WO 2015/168279 A1 | 11/2015 |
| WO | WO 2015/173164 A1 | 11/2015 |
| WO | WO 2015/179615 A1 | 11/2015 |
| WO | WO 2015/188085 A1 | 12/2015 |
| WO | WO 2016/012470 A1 | 1/2016 |
| WO | WO 2016/019232 A1 | 2/2016 |
| WO | WO 2016/023511 A1 | 2/2016 |
| WO | WO 2016/023877 A1 | 2/2016 |
| WO | WO 2016/029077 A1 | 2/2016 |
| WO | WO 2016/039749 A1 | 3/2016 |
| WO | WO 2016/055553 A1 | 4/2016 |
| WO | WO 2016/057624 A1 | 4/2016 |
| WO | WO 2016/057924 A1 | 4/2016 |
| WO | WO 2016/073738 A2 | 5/2016 |
| WO | WO 2016/075661 A1 | 5/2016 |
| WO | WO 2016/077518 A1 | 5/2016 |
| WO | WO 2016/091698 A1 | 6/2016 |
| WO | WO 2016/096778 A1 | 6/2016 |
| WO | WO 2016/100285 A1 | 6/2016 |
| WO | WO 2016/100608 A1 | 6/2016 |
| WO | WO 2016/102438 A1 | 6/2016 |
| WO | WO 2016/107536 A1 | 7/2016 |
| WO | WO 2016/107832 A1 | 7/2016 |
| WO | WO 2016/107833 A1 | 7/2016 |
| WO | WO 2016/120186 A1 | 8/2016 |
| WO | WO 2016/126646 A1 | 8/2016 |
| WO | WO 2016/128335 A1 | 8/2016 |
| WO | WO 2016/141092 A1 | 9/2016 |
| WO | WO 2016/142250 A1 | 9/2016 |
| WO | WO 2016/142833 A1 | 9/2016 |
| WO | WO 2016/142835 A1 | 9/2016 |
| WO | WO 2016/142852 A1 | 9/2016 |
| WO | WO 2016/142886 A2 | 9/2016 |

(56) References Cited

FOREIGN PATENT DOCUMENTS

| | | |
|---|---|---|
| WO | WO 2016/142894 A1 | 9/2016 |
| WO | WO 2016/149351 A1 | 9/2016 |
| WO | WO 2016/161268 A1 | 10/2016 |
| WO | WO 2016/168619 A1 | 10/2016 |
| WO | WO 2016/177655 A1 | 11/2016 |
| WO | WO 2016/180743 A1 | 11/2016 |
| WO | WO 2016/195982 A2 | 12/2016 |
| WO | WO 2017/001307 A1 | 1/2017 |
| WO | WO 2017/001655 A1 | 1/2017 |
| WO | WO 2017/001853 A1 | 1/2017 |
| WO | WO 2017/007701 A1 | 1/2017 |
| WO | WO 2017/013046 A1 | 1/2017 |
| WO | WO 2017/016960 A1 | 2/2017 |
| WO | WO 2017/017042 A1 | 2/2017 |
| WO | WO 2017/017043 A1 | 2/2017 |
| WO | WO 2017/017624 A1 | 2/2017 |
| WO | WO 2017/027434 A1 | 2/2017 |
| WO | WO 2017/034986 A1 | 3/2017 |
| WO | WO 2017/038909 A1 | 3/2017 |
| WO | WO 2017/040233 A1 | 3/2017 |
| WO | WO 2017/046112 A1 | 3/2017 |
| WO | WO 2017/047769 A1 | 3/2017 |
| WO | WO 2017/048950 A1 | 3/2017 |
| WO | WO 2017/048954 A1 | 3/2017 |
| WO | WO 2017/048962 A1 | 3/2017 |
| WO | WO 2017/061466 A1 | 4/2017 |
| WO | WO 2017/061532 A1 | 4/2017 |
| WO | WO 2017/066227 A1 | 4/2017 |
| WO | WO 2017/070089 A1 | 4/2017 |
| WO | WO 2017/176608 A1 | 4/2017 |
| WO | WO 2017/075477 A1 | 5/2017 |
| WO | WO 2017/076346 A1 | 5/2017 |
| WO | WO 2017/076988 A1 | 5/2017 |
| WO | WO 2017/079669 A1 | 5/2017 |
| WO | WO 2017/087678 A2 | 5/2017 |
| WO | WO 2017/087777 A1 | 5/2017 |
| WO | WO 2017/100108 A1 | 6/2017 |
| WO | WO 2017/106607 A1 | 6/2017 |
| WO | WO 2017/106634 A1 | 6/2017 |
| WO | WO 2017/106740 A1 | 6/2017 |
| WO | WO 2017/112730 A1 | 6/2017 |
| WO | WO 2017/161349 A1 | 9/2017 |
| WO | WO 2017/163264 A1 | 9/2017 |
| WO | WO 2017/184735 A1 | 10/2017 |
| WO | WO 2017/184746 A1 | 10/2017 |
| WO | WO 2017/186711 A1 | 11/2017 |
| WO | WO 2017/190669 A1 | 11/2017 |
| WO | WO 2017/192741 A1 | 11/2017 |
| WO | WO 2017/192961 A1 | 11/2017 |
| WO | WO 2017/198744 A1 | 11/2017 |
| WO | WO 2017/202703 A1 | 11/2017 |
| WO | WO 2017/202704 A1 | 11/2017 |
| WO | WO 2017/202798 A1 | 11/2017 |
| WO | WO 2017/205464 A1 | 11/2017 |
| WO | WO 2017/211791 A1 | 12/2017 |
| WO | WO 2017/214395 A1 | 12/2017 |
| WO | WO 2017/216054 A1 | 12/2017 |
| WO | WO 2017/216685 A1 | 12/2017 |
| WO | WO 2017/216686 A1 | 12/2017 |
| WO | WO 2017/219931 A1 | 12/2017 |
| WO | WO 2017/222976 A1 | 12/2017 |
| WO | WO 2018/001944 A1 | 1/2018 |
| WO | WO 2018/001952 A1 | 1/2018 |
| WO | WO 2018/002319 A1 | 1/2018 |
| WO | WO 2018/004163 A1 | 1/2018 |
| WO | WO 2018/005586 A1 | 1/2018 |
| WO | WO 2018/005881 A1 | 1/2018 |
| WO | WO 2018/005883 A1 | 1/2018 |
| WO | WO 2018/009466 A1 | 1/2018 |
| WO | WO 2018/009505 A1 | 1/2018 |
| WO | WO 2018/011100 A1 | 1/2018 |
| WO | WO 2018/011160 A1 | 1/2018 |
| WO | WO 2018/011162 A1 | 1/2018 |
| WO | WO 2018/011163 A1 | 1/2018 |
| WO | WO 2018/013789 A1 | 1/2018 |
| WO | WO 2018/019297 A1 | 2/2018 |
| WO | WO 2018/022282 A1 | 2/2018 |
| WO | WO 2018/026620 A1 | 2/2018 |
| WO | WO 2018/026971 A1 | 2/2018 |
| WO | WO 2018/031434 A1 | 2/2018 |
| WO | WO 2018/036941 A1 | 3/2018 |
| WO | WO 2018/038877 A1 | 3/2018 |
| WO | WO 2018/043747 A1 | 3/2018 |
| WO | WO 2018/044783 A1 | 3/2018 |
| WO | WO 2018/044963 A1 | 3/2018 |
| WO | WO 2018/045144 A1 | 3/2018 |
| WO | WO 2018/045150 A1 | 3/2018 |
| WO | WO 2018/045911 A1 | 3/2018 |
| WO | WO 2018/046460 A1 | 3/2018 |
| WO | WO 2018/047081 A1 | 3/2018 |
| WO | WO 2018/049089 A1 | 3/2018 |
| WO | WO 2018/051254 A1 | 3/2018 |
| WO | WO 2018/051255 A1 | 3/2018 |
| WO | WO 2018/060323 A1 | 4/2018 |
| WO | WO 2018/065360 A1 | 4/2018 |
| WO | WO 2018/067423 A1 | 4/2018 |
| WO | WO 2018/071849 A2 | 4/2018 |
| WO | WO 2018/073754 A1 | 4/2018 |
| WO | WO 2018/078149 A1 | 5/2018 |
| WO | WO 2018/080903 A1 | 5/2018 |
| WO | WO 2018/085750 A2 | 5/2018 |
| WO | WO 2018/086593 A1 | 5/2018 |
| WO | WO 2018/089695 A1 | 5/2018 |
| WO | WO 2018/095426 A1 | 5/2018 |
| WO | WO 2018/098203 A1 | 5/2018 |
| WO | WO 2018/100558 A2 | 6/2018 |
| WO | WO 2018/118664 A1 | 6/2018 |
| WO | WO 2018/118665 A1 | 6/2018 |
| WO | WO 2018/118826 A1 | 6/2018 |
| WO | WO 2018/118848 A1 | 6/2018 |
| WO | WO 2018/119013 A1 | 6/2018 |
| WO | WO 2018/119221 A1 | 6/2018 |
| WO | WO 2018/119236 A1 | 6/2018 |
| WO | WO 2018/119263 A1 | 6/2018 |
| WO | WO 2018/119266 A1 | 6/2018 |
| WO | WO 2018/119286 A1 | 6/2018 |
| WO | WO 2018/199338 A1 | 11/2018 |
| WO | WO 2019/200247 A1 | 10/2019 |

OTHER PUBLICATIONS

International Preliminary Report on Patentability for Application No. PCT/US2020/063479 mailed Jun. 16, 2022.
Airenne et al., Baculovirus: an insect-derived vector for diverse gene transfer applications. Mol Ther. Apr. 2013;21(4):739-49. doi: 10.1038/mt.2012.286. Epub Feb. 26, 2013.
Altschul et al., Basic local alignment search tool. J Mol Biol. Oct. 5, 1990;215(3):403-10.
Altschul et al., Gapped BLAST and PSI-BLAST: a new generation of protein database search programs. Nucleic Acids Res. Sep. 1, 1997;25(17):3389-402.
Arnould et al., Engineering of large numbers of highly specific homing endonucleases that induce recombination on novel DNA targets. J Mol Biol. Jan. 20, 2006;355(3):443-58. Epub Nov. 15, 2005.
Benoist et al., In vivo sequence requirements of the SV40 early promotor region. Nature. Mar. 26, 1981;290(5804):304-10.
Bloom et al., Inactivation of hepatitis B virus replication in cultured cells and in vivo with engineered transcription activator-like effector nucleases. Mol Ther. Oct. 2013;21(10):1889-97. doi: 10.1038/mt.2013.170. Epub Jul. 25, 2013.
Cahill et al., Mechanisms of eukaryotic DNA double strand break repair. Front Biosci. May 1, 2006;11:1958-76.
Chames et al., In vivo selection of engineered homing endonucleases using double-strand break induced homologous recombination. Nucleic Acids Res. Nov. 23, 2005;33(20):e178.
Chang et al., Inducible retroviral vectors regulated by lac repressor in mammalian cells. Gene. Dec. 12, 1996;183(1-2):137-42.
Chen et al., A novel adenoviral vector carrying an all-in-one Tet-On system with an autoregulatory loop for tight, inducible transgene expression. BMC Biotechnol. Feb. 13, 2015;15:4. doi: 10.1186/s12896-015-0121-4.

(56) References Cited

OTHER PUBLICATIONS

Chen, Exploiting the Intron-splicing Mechanism of Insect Cells to Produce Viral Vectors Harboring Toxic Genes for Suicide Gene Therapy. Mol Ther Nucleic Acids. Nov. 27, 2012;1:e57. doi: 10.1038/mtna.2012.48.

Cheng et al., Dendrimers as drug carriers: applications in different routes of drug administration. J Pharm Sci. Jan. 2008;97(1):123-43.

Cheng et al., Multifactorial heterogeneity of virus-specific T cells and association with the progression of human chronic hepatitis B infection. Sci Immunol. Feb. 8, 2019; 4(32). pii: eaau6905. doi: 10.1126/sciimmunol.aau6905.

Chevalier et al., Homing endonucleases: structural and functional insight into the catalysts of intron/intein mobility. Nucleic Acids Res. Sep. 15, 2001;29(18):3757-74.

Cots et al., Helper dependent adenovirus vectors: progress and future prospects. Curr Gene Ther. Oct. 2013; 13(5):370-81.

Deshayes et al., Cell-penetrating peptides: tools for intracellular delivery of therapeutics. Cell Mol Life Sci. Aug. 2005;62(16):1839-49.

Deshayes et al., Primary amphipathic cell-penetrating peptides: structural requirements and interactions with model membranes. Biochemistry. Jun. 22, 2004;43(24):7698-706.

Dinda et al., Nanobiotechnology-based drug delivery in brain targeting. Curr Pharm Biotechnol. 2013;14(15):1264-74.

Dingermann et al., Establishment of a system for conditional gene expression using an inducible tRNA suppressor gene. Mol Cell Biol. Sep. 1992;12(9):4038-45.

Gao et al., Efficient gene delivery into mammalian cells mediated by a recombinant baculovirus containing a whispovirus iel promoter, a novel shuttle promoter between insect cells and mammalian cells. J Biotechnol. Aug. 31, 2007;131(2):138-43. Epub Jun. 19, 2007.

Gish et al., Identification of protein coding regions by database similarity search. Nat Genet. Mar. 1993;3(3):266-72.

Grizot et al., Efficient targeting of a SCID gene by an engineered single-chain homing endonuclease. Nucleic Acids Res. Sep. 2009;37(16):5405-19. doi: 10.1093/nar/gkp548. Epub Jul. 7, 2009.

Haase et al., Generation of a tumor- and tissue-specific episomal non-viral vector system. BMC Biotechnol. Jun. 4, 2013;13:49. doi: 10.1186/1472-6750-13-49.

Hudecz et al., Medium-sized peptides as built in carriers for biologically active compounds. Med Res Rev. Nov. 2005;25(6):679-736.

Jacox et al., Tissue-specific and ubiquitous expression patterns from alternative promoters of human genes. PLoS One. Aug. 18, 2010;5(8):e12274. doi: 10.1371/journal.pone.0012274.

Jearawiriyapaisam et al., Sustained dystrophin expression induced by peptide-conjugated morpholino oligomers in the muscles of mdx mice. Mol Ther. Sep. 2008;16(9):1624-9. doi: 10.1038/mt.2008.120. Epub Jun. 10, 2008.

Jiang et al., Cationic core-shell liponanoparticles for ocular gene delivery. Biomaterials. Oct. 2012;33(30):7621-30. doi: 10.1016/j.biomaterials.2012.06.079. Epub Jul. 11, 2012.

Kang Derwent et al., Thermoresponsive hydrogels as a new ocular drug delivery platform to the posterior segment of the eye. Trans Am Ophthalmol Soc. 2008; 106:206-13; discussion 213-4.

Kang et al., Harnessing the capacity of cell-penetrating peptides for drug delivery to the central nervous system. Curr Pharm Biotechnol. 2014; 15(3):220-30.

Kramer et al., In vitro and in vivo comparative study of chimeric liver-specific promoters. Mol Ther. Mar. 2003;7(3):375-85.

Kunkel et al., Rapid and efficient site-specific mutagenesis without phenotypic selection. Methods Enzymol. 1987;154:367-82.

Kunkel, Rapid and efficient site-specific mutagenesis without phenotypic selection. Proc Natl Acad Sci U S A. Jan. 1985;82(2):488-92.

Ladner et al., Inducible expression of human hepatitis B virus (HBV) in stably transfected hepatoblastoma cells: a novel system for screening potential inhibitors of HBV replication. Antimicrob Agents Chemother. Aug. 1997; 41(8):1715-20.

Lentz et al., Viral vectors for gene delivery to the central nervous system. Neurobiol Dis. Nov. 2012;48(2):179-88. doi: 10.1016/j.nbd.2011.09.014. Epub Oct. 7, 2011.

Li et al., Generation of single-chain LAGLIDADG homing endonucleases from native homodimeric precursor proteins. Nucleic Acids Res. Apr. 2009;37(5):1650-62. doi: 10.1093/nar/gkp004. Epub Jan. 19, 2009.

Lin et al., The CRISPR/Cas9 system facilitates clearance of the intrahepatic HBV templates in vivo. Mol Ther Nucleic Acids. Aug. 19, 2014;3(8):e186. doi: 10.1038/mtna.2014.38.

Liu et al., Therapeutic levels of factor IX expression using a muscle-specific promoter and adeno-associated virus serotype 1 vector. Hum Gene Ther. Aug. 2004; 15(8):783-92.

Low et al., Binding of TCR multimers and a TCR-like antibody with distinct fine-specificities is dependent on the surface density of HLA complexes. PLOS One. 2012; 7(12):e51397. doi: 10.1371/journal.pone.0051397. Epub Dec. 10, 2012.

Madden et al., Applications of network BLAST server. Methods Enzymol. 1996;266:131-41.

Martin et al., Gene delivery to the eye using adeno-associated viral vectors. Methods. Oct. 2002;28(2):267-75.

Mastorakos et al., Hydroxyl PAMAM dendrimer-based gene vectors for transgene delivery to human retinal pigment epithelial cells. Nanoscale. Mar. 7, 2015;7(9):3845-56. doi: 10.1039/c4nr04284k.

Mccall et al., Pathogen-inspired drug delivery to the central nervous system. Tissue Barriers. Aug. 8, 2014;2(4):e944449. doi: 10.4161/21688362.2014.944449. eCollection 2014.

Mccarty et al., Self-complementary recombinant adeno-associated virus (scAAV) vectors promote efficient transduction independently of DNA synthesis. Gene Ther. Aug. 2001;8(16):1248-54.

Mishra et al., Recent applications of liposomes in ophthalmic drug delivery. J Drug Deliv. 2011;2011:863734. doi: 10.1155/2011/863734. Epub Mar. 1, 2011.

Qian et al., Improved brain uptake of peptide-based CNS drugs via alternative routes of administrations of its nanocarrier delivery systems: a promising strategy for CNS targeting delivery of peptides. Expert Opin Drug Metab Toxicol. Nov. 2014;10(11):1491-508. doi: 10.1517/17425255.2014.956080. Epub Sep. 6, 2014.

Sands, AAV-mediated liver-directed gene therapy. Methods Mol Biol. 2011;807:141-57. doi: 10.1007/978-1-61779-370-7_6.

Sastry et al., Targeting hepatitis B virus-infected cells with a T-cell receptor-like antibody. J Virol. Mar. 2011; 85(5):1935-42. doi: 10.1128/JVI.01990-10. Epub Dec. 15, 2010.

Seligman et al., Mutations altering the cleavage specificity of a homing endonuclease. Nucleic Acids Res. Sep. 1, 2002;30(17):3870-9.

Sharma et al., Formulation and optimization of polymeric nanoparticles for intranasal delivery of lorazepam using Box-Behnken design: in vitro and in vivo evaluation. Biomed Res Int. 2014;2014:156010. doi: 10.1155/2014/156010. Epub Jul. 14, 2014.

Shen et al., Frequency and reactivity of antigen-specific T cells were concurrently measured through the combination of artificial antigen-presenting cell, MACS and ELISPOT. Sci Rep. Nov. 27, 2017; 7(1):16400. doi: 10.1038/s41598-017-16549-1.

Silva et al., Meganucleases and other tools for targeted genome engineering: perspectives and challenges for gene therapy. Curr Gene Ther. Feb. 2011;11(1):11-27. doi: 10.2174/156652311794520111.

Simeoni et al., Insight into the mechanism of the peptide-based gene delivery system MPG: implications for delivery of siRNA into mammalian cells. Nucleic Acids Res. Jun. 1, 2003;31(11):2717-24.

Sowa et al., In vitro and in vivo testing of a novel regulatory system for gene therapy for intervertebral disc degeneration. Spine (Phila Pa 1976). May 1, 2011;36(10):E623-8. doi: 10.1097/BRS.0b013e3181ed11c1.

Stoddard, Homing endonuclease structure and function. Q Rev Biophys. Feb. 2005;38(1):49-95. Epub Dec. 9, 2005.

Sussman et al., Isolation and characterization of new homing endonuclease specificities at individual target site positions. J Mol Biol. Sep. 3, 2004;342(1):31-41.

Tamboli et al., Polymeric vectors for ocular gene delivery. Ther Deliv. Apr. 2011;2(4):523-36. doi: 10.4155/tde.11.20. Author manuscript.

(56) References Cited

OTHER PUBLICATIONS

Thomsen et al., Promoter-regulatory region of the major immediate early gene of human cytomegalovirus. Proc Natl Acad Sci U S A. Feb. 1984;81(3):659-63.

Tong et al., Eye drop delivery of nano-polymeric micelle formulated genes with cornea-specific promoters. J Gene Med. Nov. 2007;9(11):956-66.

Vannucci et al., Viral vectors: a look back and ahead on gene transfer technology. New Microbiol. Jan. 2013;36(1):1-22. Epub Jan. 1, 2013.

Weber et al., AAV-mediated delivery of zinc finger nucleases targeting hepatitis B virus inhibits active replication. PLoS One. May 14, 2014;9(5):e97579. doi: 10.1371/journal.pone.0097579.

Yuasa et al., Adeno-associated virus vector-mediated gene transfer into dystrophin-deficient skeletal muscles evokes enhanced immune response against the transgene product. Gene Ther. Dec. 2002;9(23):1576-88.

Zhang et al., A greedy algorithm for aligning DNA sequences. J Comput Biol. Feb.-Apr. 2000;7(1-2):203-14.

Zhao et al., Nonstimulatory peptide-MHC enhances human T-cell antigen-specific responses by amplifying proximal TCR signaling. Nat Commun. Jul. 13, 2018; 9(1):2716. doi: 10.1038/s41467-018-05288-0.

Zhu et al., Quantum dot/pMHC multimers vs. phycoerythrin/pMHC tetramers for identification of HLA-A*0201-restricted pHBV core antigen18-27-specific T cells. Mol Med Rep. Dec. 2017; 16(6):8605-8612. doi: 10.3892/mmr.2017.7126. Epub Aug. 1, 2017.

Zischewski et al., Detection of on-target and off-target mutations generated by CRISPR/Cas9 and other sequence-specific nucleases. Biotechnol Adv. Jan.-Feb. 2017;35(1):95-104. doi: 10.1016/j.biotechadv.2016.12.003. Epub Dec. 21, 2016.

Zuris et al., Cationic lipid-mediated delivery of proteins enables efficient protein-based genome editing in vitro and in vivo. Nat Biotechnol. Jan. 2015;33(1):73-80. doi: 10.1038/nbt.3081. Epub Oct. 30, 2014.

\* cited by examiner

```
                         HBV11            HBV12
                       Half-Site        Half-Site
HBV 11-12              TGCCGATCCATAC TGCGGAACT    SEQ ID NO:10
Recognition Sequence   ACGGCTAGG TATGACGCCTTGA    SEQ ID NO:11
```

FIGURE 2

| HBV 11-12  | 1259-1280 of SEQ ID NO: 3 | SEQ ID NO: |
|------------|---------------------------|------------|
| Genotype A | TGCCGATCCATACTGCGGAACT    | 10         |
| Genotype B | TGCCGATCCATACTGCGGAACT    | 10         |
| Genotype C | TGCCGATCCATACTGCGGAACT    | 10         |
| Genotype D | TGCCGATCCATACTGCGGAACT    | 10         |
| Genotype E | TGCCGATCCATACTGCGGAACT    | 10         |
| Genotype F | TGCCGATCCATACTGCGGAACT    | 10         |
| Genotype G | TGCCGATCCATACTGCGGAACT    | 10         |

FIGURE 3

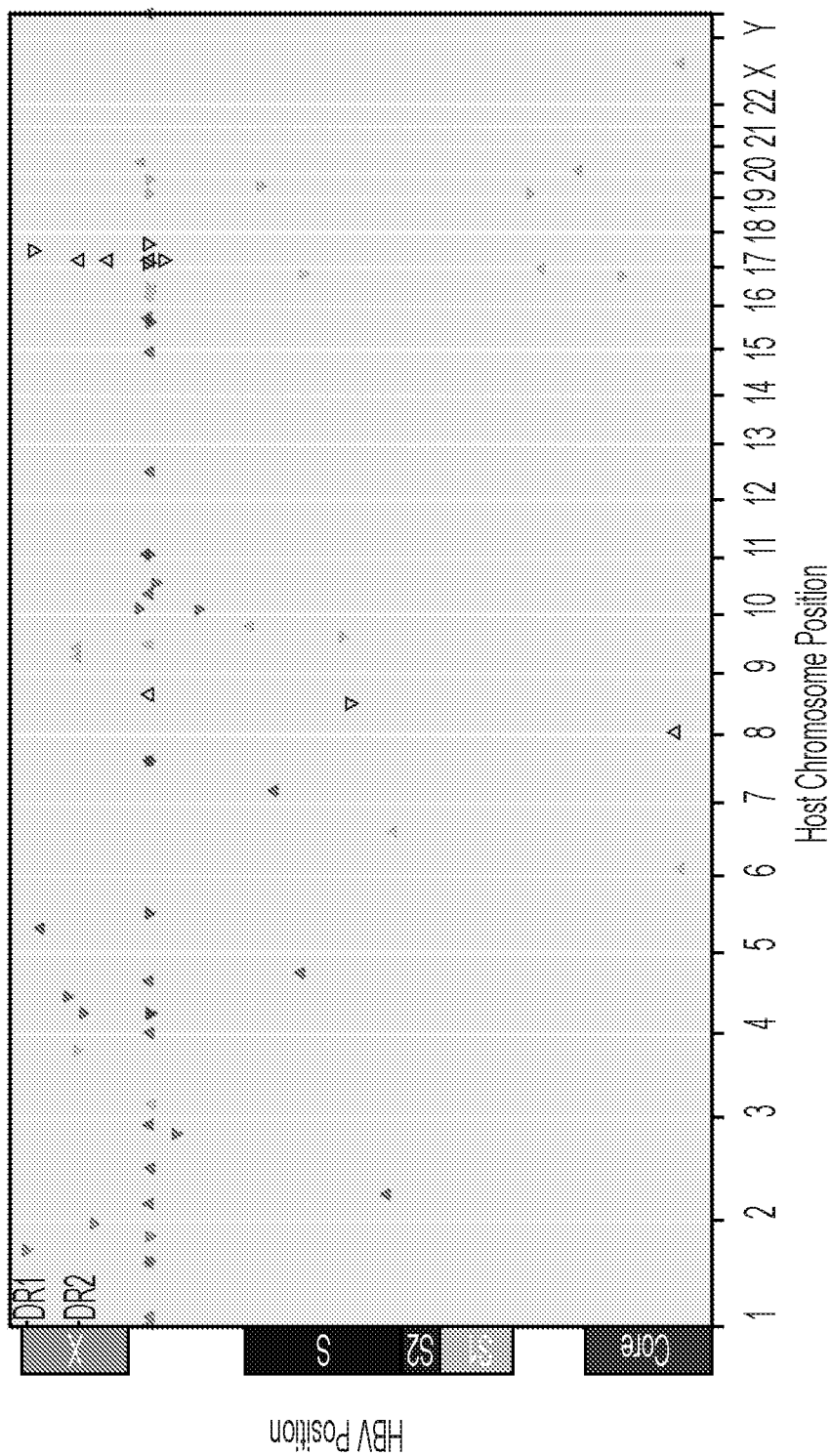

US 12,410,418 B2

OPTIMIZED ENGINEERED MEGANUCLEASES HAVING SPECIFICITY FOR A RECOGNITION SEQUENCE IN THE HEPATITIS B VIRUS GENOME

CROSS-REFERENCE TO RELATED APPLICATIONS

This Application is a national stage filing under 35 U.S.C. 371 of International Patent Application Serial No. PCT/US2020/063479, filed Dec. 4, 2020, entitled "OPTIMIZED ENGINEERED MEGANUCLEASES HAVING SPECIFICITY FOR A RECOGNITION SEQUENCE IN THE HEPATITIS B VIRUS GENOME", which claims priority to U.S. Provisional Application Ser. No. 62/944,862, filed Dec. 6, 2019, entitled "OPTIMIZED ENGINEERED MEGANUCLEASES HAVING SPECIFICITY FOR A RECOGNITION SEQUENCE IN THE HEPATITIS B VIRUS GENOME". The contents of each of these applications are incorporated herein by reference in their entireties.

FIELD OF THE INVENTION

The invention relates to the field of oncology, molecular biology and recombinant nucleic acid technology. In particular, the invention relates to optimized engineered meganucleases having specificity for a recognition sequence within the genome of genotypes A-G of the Hepatitis B virus. Such engineered meganucleases are useful in methods for treating Hepatitis B virus infections and hepatocellular carcinoma caused by Hepatitis B virus.

REFERENCE TO A SEQUENCE LISTING SUBMITTED AS A TEXT FILE VIA EFS-WEB

The instant application contains a Sequence Listing which has been submitted in ASCII format via EFS-Web and is hereby incorporated by reference in its entirety. Said ASCII copy, created on Jun. 1, 2022, is named P109070046US02-SEQ-EPG, and is 85,559 bytes in size.

BACKGROUND OF THE INVENTION

The Hepatitis B virus (HBV) is a major health problem worldwide and more than 350 million people are chronic carriers. HBV infection is a serious and common infectious disease of the liver. Chronic infection is associated with an increased risk to develop severe liver diseases, including liver cirrhosis and hepatocellular carcinoma (HCC), one of the most common forms of human cancer. The estimated risk of HCC in chronic HBV carriers is approximately 100 times greater than in uninfected individuals. About a third of the world population has been infected at one point in their lives, including 240 million to 350 million who have chronic infections. Over 750,000 people die of hepatitis B each year. About 300,000 of these are due to liver cancer. Currently available anti-HBV drugs have limitations. For example, interferon alpha administration is associated with severe adverse reactions. Nucleoside analogues are virostatic and require long-term administration.

The HBV genome exhibits genetic variability with an estimated rate of $1.4$-$3.2 \times 10^{-5}$ nucleotide substitutions per site per year. A large number of virus variants arise during replication as a result of nucleotide misincorporations in the absence of any proof reading capacity by the viral polymerase. This variability has resulted in well-recognized subtypes of the virus. HBV has been classified into well-defined genotypes on the basis of an inter-group divergence of 8% or more in the complete genomic sequence, each having a distinct geographical distribution. For example, Genotype A is widespread in sub-Saharan Africa, Northern Europe, and Western Africa; genotypes B and C are common in Asia; genotype C is primarily observed in Southeast Asia; genotype D is dominant in Africa, Europe, Mediterranean countries, and India; genotype G is reported in France, Germany, and the United States; and genotype H is commonly encountered in Central and South America. Genotype I has recently been reported in Vietnam and Laos. The newest HBV genotype, genotype J, has been identified in the Ryukyu Islands in Japan.

HBV is an enveloped DNA virus that belongs to the Hepadnaviridae family. It contains a small, partially double-stranded (DS), relaxed-circular DNA (rcDNA) genome that replicates by reverse transcription of an RNA intermediate, the pregenomic RNA (pgRNA). The circular DNA genome of HBV is unusual because the DNA is not fully double-stranded. One end of the full length strand is linked to the viral DNA polymerase. The genome is approximately 3020-3320 nucleotides long (for the full-length strand) and 1700-2800 nucleotides long (for the short length-strand). The negative-sense (non-coding) is complementary to the viral mRNA.

There are four known genes encoded by the genome, referred to as C, X, P, and S. The core protein is coded for by gene C (HBcAg), and its start codon is preceded by an upstream in-frame AUG start codon from which the pre-core protein is produced. The HBeAg is produced by proteolytic processing of the pre-core protein. The DNA polymerase is encoded by gene P. Gene S codes for the surface antigen (HBsAg). The HBsAg gene is one long open reading frame but contains three in frame "start" (ATG) codons that divide the gene into three sections: pre-S1, pre-S2, and S. Because of the multiple start codons, polypeptides of three different sizes called Large (the order from surface to the inside: pre-S1/pre-S2/S), Middle (pre-S2/S), and Small (S) are produced. The function of the protein coded for by gene X is not fully understood but it is associated with the development of liver cancer. It stimulates genes that promote cell growth and inactivates growth regulating molecules.

The viral DNA is found in the nucleus soon after infection of the cell. The partially double-stranded DNA is rendered fully double-stranded by completion of the (+) sense strand and removal of a protein molecule from the (−) sense strand and a short sequence of RNA from the (+) sense strand. Non-coding bases are removed from the ends of the (−) sense strand and the ends are rejoined.

The HBV life cycle begins when the virus attaches to the host cell and is internalized. Recent studies have demonstrated that sodium-taurocholate co-transporting polypeptide (NTCP) is a functional receptor in HBV infection. The virion relaxed circular DNA (rcDNA) is delivered to the nucleus, where it is repaired to form a covalently closed-circular DNA (cccDNA). The episomal cccDNA serves as the template for the transcription of the pregenomic RNA (pgRNA) and the other viral mRNAs by the host RNA polymerase II. The transcripts are then exported to the cytoplasm, where translation of the viral proteins occurs. Reverse transcriptase (RT) binds to pgRNA and triggers assembly of the core proteins into immature, RNA-containing nucleocapsids. The immature nucleocapsids then undergo a process of maturation whereby pgRNA is reversed transcribed by RT to make the mature rcDNA. A unique feature of hepadnavirus reverse transcription is the RT primed initiation of minus-strand DNA synthesis, which leads to the covalent linkage of RT to the 5' end of the minus-strand DNA.

The mature, rcDNA-containing nucleocapsids are then enveloped by the viral surface proteins and secreted as virions (secretion pathway) or, alternatively, are recycled back to the nucleus to further amplify the pool of cccDNA (recycling pathway). Persistence of cccDNA in hepatocytes plays a key role in viral persistence, reactivation of viral replication after cessation of antiviral therapy, and resistance to therapy.

Homing endonucleases are a group of naturally-occurring nucleases which recognize 15-40 base-pair cleavage sites commonly found in the genomes of plants and fungi. They are frequently associated with parasitic DNA elements, such as group 1 self-splicing introns and inteins. They naturally promote homologous recombination or gene insertion at specific locations in the host genome by producing a double-stranded break in the chromosome, which recruits the cellular DNA-repair machinery (Stoddard (2006), Q. Rev. Biophys. 38: 49-95). Homing endonucleases are commonly grouped into four families: the LAGLIDADG (SEQ ID NO: 2) family, the GIY-YIG family, the His-Cys box family and the HNH family. These families are characterized by structural motifs, which affect catalytic activity and recognition sequence. For instance, members of the LAGLIDADG (SEQ ID NO: 2) family are characterized by having either one or two copies of the conserved LAGLIDADG (SEQ ID NO: 2) motif (see Chevalier et al. (2001), Nucleic Acids Res. 29(18): 3757-3774). The LAGLIDADG (SEQ ID NO: 2) homing endonucleases with a single copy of the LAGLIDADG (SEQ ID NO: 2) motif form homodimers, whereas members with two copies of the LAGLIDADG (SEQ ID NO: 2) motif are found as monomers. Methods for producing homing endonucleases are known in the art.

I-CreI (SEQ ID NO: 1) is a member of the LAGLIDADG (SEQ ID NO: 2) family of homing endonucleases which recognizes and cuts a 22 basepair recognition sequence in the chloroplast chromosome of the algae *Chlamydomonas reinhardtii*. Genetic selection techniques have been used to modify the wild-type I-CreI cleavage site preference (Sussman et al. (2004), J. Mol. Biol. 342: 31-41; Chames et al. (2005), Nucleic Acids Res. 33: e178; Seligman et al. (2002), Nucleic Acids Res. 30: 3870-9, Arnould et al. (2006), J. Mol. Biol. 355: 443-58). Methods for rationally-designing mono-LAGLIDADG (SEQ ID NO: 2) homing endonucleases were described which are capable of comprehensively redesigning I-CreI and other homing endonucleases to target widely-divergent DNA sites, including sites in mammalian, yeast, plant, bacterial, and viral genomes (see, e.g., WO 2007/047859).

As first described in WO 2009/059195, I-CreI and its engineered derivatives are normally dimeric but can be fused into a single polypeptide using a short peptide linker that joins the C-terminus of a first subunit to the N-terminus of a second subunit (see also Li et al. (2009), Nucleic Acids Res. 37:1650-62; Grizot et al. (2009), Nucleic Acids Res. 37:5405-19). Thus, a functional "single-chain" meganuclease can be expressed from a single transcript.

The use of engineered meganucleases for treatment of HBV infections has been suggested. For example, WO 2010/136841 suggests the use of engineered meganucleases for cleaving the genome of non-genomically integrating viruses. Such meganucleases include variants of I-CreI targeting 22 base pair meganuclease recognition sequences which differ from those described herein, and which are only present in a few HBV genotypes.

Applicants previously disclosed in PCT/US2017/56638 and PCT/US2019/27203 a number of engineered meganucleases having specificity for recognition sequences present in the HBV genome, including the HBV 11-12 recognition sequence (SEQ ID NO: 10) which is advantageously present in the genome of at least HBV genotypes A-G (SEQ ID NOs: 3-9).

The present invention improves upon the engineered meganucleases previously described in the art in a number of aspects. When generating an endonuclease for therapeutic administration to a patient, it is critical that on-target specificity is enhanced (i.e., increased) while reducing or eliminating off-target cutting within the target cell genome. Here, Applicants have developed additional engineered meganucleases which target the HBV 11-12 recognition sequence. The meganucleases of the present invention have novel and unique sequences which were generated through extensive experimentation. Additionally, the meganucleases described herein have a number of improved and unexpected properties when compared to the previously disclosed engineered meganucleases, including a significant reduction in off-target cutting in the host cell genome. In particular, the engineered meganucleases described herein demonstrate a significant enhancement in the (i.e., increased) formation of indels (i.e., insertions or deletions within the HBV genome at the cleavage site, indicative of on-target cutting) in cell lines comprising an integrated copy of the HBV genome. Thus, the meganucleases of the invention further advance the art in a number of ways that are necessary for development of a clinical product targeting HBV infection and HBV-related hepatocellular carcinoma.

SUMMARY OF THE INVENTION

The present invention provides improved engineered meganucleases that recognize and cleave a recognition sequence conserved across multiple genotypes of Hepatitis B viruses. Cleavage at the recognition sequence by an engineered meganuclease described herein can disrupt expression of one or more viral proteins due to non-homologous end joining (NHEJ) at the cleavage site. NHEJ can result in insertions, deletions, or result in a frameshift mutation that can interfere with gene expression. Alternatively, a "suicide gene" can be introduced into a Hepatitis B virus (HBV) genome via homologous recombination. In another embodiment, the HBV genome or cccDNA may be degraded following cleavage at the HBV 11-12 recognition sequence. Accordingly, by interrupting normal gene expression, the infection and proliferation of HBV can be reduced or eliminated according to the methods described herein. Such meganucleases are, therefore, useful for treating or reducing the proliferation of HBV in infected individuals worldwide.

Suppression or eradication of the replication of HBV in the liver leads to improved liver pathology and decreased progression to liver cirrhosis and hepatocellular carcinoma (HCC). Thus, the present invention also provides pharmaceutical compositions and methods for treatment of a subject having HBV or HCC which utilize an engineered meganuclease having specificity for a recognition sequence comprising SEQ ID NO: 10 within a Hepatitis B virus genome. The present invention further provides methods of delivering the engineered meganucleases described herein, or a nucleic acid encoding the same, to a subject infected with HBV in order to reduce the level of HBV virus or HBV cccDNA and/or reduce the symptoms associated with an HBV infection. In some embodiments, the presently disclosed engineered meganucleases exhibit at least one optimized characteristic in comparison to the previously described meganucleases including, inter alia HBV 11-12x.26 or HBV 11-12L.363. Such optimized characteristics include improved (i.e., increased) specificity resulting in reduced off-target cutting, and enhanced (i.e., increased) efficiency of cleavage and indel formation at the HBV 11-12 recognition sequence, for example in cells comprising an integrated copy of the HBV genome.

Thus, in one aspect, the invention provides an engineered meganuclease that binds and cleaves the HBV 11-12 recognition sequence (SEQ ID NO: 10) within a Hepatitis B virus genome. The engineered meganuclease comprises a first subunit and a second subunit, wherein the first subunit binds to a first recognition half-site of the recognition sequence and comprises a first hypervariable (HVR1) region having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100%, sequence identity to an amino acid sequence corresponding to residues 215-270 of the presently disclosed HBV 11-12L.1090 meganuclease (the amino acid sequence of which is set forth as SEQ ID NO: 12), the presently disclosed HBV 11-12L.1036 meganuclease (the amino acid sequence of which is set forth as SEQ ID NO: 13), the presently disclosed HBV 11-12L.520 S19 meganuclease (the amino acid sequence of which is set forth as SEQ ID NO: 14), the presently disclosed HBV 11-12L.638 meganuclease (the amino acid sequence of which is set forth as SEQ ID NO: 15), the presently disclosed HBV 11-12L.638 S19 meganuclease (the amino acid sequence of which is set forth as SEQ ID NO: 16), or the presently disclosed HBV 11-12L.699 meganuclease (the amino acid sequence of which is set forth as SEQ ID NO: 17), and wherein the second subunit binds to a second recognition half-site of the recognition sequence and comprises a second hypervariable (HVR2) region having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to residues 24-79 of the presently disclosed HBV 11-12L.1090 meganuclease (the amino acid sequence of which is set forth as SEQ ID NO: 12), the presently disclosed HBV 11-12L.1036 meganuclease (the amino acid sequence of which is set forth as SEQ ID NO: 13), the presently disclosed HBV 11-12L.520 S19 meganuclease (the amino acid sequence of which is set forth as SEQ ID NO: 14), the presently disclosed HBV 11-12L.638 meganuclease (the amino acid sequence of which is set forth as SEQ ID NO: 15), the presently disclosed HBV 11-12L.638 S19 meganuclease (the amino acid sequence of which is set forth as SEQ ID NO: 16), or the presently disclosed HBV 11-12L.699 meganuclease (the amino acid sequence of which is set forth as SEQ ID NO: 17).

In some embodiments, any of the disclosed hypervariable regions (e.g., HVR1 or HVR2) has an amino acid sequence that differs by up to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 amino acid substitutions relative to any one of SEQ ID NOs: 12, 13, 14, 15, 16, and 17. These differences may comprise amino acids that have been inserted, deleted, or substituted relative to the sequence of any one of SEQ ID NOs: 12, 13, 14, 15, 16, and 17. In some embodiments, the HVR1 region contains stretches of about 10, about 20, about 30, about 40, about 50, about 60, about 75, or more than 74 amino acids in common with the sequence of any one of SEQ ID NOs: 12, 13, 14, 15, 16, and 17.

In certain embodiments, the HVR1 region has at least 92%, at least 93%, at least 94%, at least 95%, at least 96%, at least 97%, at least 98%, at least 99%, or 100% sequence identity to an amino acid sequence corresponding to residues 215-270 of SEQ ID NO: 12, at least 90%, at least 91%, at least 92%, at least 93%, at least 94%, at least 95%, at least 96%, at least 97%, at least 98%, at least 99% or 100% sequence identity to an amino acid sequence corresponding to residues 215-270 of SEQ ID NO: 13, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to an amino acid sequence corresponding to residues 215-270 of SEQ ID NO: 14, at least 99% or 100% sequence identity to an amino acid sequence corresponding to residues 215-270 of any one of SEQ ID NOs: 15 or 16, or at least 86%, at least 87%, at least 88%, at least 89%, at least 90%, at least 91%, at least 92%, at least 93%, at least 94%, at least 95%, at least 96%, at least 97%, at least 98%, or at least 99% or 100% sequence identity to an amino acid sequence corresponding to residues 215-270 of SEQ ID NO: 17.

In certain embodiments, the HVR1 region comprises an amino acid sequence corresponding to residues 215-270 of SEQ ID NOs: 12, 13, 14, 15, 16, or 17 with up to 1, 2, 3, 4, 5, 6, or 7 amino acid substitutions.

In some embodiments, the HVR1 region comprises one or more residues corresponding to residues 215, 217, 219, 221, 223, 224, 229, 231, 233, 235, 237, 259, 261, 266, and 268 of any one of SEQ ID NOs: 12, 13, 14, 15, 16, and 17.

In some embodiments, the HVR1 region comprises residues corresponding to residues 215, 217, 219, 221, 223, 224, 229, 231, 233, 235, 237, 259, 261, 266, and 268 of any one of SEQ ID NOs: 12, 13, 14, 15, 16, and 17.

In some embodiments, the HVR1 region comprises one or more residues corresponding to residues 262, 263, and 264 of SEQ ID NO: 12 or 13.

In some embodiments, the HVR1 region comprises residues corresponding to residues 262, 263, and 264 of SEQ ID NO: 12 or 13.

In some embodiments, the HVR1 region comprises one or more residues corresponding to residues 239, 241, 262, 263, and 264 of SEQ ID NO: 15 or 16.

In some embodiments, the HVR1 region comprises residues corresponding to residues 239, 241, 262, 263, and 264 of SEQ ID NO: 15 or 16.

In some embodiments, the HVR1 region comprises residues corresponding to residues 241, 262, 263, and 264 of SEQ ID NO: 17.

In some embodiments, the HVR1 region comprises one or more residues corresponding to residues 241, 262, 263, and 264 of SEQ ID NO: 17.

In certain embodiments, the HVR1 region comprises Y, R, K, or D at a residue corresponding to residue 257 of any one of SEQ ID NOs: 12, 13, 14, 15, 16, and 17.

In certain embodiments, the HVR1 region comprises residues 215-270 of any one of SEQ ID NOs: 12, 13, 14, 15, 16, and 17.

In particular embodiments, the first subunit comprises an amino acid sequence having at least 80%, at least 85%, at least 90%, at least 91%, at least 92%, at least 93%, at least 94%, at least 95%, at least 96%, at least 97%, at least 98%, at least 99% or 100%, sequence identity to an amino acid sequence corresponding to residues 198-344 of SEQ ID NO:

12, 13, 14, 15, 16, or 17. In certain embodiments, the first subunit comprises an amino acid sequence having at least 96% sequence identity to residues 198-344 of SEQ ID NO: 12, 13, 14, 15, 16, or 17. In some embodiments, the first subunit comprises an amino acid sequence corresponding to residues 198-344 of SEQ ID NOs: 12, 13, 14, 15, 16, or 17 with up to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 amino acid substitutions.

In certain embodiments, the first subunit comprises G, S, or A at a residue corresponding to residue 210 of SEQ ID NO: 12, 13, 14, 15, 16, or 17.

In certain embodiments, the first subunit comprises a residue corresponding to residue 210 of SEQ ID NO: 14 or SEQ ID NO: 16.

In certain embodiments, the first subunit comprises E, Q, or K at a residue corresponding to residue 271 of SEQ ID NO: 12, 13, 14, 15, 16, or 17.

In certain embodiments, the first subunit comprises a residue corresponding to residue 271 of SEQ ID NO: 12.

In certain embodiments, the first subunit comprises a residue corresponding to residue 330 of SEQ ID NO: 13.

In particular embodiments, the first subunit comprises residues 198-344 of SEQ ID NO: 12, 13, 14, 15, 16, or 17.

In some such embodiments, the HVR2 region comprises an amino acid sequence having at least 80%, at least 85%, at least 90%, at least 91%, at least 92%, at least 93%, at least 94%, at least 95%, at least 96%, at least 97%, at least 98%, at least 99% or 100%, sequence identity to an amino acid sequence corresponding to residues 24-79 of SEQ ID NO: 12, 13, 14, 15, 16, or 17. In certain embodiments, the HVR2 region comprises an amino acid sequence corresponding to residues 24-79 of SEQ ID NOs: 12, 13, 14, 15, 16, or 17 with up to 1, 2, 3, 4, 5, 6, 7, 8, 9, 10, or 11 amino acid substitutions.

In certain embodiments, the HVR2 region comprises one or more residues corresponding to residues 24, 26, 28, 30, 32, 33, 38, 40, 42, 44, 46, 68, 70, 75, and 77 of SEQ ID NO: 12, 13, 14, 15, 16, or 17.

In certain embodiments, the HVR2 region comprises residues corresponding to residues 24, 26, 28, 30, 32, 33, 38, 40, 42, 44, 46, 68, 70, 75, and 77 of SEQ ID NO: 12, 13, 14, 15, 16, or 17.

In certain embodiments, the HVR2 region comprises a residue corresponding to residue 51 of SEQ ID NO: 12.

In certain embodiments, the HVR2 region comprises Y, R, K, or D at a residue corresponding to residue 66 of SEQ ID NO: 12, 13, 14, 15, 16, or 17.

In particular embodiments, the HVR2 region comprises residues 24-79 of SEQ ID NO: 12, 13, 14, 15, 16, or 17.

In some embodiments, the second subunit comprises an amino acid sequence having at least 80%, at least 85%, at least 90%, at least 91%, at least 92%, at least 93%, at least 94%, at least 95%, at least 96%, at least 97%, at least 98%, at least 99% or 100%, sequence identity to an amino acid sequence corresponding to residues 7-153 of SEQ ID NO: 12, 13, 14, 15, 16, or 17. In certain embodiments, the second subunit comprises an amino acid sequence having at least 99% sequence identity to an amino acid sequence corresponding to residues 7-153 of SEQ ID NO: 12, 13, 14, 15, 16, or 17. In particular embodiments, the second subunit comprises an amino acid sequence corresponding to residues 7-153 of SEQ ID NOs: 12, 13, 14, 15, 16, or 17 with up to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 amino acid substitutions.

In certain embodiments, the second subunit comprises G, S, or A at a residue corresponding to residue 19 of SEQ ID NO: 12, 13, 14, 15, 16, or 17.

In certain embodiments, the second subunit comprises a residue corresponding to residue 19 of SEQ ID NO: 12 or SEQ ID NO: 13.

In certain embodiments, the second subunit comprises E, Q, or K at a residue corresponding to residue 80 of SEQ ID NO: 12, 13, 14, 15, 16, or 17.

In certain embodiments, the second subunit comprises a residue corresponding to residue 80 of SEQ ID NO: 12, 13, 14, 15, 16, or 17.

In particular embodiments, the second subunit comprises residues 7-153 of SEQ ID NO: 12, 13, 14, 15, 16, or 17.

In some embodiments, the first subunit of the engineered meganuclease has at least 80%, at least 85%, at least 90%, at least 91%, at least 92%, at least 93%, at least 94%, at least 95%, at least 96%, at least 97%, at least 98%, at least 99% or 100%, sequence identity to an amino acid sequence corresponding to residues 198-344 of SEQ ID NO: 12, 13, 14, 15, 16, or 17, and the second subunit comprises an amino acid sequence having at least 80%, at least 85%, at least 90%, at least 91%, at least 92%, at least 93%, at least 94%, at least 95%, at least 96%, at least 97%, at least 98%, at least 99% or 100%, sequence identity to an amino acid sequence corresponding to residues 7-153 of SEQ ID NO: 12, 13, 14, 15, 16, or 17. In particular embodiments, the first subunit of the engineered meganuclease has at least 96% sequence identity to an amino acid sequence corresponding to residues 198-344 of SEQ ID NO: 12, 13, 14, 15, 16, or 17, and the second subunit comprises an amino acid sequence having at least 99% sequence identity to an amino acid sequence corresponding to residues 7-153 of SEQ ID NO: 12, 13, 14, 15, 16, or 17. In certain embodiments, the first subunit and/or the second subunit comprises up to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 amino acid substitutions relative to residues 198-344 and residues 7-153, respectively, of SEQ ID NOs: 12, 13, 14, 15, 16, or 17.

In certain embodiments, the engineered meganuclease comprises a linker, wherein the linker covalently joins the first subunit and the second subunit.

In some embodiments, the engineered meganuclease comprises an amino acid sequence having at least about 90%, about 91%, about 92%, about 93%, about 94%, about 95%, about 96%, about 97%, about 98%, about 99%, or 100% sequence identity to the amino acid sequence of SEQ ID NO: 12, 13, 14, 15, 16, or 17. In certain embodiments, the engineered meganuclease comprises an amino acid sequence having at least 97% sequence identity to the amino acid sequence of SEQ ID NO: 12, 13, 14, 15, 16, or 17.

In particular embodiments, the engineered meganuclease comprises the amino acid sequence of SEQ ID NO: 12, 13, 14, 15, 16 or 17.

In some embodiments, the engineered meganuclease is encoded by a nucleic sequence having at least 80%, 85%, 90%, 91%, 92%, 93%, 94%, 95%, 96%, 97%, 98%, 99% or more sequence identity to a nucleic acid sequence set forth in any one of SEQ ID NOs: 45, 46, 47, 48, 49, or 50. In some embodiments, the engineered meganuclease is encoded by a nucleic sequence set forth in any one of SEQ ID NOs: 45, 46, 47, 48, 49, or 50.

In each of the embodiments above, the engineered meganuclease can comprise a nuclear localization signal. In some embodiments, the nuclear localization signal is at the N-terminus of the engineered meganuclease. In some embodiments, the nuclear localization signal comprises an amino acid sequence having at least 80% or at least 90% sequence identity to SEQ ID NO: 51. In some embodiments, the nuclear localization signal comprises SEQ ID NO: 51.

In some embodiments, the engineered meganuclease described herein exhibit at least one of the following optimized characteristics as compared to the HBV 11-12x.26 meganuclease set forth as SEQ ID NO: 39 or the HBV 11-12L.363 meganuclease set forth in SEQ ID NO: 40: improved specificity, enhanced efficiency of cleavage, and enhanced efficiency of indel formation. In some embodiments, the engineered meganuclease described herein exhibits improved specificity as compared to the HBV 11-12x.26 meganuclease set forth as SEQ ID NO: 39 or the HBV 11-12L.363 meganuclease set forth in SEQ ID NO: 40. In some embodiments, the engineered meganuclease described herein exhibits enhanced efficiency of cleavage as compared to the HBV 11-12x.26 meganuclease set forth as SEQ ID NO: 39 or the HBV 11-12L.363 meganuclease set forth in SEQ ID NO: 40. In some embodiments, the engineered meganuclease described herein exhibits enhanced indel formation as compared to the HBV 11-12x.26 meganuclease set forth as SEQ ID NO: 39 or the HBV 11-12L.363 meganuclease set forth in SEQ ID NO: 40.

In another aspect, the invention provides a polynucleotide comprising a nucleic acid sequence encoding an engineered meganuclease described herein.

In certain embodiments, the polynucleotide is an mRNA.

In further embodiments, the mRNA is a polycistronic mRNA encoding one or more engineered meganucleases described herein. In certain embodiments, the polycistronic mRNA encodes at least one of the presently disclosed engineered meganucleases which binds and cleaves a recognition sequence comprising SEQ ID NO: 10, and a second engineered meganuclease which binds and cleaves a second recognition sequence which is present in a Hepatitis B virus genome but differs from SEQ ID NO: 10. In some embodiments, the polycistronic mRNA encodes at least one of the presently disclosed engineered meganucleases which binds and cleaves a recognition sequence comprising SEQ ID NO: 10; and an additional one or more engineered meganucleases which bind and cleave an additional one or more recognition sequences which is present in a Hepatitis B virus genome but differ from SEQ ID NO: 10. In some of these embodiments, the second recognition sequence comprises the HBV 5-6 recognition sequence (which is set forth as SEQ ID NO: 30).

In further embodiments, a polycistronic mRNA of the invention encodes one or more engineered meganucleases described herein and one or more additional proteins that induce a therapeutically beneficial effect in an HBV-infected cell and/or HBV-infected subject.

In another aspect, the invention provides a recombinant DNA construct comprising a polynucleotide comprising a nucleic acid sequence encoding an engineered meganuclease described herein. In some embodiments, the recombinant DNA construct comprises a cassette comprising a promoter and a nucleic acid sequence encoding an engineered meganuclease described herein. In other embodiments, the recombinant DNA construct comprises at least a first cassette and a second cassette, wherein the first cassette comprises a promoter and a nucleic acid sequence encoding an engineered meganuclease described herein, and wherein the second cassette comprises a promoter and a nucleic acid sequence encoding a second engineered meganuclease which binds and cleaves a second recognition sequence which is present in a Hepatitis B virus genome but differs from SEQ ID NO: 10. In some embodiments, the recombinant DNA construct comprises at least a first cassette and one or more additional cassettes, wherein the first cassette comprises a promoter and a nucleic acid sequence encoding an engineered meganuclease described herein, and wherein the one or more additional cassettes comprise a promoter and a nucleic acid sequence encoding an additional one or more engineered meganucleases which bind and cleave an additional one or more recognition sequences which are present in a Hepatitis B virus genome but differ from SEQ ID NO: 10. In some of these embodiments, the second recognition sequence comprises SEQ ID NO: 30.

In other embodiments, the recombinant DNA construct comprises a cassette comprising a promoter and a polycistronic nucleic acid sequence, wherein the promoter drives expression of the polycistronic nucleic acid sequence to generate a polycistronic mRNA described herein in a target cell. In some embodiments, the target cell is a hepatocyte. In some embodiments, the target cell is a primary human hepatocyte (PHH).

In some embodiments, the promoter is a liver specific promoter.

In some embodiments, the promoter comprises a human thyroxine binding globulin (TBG) promoter, a human alpha-1 antitrypsin promoter, a hybrid liver-specific promoter, or an apolipoprotein A-II promoter.

In certain embodiments, the recombinant DNA construct encodes a recombinant virus comprising the polynucleotide comprising a nucleic acid sequence encoding an engineered meganuclease described herein. In particular embodiments, the recombinant virus is a recombinant adenovirus, a recombinant lentivirus, a recombinant retrovirus, or a recombinant adeno-associated virus (AAV). In some embodiments, the recombinant virus is a recombinant AAV. In some embodiments, the recombinant AAV has an AAV8 serotype.

In another aspect, the invention provides a recombinant virus comprising a polynucleotide comprising a nucleic acid sequence encoding an engineered meganuclease described herein. In particular embodiments, the recombinant virus is a recombinant adenovirus, a recombinant lentivirus, a recombinant retrovirus, or a recombinant AAV.

In some embodiments, the recombinant virus comprises a cassette comprising a promoter and a nucleic acid sequence encoding an engineered meganuclease described herein. In other embodiments, the viral vector comprises at least a first cassette and a second cassette, wherein the first cassette comprises a promoter and a nucleic acid sequence encoding an engineered meganuclease described herein, and wherein the second cassette comprises a promoter and a nucleic acid sequence encoding a second engineered meganuclease which binds and cleaves a second recognition sequence that is present in a Hepatitis B virus genome and differs from SEQ ID NO: 10. In some embodiments, the recombinant virus comprises at least a first cassette and one or more additional cassettes, wherein the first cassette comprises a promoter and a nucleic acid sequence encoding an engineered meganuclease described herein, and wherein the one or more additional cassettes comprise a promoter and a nucleic acid sequence encoding one or more additional engineered meganucleases which bind and cleave a second recognition sequence that is present in a Hepatitis B virus genome and differs from SEQ ID NO: 10. In some of these embodiments, the second recognition sequence comprises SEQ ID NO: 30.

In other embodiments, the recombinant virus comprises one cassette comprising a promoter and a polycistronic nucleic acid sequence, wherein the promoter drives expression of the polycistronic nucleic acid sequence to generate a polycistronic mRNA described herein in a target cell.

In some embodiments, the promoter is a liver specific promoter. In some embodiments, the promoter comprises a human thyroxine binding globulin (TBG) promoter, a human alpha-1 antitrypsin promoter, a hybrid liver-specific promoter, or an apolipoprotein A-II promoter.

In some embodiments, the polycistronic mRNA is any polycistronic mRNA described herein.

In another aspect, the invention provides a pharmaceutical composition comprising, the pharmaceutical composition comprising a pharmaceutically acceptable carrier and: (a) a polynucleotide comprising a nucleic acid sequence encoding an engineered meganuclease described herein; or (b) an engineered meganuclease described herein. In some embodiments, the pharmaceutical composition is used for treatment of a subject having Hepatitis B virus or hepatocellular carcinoma caused by Hepatitis B virus.

In one embodiment, the nucleic acid sequence of the pharmaceutical composition encoding an engineered meganuclease described herein is an mRNA described herein. In some such embodiments, the mRNA is a polycistronic mRNA described herein, such that an engineered meganuclease described herein is expressed in the target cell in vivo, along with a second engineered meganuclease which binds and cleaves a second recognition sequence that is present in a Hepatitis B virus genome and differs from SEQ ID NO: 10. In some of these embodiments, the second recognition sequence comprises SEQ ID NO: 30.

In another embodiment, the pharmaceutical composition comprises a recombinant DNA construct described herein comprising a polynucleotide comprising a nucleic acid sequence encoding an engineered meganuclease described herein. In some such embodiments, the recombinant DNA construct comprises a cassette comprising a promoter and a nucleic acid sequence encoding an engineered meganuclease of the invention. In other embodiments, the recombinant DNA construct of the pharmaceutical composition comprises at least a first cassette and a second cassette, wherein the first cassette comprises a promoter and a nucleic acid sequence encoding an engineered meganuclease described herein, and wherein the second cassette comprises a promoter and a nucleic acid sequence encoding a second engineered meganuclease which binds and cleaves a second recognition sequence that is present in a Hepatitis B virus genome and differs from SEQ ID NO: 10. In some of these embodiments, the second recognition sequence comprises SEQ ID NO: 30.

In other embodiments, the recombinant DNA construct of the pharmaceutical composition comprises a cassette comprising a promoter and a polycistronic nucleic acid sequence, wherein the promoter drives expression of the polycistronic nucleic acid sequence to generate a polycistronic mRNA described herein in the target cell in vivo.

In another embodiment, the pharmaceutical composition comprises a recombinant virus comprising a polynucleotide comprising a nucleic acid sequence encoding an engineered meganuclease described herein. In one such embodiment, the recombinant virus is a recombinant adenovirus, a recombinant lentivirus, a recombinant retrovirus, or a recombinant AAV.

In some such embodiments, the recombinant virus comprises a cassette comprising a promoter and a nucleic acid sequence encoding an engineered meganuclease described herein. In other embodiments, the recombinant virus comprises at least a first cassette and a second cassette, wherein the first cassette comprises a promoter and a nucleic acid sequence encoding an engineered meganuclease described herein, and wherein the second cassette comprises a promoter and a nucleic acid sequence encoding a second engineered meganuclease which binds and cleaves a second recognition sequence that is present in a Hepatitis B virus genome and differs from SEQ ID NO: 10. In some of these embodiments, the second recognition sequence comprises SEQ ID NO: 30.

In other such embodiments, the recombinant virus comprises one cassette comprising a promoter and a polycistronic nucleic acid sequence, wherein the promoter drives expression of the polycistronic nucleic acid sequence to generate a polycistronic mRNA described herein in the target cell in vivo.

In other embodiments, the pharmaceutical composition comprises an engineered meganuclease described herein. In various embodiments, the pharmaceutical composition comprises an engineered meganuclease described herein and a second engineered meganuclease which binds and cleaves a second recognition sequence which is present in a Hepatitis B virus genome but differs from SEQ ID NO: 10. In other embodiments, the pharmaceutical composition comprises an engineered meganuclease described herein and an additional one or more engineered meganucleases which bind and cleave an additional one or more recognition sequences which are present in a Hepatitis B virus genome but differ from SEQ ID NO: 10. In some of these embodiments, the second recognition sequence comprises SEQ ID NO: 30.

In still other embodiments, the pharmaceutical composition comprises a polynucleotide comprising a nucleic acid sequence encoding an engineered meganuclease described herein and a nucleic acid sequence encoding a second engineered meganuclease which binds and cleaves a second recognition sequence that is present in a Hepatitis B virus genome and differs from SEQ ID NO: 10. In further embodiments, the pharmaceutical composition comprises a polynucleotide comprising a nucleic acid sequence encoding an engineered meganuclease described herein and a nucleic acid sequence encoding an additional one or more engineered meganucleases which bind and cleave a second recognition sequence that is present in a Hepatitis B virus genome and differs from SEQ ID NO: 10. In some of these embodiments, the second recognition sequence comprises SEQ ID NO: 30. In such embodiments, the polynucleotides comprising two nucleic acid sequences may be comprised by mRNAs described herein, the recombinant DNA constructs described herein, and/or the recombinant viruses described herein.

In some embodiments, the pharmaceutical composition comprises one or more mRNAs described herein encapsulated within lipid nanoparticles. In particular embodiments, the lipid nanoparticles of the pharmaceutical composition comprise at least a first mRNA and at least a second mRNA, wherein the first mRNA encodes an engineered meganuclease described herein, and the second mRNA encodes a second engineered meganuclease which binds and cleaves a second recognition sequence which is present in a Hepatitis B virus genome but differs from SEQ ID NO: 10. In some of these embodiments, the second recognition sequence comprises SEQ ID NO: 30. In other embodiments, the lipid nanoparticles of the pharmaceutical composition comprise one or more polycistronic mRNAs described herein, wherein the polycistronic mRNA encodes an engineered meganuclease described herein and a second engineered meganuclease which binds and cleaves a second recognition sequence that is present in a Hepatitis B virus genome and differs from SEQ ID NO: 10. In some of these embodiments, the second recognition sequence comprises SEQ ID NO: 30. In some embodiments, the lipid nanoparticles have a composition which enhances delivery and uptake in the liver, and specifically within hepatocytes.

In another aspect, the invention provides a lipid nanoparticle, or a lipid nanoparticle formulation, comprising mRNA encoding at least one engineered meganuclease described herein.

In particular embodiments, the lipid nanoparticles comprise at least a first mRNA and at least a second mRNA, wherein the first mRNA encodes an engineered meganuclease described herein, and the second mRNA encodes a second engineered meganuclease which binds and cleaves a second recognition sequence that is present in a Hepatitis B virus genome and differs from SEQ ID NO: 10. In some of these embodiments, the second recognition sequence comprises SEQ ID NO: 30.

In other embodiments, the lipid nanoparticles of the pharmaceutical composition comprises one or more polycistronic mRNAs described herein, wherein the polycistronic mRNA encodes an engineered meganuclease described herein and a second engineered meganuclease which binds and cleaves a second recognition sequence that is present in a Hepatitis B virus genome and differs from SEQ ID NO: 10. In some of these embodiments, the second recognition sequence comprises SEQ ID NO: 30.

In some embodiments, the lipid nanoparticles have a composition which enhances delivery and uptake in the liver, and specifically within hepatocytes.

In another aspect, the invention provides a method for treating a subject having HBV or hepatocellular carcinoma caused by HBV. Likewise, provided herein is a method for reducing the level and/or proliferation of HBV, or reducing the symptoms associated with HBV. The methods comprise delivering to a target cell in the subject: (a) a therapeutically effective amount of a polynucleotide comprising a nucleic acid sequence encoding an engineered meganuclease described herein, wherein the engineered meganuclease is expressed in the target cell in vivo; or (b) a therapeutically effective amount of an engineered meganuclease protein described herein; wherein the engineered meganuclease binds and cleaves a recognition sequence comprising SEQ ID NO: 10 within the HBV genome in the target cell. The method can reduce or eliminate the infection and/or proliferation of HBV in the subject.

In certain embodiments, the methods reduce circulating HBsAg levels, circulating HBeAg levels, circulating HBV DNA levels, and/or hepatic cccDNA levels.

In another aspect, the invention provides a method for treating a subject having HCC caused by HBV. The methods comprise delivering to a target cell in the subject: (1) (a) a polynucleotide comprising a nucleic acid sequence encoding an engineered meganuclease described herein, wherein the engineered meganuclease is expressed in the target cell in vivo; or (b) an engineered meganuclease protein; and (2) a polynucleotide comprising a nucleic acid sequence encoding a suicide gene and sequences homologous to sequences flanking the meganuclease cleavage site; wherein the engineered meganuclease binds and cleaves a recognition sequence comprising SEQ ID NO: 10 within the Hepatitis B virus genome, thus cleaving the HBV genome in the target cell; wherein the suicide gene is inserted into the cleaved HBV genome by homologous recombination; and wherein expression of the suicide gene kills the target cell.

In some embodiments, the suicide gene is directly lethal to the target cell. In some such embodiments, the directly lethal suicide gene encodes a toxic polypeptide or a pro-apoptotic protein. In some embodiments, the suicide gene is indirectly lethal to the target cell, and directs the subject's own immune system to kill the target cell. In some such embodiments, the indirectly lethal suicide gene encodes a cell surface protein which is recognized as foreign by the subject's immune system and is targeted by a humoral or cellular immune response. In other such embodiments, the indirectly lethal suicide gene encodes a polypeptide which is presented by an MHC Class I molecule, is recognized as foreign by the subject's immune system, and is targeted by a cytotoxic immune response.

In further embodiments, the methods of treatment for HBV infection or HCC comprise administering to the subject any pharmaceutical composition of the invention described herein which comprises, at least, a pharmaceutically acceptable carrier and (a) a polynucleotide comprising a nucleic acid sequence encoding an engineered meganuclease described herein, wherein the engineered meganuclease is expressed in a target cell in vivo; or (b) an engineered meganuclease protein described herein.

In some embodiments of the methods of treatment for HBV infection or HCC, the engineered meganuclease, or a polynucleotide comprising a nucleic acid sequence encoding the engineered meganuclease, can be delivered to a target hepatocyte cell. In particular embodiments, an effective amount of the engineered meganuclease, or the polynucleotide comprising a nucleic acid sequence encoding the engineered meganuclease, can be delivered to a target hepatocyte cell.

In some embodiments, the method further comprises administering a therapeutically effective amount of a polynucleotide comprising a nucleic acid sequence encoding one or more additional engineered meganucleases or a therapeutically effective amount of one or more additional engineered meganucleases, wherein the one or more additional engineered meganucleases bind and cleave a recognition sequence other than SEQ ID NO: 10.

In some embodiments, the polynucleotide comprising a nucleic acid sequence encoding one or more additional engineered meganucleases or the one or more additional engineered meganucleases are administered concurrently with the administration of the nucleic acid encoding an engineered meganuclease described herein or an engineered meganuclease described herein (e.g., an engineered meganuclease set forth in SEQ ID NOs: 12, 13, 14, 15, 16, or 17).

In some embodiments, the polynucleotide comprising a nucleic acid sequence encoding one or more additional engineered meganucleases or the one or more additional engineered meganucleases are administered separately from the administration of the nucleic acid encoding an engineered meganuclease described herein or an engineered meganuclease described herein (e.g., an engineered meganuclease set forth in SEQ ID NOs: 12, 13, 14, 15, 16, or 17).

In some embodiments, the one or more additional engineered meganucleases are encoded in a polynucleotide that encodes an engineered meganuclease described herein (e.g., an engineered meganuclease set forth in SEQ ID NOs: 12, 13, 14, 15, 16, or 17).

In some embodiments, the one or more additional engineered meganucleases are encoded in a different polynucleotide from a polynucleotide that encodes an engineered meganuclease described herein (e.g., an engineered meganuclease set forth in SEQ ID NOs: 12, 13, 14, 15, 16, or 17).

In some embodiments, the polynucleotide encoding one or more additional engineered meganucleases or the one or more additional engineered meganucleases are administered as a part of a pharmaceutical composition. In some embodiments, the pharmaceutical composition is different from the pharmaceutical composition including an engineered meganuclease described herein (e.g., an engineered meganuclease set forth in SEQ ID NOs: 12, 13, 14, 15, 16, or 17).

In some embodiments, the polynucleotide administered in the methods described herein is an mRNA. In some embodiments, the polynucleotide is part of a recombinant DNA construct. In some embodiments, the recombinant DNA construct encodes a recombinant virus comprising the polynucleotide comprising the nucleic acid sequence encoding an engineered meganuclease described herein. In some embodiments, the recombinant virus is a recombinant adenovirus, a recombinant lentivirus, a recombinant retrovirus, or a recombinant AAV.

In certain embodiments, the methods reduce circulating HBsAg levels, circulating HBeAg levels, circulating HBV DNA levels, and/or hepatic cccDNA levels.

In some embodiments, the methods described herein further comprise administering one or more additional therapeutic agents that are effective in treating an HBV infection.

In particular embodiments, delivery to a hepatocyte cell occurs ex vivo, wherein an effective amount of the hepatocyte cells having been delivered the engineered meganuclease, or the nucleic acid encoding the engineered meganuclease, are administered to a subject.

In some embodiments, a hepatotoxic protein, or a nucleic acid or AAV encoding a hepatotoxic protein, is administered with the pharmaceutical compositions described herein.

In particular embodiments of the methods, the engineered meganuclease comprises the amino acid sequence of SEQ ID NO: 12, 13, 14, 15, 16, or 17.

In particular embodiments of the methods, the subject is a mammal, such as a human.

In another aspect, the invention provides an engineered meganuclease described herein for use as a medicament. The invention further provides the use of an engineered meganuclease, described herein in the manufacture of a medicament for treating HBV, for reducing the level or proliferation of HBV, reducing the symptoms associated with HBV, or treating HCC.

In another aspect, the invention provides an isolated polynucleotide for use as a medicament, wherein the isolated polynucleotide comprises a nucleic acid sequence encoding an engineered meganuclease described herein. The invention further provides the use of an isolated polynucleotide in the manufacture of a medicament for treating HBV, for reducing the level or proliferation of HBV, reducing the symptoms associated with HBV, or treating HCC.

In another aspect, the invention provides a recombinant AAV for use as a medicament, wherein the recombinant AAV comprises a polynucleotide, and wherein the polynucleotide comprises a nucleic acid sequence encoding an engineered meganuclease described herein. The invention further provides the use of a recombinant AAV in the manufacture of a medicament for treating HBV, for reducing the level or proliferation of HBV, reducing the symptoms associated with HBV, or treating HCC, wherein the recombinant AAV comprises a polynucleotide, and wherein the polynucleotide comprises a nucleic acid sequence encoding an engineered meganuclease described herein.

BRIEF DESCRIPTION OF THE FIGURES

FIG. 2. HBV 11-12 recognition sequence in the HBV genome. The HBV 11-12 recognition sequence, targeted by engineered meganucleases of the invention, comprises two recognition half-sites. Each recognition half-site comprises 9 base pairs, separated by a 4 base pair central sequence. The HBV 11-12 recognition sequence (SEQ ID NO: 10) comprises two recognition half-sites referred to as HBV11 and HBV12.

FIG. 3. Alignment of HBV recognition sequences in HBV genotypes A-G. The HBV 11-12 recognition sequence targeted by engineered meganucleases of the invention is conserved across multiple HBV genotypes. The HBV 11-12 recognition sequence spans residues 1259-1280 of HBV genotype A set forth in SEQ ID NO: 3, and this recognition sequence is fully conserved in genotypes B, C, D, E, F, and G (SEQ ID NOs: 4-9).

FIG. 16A). A Southern blot detecting the presence of rcDNA, dslDNA, cccDNA, and control mtDNA of HBV infected PHH samples taken at 3, 6, 9, 12, and 17 days following the first mRNA delivery of either a mCherry mock transfection, HBV 11-12L.520S19 or a non-targeting PCSK9 control meganuclease PCS 7-8 L.197. FIG. 16B). A Southern blot detecting the presence of rcDNA, dslDNA, cccDNA, and control mtDNA of HBV infected PHH samples taken at 3, 6, 9, 12, and 17 days following the first mRNA delivery of either a HBV 11-12L.1036, HBV 11-12L.1090, or the control PCS 7-8 L.197 meganuclease.

FIG. 17A). Bar graph showing the effectiveness of the HBV 11-12L.520S19 or a non-targeting PCSK9 control meganuclease PCS 7-8 L.197 in reducing the percent cccDNA in HBV infected PHH normalized to a mock transfection control. FIG. 17B). Bar graph showing the effectiveness of the HBV 11-12L.1036 or HBV 11-12L.1090 or a non-targeting PCSK9 control meganuclease PCS 7-8 L.197 in reducing the percent cccDNA in HBV infected PHH normalized to a mock transfection control. The levels of cccDNA shown were measured at 3, 6, 9, 12, and 17 days following the second transfection of the respective meganucleases.

FIGS. 18A-18D. Diagrams showing HBV integration events, which were detected as chimeric sequence reads between a host genomic fragment and HBV genomic fragment. Each event is represented by a small triangle. The Y-axis provides the location of the HBV genome that is integrated within the host genome and the X-axis provides the host chromosome number. Each line indicates the start and stop point of an HBV integrant. Non-vertical lines between individual triangles indicate a translocation of HBV genomic material between chromosomes. The lack of a line between triangles indicates that only one genomic/HBV junction was present in the sequencing read and the full extent of the integration at that chromosomal location could not be determined. FIG. 18A represents integration and translocation information from infected PHH that were mock transfected. FIGS. 18B, 18C, and 18D shows the integration and translocation events of infected PHH that were transfected with the HBV 11-12L.520S19, HBV 11-12L.1036, and HBV 11-12L.1090 meganucleases, respectively.

BRIEF DESCRIPTION OF THE SEQUENCES

Figure 1:
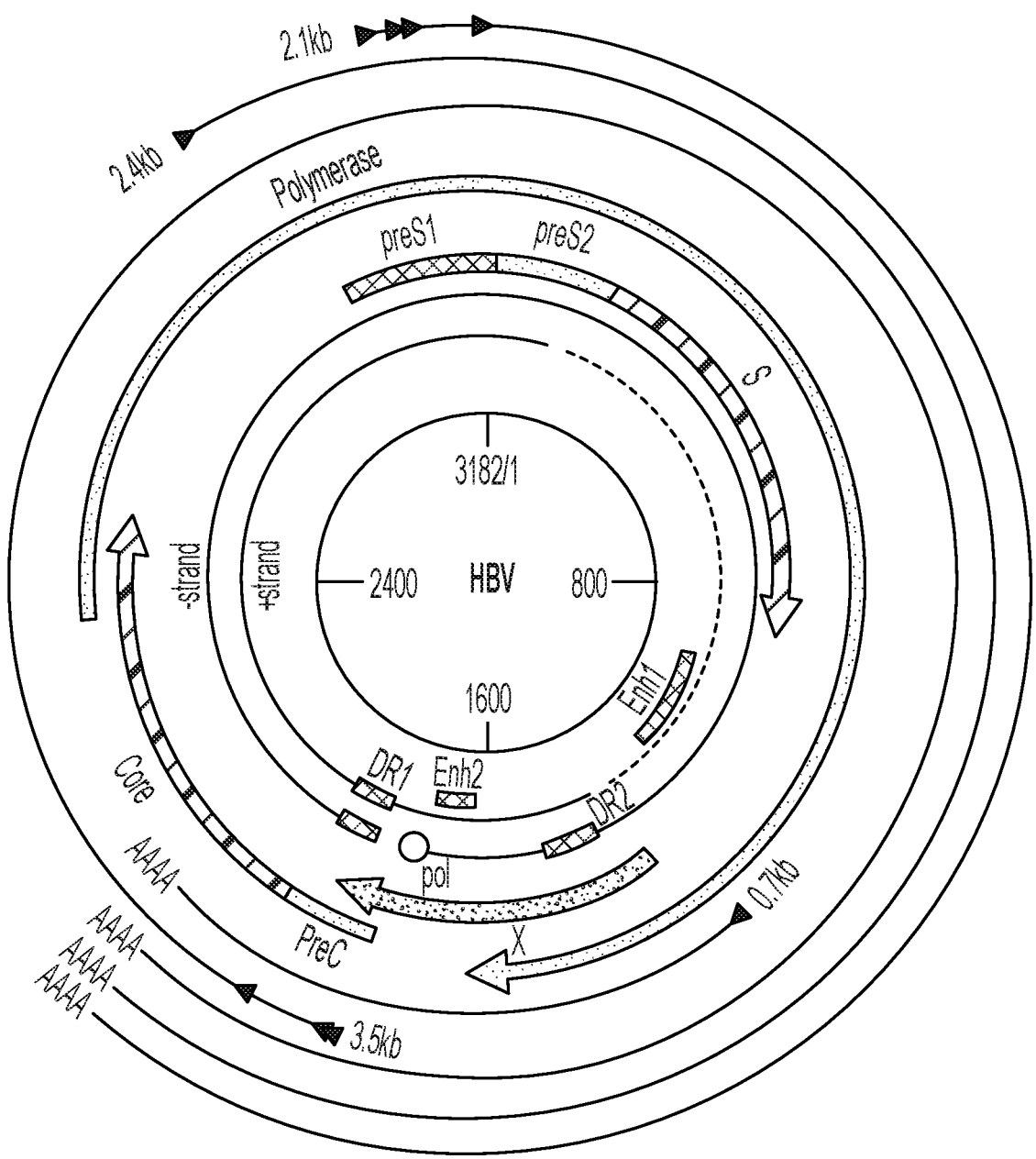
FIG. 1 shows a genomic map of the HBV genome and identifies all ORFs. Virus particles have a partially double-stranded genome (indicated by a dashed line) with a cohesive overlap that spans the 5' regions of each strand and that is flanked by direct repeat sequences (DR1 and DR2). The gene S encodes the major hepatitis B surface antigen (HBsAg) protein and its glycosylated partner, which are transmembrane proteins in the virus envelope. In-frame sequences upstream from the S gene encode the pre-S domains, which are translated with the S sequences to make the pre-S and S polypeptides (middle and large proteins) that contain the virus receptor for infection of hepatocytes. Gene C encodes the hepatitis B core antigen (HBcAg) which forms the nucleocapsid of the virus. The P region encodes the virus reverse transcriptase that also has DNA-dependent DNA polymerase activity and RNase H activity required for virus replication. Although HBV is a DNA virus, it replicates through a pre-genomic RNA intermediate. Finally, the X gene encodes the small regulatory protein of the virus, the hepatitis B x (HBx) antigen. HBx is a transactivating protein that stimulates virus gene expression and replication, protects virus-infected cells against immune-mediated destruction and contributes to the development of hepatocellular carcinoma.
Figure 4:
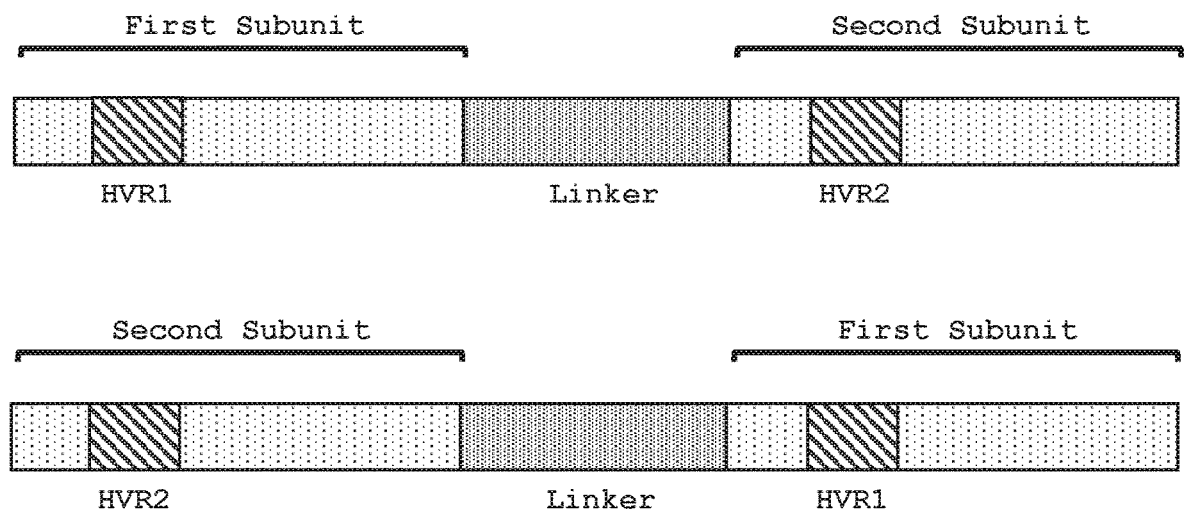
FIG. 4. The engineered meganucleases of the invention comprise two subunits, wherein the first subunit comprising the HVR1 region binds to a first recognition half-site (e.g., HBV11) and the second subunit comprising the HVR2 region binds to a second recognition half-site (e.g., HBV12). In embodiments where the engineered meganuclease is a single-chain meganuclease, the first subunit comprising the HVR1 region can be positioned as either the N-terminal or C-terminal subunit. Likewise, the second subunit comprising the HVR2 region can be positioned as either the N-terminal or C-terminal subunit.

SEQ ID NO: 1 sets forth the amino acid sequence of the wild-type I-CreI meganuclease from *Chlamydomonas reinhardtii*.

SEQ ID NO: 2 sets forth the amino acid sequence of the LAGLIDADG motif.

SEQ ID NO: 3 sets forth the nucleic acid sequence of HBV genotype A.

SEQ ID NO: 4 sets forth the nucleic acid sequence of HBV genotype B.

SEQ ID NO: 5 sets forth the nucleic acid sequence of HBV genotype C.

SEQ ID NO: 6 sets forth the nucleic acid sequence of HBV genotype D.

SEQ ID NO: 7 sets forth the nucleic acid sequence of HBV genotype E.

SEQ ID NO: 8 sets forth the nucleic acid sequence of HBV genotype F.

SEQ ID NO: 9 sets forth the nucleic acid sequence of HBV genotype G.

SEQ ID NO: 10 sets forth the nucleic acid sequence of the sense strand of the HBV 11-12 recognition sequence.

SEQ ID NO: 11 sets forth the nucleic acid sequence of the antisense strand of the HBV 11-12 recognition sequence.

SEQ ID NO: 12 sets forth the amino acid sequence of the HBV 11-12L.1090 meganuclease.

SEQ ID NO: 13 sets forth the amino acid sequence of the HBV 11-12L.1036 meganuclease.

SEQ ID NO: 14 sets forth the amino acid sequence of the HBV 11-12L.520 S19 meganuclease.

SEQ ID NO: 15 sets forth the amino acid sequence of the HBV 11-12L.638 meganuclease.

SEQ ID NO: 16 sets forth the amino acid sequence of the HBV 11-12L.638 S19 meganuclease.

SEQ ID NO: 17 sets forth the amino acid sequence of the HBV 11-12L.699 meganuclease.

SEQ ID NO: 18 sets forth the amino acid sequence of the HBV 11-12L.1090 meganuclease HBV11-binding subunit.

SEQ ID NO: 19 sets forth the amino acid sequence of the HBV 11-12L.1036 meganuclease HBV11-binding subunit.

SEQ ID NO: 20 sets forth the amino acid sequence of the HBV 11-12L.520 S19 meganuclease HBV 11-binding subunit.

SEQ ID NO: 21 sets forth the amino acid sequence of the HBV 11-12L.638 meganuclease HBV 11-binding subunit.

SEQ ID NO: 22 sets forth the amino acid sequence of the HBV 11-12L.638 S19 meganuclease HBV 11-binding subunit.

SEQ ID NO: 23 sets forth the amino acid sequence of the HBV 11-12L.699 meganuclease HBV 11-binding subunit.

SEQ ID NO: 24 sets forth the amino acid sequence of the HBV 11-12L.1090 meganuclease HBV12-binding subunit.

SEQ ID NO: 25 sets forth the amino acid sequence of the HBV 11-12L.1036 meganuclease HBV12-binding subunit.

SEQ ID NO: 26 sets forth the amino acid sequence of the HBV 11-12L.520 S19 meganuclease HBV12-binding subunit.

SEQ ID NO: 27 sets forth the amino acid sequence of the HBV 11-12L.638 meganuclease HBV12-binding subunit.

SEQ ID NO: 28 sets forth the amino acid sequence of the HBV 11-12L.638 S19 meganuclease HBV12-binding subunit.

SEQ ID NO: 29 sets forth the amino acid sequence of the HBV 11-12L.699 meganuclease HBV12-binding subunit.

SEQ ID NO: 30 sets forth the nucleic acid sequence of the HBV 5-6 recognition sequence (sense).

SEQ ID NO: 31 sets forth the nucleic acid sequence of the HBV 5-6 recognition sequence (antisense).

SEQ ID NO: 32 sets forth the nucleic acid sequence of the P1 PCR primer.

SEQ ID NO: 33 sets forth the nucleic acid sequence of the F1 PCR primer.

SEQ ID NO: 34 sets forth the nucleic acid sequence of the R1 PCR primer.

SEQ ID NO: 35 sets forth the nucleic acid sequence of the P2 PCR primer.

SEQ ID NO: 36 sets forth the nucleic acid sequence of the F2 PCR primer.

SEQ ID NO: 37 sets forth the nucleic acid sequence of the R2 PCR primer.

SEQ ID NO: 38 sets forth the amino acid sequence of a polypeptide linker.

SEQ ID NO: 39 sets forth the amino acid sequence of the HBV 11-12x.26 meganuclease.

SEQ ID NO: 40 sets forth the amino acid sequence of the HBV 11-12L.363 meganuclease.

SEQ ID NO: 41 sets forth the nucleic acid sequence of the HBV 1-2 recognition sequence (sense).

SEQ ID NO: 42 sets forth the nucleic acid sequence of the HBV 1-2 recognition sequence (antisense).

SEQ ID NO: 43 sets forth the nucleic acid sequence of the HBV 7-8 recognition sequence (sense).

SEQ ID NO: 44 sets forth the nucleic acid sequence of the HBV 7-8 recognition sequence (antisense).

SEQ ID NO: 45 sets forth a nucleic acid sequence encoding the HBV 11-12L.1090 engineered meganuclease.

SEQ ID NO: 46 sets forth a nucleic acid sequence encoding the HBV 11-12L.1036 engineered meganuclease.

SEQ ID NO: 47 sets forth a nucleic acid sequence encoding the HBV 11-12L.520 S19 engineered meganuclease.

SEQ ID NO: 48 sets forth a nucleic acid sequence encoding the HBV 11-12L.638 engineered meganuclease.

SEQ ID NO: 49 sets forth a nucleic acid sequence encoding the HBV 11-12L.638 S19 engineered meganuclease.

SEQ ID NO: 50 sets forth a nucleic acid sequence encoding the HBV 11-12L.699 engineered meganuclease.

SEQ ID NO: 51 sets forth the amino acid sequence of a nuclear localization signal.

DETAILED DESCRIPTION OF THE INVENTION

1.1 References and Definitions

The patent and scientific literature referred to herein establishes knowledge that is available to those of skill in the art. The issued US patents, allowed applications, published foreign applications, and references, including GenBank database sequences, which are cited herein are hereby incorporated by reference to the same extent as if each was specifically and individually indicated to be incorporated by reference.

The present invention can be embodied in different forms and should not be construed as limited to the embodiments set forth herein. Rather, these embodiments are provided so that this disclosure will be thorough and complete, and will fully convey the scope of the invention to those skilled in the art. For example, features illustrated with respect to one embodiment can be incorporated into other embodiments, and features illustrated with respect to a particular embodiment can be deleted from that embodiment. In addition, numerous variations and additions to the embodiments suggested herein will be apparent to those skilled in the art in light of the instant disclosure, which do not depart from the instant invention.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

All publications, patent applications, patents, and other references mentioned herein are incorporated by reference herein in their entirety.

As used herein, "a," "an," or "the" can mean one or more than one. For example, "a" cell can mean a single cell or a multiplicity of cells.

As used herein, unless specifically indicated otherwise, the word "or" is used in the inclusive sense of "and/or" and not the exclusive sense of "either/or."

As used herein, the terms "nuclease" and "endonuclease" are used interchangeably to refer to naturally-occurring or engineered enzymes, which cleave a phosphodiester bond within a polynucleotide chain.

As used herein, the terms "cleave" or "cleavage" refer to the hydrolysis of phosphodiester bonds within the backbone of a recognition sequence within a target sequence that results in a double-stranded break within the target sequence, referred to herein as a "cleavage site".

As used herein, the term "meganuclease" refers to an endonuclease that binds double-stranded DNA at a recognition sequence that is greater than 12 base pairs. In some embodiments, the recognition sequence for a meganuclease of the present disclosure is 22 base pairs. A meganuclease can be an endonuclease that is derived from I-CreI (SEQ ID NO: 1), and can refer to an engineered variant of I-CreI that has been modified relative to natural I-CreI with respect to, for example, DNA-binding specificity, DNA cleavage activity, DNA-binding affinity, or dimerization properties. Methods for producing such modified variants of I-CreI are known in the art (e.g., WO 2007/047859, incorporated by reference in its entirety). A meganuclease as used herein binds to double-stranded DNA as a heterodimer. A meganuclease may also be a "single-chain meganuclease" in which a pair of DNA-binding domains is joined into a single polypeptide using a peptide linker. The term "homing endonuclease" is synonymous with the term "meganuclease." Meganucleases of the present disclosure are substantially non-toxic when expressed in the targeted cells as described herein such that cells can be transfected and maintained at 37° C. without observing deleterious effects on cell viability or significant reductions in meganuclease cleavage activity when measured using the methods described herein.

As used herein, the term "single-chain meganuclease" refers to a polypeptide comprising a pair of nuclease subunits joined by a linker. A single-chain meganuclease has the organization: N-terminal subunit—Linker—C-terminal subunit. The two meganuclease subunits will generally be non-identical in amino acid sequence and will bind non-identical DNA sequences. Thus, single-chain meganucleases typically cleave pseudo-palindromic or non-palindromic recognition sequences. A single-chain meganuclease may be referred to as a "single-chain heterodimer" or "single-chain heterodimeric meganuclease" although it is not, in fact, dimeric. For clarity, unless otherwise specified, the term "meganuclease" can refer to a dimeric or single-chain meganuclease.

As used herein, the term "linker" refers to an exogenous peptide sequence used to join two nuclease subunits into a single polypeptide. A linker may have a sequence that is found in natural proteins or may be an artificial sequence that is not found in any natural protein. A linker may be flexible and lacking in secondary structure or may have a propensity to form a specific three-dimensional structure under physiological conditions. A linker can include, without limitation, those encompassed by U.S. Pat. Nos. 8,445,251, 9,340,777, 9,434,931, and 10,041,053, each of which is incorporated by reference in its entirety. In some embodiments, a linker may have at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO: 38, which sets forth residues 154-195 of any one of SEQ ID NOs: 12-17. In some embodiments, a linker may have an amino acid sequence comprising SEQ ID NO: 38, which sets forth residues 154-195 of any one of SEQ ID NOs: 12-17.

As used herein, the terms "recombinant" or "engineered," with respect to a protein, means having an altered amino acid sequence as a result of the application of genetic engineering techniques to nucleic acids that encode the protein and cells or organisms that express the protein. With respect to a nucleic acid, the term "recombinant" or "engineered" means having an altered nucleic acid sequence as a result of the application of genetic engineering techniques. Genetic engineering techniques include, but are not limited to, PCR and DNA cloning technologies; transfection, transformation, and other gene transfer technologies; homologous recombination; site-directed mutagenesis; and gene fusion. In accordance with this definition, a protein having an amino acid sequence identical to a naturally-occurring protein, but produced by cloning and expression in a heterologous host, is not considered recombinant or engineered.

As used herein, the term "wild-type" refers to the most common naturally occurring allele (i.e., polynucleotide sequence) in the allele population of the same type of gene, wherein a polypeptide encoded by the wild-type allele has its original functions. The term "wild-type" also refers to a polypeptide encoded by a wild-type allele. Wild-type alleles (i.e., polynucleotides) and polypeptides are distinguishable from mutant or variant alleles and polypeptides, which comprise one or more mutations and/or substitutions relative to the wild-type sequence(s). Whereas a wild-type allele or polypeptide can confer a normal phenotype in an organism, a mutant or variant allele or polypeptide can, in some instances, confer an altered phenotype. Wild-type nucleases are distinguishable from recombinant or non-naturally-occurring nucleases. The term "wild-type" can also refer to a cell, an organism, and/or a subject which possesses a wild-type allele of a particular gene, or a cell, an organism, and/or a subject used for comparative purposes.

As used herein, the term "genetically-modified" refers to a cell or organism in which, or in an ancestor of which, a genomic DNA sequence has been deliberately modified by recombinant technology. As used herein, the term "genetically-modified" encompasses the term "transgenic."

As used herein, the term with respect to recombinant proteins, the term "modification" means any insertion, deletion, or substitution of an amino acid residue in the recombinant sequence relative to a reference sequence (e.g., a wild-type or a native sequence).

As used herein, the terms "recognition sequence" or "recognition site" refers to a DNA sequence that is bound and cleaved by a nuclease. In the case of a meganuclease, a recognition sequence comprises a pair of inverted, 9 basepair "half sites" which are separated by four basepairs. In the case of a single-chain meganuclease, the N-terminal domain of the protein contacts a first half-site and the C-terminal domain of the protein contacts a second half-site. Cleavage by a meganuclease produces four basepair 3' "overhangs". "Overhangs," or "sticky ends" are short, single-stranded DNA segments that can be produced by endonuclease cleavage of a double-stranded DNA sequence. In the case of meganucleases and single-chain meganucleases derived from I-CreI, the overhang comprises bases 10-13 of the 22 basepair recognition sequence.

As used herein, the terms "target site" or "target sequence" refers to a region of the chromosomal DNA of a cell comprising a recognition sequence for a nuclease.

As used herein, the terms "DNA-binding affinity" or "binding affinity" means the tendency of a meganuclease to non-covalently associate with a reference DNA molecule (e.g., a recognition sequence or an arbitrary sequence). Binding affinity is measured by a dissociation constant, Kd. As used herein, a nuclease has "altered" binding affinity if the Kd of the nuclease for a reference recognition sequence is increased or decreased by a statistically significant percent change relative to a reference nuclease.

As used herein, the term "specificity" refers to the ability of a nuclease to recognize and cleave double-stranded DNA molecules only at a particular sequence of base pairs referred to as the recognition sequence, or only at a particular set of recognition sequences. The set of recognition sequences will share certain conserved positions or sequence motifs, but may be degenerate at one or more positions. A highly-specific nuclease is capable of cleaving only one or a very few recognition sequences. Specificity can be determined by any method known in the art, such as unbiased identification of DSBs enabled by sequencing (GUIDE-seq), oligonucleotide (oligo) capture assay, whole genome sequencing, and long-range next generation sequencing of the recognition sequence. In some embodiments, specificity is measured using GUIDE-seq. As used herein, "specificity" is synonymous with a low incidence of cleavage of sequences different from the target sequences (non-target sequences), i.e., off-target cutting. A low incidence of off-target cutting may comprise an incidence of cleavage of non-target sequences of less than 25%, less than 20%, less than 18%, less than 15%, less than 12.5%, less than 10%, less than 9%, less than 8%, less than 7%, less than 6%, less than 5%, less than 4%, less than 3%, less than 2.5%, less than 2%, less than 1.5%, less than 1%, less than 0.75%, less than 0.5%, or less than 0.25%.

As used herein, a meganuclease has "altered" specificity if it binds to and cleaves a recognition sequence which is not bound to and cleaved by a reference meganuclease (e.g., a wild-type) under physiological conditions, or if the rate of cleavage of a recognition sequence is increased or decreased by a biologically significant amount (e.g., at least 2×, or 2×-10×) relative to a reference meganuclease.

In some embodiments, the presently disclosed engineered meganucleases have improved (i.e., increased) specificity for the target recognition sequence that comprises SEQ ID NO: 10 (i.e., HBV 11-12) as compared to the HBV 11-12x.26 meganuclease (the amino acid sequence of which is set forth as SEQ ID NO: 39). Thus, in certain embodiments, the presently disclosed engineered meganucleases exhibit reduced off-target cleavage as compared to the HBV 11-12x.26 meganuclease. In some embodiments, the presently disclosed engineered meganucleases have improved (i.e., increased) specificity for the target recognition sequence that comprises SEQ ID NO: 10 (i.e., HBV 11-12) as compared to the HBV 11-12L.363 meganuclease (the amino acid sequence of which is set forth as SEQ ID NO: 40). Thus, in certain embodiments, the presently disclosed engineered meganucleases exhibit reduced off-target cleavage as compared to the HBV 11-12L.363 meganuclease. Off-target cleavage by a meganuclease can be measured using any method known in the art, including for example, oligo capture analysis as described here, a T7 endonuclease (T7E) assay as described herein, digital PCR as described herein, targeted sequencing of particular off-target sites, exome sequencing, whole genome sequencing, direct in situ breaks labeling enrichment on streptavidin and next-generation sequencing (BLESS), genome-wide, GUIDE-seq, and linear amplification-mediated high-throughput genome-wide translocation sequencing (LAM-HTGTS) (see, e.g., Zischewski et al. (2017), Biotechnology Advances 35(1): 95-104, which is incorporated by reference in its entirety).

As used herein, the term "efficiency of cleavage" refers to the incidence by which a meganuclease cleaves a recognition sequence in a double-stranded DNA molecule relative to the incidence of all cleavage events by the meganuclease on the DNA molecule. "Efficiency of cleavage" is synonymous with DNA editing efficiency or on-target editing. Efficiency of cleavage and/or indel formation by a meganuclease can be measured using any method known in the art, including T7E assay, digital PCR (ddPCR), mismatch detection assays, mismatch cleavage assay, high-resolution melting analysis (HRMA), heteroduplex mobility assay, sequencing, and fluorescent PCR capillary gel electrophoresis (see, e.g., Zischewski et al. (2017) Biotechnology Advances 35(1):95-104, which is incorporated by reference in its entirety). In some embodiments, efficiency of cleavage is measured by ddPCR. In some embodiments, the disclosed meganucleases generate efficiencies of cleavage of at least about 35%, 40%, 50%, 60%, 70%, 80%, 85%, 90%, 95%, 98%, or 99% at the recognition sequence.

An "indel", as used herein, refers to the insertion or deletion of a nucleobase within a nucleic acid, such as DNA. In some embodiments, it is desirable to generate one or more insertions or deletions (i.e., indels) in the nucleic acid, e.g., in a foreign nucleic acid such as viral DNA. Accordingly, as used herein, "efficiency of indel formation" refers to the incidence by which a meganuclease generates one or more indels through cleavage of a recognition sequence relative to the incidence of all cleavage events by the meganuclease on the DNA molecule. In some embodiments, efficiency of indel formation is measured by ddPCR. In some embodiments, the disclosed meganucleases generate efficiencies of indel formation of at least about 35%, 40%, 50%, 60%, 70%, 80%, 85%, 90%, 95%, 98%, or 99% at the recognition sequence. The disclosed meganucleases may generate efficiencies of cleavage and/or efficiencies of indel formation of at least about 60%, 61%, 62%, 63%, 64%, 65%, 66%, 67%, 68%, 69%, 70%, 71%, 72%, 73%, 74%, or 75% at the recognition sequence.

As used herein, the term "homologous recombination" or "HR" refers to the natural, cellular process in which a double-stranded DNA-break is repaired using a homologous DNA sequence as the repair template (see, e.g. Cahill et al. (2006), Front. Biosci. 11:1958-1976). The homologous DNA sequence may be an endogenous chromosomal sequence or an exogenous nucleic acid that was delivered to the cell.

As used herein, the term "non-homologous end-joining" or "NHEJ" refers to the natural, cellular process in which a double-stranded DNA-break is repaired by the direct joining of two non-homologous DNA segments (see, e.g. Cahill et al. (2006), Front. Biosci. 11:1958-1976). DNA repair by non-homologous end-joining is error-prone and frequently results in the untemplated addition or deletion of DNA sequences at the site of repair. In some instances, cleavage at a target recognition sequence results in NHEJ at a target recognition site. Nuclease-induced cleavage of a target site in the coding sequence of a gene followed by DNA repair by NHEJ can introduce mutations into the coding sequence, such as frameshift mutations, that disrupt gene function. Thus, engineered meganucleases can be used to effectively knock-out a gene in a population of cells.

As used herein, the term "homology arms" or "sequences homologous to sequences flanking a meganuclease cleavage site" refer to sequences flanking the 5' and 3' ends of a nucleic acid molecule which promote insertion of the nucleic acid molecule into a cleavage site generated by a meganuclease. In general, homology arms can have a length of at least 50 base pairs, preferably at least 100 base pairs, and up to 2000 base pairs or more, and can have at least 90%, preferably at least 95%, or more, sequence homology to their corresponding sequences in the genome. In some embodiments, the homology arms are about 500 base pairs.

As used herein with respect to both amino acid sequences and nucleic acid sequences, the terms "percent identity," "sequence identity," "percentage similarity," "sequence similarity" and the like refer to a measure of the degree of similarity of two sequences based upon an alignment of the sequences that maximizes similarity between aligned amino acid residues or nucleotides, and which is a function of the number of identical or similar residues or nucleotides, the number of total residues or nucleotides, and the presence and length of gaps in the sequence alignment. A variety of algorithms and computer programs are available for determining sequence similarity using standard parameters. As used herein, sequence similarity is measured using the BLASTp program for amino acid sequences and the BLASTn program for nucleic acid sequences, both of which are available through the National Center for Biotechnology Information (www.ncbi.nlm.nih.gov/), and are described in, for example, Altschul et al. (1990), J. Mol. Biol. 215:403-410; Gish and States (1993), Nature Genet. 3:266-272; Madden et al. (1996), Meth. Enzymol.266:131-141; Altschul et al. (1997), Nucleic Acids Res. 25:33 89-3402); Zhang et al. (2000), J. Comput. Biol. 7(1-2):203-14. As used herein, percent similarity of two amino acid sequences is the score based upon the following parameters for the BLASTp algorithm: word size=3; gap opening penalty=−11; gap extension penalty=−1; and scoring matrix=BLOSUM62. As used herein, percent similarity of two nucleic acid sequences is the score based upon the following parameters for the BLASTn algorithm: word size=11; gap opening penalty=−5; gap extension penalty=−2; match reward=1; and mismatch penalty=−3.

As used herein, the term "corresponding to" with respect to modifications of two proteins or amino acid sequences, is used to indicate that a specified modification in the first protein is a substitution of the same amino acid residue as in the modification in the second protein, and that the amino acid position of the modification in the first protein corresponds to or aligns with the amino acid position of the modification in the second protein when the two proteins are subjected to standard sequence alignments (e.g., using the BLASTp program). Thus, the modification of residue "X" to amino acid "A" in the first protein will correspond to the modification of residue "Y" to amino acid "A" in the second protein if residues X and Y correspond to each other in a sequence alignment, and despite the fact that X and Y may be different numbers.

As used herein, the term "recognition half-site," "recognition sequence half-site," or simply "half-site" means a nucleic acid sequence in a double-stranded DNA molecule that is recognized and bound by a monomer of a homodimeric or heterodimeric meganuclease or by one subunit of a single-chain meganuclease or by one subunit of a single-chain meganuclease.

As used herein, the term "hypervariable region" refers to a localized sequence within a meganuclease monomer or subunit that comprises amino acids with relatively high variability. A hypervariable region can comprise about 50-60 contiguous residues, about 53-57 contiguous residues, or preferably about 56 residues. In some embodiments, the residues of a hypervariable region may correspond to positions 24-79 or positions 215-270 of SEQ ID NO: 12, 13, 14, 15, 16, or 17. A hypervariable region can comprise one or more residues that contact DNA bases in a recognition sequence and can be modified to alter base preference of the monomer or subunit. A hypervariable region can also comprise one or more residues that bind to the DNA backbone when the meganuclease associates with a double-stranded DNA recognition sequence. Such residues can be modified to alter the binding affinity of the meganuclease for the DNA backbone and the target recognition sequence. In different embodiments of the invention, a hypervariable region may comprise between 1-20 residues that exhibit variability and can be modified to influence base preference and/or DNA-binding affinity. In particular embodiments, a hypervariable region comprises between about 15-20 residues that exhibit variability and can be modified to influence base preference and/or DNA-binding affinity.

In some embodiments, variable residues within a hypervariable region correspond to one or more of positions 24, 26, 28, 30, 32, 33, 38, 40, 42, 44, 46, 68, 70, 75, and 77 of SEQ ID NO: 12, 13, 14, 15, 16, or 17.

In some embodiments, variable residues within a hypervariable region correspond to one or more of positions 215, 217, 219, 221, 223, 224, 229, 231, 233, 235, 237, 259, 261, 266, and 268 of SEQ ID NO: 12, 13, 14, 15, 16, or 17. In some embodiments, variable residues within a hypervariable region further correspond to one or more of positions 262, 263, and 264 of SEQ ID NO: 12 or 13, one or more of positions 239, 241, 262, 263, and 264 of SEQ ID NO: 15 or 16, or one or more of positions 241, 262, 263, and 264 of SEQ ID NO: 17. In other embodiments, variable residues within a hypervariable region correspond to one or more of positions In other embodiments, variable residues within a hypervariable region correspond to one or more of positions 215, 217, 219, 221, 223, 224, 229, 231, 233, 235, 237, 239, 241, 259, 261, 262, 263, 264, 266, and 268 of SEQ ID NO: 12, 13, 14, 15, 16, or 17.

The terms "recombinant DNA construct," "recombinant construct," "expression cassette," "cassette," "expression construct," "chimeric construct," "construct," and "recombinant DNA fragment" are used interchangeably herein and are single or double-stranded polynucleotides. A recombinant construct comprises an artificial combination of nucleic acid fragments, including, without limitation, regulatory and coding sequences that are not found together in nature. For example, a recombinant DNA construct may comprise regulatory sequences and coding sequences that are derived from different sources, or regulatory sequences and coding sequences derived from the same source and arranged in a manner different than that found in nature. Such a construct may be used by itself or may be used in conjunction with a vector.

As used herein, a "vector" or "recombinant DNA vector" may be a construct that includes a replication system and sequences that are capable of transcription and translation of a polypeptide-encoding sequence in a given host cell. If a vector is used, then the choice of vector is dependent upon the method that will be used to transform host cells as is well known to those skilled in the art. Vectors can include, without limitation, plasmid vectors and recombinant AAV vectors, or any other vector known in the art suitable for delivering a gene to a target cell. The skilled artisan is well aware of the genetic elements that must be present on the vector in order to successfully transform, select and propagate host cells comprising any of the isolated nucleotides or nucleic acid sequences of the invention. In some embodiments, a "vector" also refers to a viral vector. Viral vectors can include, without limitation, retroviral vectors, lentiviral vectors, adenoviral vectors, and adeno-associated viral vectors (AAV).

As used herein, a "polycistronic" mRNA refers to a single messenger RNA that comprises two or more coding sequences (i.e., cistrons) and encodes more than one protein. A polycistronic mRNA can comprise any element known in the art to allow for the translation of two or more genes from the same mRNA molecule including, but not limited to, an IRES element, a T2A element, a P2A element, an E2A element, and an F2A element.

As used herein, the term "operably linked" is intended to mean a functional linkage between two or more elements. For example, an operable linkage between a nucleic acid sequence encoding a nuclease as described herein and a regulatory sequence (e.g., a promoter) is a functional link that allows for expression of the nucleic acid sequence encoding the nuclease. Operably linked elements may be contiguous or non-contiguous. When used to refer to the joining of two protein coding regions, by operably linked is intended that the coding regions are in the same reading frame.

As used herein, a "control" or "control cell" refers to a cell that provides a reference point for measuring changes in genotype or phenotype of a genetically-modified cell. A control cell may comprise, for example: (a) a wild-type cell, i.e., of the same genotype as the starting material for the genetic alteration which resulted in the genetically-modified cell; (b) a cell of the same genotype as the genetically-modified cell but which has been transformed with a null construct (i.e., with a construct which has no known effect on the trait of interest); or, (c) a cell genetically identical to the genetically-modified cell but which is not exposed to conditions or stimuli or further genetic modifications that would induce expression of altered genotype or phenotype. A control subject may comprise, for example: a wild-type subject, i.e., a subject not having an HBV infection, which is not exposed to conditions or stimuli or further genetic modifications (e.g., administration of an engineered meganuclease described herein). Alternatively, a control subject may comprise, for example: a subject having an HBV infection, which is not exposed to conditions or stimuli or further genetic modifications (e.g., administration of an engineered meganuclease described herein) that can alter the HBV infection status of the subject.

As used herein, the terms "treatment" or "treating a subject" refers to the administration of an engineered meganuclease of the invention, or a nucleic acid encoding an engineered meganuclease of the invention to a subject infected with HBV for the purpose of slowing or stopping the rate of HBV proliferation of the virus by cleaving the genome of at least one HBV particle. Such treatment reduces or prevents transfection and replication of HBV in the subject, and provides either partial or complete relief of one or more symptoms of HBV in the subject. Means to assess alleviation of symptoms of HBV infection may include measurement of liver functions by determining levels of the enzyme alanine aminotransferase (ALT) or by measuring sero conversion, namely disappearance and/or reduction of the circulating HBeAg and/or HBsAg levels. Further, alleviation or reduction of symptoms of HBV can be determined by examining liver biopsies and measuring the level of tissue fibrosis by methods well known in the art. The number of circulating viral particles can be determined for example by measuring HBV DNA levels using PCR or by detecting HBsAg levels in the blood. The terms "treatment" or "treating a subject" can further refer to the administration of a cell (e.g., hepatocyte cell) comprising a nucleic acid encoding an engineered meganuclease, wherein the cell is delivered to a target tissue (e.g., liver) and produces the engineered meganuclease in an amount sufficient to treat an HBV infection in the subject, thereby resulting in either partial or complete relief of one or more symptoms of HBV. In some aspects, an engineered meganuclease of the invention, a nucleic acid encoding the same, or a genetically-modified cell or population of genetically-modified cells described herein is administered during treatment in the form of a pharmaceutical composition of the invention.

The term "Hepatitis B Virus infection" refers to any condition related to or resulting from infection with a Hepatitis B virus, such as chronic liver diseases/disorders, inflammations, fibrotic conditions and proliferative disorders, such as liver cancers. Chronic persistent HBV infection can cause fatigue, liver damage, cirrhosis of the liver, and hepatocellular carcinoma, a primary liver cancer.

The terms "proliferating" and "proliferation" as used herein refer to HBV viruses or HBV covalently closed circular DNA (cccDNA) actively dividing and/or infecting human cells. Thus, reduction in proliferation refers to any decrease in the proliferation of HBV including reduction of at least 1%, 2%, 3%, 4%, 5%, 10%, 15%, 20%, 25%, 30%, 40%, 50%, 60%, 70%, 80%, 90%, 91%, 92%, 93%, 94%, 95%, 96%, 97%, 98%, 99%, or 100% when compared to an appropriate control not having been administered the engineered meganuclease, or nucleic acid encoding the engineered meganuclease, described herein. Throughout this application, the term "proliferative disorder" refers to any disease/disorder marked by unwanted or aberrant proliferation of cells or tissue. As used herein, the term "proliferative disorder" also refers to conditions in which the unregulated and/or abnormal growth of cells can lead to the development of an unwanted condition or disease, which can be cancerous or non-cancerous.

As used herein, the term "effective amount" or "therapeutically effective amount" refers to an amount sufficient to effect beneficial or desirable biological and/or clinical results. The therapeutically effective amount will vary depending on the formulation or composition used, the disease and its severity and the age, weight, physical condition and responsiveness of the subject to be treated. In specific embodiments, an effective amount of the engineered meganuclease or pharmaceutical compositions described herein reduces the level or proliferation of HBV or reduces at least one symptom of HBV in a subject with an HBV infection.

The term "gc/kg" or "gene copies/kilogram" refers to the number of copies of a nucleic acid encoding an engineered meganuclease described herein per weight in kilograms of a subject that is administered the nucleic acid encoding the engineered meganuclease.

The term "lipid nanoparticle" refers to a lipid composition having a typically spherical structure with an average diameter between 10 and 1000 nanometers. In some formulations, lipid nanoparticles can comprise at least one cationic lipid, at least one non-cationic lipid, and at least one conjugated lipid. Lipid nanoparticles known in the art that are suitable for encapsulating nucleic acids, such as mRNA, are contemplated for use in the invention.

As used herein, the recitation of a numerical range for a variable is intended to convey that the present disclosure may be practiced with the variable equal to any of the values within that range. Thus, for a variable which is inherently discrete, the variable can be equal to any integer value within the numerical range, including the end-points of the range. Similarly, for a variable which is inherently continuous, the variable can be equal to any real value within the numerical range, including the end-points of the range. As an example, and without limitation, a variable which is described as having values between 0 and 2 can take the values 0, 1 or 2 if the variable is inherently discrete, and can take the values 0.0, 0.1, 0.01, 0.001, or any other real values $\geq 0$ and $\leq 2$ if the variable is inherently continuous.

2.1 Principle of the Invention

The present invention is based, in part, on the discovery of HBV 11-12 meganucleases which have improved properties when compared to previously described HBV 11-12 meganucleases, such as improved (i.e., increased) specificity resulting in reduced off-target cutting, and enhanced (i.e., increased) efficiency of cleavage and indel formation at the HBV 11-12 recognition sequence, particularly in cells comprising an integrated copy of the HBV genome.

The presently disclosed HBV 11-12 meganucleases of the invention recognize the HBV 11-12 recognition sequence (SEQ ID NO: 10) in the P gene of the Hepatitis B virus that encodes the viral DNA polymerase. The HBV 11-12 recognition sequence is conserved across at least HBV genotypes A-G (SEQ ID NOs: 3-9), which advantageously allows for the presently disclosed engineered meganucleases to target HBV infections around the globe.

Cleavage at the HBV 11-12 recognition sequence can allow for non-homologous end joining (NHEJ) at the cleavage site and can disrupt expression of one or more viral proteins (e.g., viral DNA polymerase) due to NHEJ at the cleavage site that results in insertions, deletions, or frame-shift mutations. Alternatively, cleavage of the HBV genome at the HBV 11-12 recognition sequence may promote degradation of the HBV genome and/or HBV cccDNA. Disruption of the expression of the viral protein(s) can reduce or eliminate the infection and/or proliferation of HBV.

Additionally, cleavage at the HBV 11-12 recognition sequence can further allow for homologous recombination of exogenous nucleic acid sequences directly into the HBV genome to disrupt the expression of one or more viral proteins. For example, a "suicide gene" can be introduced into a HBV genome via homologous recombination.

Thus, the present invention encompasses engineered meganucleases which recognize and cleave the HBV 11-12 recognition sequence within a HBV genome. The present invention also encompasses methods of using such engineered meganucleases in a pharmaceutical composition and in methods for treating HBV infection. Further, the invention encompasses pharmaceutical compositions comprising engineered meganuclease proteins, or nucleic acids encoding engineered meganucleases, and the use of such compositions for the treatment of HBV infection and hepatocellular carcinoma (HCC).

2.2 Optimized Meganucleases that Recognize and Cleave the HBV 11-12 Recognition Sequence within the Genome of HBV It is known in the art that it is possible to use a site-specific nuclease to make a DNA break in the genome of a virus, and that such a DNA break can result in permanent modification of the genome via NHEJ such that the HBV virion can no longer divide/replicate or infect human cells. Thus, in some embodiments, the invention can be practiced using engineered meganucleases.

In particular embodiments, the nucleases used to practice the invention are single-chain meganucleases. A single-chain meganuclease comprises an N-terminal subunit and a C-terminal subunit joined by a linker peptide. Each of the two domains recognizes half of the recognition sequence (i.e., a recognition half-site) and the site of DNA cleavage is at the middle of the recognition sequence near the interface of the two subunits. DNA strand breaks are offset by four base pairs such that DNA cleavage by a meganuclease generates a pair of four base pair, 3' single-strand overhangs.

The engineered meganucleases of the invention have been engineered to recognize and cleave the HBV 11-12 recognition sequence (SEQ ID NO: 10). The HBV 11-12 recognition sequence is positioned within the P protein ORF of multiple HBV genotypes. The HBV 11-12 recognition sequence can at least be found in the genome of multiple HBV genotypes, including genotypes A, B, C, D, E, F, and G (e.g., SEQ ID NOs: 3-9, respectively).

Engineered meganucleases of the invention comprise a first subunit, comprising a first hypervariable (HVR1) region, and a second subunit, comprising a second hypervariable (HVR2) region. Further, the first subunit binds to a first recognition half-site in the recognition sequence (i.e., the HBV11 half-site), and the second subunit binds to a second recognition half-site in the recognition sequence (i.e., the HBV12 half-site). In embodiments where the engineered meganuclease is a single-chain meganuclease, the first and second subunits can be oriented such that the first subunit, which comprises the HVR1 region and binds the first half-site, is positioned as the N-terminal subunit, and the second subunit, which comprises the HVR2 region and binds the second half-site, is positioned as the C-terminal subunit. In alternative embodiments, the first and second subunits can be oriented such that the first subunit, which comprises the HVR1 region and binds the first half-site, is positioned as the C-terminal subunit, and the second subunit, which comprises the HVR2 region and binds the second half-site, is positioned as the N-terminal subunit. Exemplary engineered meganucleases that recognize and cleave the HBV 11-12 recognition sequence are provided in Tables 1 and 2.

TABLE 1

Exemplary engineered meganucleases that bind and cleave the HBV 11-12 recognition sequence (SEQ ID NO: 10).

| Meganuclease | AA SEQ ID | HBV11 Subunit Residues | HBV11 Subunit SEQ ID | *HBV11 Subunit % | HBV12 Subunit Residues | HBV12 Subunit SEQ ID | *HBV12 Subunit % |
|---|---|---|---|---|---|---|---|
| HBV 11-12L.1090 | 12 | 198-344 | 19 | 100 | 7-153 | 26 | 100 |
| HBV 11-12L.1036 | 13 | 198-344 | 20 | 97.96 | 7-153 | 27 | 97.28 |
| HBV 11-12L.520 S19 | 14 | 198-344 | 21 | 95.24 | 7-153 | 28 | 97.96 |
| HBV 11-12L.638 | 15 | 198-344 | 22 | 96.6 | 7-153 | 29 | 96.6 |
| HBV 11-12L.638 S19 | 16 | 198-344 | 23 | 95.92 | 7-153 | 30 | 96.6 |
| HBV 11-12L.699 | 17 | 198-344 | 24 | 94.56 | 7-153 | 31 | 96.6 |

"HBV 11 Subunit %" and "HBV 12 Subunit %" represent the amino acid sequence identity between the HBV 11-binding and HBV12-binding subunit regions of each meganuclease and the HBV 11-binding and HB V12-binding subunit regions, respectively, of the HBV 11-12L.1090 meganuclease.

TABLE 2

Exemplary engineered meganucleases which recognize and cleave the HBV 11-12 recognition sequence (SEQ ID NO: 10).

| Meganuclease | AA SEQ ID | HBV11 Subunit Residues | HBV11 Subunit SEQ ID | HVR1 Residues | *HVR1 % | HBV12 Subunit Residues | HBV12 Subunit SEQ ID | HVR2 Residues | *HVR2 % |
|---|---|---|---|---|---|---|---|---|---|
| HBV 11-12L.1090 | 12 | 198-344 | 19 | 215-270 | 100 | 7-153 | 26 | 24-79 | 100 |
| HBV 11-12L.1036 | 13 | 198-344 | 20 | 215-270 | 98.21 | 7-153 | 27 | 24-79 | 94.64 |

TABLE 2-continued Exemplary engineered meganucleases which recognize and cleave the HBV 11-12 recognition sequence (SEQ ID NO: 10).

| Meganuclease | AA SEQ ID | HBV11 Subunit Residues | HBV11 Subunit SEQ ID | HVR1 Residues | *HVR1 % | HBV12 Subunit Residues | HBV12 Subunit SEQ ID | HVR2 Residues | *HVR2 % |
|---|---|---|---|---|---|---|---|---|---|
| HBV 11-12L.520 S19 | 14 | 198-344 | 21 | 215-270 | 91.07 | 7-153 | 28 | 24-79 | 96.43 |
| HBV 11-12L.638 | 15 | 198-344 | 22 | 215-270 | 92.86 | 7-153 | 29 | 24-79 | 92.86 |
| HBV 11-12L.638 S19 | 16 | 198-344 | 23 | 215-270 | 92.86 | 7-153 | 30 | 24-79 | 92.86 |
| HBV 11-12L.699 | 17 | 198-344 | 24 | 215-270 | 87.5 | 7-153 | 31 | 24-79 | 92.86 |

*"HVR1 %" and "HVR2 %" represent the amino acid sequence identity between the HVR1 and HVR2 regions, respectively, of each meganuclease and the HVR1 and HVR2 regions, respectively, of the HBV 11-12L.1090 meganuclease.

In some embodiments, the presently disclosed engineered meganucleases exhibit at least one optimized characteristic in comparison to the previously described meganuclease HBV 11-12x.26 or HBV 11-12L.363. Such optimized characteristics include improved (i.e. increased) specificity resulting in reduced off-target cutting, and enhanced (i.e., increased) efficiency of cleavage and indel (i.e., insertion or deletion) formation at the HBV 11-12 recognition sequence, particularly in cells comprising an integrated copy of the HBV genome. Thus, in particular embodiments, the presently disclosed engineered meganucleases, when delivered to a population of HBV-infected target cells, is able to generate a greater percentage of virions or cells with a cleavage and/or an indel in the HBV genome (either incorporated or unincorporated). In some of these embodiments, the population of HBV or target cells comprises at least 40%, at least 45%, at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% of HBV or target cells comprising a cleavage and/or an indel in the HBV genome (either incorporated or unincorporated). Cleavage and/or indel formation by a meganuclease can be measured using any method known in the art, including T7E assay, digital PCR, mismatch detection assays, mismatch cleavage assay, high-resolution melting analysis (HRMA), heteroduplex mobility assay, sequencing, and fluorescent PCR capillary gel electrophoresis (see, e.g., Zischewski et al. (2017) Biotechnology Advances 35(1):95-104, which is incorporated by reference in its entirety).

In some embodiments, the target cell is a hepatocyte. In some embodiments, the target cell is a primary human hepatocyte (PHH). In some embodiments, the target cell is a non-human, mammalian hepatocyte.

In certain embodiments of the invention, the engineered meganuclease binds and cleaves a recognition sequence comprising SEQ ID NO: 10 (i.e., the HBV 11-12 recognition sequence) within the HBV genome, wherein the engineered meganuclease comprises a first subunit and a second subunit, wherein the first subunit binds to a first recognition half-site of the recognition sequence and comprises a first hypervariable (HVR1) region, and wherein the second subunit binds to a second recognition half-site of the recognition sequence and comprises a second hypervariable (HVR2) region. Exemplary HBV 11-12 meganucleases are described below.

HBV 11-12L.1090 (SEQ ID NO: 12)

In some embodiments, the HVR1 region comprises an amino acid sequence having at least 80%, 85%, 90%, 91%, 92%, 93%, 94%, 95%, 96%, 97%, 98%, 99% or more sequence identity to an amino acid sequence corresponding to residues 215-270 of SEQ ID NO: 12. In some embodiments, the HVR1 region comprises one or more residues corresponding to residues 215, 217, 219, 221, 223, 224, 229, 231, 233, 235, 237, 259, 261, 266, and 268 of SEQ ID NO: 12. In some embodiments, the HVR1 region comprises residues corresponding to residues 215, 217, 219, 221, 223, 224, 229, 231, 233, 235, 237, 259, 261, 266, and 268 of SEQ ID NO: 12. In some embodiments, the HVR1 region comprises Y, R, K, or D at a residue corresponding to residue 257 of SEQ ID NO: 12. In some embodiments, the HVR1 region comprises a residue corresponding to residue 262 of SEQ ID NO: 12. In some embodiments, the HVR1 region comprises a residue corresponding to residue 263 of SEQ ID NO: 12. In some embodiments, the HVR1 region comprises a residue corresponding to residue 264 of SEQ ID NO: 12. In some embodiments, the HVR1 region comprises residues 215-270 of SEQ ID NO: 12 with up to 1, 2, 3, 4, 5, 6, 7, 8, 9, 10, or 11 amino acid substitutions. In some embodiments, the HVR1 region comprises residues 215-270 of SEQ ID NO: 12.

In some embodiments, the first subunit comprises an amino acid sequence having at least 80%, 85%, 90%, 91%, 92%, 93%, 94%, 95%, 96%, 97%, 98%, 99% or more sequence identity to residues 198-344 of SEQ ID NO: 12. In some embodiments, the first subunit comprises G, S, or A at a residue corresponding to residue 210 of SEQ ID NO: 12. In some embodiments, the first subunit comprises E, Q, or K at a residue corresponding to residue 271 of SEQ ID NO: 12. In some embodiments, the first subunit comprises a residue corresponding to residue 271 of SEQ ID NO: 12. In some embodiments, the first subunit comprises residues 198-344 of SEQ ID NO: 12 with up to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 amino acid substitutions. In some embodiments, the first subunit comprises residues 198-344 of SEQ ID NO: 12.

In some embodiments, the HVR2 region comprises an amino acid sequence having at least 80%, 85%, 90%, 91%, 92%, 93%, 94%, 95%, 96%, 97%, 98%, 99% or more sequence identity to an amino acid sequence corresponding to residues 24-79 of SEQ ID NO: 12. In some embodiments, the HVR2 region comprises one or more residues corresponding to residues 24, 26, 28, 30, 32, 33, 38, 40, 42, 44, 46, 68, 70, 75, and 77 of SEQ ID NO: 12. In some embodiments, the HVR2 region comprises residues corresponding to residues 24, 26, 28, 30, 32, 33, 38, 40, 42, 44, 46, 68, 70, 75, and 77 of SEQ ID NO: 12. In some embodiments, the HVR2 region comprises Y, R, K, or D at a residue corresponding to residue 66 of SEQ ID NO: 12. In some embodiments, the HVR2 region comprises at a residue corresponding to residue 51 of SEQ ID NO: 12. In some embodiments, the HVR2 region comprises residues 24-79 of SEQ ID NO: 12 with up to 1, 2, 3, 4, 5, 6, 7, 8, 9, 10, or 11 amino acid substitutions. In some embodiments, the HVR2 region comprises residues 24-79 of SEQ ID NO: 12.

In some embodiments, the second subunit comprises an amino acid sequence having at least 80%, 85%, 90%, 91%, 92%, 93%, 94%, 95%, 96%, 97%, 98%, 99% or more sequence identity to residues 7-153 of SEQ ID NO: 12. In some embodiments, the second subunit comprises G, S, or A at a residue corresponding to residue 19 of SEQ ID NO: 12. In some embodiments, the second subunit comprises a residue corresponding to residue 19 of SEQ ID NO: 12. In some embodiments, the second subunit comprises E, Q, or K at a residue corresponding to residue 80 of SEQ ID NO: 12. In some embodiments, the second subunit comprises a residue corresponding to residue 80 of SEQ ID NO: 12. In some embodiments, the second subunit comprises residues 7-153 of SEQ ID NO: 12 with up to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 amino acid substitutions. In some embodiments, the second subunit comprises residues 7-153 of SEQ ID NO: 12.

In some embodiments, the engineered meganuclease is a single-chain meganuclease comprising a linker, wherein the linker covalently joins said first subunit and said second subunit. In some embodiments, the engineered meganuclease comprises an amino acid sequence having at least 80%, 85%, 90%, 91%, 92%, 93%, 94%, 95%, 96%, 97%, 98%, 99% or more sequence identity SEQ ID NO: 12. In some embodiments, the engineered meganuclease comprises an amino acid sequence of SEQ ID NO: 12. In some embodiments, the engineered meganuclease is encoded by a nucleic sequence having at least 80%, 85%, 90%, 91%, 92%, 93%, 94%, 95%, 96%, 97%, 98%, 99% or more sequence identity to a nucleic acid sequence set forth in SEQ ID NO: 45. In some embodiments, the engineered meganuclease is encoded by a nucleic acid sequence set forth in SEQ ID NO: 45.

HBV 11-12L.1036 (SEQ ID NO: 13)

In some embodiments, the HVR1 region comprises an amino acid sequence having at least 80%, 85%, 90%, 91%, 92%, 93%, 94%, 95%, 96%, 97%, 98%, 99% or more sequence identity to an amino acid sequence corresponding to residues 215-270 of SEQ ID NO: 13. In some embodiments, the HVR1 region comprises one or more residues corresponding to residues 215, 217, 219, 221, 223, 224, 229, 231, 233, 235, 237, 259, 261, 266, and 268 of SEQ ID NO: 13. In some embodiments, the HVR1 region comprises residues corresponding to residues 215, 217, 219, 221, 223, 224, 229, 231, 233, 235, 237, 259, 261, 266, and 268 of SEQ ID NO: 13. In some embodiments, the HVR1 region comprises Y, R, K, or D at a residue corresponding to residue 257 of SEQ ID NO: 13. In some embodiments, the HVR1 region comprises a residue corresponding to residue 262 of SEQ ID NO: 13. In some embodiments, the HVR1 region comprises a residue corresponding to residue 263 of SEQ ID NO: 13. In some embodiments, the HVR1 region comprises a residue corresponding to residue 264 of SEQ ID NO: 13. In some embodiments, the HVR1 region comprises residues 215-270 of SEQ ID NO: 13 with up to 1, 2, 3, 4, 5, 6, 7, 8, 9, 10, or 11 amino acid substitutions. In some embodiments, the HVR1 region comprises residues 215-270 of SEQ ID NO: 13.

In some embodiments, the first subunit comprises an amino acid sequence having at least 80%, 85%, 90%, 91%, 92%, 93%, 94%, 95%, 96%, 97%, 98%, 99% or more sequence identity to residues 198-344 of SEQ ID NO: 13. In some embodiments, the first subunit comprises G, S, or A at a residue corresponding to residue 210 of SEQ ID NO: 13. In some embodiments, the first subunit comprises E, Q, or K at a residue corresponding to residue 271 of SEQ ID NO: 13. In some embodiments, the first subunit comprises a residue corresponding to residue 330 of SEQ ID NO: 13. In some embodiments, the first subunit comprises residues 198-344 of SEQ ID NO: 13 with up to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 amino acid substitutions. In some embodiments, the first subunit comprises residues 198-344 of SEQ ID NO: 13.

In some embodiments, the HVR2 region comprises an amino acid sequence having at least 80%, 85%, 90%, 91%, 92%, 93%, 94%, 95%, 96%, 97%, 98%, 99% or more sequence identity to an amino acid sequence corresponding to residues 24-79 of SEQ ID NO: 13. In some embodiments, the HVR2 region comprises one or more residues corresponding to residues 24, 26, 28, 30, 32, 33, 38, 40, 42, 44, 46, 68, 70, 75, and 77 of SEQ ID NO: 13. In some embodiments, the HVR2 region comprises residues corresponding to residues 24, 26, 28, 30, 32, 33, 38, 40, 42, 44, 46, 68, 70, 75, and 77 of SEQ ID NO: 13. In some embodiments, the HVR2 region comprises Y, R, K, or D at a residue corresponding to residue 66 of SEQ ID NO: 13. In some embodiments, the HVR2 region comprises residues 24-79 of SEQ ID NO: 13 with up to 1, 2, 3, 4, 5, 6, 7, 8, 9, 10, or 11 amino acid substitutions. In some embodiments, the HVR2 region comprises residues 24-79 of SEQ ID NO: 13.

In some embodiments, the second subunit comprises an amino acid sequence having at least 80%, 85%, 90%, 91%, 92%, 93%, 94%, 95%, 96%, 97%, 98%, 99% or more sequence identity to residues 7-153 of SEQ ID NO: 13. In some embodiments, the second subunit comprises G, S, or A at a residue corresponding to residue 19 of SEQ ID NO: 13. In some embodiments, the second subunit comprises a residue corresponding to residue 19 of SEQ ID NO: 13. In some embodiments, the second subunit comprises E, Q, or K at a residue corresponding to residue 80 of SEQ ID NO: 13. In some embodiments, the second subunit comprises a residue corresponding to residue 80 of SEQ ID NO: 13. In some embodiments, the second subunit comprises residues 7-153 of SEQ ID NO: 13 with up to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 amino acid substitutions. In some embodiments, the second subunit comprises residues 7-153 of SEQ ID NO: 13.

In some embodiments, the engineered meganuclease is a single-chain meganuclease comprising a linker, wherein the linker covalently joins said first subunit and said second subunit. In some embodiments, the engineered meganuclease comprises an amino acid sequence having at least 80%, 85%, 90%, 91%, 92%, 93%, 94%, 95%, 96%, 97%, 98%, 99% or more sequence identity SEQ ID NO: 13. In some embodiments, the engineered meganuclease comprises an amino acid sequence of SEQ ID NO: 13. In some embodiments, the engineered meganuclease is encoded by a nucleic sequence having at least 80%, 85%, 90%, 91%, 92%, 93%, 94%, 95%, 96%, 97%, 98%, 99% or more sequence identity to a nucleic acid sequence set forth in SEQ ID NO: 46. In some embodiments, the engineered meganuclease is encoded by a nucleic acid sequence set forth in SEQ ID NO: 46.

HBV 11-12L.520 S19 (SEQ ID NO: 14)

In some embodiments, the HVR1 region comprises an amino acid sequence having at least 80%, 85%, 90%, 91%, 92%, 93%, 94%, 95%, 96%, 97%, 98%, 99% or more sequence identity to an amino acid sequence corresponding to residues 215-270 of SEQ ID NO: 14. In some embodiments, the HVR1 region comprises one or more residues corresponding to residues 215, 217, 219, 221, 223, 224, 229, 231, 233, 235, 237, 259, 261, 266, and 268 of SEQ ID NO: 14. In some embodiments, the HVR1 region comprises residues corresponding to residues 215, 217, 219, 221, 223, 224, 229, 231, 233, 235, 237, 259, 261, 266, and 268 of SEQ ID NO: 14. In some embodiments, the HVR1 region comprises Y, R, K, or D at a residue corresponding to residue 257 of SEQ ID NO: 14. In some embodiments, the HVR1 region comprises residues 215-270 of SEQ ID NO: 14 with up to 1, 2, 3, 4, 5, 6, 7, 8, 9, 10, or 11 amino acid substitutions. In some embodiments, the HVR1 region comprises residues 215-270 of SEQ ID NO: 14.

In some embodiments, the first subunit comprises an amino acid sequence having at least 80%, 85%, 90%, 91%, 92%, 93%, 94%, 95%, 96%, 97%, 98%, 99% or more sequence identity to residues 198-344 of SEQ ID NO: 14. In some embodiments, the first subunit comprises G, S, or A at a residue corresponding to residue 210 of SEQ ID NO: 14. In some embodiments, the first subunit comprises a residue corresponding to residue 210 of SEQ ID NO: 14. In some embodiments, the first subunit comprises E, Q, or K at a residue corresponding to residue 271 of SEQ ID NO: 14. In some embodiments, the first subunit comprises residues 198-344 of SEQ ID NO: 14 with up to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 amino acid substitutions. In some embodiments, the first subunit comprises residues 198-344 of SEQ ID NO: 14.

In some embodiments, the HVR2 region comprises an amino acid sequence having at least 80%, 85%, 90%, 91%, 92%, 93%, 94%, 95%, 96%, 97%, 98%, 99% or more sequence identity to an amino acid sequence corresponding to residues 24-79 of SEQ ID NO: 14. In some embodiments, the HVR2 region comprises one or more residues corresponding to residues 24, 26, 28, 30, 32, 33, 38, 40, 42, 44, 46, 68, 70, 75, and 77 of SEQ ID NO: 14. In some embodiments, the HVR2 region comprises residues corresponding to residues 24, 26, 28, 30, 32, 33, 38, 40, 42, 44, 46, 68, 70, 75, and 77 of SEQ ID NO: 14. In some embodiments, the HVR2 region comprises Y, R, K, or D at a residue corresponding to residue 66 of SEQ ID NO: 14. In some embodiments, the HVR2 region comprises residues 24-79 of SEQ ID NO: 14 with up to 1, 2, 3, 4, 5, 6, 7, 8, 9, 10, or 11 amino acid substitutions. In some embodiments, the HVR2 region comprises residues 24-79 of SEQ ID NO: 14.

In some embodiments, the second subunit comprises an amino acid sequence having at least 80%, 85%, 90%, 91%, 92%, 93%, 94%, 95%, 96%, 97%, 98%, 99% or more sequence identity to residues 7-153 of SEQ ID NO: 14. In some embodiments, the second subunit comprises G, S, or A at a residue corresponding to residue 19 of SEQ ID NO: 14. In some embodiments, the second subunit comprises E, Q, or K at a residue corresponding to residue 80 of SEQ ID NO: 14. In some embodiments, the second subunit comprises a residue corresponding to residue 80 of SEQ ID NO: 14. In some embodiments, the second subunit comprises residues 7-153 of SEQ ID NO: 14 with up to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 amino acid substitutions. In some embodiments, the second subunit comprises residues 7-153 of SEQ ID NO: 14.

In some embodiments, the engineered meganuclease is a single-chain meganuclease comprising a linker, wherein the linker covalently joins said first subunit and said second subunit. In some embodiments, the engineered meganuclease comprises an amino acid sequence having at least 80%, 85%, 90%, 91%, 92%, 93%, 94%, 95%, 96%, 97%, 98%, 99% or more sequence identity SEQ ID NO: 14. In some embodiments, the engineered meganuclease comprises an amino acid sequence of SEQ ID NO: 14. In some embodiments, the engineered meganuclease is encoded by a nucleic acid sequence having at least 80%, 85%, 90%, 91%, 92%, 93%, 94%, 95%, 96%, 97%, 98%, 99% or more sequence identity to a nucleic acid sequence set forth in SEQ ID NO: 47. In some embodiments, the engineered meganuclease is encoded by a nucleic acid sequence set forth in SEQ ID NO: 47.

HBV 11-12L.638 (SEQ ID NO: 15)

In some embodiments, the HVR1 region comprises an amino acid sequence having at least 80%, 85%, 90%, 91%, 92%, 93%, 94%, 95%, 96%, 97%, 98%, 99% or more sequence identity to an amino acid sequence corresponding to residues 215-270 of SEQ ID NO: 15. In some embodiments, the HVR1 region comprises one or more residues corresponding to residues 215, 217, 219, 221, 223, 224, 229, 231, 233, 235, 237, 259, 261, 266, and 268 of SEQ ID NO: 15. In some embodiments, the HVR1 region comprises residues corresponding to residues 215, 217, 219, 221, 223, 224, 229, 231, 233, 235, 237, 259, 261, 266, and 268 of SEQ ID NO: 15. In some embodiments, the HVR1 region comprises Y, R, K, or D at a residue corresponding to residue 257 of SEQ ID NO: 15. In some embodiments, the HVR1 region comprises residues 215-270 of SEQ ID NO: 15 with up to 1, 2, 3, 4, 5, 6, 7, 8, 9, 10, or 11 amino acid substitutions. In some embodiments, the HVR1 region comprises a residue corresponding to residue 239 of SEQ ID NO: 15. In some embodiments, the HVR1 region comprises a residue corresponding to residue 241 of SEQ ID NO: 15. In some embodiments, the HVR1 region comprises a residue corresponding to residue 262 of SEQ ID NO: 15. In some embodiments, the HVR1 region comprises a residue corresponding to residue 263 of SEQ ID NO: 15. In some embodiments, the HVR1 region comprises a residue corresponding to residue 264 of SEQ ID NO: 15. In some embodiments, the HVR1 region comprises residues 215-270 of SEQ ID NO: 15.

In some embodiments, the first subunit comprises an amino acid sequence having at least 80%, 85%, 90%, 91%, 92%, 93%, 94%, 95%, 96%, 97%, 98%, 99% or more sequence identity to residues 198-344 of SEQ ID NO: 15. In some embodiments, the first subunit comprises G, S, or A at a residue corresponding to residue 210 of SEQ ID NO: 15. In some embodiments, the first subunit comprises E, Q, or K at a residue corresponding to residue 271 of SEQ ID NO: 15. In some embodiments, the first subunit comprises residues 198-344 of SEQ ID NO: 15 with up to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 amino acid substitutions. In some embodiments, the first subunit comprises residues 198-344 of SEQ ID NO: 15.

In some embodiments, the HVR2 region comprises an amino acid sequence having at least 80%, 85%, 90%, 91%, 92%, 93%, 94%, 95%, 96%, 97%, 98%, 99% or more sequence identity to an amino acid sequence corresponding to residues 24-79 of SEQ ID NO: 15. In some embodiments, the HVR2 region comprises one or more residues corresponding to residues 24, 26, 28, 30, 32, 33, 38, 40, 42, 44, 46, 68, 70, 75, and 77 of SEQ ID NO: 15. In some embodiments, the HVR2 region comprises residues corresponding to residues 24, 26, 28, 30, 32, 33, 38, 40, 42, 44, 46, 68, 70, 75, and 77 of SEQ ID NO: 15. In some embodiments, the HVR2 region comprises Y, R, K, or D at a residue corresponding to residue 66 of SEQ ID NO: 15. In some embodiments, the HVR2 region comprises residues 24-79 of SEQ ID NO: 15 with up to 1, 2, 3, 4, 5, 6, 7, 8, 9, 10, or 11 amino acid substitutions. In some embodiments, the HVR2 region comprises residues 24-79 of SEQ ID NO: 15.

In some embodiments, the second subunit comprises G, S, or A at a residue corresponding to residue 19 of SEQ ID NO: 15. In some embodiments, the second subunit comprises E, Q, or K at a residue corresponding to residue 80 of SEQ ID NO: 15. In some embodiments, the second subunit comprises a residue corresponding to residue 80 of SEQ ID NO: 15. In some embodiments, the second subunit comprises residues 7-153 of SEQ ID NO: 15 with up to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 amino acid substitutions. In some embodiments, the second subunit comprises residues 7-153 of SEQ ID NO: 15.

In some embodiments, the engineered meganuclease is a single-chain meganuclease comprising a linker, wherein the linker covalently joins said first subunit and said second subunit. In some embodiments, the engineered meganuclease comprises an amino acid sequence having at least 80%, 85%, 90%, 91%, 92%, 93%, 94%, 95%, 96%, 97%, 98%, 99% or more sequence identity SEQ ID NO: 15. In some embodiments, the engineered meganuclease comprises an amino acid sequence of SEQ ID NO: 15. In some embodiments, the engineered meganuclease is encoded by a nucleic sequence having at least 80%, 85%, 90%, 91%, 92%, 93%, 94%, 95%, 96%, 97%, 98%, 99% or more sequence identity to a nucleic acid sequence set forth in SEQ ID NO: 48. In some embodiments, the engineered meganuclease is encoded by a nucleic acid sequence set forth in SEQ ID NO: 48.

HBV 11-12L.638 S19 (SEQ ID NO: 16)

In some embodiments, the HVR1 region comprises an amino acid sequence having at least 80%, 85%, 90%, 91%, 92%, 93%, 94%, 95%, 96%, 97%, 98%, 99% or more sequence identity to an amino acid sequence corresponding to residues 215-270 of SEQ ID NO: 16. In some embodiments, the HVR1 region comprises one or more residues corresponding to residues 215, 217, 219, 221, 223, 224, 229, 231, 233, 235, 237, 259, 261, 266, and 268 of SEQ ID NO: 16. In some embodiments, the HVR1 region comprises residues corresponding to residues 215, 217, 219, 221, 223, 224, 229, 231, 233, 235, 237, 259, 261, 266, and 268 of SEQ ID NO: 16. In some embodiments, the HVR1 region comprises Y, R, K, or D at a residue corresponding to residue 257 of SEQ ID NO: 16. In some embodiments, the HVR1 region comprises residues 215-270 of SEQ ID NO: 16 with up to 1, 2, 3, 4, 5, 6, 7, 8, 9, 10, or 11 amino acid substitutions. In some embodiments, the HVR1 region comprises a residue corresponding to residue 239 of SEQ ID NO: 16. In some embodiments, the HVR1 region comprises a residue corresponding to residue 241 of SEQ ID NO: 16. In some embodiments, the HVR1 region comprises a residue corresponding to residue 262 of SEQ ID NO: 16. In some embodiments, the HVR1 region comprises a residue corresponding to residue 263 of SEQ ID NO: 16. In some embodiments, the HVR1 region comprises a residue corresponding to residue 264 of SEQ ID NO: 16. In some embodiments, the HVR1 region comprises residues 215-270 of SEQ ID NO: 16.

In some embodiments, the first subunit comprises an amino acid sequence having at least 80%, 85%, 90%, 91%, 92%, 93%, 94%, 95%, 96%, 97%, 98%, 99% or more sequence identity to residues 198-344 of SEQ ID NO: 16. In some embodiments, the first subunit comprises G, S, or A at a residue corresponding to residue 210 of SEQ ID NO: 16. In some embodiments, the first subunit comprises a residue corresponding to residue 210 of SEQ ID NO: 16. In some embodiments, the first subunit comprises E, Q, or K at a residue corresponding to residue 271 of SEQ ID NO: 16. In some embodiments, the first subunit comprises residues 198-344 of SEQ ID NO: 16 with up to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 amino acid substitutions. In some embodiments, the first subunit comprises residues 198-344 of SEQ ID NO: 16.

In some embodiments, the HVR2 region comprises an amino acid sequence having at least 80%, 85%, 90%, 91%, 92%, 93%, 94%, 95%, 96%, 97%, 98%, 99% or more sequence identity to an amino acid sequence corresponding to residues 24-79 of SEQ ID NO: 16. In some embodiments, the HVR2 region comprises one or more residues corresponding to residues 24, 26, 28, 30, 32, 33, 38, 40, 42, 44, 46, 68, 70, 75, and 77 of SEQ ID NO: 16. In some embodiments, the HVR2 region comprises residues corresponding to residues 24, 26, 28, 30, 32, 33, 38, 40, 42, 44, 46, 68, 70, 75, and 77 of SEQ ID NO: 16. In some embodiments, the HVR2 region comprises Y, R, K, or D at a residue corresponding to residue 66 of SEQ ID NO: 16. In some embodiments, the HVR2 region comprises residues 24-79 of SEQ ID NO: 16 with up to 1, 2, 3, 4, 5, 6, 7, 8, 9, 10, or 11 amino acid substitutions. In some embodiments, the HVR2 region comprises residues 24-79 of SEQ ID NO: 16.

In some embodiments, the second subunit comprises an amino acid sequence having at least 80%, 85%, 90%, 91%, 92%, 93%, 94%, 95%, 96%, 97%, 98%, 99% or more sequence identity to residues 7-153 of SEQ ID NO: 16. In some embodiments, the second subunit comprises G, S, or A at a residue corresponding to residue 19 of SEQ ID NO: 16. In some embodiments, the second subunit comprises E, Q, or K at a residue corresponding to residue 80 of SEQ ID NO: 16. In some embodiments, the second subunit comprises a residue corresponding to residue 80 of SEQ ID NO: 16. In some embodiments, the second subunit comprises residues 7-153 of SEQ ID NO: 16 with up to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 amino acid substitutions. In some embodiments, the second subunit comprises residues 7-153 of SEQ ID NO: 16.

In some embodiments, the engineered meganuclease is a single-chain meganuclease comprising a linker, wherein the linker covalently joins said first subunit and said second subunit. In some embodiments, the engineered meganuclease comprises an amino acid sequence having at least 80%, 85%, 90%, 91%, 92%, 93%, 94%, 95%, 96%, 97%, 98%, 99% or more sequence identity SEQ ID NO: 16. In some embodiments, the engineered meganuclease comprises an amino acid sequence of SEQ ID NO: 16. In some embodiments, the engineered meganuclease is encoded by a nucleic sequence having at least 80%, 85%, 90%, 91%, 92%, 93%, 94%, 95%, 96%, 97%, 98%, 99% or more sequence identity to a nucleic acid sequence set forth in SEQ ID NO: 49. In some embodiments, the engineered meganuclease is encoded by a nucleic acid sequence set forth in SEQ ID NO: 49.

HBV 11-12L.699 (SEQ ID NO: 17)

In some embodiments, the HVR1 region comprises an amino acid sequence having at least 80%, 85%, 90%, 91%, 92%, 93%, 94%, 95%, 96%, 97%, 98%, 99% or more sequence identity to an amino acid sequence corresponding to residues 215-270 of SEQ ID NO: 17. In some embodiments, the HVR1 region comprises one or more residues corresponding to residues 215, 217, 219, 221, 223, 224, 229, 231, 233, 235, 237, 259, 261, 266, and 268 of SEQ ID NO: 17. In some embodiments, the HVR1 region comprises residues corresponding to residues 215, 217, 219, 221, 223, 224, 229, 231, 233, 235, 237, 259, 261, 266, and 268 of SEQ ID NO: 17. In some embodiments, the HVR1 region comprises Y, R, K, or D at a residue corresponding to residue 257 of SEQ ID NO: 17. In some embodiments, the HVR1 region comprises residues 215-270 of SEQ ID NO: 17 with up to 1, 2, 3, 4, 5, 6, 7, 8, 9, 10, or 11 amino acid substitutions. In some embodiments, the HVR1 region comprises a residue corresponding to residue 241 of SEQ ID NO: 17. In some embodiments, the HVR1 region comprises a residue corresponding to residue 262 of SEQ ID NO: 17. In some embodiments, the HVR1 region comprises a residue corresponding to residue 263 of SEQ ID NO: 17. In some embodiments, the HVR1 region comprises a residue corresponding to residue 264 of SEQ ID NO: 17. In some embodiments, the HVR1 region comprises residues 215-270 of SEQ ID NO: 17.

In some embodiments, the first subunit comprises G, S, or A at a residue corresponding to residue 210 of SEQ ID NO: 17. In some embodiments, the first subunit comprises E, Q, or K at a residue corresponding to residue 271 of SEQ ID NO: 17. In some embodiments, the first subunit comprises residues 198-344 of SEQ ID NO: 17 with up to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 amino acid substitutions. In some embodiments, the first subunit comprises residues 198-344 of SEQ ID NO: 17.

In some embodiments, the HVR2 region comprises an amino acid sequence having at least 80%, 85%, 90%, 91%, 92%, 93%, 94%, 95%, 96%, 97%, 98%, 99% or more sequence identity to an amino acid sequence corresponding to residues 24-79 of SEQ ID NO: 17. In some embodiments, the HVR2 region comprises one or more residues corresponding to residues 24, 26, 28, 30, 32, 33, 38, 40, 42, 44, 46, 68, 70, 75, and 77 of SEQ ID NO: 17. In some embodiments, the HVR2 region comprises residues corresponding to residues 24, 26, 28, 30, 32, 33, 38, 40, 42, 44, 46, 68, 70, 75, and 77 of SEQ ID NO: 17. In some embodiments, the HVR2 region comprises Y, R, K, or D at a residue corresponding to residue 66 of SEQ ID NO: 17. In some embodiments, the HVR2 region comprises residues 24-79 of SEQ ID NO: 17 with up to 1, 2, 3, 4, 5, 6, 7, 8, 9, 10, or 11 amino acid substitutions. In some embodiments, the HVR2 region comprises residues 24-79 of SEQ ID NO: 17.

In some embodiments, the second subunit comprises G, S, or A at a residue corresponding to residue 19 of SEQ ID NO: 17. In some embodiments, the second subunit comprises E, Q, or K at a residue corresponding to residue 80 of SEQ ID NO: 17. In some embodiments, the second subunit comprises a residue corresponding to residue 80 of SEQ ID NO: 17. In some embodiments, the second subunit comprises residues 7-153 of SEQ ID NO: 17 with up to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 amino acid substitutions. In some embodiments, the second subunit comprises residues 7-153 of SEQ ID NO: 17.

In some embodiments, the engineered meganuclease is a single-chain meganuclease comprising a linker, wherein the linker covalently joins said first subunit and said second subunit. In some embodiments, the engineered meganuclease comprises an amino acid sequence having at least 80%, 85%, 90%, 91%, 92%, 93%, 94%, 95%, 96%, 97%, 98%, 99% or more sequence identity SEQ ID NO: 17. In some embodiments, the engineered meganuclease comprises an amino acid sequence of SEQ ID NO: 17. In some embodiments, the engineered meganuclease is encoded by a nucleic sequence having at least 80%, 85%, 90%, 91%, 92%, 93%, 94%, 95%, 96%, 97%, 98%, 99% or more sequence identity to a nucleic acid sequence set forth in SEQ ID NO: 50. In some embodiments, the engineered meganuclease is encoded by a nucleic acid sequence set forth in SEQ ID NO: 50.

In each of the embodiments above, the engineered meganuclease can comprise a nuclear localization signal. In some embodiments, the nuclear localization signal is at the N-terminus of the engineered meganuclease. In some embodiments, the nuclear localization signal comprises an amino acid sequence having at least 80% or at least 90% sequence identity to SEQ ID NO: 51. In some embodiments, the nuclear localization signal comprises SEQ ID NO: 51.

2.3 Methods for Delivering and Expressing Optimized Engineered Meganucleases

Described herein are methods for treating an HBV infection or HCC in a subject. Likewise, methods are provided for reducing the symptoms of an HBV infection and reducing the amount of HBV, reducing the rate of proliferation of HBV or treating HCC in a subject comprising administering a pharmaceutical composition comprising a pharmaceutically acceptable carrier and an engineered meganuclease described herein (or a nucleic acid encoding the engineered meganuclease or a cell expressing the engineered meganuclease). In the methods of the invention, an engineered meganuclease described herein can be delivered to and/or expressed from DNA/RNA in target cells that can provide the engineered meganuclease to the HBV genome.

Introduction of Engineered Meganucleases into Cells

Engineered meganuclease proteins described herein, or polynucleotides encoding the same, can be delivered into cells to cleave genomic DNA by a variety of different mechanisms known in the art, including those further detailed herein below.

Engineered meganucleases described herein can be delivered into a cell in the form of protein or, preferably, as a polynucleotide comprising a nucleic acid sequence encoding the engineered meganuclease. Such polynucleotides can be, for example, DNA (e.g., circular or linearized plasmid DNA, PCR products, or viral genomes) or RNA (e.g., mRNA).

For embodiments in which the engineered meganuclease coding sequence is delivered in DNA form, it should be operably linked to a promoter to facilitate transcription of the meganuclease gene. Mammalian promoters suitable for the invention include constitutive promoters such as the cytomegalovirus early (CMV) promoter (Thomsen et al. (1984), *Proc Natl Acad Sci USA.* 81(3):659-63) or the SV40 early promoter (Benoist and Chambon (1981), *Nature.* 290 (5804):304-10) as well as inducible promoters such as the tetracycline-inducible promoter (Dingermann et al. (1992), *Mol Cell Biol.* 12(9):4038-45). An engineered meganuclease of the invention can also be operably linked to a synthetic promoter. Synthetic promoters can include, without limitation, the JeT promoter (WO 2002/012514). In specific embodiments, a nucleic acid sequence encoding an engineered meganuclease as described herein can be operably linked to a liver-specific promoter. Examples of liver-specific promoters include, without limitation, human alpha-1 antitrypsin promoter, hybrid liver-specific promoter (hepatic locus control region from ApoE gene (ApoE-HCR) and a liver-specific alpha1-antitrypsin promoter), human thyroxine binding globulin (TBG) promoter, and apolipoprotein A-II promoter.

In some embodiments, wherein a single polynucleotide comprises two separate nucleic acid sequences each encoding an engineered meganuclease described herein, the meganuclease genes are operably linked to two separate promoters. In alternative embodiments, the two meganuclease genes are operably linked to a single promoter, and in some examples can be separated by an internal-ribosome entry site (IRES) or a 2A peptide sequence (Szymczak and Vignali (2005) *Expert Opin Biol Ther.* 5:627-38). Such 2A peptide sequences can include, for example, a T2A, P2A, E2A, or F2A sequence.

In specific embodiments, a polynucleotide comprising a nucleic acid sequence encoding at least one engineered meganuclease described herein is delivered on a recombinant DNA construct or expression cassette. For example, the recombinant DNA construct can comprise an expression cassette (i.e., "cassette") comprising a promoter and a nucleic acid sequence encoding an engineered meganuclease described herein.

In other embodiments, the recombinant DNA construct comprises at least a first cassette and a second cassette, wherein the first cassette comprises a promoter and a nucleic acid sequence encoding an engineered meganuclease described herein, and wherein the second cassette comprises a promoter and a nucleic acid sequence encoding a second engineered meganuclease which binds and cleaves a second recognition sequence which is present in a Hepatitis B virus genome but differs from SEQ ID NO: 10. Non-limiting examples of other recognition sequences within the genome of a Hepatitis B virus include the HBV 5-6 recognition sequence (set forth as SEQ ID NO: 30).

In other embodiments, the recombinant DNA construct comprises a cassette comprising a promoter and a polycistronic nucleic acid sequence, wherein the promoter drives expression of the polycistronic nucleic acid sequence to generate a polycistronic mRNA described herein in a target cell.

In another particular embodiment, a polynucleotide comprising a nucleic acid sequence encoding an engineered meganuclease described herein is introduced into the cell using a single-stranded DNA template. The single-stranded DNA can further comprise a 5' and/or a 3' AAV inverted terminal repeat (ITR) upstream and/or downstream of the sequence encoding the engineered nuclease. The single-stranded DNA can further comprise a 5' and/or a 3' homology arm upstream and/or downstream of the sequence encoding the engineered meganuclease.

In another particular embodiment, a polynucleotide comprising a nucleic acid sequence encoding an engineered meganuclease described herein can be introduced into a cell using a linearized DNA template. Such linearized DNA templates can be produced by methods known in the art. For example, a plasmid DNA encoding a nuclease can be digested by one or more restriction enzymes such that the circular plasmid DNA is linearized prior to being introduced into a cell.

In some embodiments, mRNA encoding an engineered meganuclease is delivered to a cell because this reduces the likelihood that the gene encoding the engineered meganuclease will integrate into the genome of the cell.

Such mRNA can be produced using methods known in the art such as in vitro transcription. In some embodiments, the mRNA is 5' capped using 7-methyl-guanosine, anti-reverse cap analogs (ARCA) (U.S. Pat. No. 7,074,596), CleanCap® analogs such as Cap 1 analogs (Trilink, San Diego, CA), or enzymatically capped using vaccinia capping enzyme or similar. In some embodiments, the mRNA may be polyadenylated. The mRNA may contain various 5' and 3' untranslated sequence elements to enhance expression the encoded engineered meganuclease and/or stability of the mRNA itself. Such elements can include, for example, posttranslational regulatory elements such as a woodchuck hepatitis virus posttranslational regulatory element. The mRNA may contain nucleoside analogs or naturally-occurring nucleosides, such as pseudouridine, 5-methylcytidine, N6-methyladenosine, 5-methyluridine, or 2-thiouridine. Additional nucleoside analogs include, for example, those described in U.S. Pat. No. 8,278,036.

In particular embodiments, an mRNA encoding an engineered nuclease of the invention can be a polycistronic mRNA encoding two or more of the presently disclosed meganucleases which are simultaneously expressed in a cell. In some embodiments, a polycistronic mRNA can encode at least a first and a second engineered meganuclease, wherein the first engineered meganuclease is an engineered meganuclease described herein, and wherein the second engineered meganuclease binds and cleaves a second recognition sequence in the HBV genome that differs from SEQ ID NO: 10 (e.g., the HBV 5-6 recognition sequence), such that the HBV genome is cleaved at multiple sites. In some embodiments, a polycistronic mRNA can encode an engineered meganuclease described herein and at least one additional protein which induces a therapeutically beneficial effect in the cell. A polycistronic mRNA of the invention can comprise any element known in the art to allow for the translation of two or more genes from the same mRNA molecule including, but not limited to, an IRES element, a T2A element, a P2A element, an E2A element, and an F2A element.

In some embodiments, the methods comprise delivering an engineered meganuclease described herein (or a nucleic acid encoding the same) and a nucleic acid comprising a polynucleotide sequence encoding a suicide gene and sequences homologous to sequences flanking the meganuclease cleavage site, wherein the engineered meganuclease binds and cleaves a recognition sequence comprising SEQ ID NO: 10 within the Hepatitis B virus genome, thus cleaving the HBV genome, wherein the suicide gene is inserted into the cleaved HBV genome by homologous recombination.

A suicide gene is a nucleic acid that encodes a product that causes cell death by itself or in the presence of other compounds. A representative example of such a suicide gene is one that encodes thymidine kinase of herpes simplex virus. Additional examples are genes that encode thymidine kinase of varicella zoster virus and the bacterial gene cytosine deaminase that can convert 5-fluorocytosine to the highly toxic compound 5-fluorouracil. Suicide genes also include as non-limiting examples genes that encode caspase-9, caspase-8, or cytosine deaminase. In some examples, caspase-9 can be activated using a specific chemical inducer of dimerization (CID). In some embodiments, the suicide gene is directly lethal to the HBV or a target cell (e.g., HCC cell). In some such embodiments, the directly lethal suicide gene encodes a toxic polypeptide or a pro-apoptotic protein. In some embodiments, the suicide gene is indirectly lethal to the target cell, and directs the subject's own immune system to kill the target cell. In some such embodiments, the indirectly lethal suicide gene encodes a cell surface protein which is recognized as foreign by the subject's immune system and is targeted by a humoral or cellular immune response. In other such embodiments, the indirectly lethal suicide gene encodes a polypeptide which is presented by an MHC Class I molecule, is recognized as foreign by the subject's immune system, and is targeted by a cytotoxic immune response.

Purified meganuclease proteins can be delivered into cells to cleave genomic DNA by a variety of different mechanisms known in the art, including those further detailed herein below.

The target tissue(s) for delivery of engineered meganucleases of the invention include, without limitation, cells of the liver, such as a hepatocyte cell or preferably a primary hepatocyte, more preferably a human hepatocyte or a human primary hepatocyte, a HepG2.2.15 or a HepG2-hNTCP cell. As discussed, meganucleases of the invention can be delivered as purified protein or as RNA or DNA encoding the meganuclease. In one embodiment, meganuclease proteins, or mRNA, or DNA vectors encoding meganucleases, are supplied to target cells (e.g., cells in the liver) via injection directly to the target tissue. Alternatively, meganuclease protein, mRNA, DNA, or cells expressing meganucleases can be delivered systemically via the circulatory system.

In some embodiments, the meganuclease proteins, or DNA/mRNA encoding the meganuclease, are coupled to a cell penetrating peptide or targeting ligand to facilitate cellular uptake. Examples of cell penetrating peptides known in the art include poly-arginine (Jearawiriyapaisarn, et al. (2008) Mol Ther. 16:1624-9), TAT peptide from the HIV virus (Hudecz et al. (2005), Med. Res. Rev. 25: 679-736), MPG (Simeoni, et al. (2003) Nucleic Acids Res. 31:2717-2724), Pep-1 (Deshayes et al. (2004) Biochemistry 43: 7698-7706, and HSV-1 VP-22 (Deshayes et al. (2005) Cell Mol Life Sci. 62:1839-49. In an alternative embodiment, meganuclease proteins, or DNA/mRNA encoding meganucleases, are coupled covalently or non-covalently to an antibody that recognizes a specific cell-surface receptor expressed on target cells such that the meganuclease protein/DNA/mRNA binds to and is internalized by the target cells. Alternatively, meganuclease protein/DNA/mRNA can be coupled covalently or non-covalently to the natural ligand (or a portion of the natural ligand) for such a cell-surface receptor. (McCall, et al. (2014) Tissue Barriers. 2(4): e944449; Dinda, et al. (2013) Curr Pharm Biotechnol. 14:1264-74; Kang, et al. (2014) Curr Pharm Biotechnol. 15(3):220-30; Qian et al. (2014) Expert Opin Drug Metab Toxicol. 10(11):1491-508).

In some embodiments, meganuclease proteins, or DNA/mRNA encoding meganucleases, are encapsulated within biodegradable hydrogels for injection or implantation within the desired region of the liver (e.g., in proximity to hepatic sinusoidal endothelial cells or hematopoietic endothelial cells, or progenitor cells which differentiate into the same). Hydrogels can provide sustained and tunable release of the therapeutic payload to the desired region of the target tissue without the need for frequent injections, and stimuli-responsive materials (e.g., temperature- and pH-responsive hydrogels) can be designed to release the payload in response to environmental or externally applied cues (Kang Derwent et al. (2008) Trans Am Ophthalmol Soc. 106:206-214).

In some embodiments, meganuclease proteins, or DNA/mRNA encoding meganucleases, are coupled covalently or, preferably, non-covalently to a nanoparticle or encapsulated within such a nanoparticle using methods known in the art (Sharma, et al. (2014) Biomed Res Int. 2014). A nanoparticle is a nanoscale delivery system whose length scale is <1 μm, preferably <100 nm. Such nanoparticles may be designed using a core composed of metal, lipid, polymer, or biological macromolecule, and multiple copies of the meganuclease proteins, mRNA, or DNA can be attached to or encapsulated with the nanoparticle core. This increases the copy number of the protein/mRNA/DNA that is delivered to each cell and, so, increases the intracellular expression of each meganuclease to maximize the likelihood that the target recognition sequences will be cut. The surface of such nanoparticles may be further modified with polymers or lipids (e.g., chitosan, cationic polymers, or cationic lipids) to form a core-shell nanoparticle whose surface confers additional functionalities to enhance cellular delivery and uptake of the payload (Jian et al. (2012) Biomaterials. 33(30): 7621-30). Nanoparticles may additionally be advantageously coupled to targeting molecules to direct the nanoparticle to the appropriate cell type and/or increase the likelihood of cellular uptake. Examples of such targeting molecules include antibodies specific for cell-surface receptors and the natural ligands (or portions of the natural ligands) for cell surface receptors.

In some embodiments, the meganuclease proteins or DNA/mRNA encoding the meganucleases are encapsulated within liposomes or complexed using cationic lipids (see, e.g., LIPOFECTAMINE, Life Technologies Corp., Carlsbad, CA; Zuris et al. (2015) Nat Biotechnol. 33: 73-80; Mishra et al. (2011) J Drug Deliv. 2011:863734). The liposome and lipoplex formulations can protect the payload from degradation, enhance accumulation and retention at the target site, and facilitate cellular uptake and delivery efficiency through fusion with and/or disruption of the cellular membranes of the target cells.

In some embodiments, meganuclease proteins, or DNA/mRNA encoding meganucleases, are encapsulated within polymeric scaffolds (e.g., PLGA) or complexed using cationic polymers (e.g., PEI, PLL) (Tamboli et al. (2011) Ther Deliv. 2(4): 523-536). Polymeric carriers can be designed to provide tunable drug release rates through control of polymer erosion and drug diffusion, and high drug encapsulation efficiencies can offer protection of the therapeutic payload until intracellular delivery to the desired target cell population.

In some embodiments, meganuclease proteins, or DNA/mRNA encoding engineered meganucleases, are combined with amphiphilic molecules that self-assemble into micelles (Tong et al. (2007) J Gene Med. 9(11): 956-66). Polymeric micelles may include a micellar shell formed with a hydrophilic polymer (e.g., polyethyleneglycol) that can prevent aggregation, mask charge interactions, and reduce nonspecific interactions.

In some embodiments, meganuclease proteins, or DNA/mRNA encoding meganucleases, are formulated into an emulsion or a nanoemulsion (i.e., having an average particle diameter of <1 nm) for administration and/or delivery to the target cell. The term "emulsion" refers to, without limitation, any oil-in-water, water-in-oil, water-in-oil-in-water, or oil-in-water-in-oil dispersions or droplets, including lipid structures that can form as a result of hydrophobic forces that drive apolar residues (e.g., long hydrocarbon chains) away from water and polar head groups toward water, when a water immiscible phase is mixed with an aqueous phase. These other lipid structures include, but are not limited to, unilamellar, paucilamellar, and multilamellar lipid vesicles, micelles, and lamellar phases. Emulsions are composed of an aqueous phase and a lipophilic phase (typically containing an oil and an organic solvent). Emulsions also frequently contain one or more surfactants. Nanoemulsion formulations are well known, e.g., as described in U.S. Pat. Nos. 6,015,832, 6,506,803, 6,635,676, 6,559,189, and 7,767,216, each of which is incorporated herein by reference in its entirety.

In some embodiments, meganuclease proteins, or DNA/mRNA encoding meganucleases, are covalently attached to, or non-covalently associated with, multifunctional polymer conjugates, DNA dendrimers, and polymeric dendrimers (Mastorakos et al. (2015) Nanoscale. 7(9): 3845-56; Cheng et al. (2008) J Pharm Sci. 97(1): 123-43). The dendrimer generation can control the payload capacity and size, and can provide a high drug payload capacity. Moreover, display of multiple surface groups can be leveraged to improve stability, reduce nonspecific interactions, and enhance cell-specific targeting and drug release.

In some embodiments, polynucleotides comprising a nucleic acid sequence encoding an engineered meganuclease described herein are introduced into a cell using a recombinant virus (i.e., a recombinant viral vector). Such recombinant viruses are known in the art and include recombinant retroviruses, recombinant lentiviruses, recombinant adenoviruses, and recombinant adeno-associated viruses (AAVs) (reviewed in Vannucci, et al. (2013 *New Microbiol.* 36:1-22). Recombinant AAVs useful in the invention can have any serotype that allows for transduction of the virus into a target cell type and expression of the meganuclease gene in the target cell. For example, in some embodiments, recombinant AAVs have a serotype (i.e. capsid) of AAV1, AAV2, AAV5 AAV6, AAV7, AAV8, AAV9, and AAV12. It is known in the art that different AAVs tend to localize to different tissues (Wang et al., *Expert Opin Drug Deliv* 11(3). 2014). In some embodiments, the viral vectors are injected directly into target tissues (e.g., liver tissue). In alternative embodiments, the viral vectors are delivered systemically via the circulatory system. It is known in the art that different AAV vectors tend to localize to different tissues. In liver target tissues, effective transduction of hepatocytes has been shown, for example, with AAV serotypes 2, 8, and 9 (Sands (2011) Methods Mol. Biol. 807:141-157). In some embodiments, the AAV serotype is AAV2. In some embodiments, the AAV serotype is AAV8. In some embodiments, the AAV serotype is AAV9. AAVs can also be self-complementary such that they do not require second-strand DNA synthesis in the host cell (McCarty, et al. (2001) Gene Ther. 8:1248-54). Polynucleotides delivered by recombinant AAVs can include left (5') and right (3') inverted terminal repeats as part of the viral genome. In some embodiments, the recombinant viruses are injected directly into target tissues. In alternative embodiments, the recombinant viruses are delivered systemically via the circulatory system.

In one embodiment, a recombinant virus used for meganuclease gene delivery is a self-limiting recombinant virus. A self-limiting virus can have limited persistence time in a cell or organism due to the presence of a recognition sequence for an engineered meganuclease within the viral genome. Thus, a self-limiting recombinant virus can be engineered to provide a coding sequence for a promoter, an engineered meganuclease described herein, and a meganuclease recognition site within the ITRs. The self-limiting recombinant virus delivers the meganuclease gene to a cell, tissue, or organism, such that the meganuclease is expressed and able to cut the genome of the cell at an endogenous recognition sequence within the genome. The delivered meganuclease will also find its target site within the self-limiting recombinant viral genome, and cut the recombinant viral genome at this target site. Once cut, the 5' and 3' ends of the viral genome will be exposed and degraded by exonucleases, thus killing the virus and ceasing production of the meganuclease.

If a polynucleotide comprising a nucleic acid sequence encoding an engineered meganuclease described herein is delivered to a cell by a recombinant virus (e.g. an AAV), the nucleic acid sequence encoding the engineered meganuclease can be operably linked to a promoter. In some embodiments, this can be a viral promoter such as endogenous promoters from the recombinant virus (e.g. the LTR of a lentivirus) or the well-known cytomegalovirus—or SV40 virus-early promoters. In particular embodiments, the nucleic acid sequence encoding the engineered meganuclease is operably linked to a promoter that drives gene expression preferentially in the target cells. Examples of liver-specific promoters include, without limitation, human alpha-1 antitrypsin promoter, hybrid liver-specific promoter (hepatic locus control region from ApoE gene (ApoE-HCR) and a liver-specific alpha1-antitrypsin promoter), human thyroxine binding globulin (TBG) promoter, and apolipoprotein A-II promoter.

In particular embodiments, the viral vector comprises a cassette comprising a promoter and a nucleic acid sequence encoding an engineered meganuclease described herein. The viral vector could also comprise two or more cassettes, wherein at least a first cassette comprises a promoter and a nucleic acid sequence encoding an engineered meganuclease described herein, and wherein at least a second cassette comprises a promoter and a nucleic acid sequence encoding an engineered meganuclease that has specificity for a different HBV recognition sequence other than the HBV 11-12 recognition sequence. In some embodiments, the viral vector comprises one cassette comprising a promoter and a polycistronic nucleic acid sequence, wherein the promoter drives expression of the polycistronic nucleic acid sequence to generate a polycistronic mRNA, such as polycistronic mRNA encoding an engineered meganuclease, described herein in a target cell.

Methods and compositions are provided for delivering a meganuclease described herein to the liver of a subject infected with HBV. In one embodiment, native hepatocytes which have been removed from the mammal can be transduced with a vector which encodes the engineered meganuclease. Alternatively, native hepatocytes of the HBV-infected subject can be transduced ex vivo with an adenoviral vector (i.e., an AAV vector) which encodes the engineered meganuclease and/or a molecule that stimulates liver regeneration, such as a hepatotoxin. Preferably the hepatotoxin is uPA, and has been modified to inhibit its secretion from the hepatocyte once expressed by the viral vector. In another embodiment, the vector encodes tPA, which can stimulate hepatocyte regeneration de novo. The transduced hepatocytes which have been removed from the mammal can then be returned to the mammal, where conditions are provided which are conducive to expression of the engineered meganuclease. Typically, the transduced hepatocytes can be returned to the patient by infusion through the spleen or portal vasculature, and administration may be single or multiple over a period of 1 to 5 or more days.

Administration

In an in vivo aspect of the methods of the invention, a retroviral, pseudotype or adenoviral associated virus (i.e., an AAV) is constructed which encodes the engineered meganuclease and is administered to the subject. Administration of a vector encoding the engineered meganuclease can occur with administration of an adenoviral vector that encodes a secretion-impaired hepatotoxin, or encodes tPA, which stimulates hepatocyte regeneration without acting as a hepatotoxin.

In various embodiments of the methods and compositions described herein, such as the engineered meganucleases described herein, polynucleotides encoding the same, recombinant viruses comprising such polynucleotides, or lipid nanoparticles comprising such polynucleotides, can be administered via any suitable route of administration known in the art. Such routes of administration can include, for example, intravenous, intramuscular, intraperitoneal, subcutaneous, intrahepatic, transmucosal, transdermal, intraarterial, and sublingual. In some embodiments, the engineered meganuclease proteins, polynucleotides encoding the same, recombinant viruses comprising such polynucleotides, or lipid nanoparticles comprising such polynucleotides, are supplied to target cells (e.g., liver cells) via injection directly to the target tissue (e.g., liver tissue). Other suitable routes of administration can be readily determined by the treating physician as necessary.

In some embodiments, a therapeutically effective amount of an engineered meganuclease described herein, or a polynucleotide encoding the same, is administered to a subject in need thereof for the treatment of a disease. Such administration may be carried out until sAg is no longer detectable in the serum or plasma of the subject. In some embodiments, after one or more administrations of the one or more engineered meganucleases, polynucleotides encoding such engineered meganucleases, lipid nanoparticles or recombinant viruses comprising one or more polynucleotides encoding such engineered meganucleases, as described herein, optionally with one or more additional therapeutic agents, described herein, the subject does not exhibit symptoms of HBV in the absence of antiviral treatment. In some embodiments, after one or more administrations of the one or more engineered meganucleases, polynucleotides encoding such engineered meganucleases, or vectors comprising one or more polynucleotides encoding such engineered meganucleases, as described herein, optionally with one or more additional therapeutic agents, described herein, sAg is no longer detectable in the serum or plasma of the subject, in the absence of antiviral treatment.

In some embodiments, a subject is administered a pharmaceutical composition comprising a polynucleotide comprising a nucleic acid sequence encoding an engineered meganuclease described herein, wherein the encoding nucleic acid sequence is administered at a dose of about $1 \times 10^{10}$ gc/kg to about $1 \times 10^{14}$ gc/kg (e.g., about $1 \times 10^{10}$ gc/kg, about $1 \times 10^{11}$ gc/kg, about $1 \times 10^{12}$ gc/kg, about $1 \times 10^{13}$ gc/kg, or about $1 \times 10^{14}$ gc/kg). In some embodiments, a subject is administered a pharmaceutical composition comprising a polynucleotide comprising a nucleic acid sequence encoding an engineered meganuclease described herein, wherein the encoding nucleic acid sequence is administered at a dose of about $1 \times 10^{10}$ gc/kg, about $1 \times 10^{11}$ gc/kg, about $1 \times 10^{12}$ gc/kg, about $1 \times 10^{13}$ gc/kg, or about $1 \times 10^{14}$ gc/kg. In some embodiments, a subject is administered a pharmaceutical composition comprising a polynucleotide comprising a nucleic acid sequence encoding an engineered meganuclease described herein, wherein the encoding nucleic acid sequence is administered at a dose of about $1 \times 10^{10}$ gc/kg to about $1 \times 10^{11}$ gc/kg, about $1 \times 10^{11}$ gc/kg to about $1 \times 10^{12}$ gc/kg, about $1 \times 10^{12}$ gc/kg to about $1 \times 10^{13}$ gc/kg, or about $1 \times 10^{13}$ gc/kg to about $1 \times 10^{14}$ gc/kg. It should be understood that these doses can relate to the administration of a single polynucleotide comprising a single nucleic acid sequence encoding a single engineered meganuclease described herein or, alternatively, can relate to a single polynucleotide comprising a first nucleic acid sequence encoding a first engineered meganuclease described herein and a second nucleic acid sequence encoding a second engineered meganuclease described herein, wherein each of the two encoding nucleic acid sequences is administered at the indicated dose.

In some embodiments, a subject is administered a lipid nanoparticle formulation comprising an mRNA comprising a nucleic acid sequence encoding an engineered meganuclease described herein, wherein the dose of the mRNA is about 0.1 mg/kg to about 3 mg/kg. In some embodiments, a subject is administered a lipid nanoparticle formulation comprising an mRNA comprising a nucleic acid sequence encoding an engineered meganuclease described herein, wherein the dose of the mRNA is about 0.1 mg/kg, about 0.25 mg/kg, about 0.5 mg/kg, about 0.75 mg/kg, about 1.0 mg/kg, about 1.5 mg/kg, about 2.0 mg/kg, about 2.5 mg/kg, or about 3.0 mg/kg. In some embodiments, a subject is administered a lipid nanoparticle formulation comprising an mRNA comprising a nucleic acid sequence encoding an engineered meganuclease described herein, wherein the dose of the mRNA is about 0.1 mg/kg to about 0.25 mg/kg, about 0.25 mg/kg to about 0.5 mg/kg, about 0.5 mg/kg to about 0.75 mg/kg, about 0.75 mg/kg to about 1.0 mg/kg, about 1.0 mg/kg to about 1.5 mg/kg, about 1.5 mg/kg to about 2.0 mg/kg, about 2.0 mg/kg to about 2.5 mg/kg, or about 2.5 mg/kg to about 3.0 mg/kg.

As appropriate, the dosage or dosing frequency of the engineered meganuclease, or the polynucleotide encoding the same, may be adjusted over the course of the treatment, based on the judgment of the administering physician. Appropriate doses will depend, among other factors, on the specifics of any AAV chosen (e.g., serotype, etc.), any lipid nanoparticle chosen, on the route of administration, on the subject being treated (i.e., age, weight, sex, and general condition of the subject), and the mode of administration. Thus, the appropriate dosage may vary from patient to patient. An appropriate effective amount can be readily determined by one of skill in the art or treating physician. Dosage treatment may be a single dose schedule or, if multiple doses are required, a multiple dose schedule. Moreover, the subject may be administered as many doses as appropriate. One of skill in the art can readily determine an appropriate number of doses. The dosage may need to be adjusted to take into consideration an alternative route of administration or balance the therapeutic benefit against any side effects.

2.4 Pharmaceutical Compositions

In some embodiments, the invention provides a pharmaceutical composition comprising a pharmaceutically acceptable carrier and an engineered meganuclease described herein, or a pharmaceutically acceptable carrier and a polynucleotide described herein that comprises a nucleic acid sequence encoding an engineered meganuclease described herein. Such polynucleotides can be, for example, mRNA or DNA as described herein. In some such examples, the polynucleotide in the pharmaceutical composition can be comprised by a lipid nanoparticle or can be comprised by a recombinant virus (e.g., a recombinant AAV). In other embodiments, the disclosure provides a pharmaceutical composition comprising a pharmaceutically acceptable carrier and a genetically-modified cell of the invention, which can be delivered to a target tissue where the cell expresses the engineered meganuclease as described herein. Pharmaceutical compositions of the invention can be useful for treating a subject having HBV, reducing the level or proliferation of HBV, reducing at least one symptom of HBV, or treating HCC.

Pharmaceutical compositions can be designed or selected according to the genotype of the target HBV strain. As described in detail herein, the meganucleases of the invention have been engineered to recognize and cleave a recognition sequence in specific genotypes of HBV. HBV 11-12 meganucleases (e.g., SEQ ID NOs: 12, 13, 14, 15, 16, and 17), recognize and cleave the HBV 11-12 recognition sequence that is at least found in the genome of HBV genotypes A, B, C, D, E, F, and G (e.g., SEQ ID NOs: 3-9, respectively). Further, recognition sequences of the engineered meganucleases described herein can be found in isolates of HBV genotypes A, B, C, D, E, F, and G that do not share 100% sequence identity to the respective genotype examples provided in SEQ ID NOs: 3-9. As used herein, HBV "isolates" can share at least 80%, at least 85%, at least 90%, at least 91%, at least 92%, at least 93%, at least 94%, at least 95%, at least 96%, at least 97%, at least 98%, at least 99% or 100% sequence identity with the corresponding genotype example provided in any of SEQ ID NOs: 3-9. In some embodiments, the pharmaceutical compositions described herein can be administered to a subject having any genotype of HBV comprising a recognition sequence set forth in SEQ ID NO: 10.

Such pharmaceutical compositions can be prepared in accordance with known techniques. See, e.g., Remington, The Science And Practice of Pharmacy (21st ed., Philadelphia, Lippincott, Williams & Wilkins, 2005). In the manufacture of a pharmaceutical formulation according to the invention, engineered meganucleases described herein, polynucleotides encoding the same, or cells expressing the same, are typically admixed with a pharmaceutically acceptable carrier and the resulting composition is administered to a subject. The carrier must be acceptable in the sense of being compatible with any other ingredients in the formulation and must not be deleterious to the subject. The carrier can be a solid or a liquid, or both, and can be formulated with the compound as a unit-dose formulation.

In some embodiments, pharmaceutical compositions of the invention can further comprise one or more additional agents or biological molecules useful in the treatment of a disease in the subject. Likewise, the additional agent(s) and/or biological molecule(s) can be co-administered as a separate composition.

Given that the presently disclosed engineered meganucleases can have improved (i.e., increased) specificity resulting in reduced off-target cutting, and enhanced (i.e., increased) efficiency of cleavage and indel formation, particularly in cells comprising an integrated copy of the HBV genome, as compared to the HBV 11-12x.26 or HBV 11-12L.363 meganuclease, in some embodiments, the presently disclosed pharmaceutical compositions comprising optimized engineered meganucleases, nucleic acid sequences encoding the same, or cells expressing the same, also have improved (i.e., increased) efficacy in treating HBV, reducing the level or proliferation of HBV, reducing at least one symptom of HBV, or treating HCC in a subject, when compared to the administration of pharmaceutical compositions comprising the HBV 11-12x.26 or HBV 11-12L.363 meganuclease.

In particular embodiments, pharmaceutical compositions of the invention can include combinations of the engineered meganucleases described herein (or nucleic acids encoding engineered meganucleases or cells expressing engineered meganucleases). In other embodiments, pharmaceutical compositions of the invention can include at least two engineered meganucleases (or nucleic acids encoding engineered meganucleases or cells expressing engineered meganucleases), wherein at least a first engineered meganuclease is one described herein that binds and cleaves the HBV 11-12 recognition sequence, and wherein at least a second engineered meganuclease binds and cleaves a second recognition sequence in the HBV genome other than the HBV 11-12 recognition sequence, such that a single pharmaceutical composition is broadly useful for the treatment of a wide array of HBV genotypes and/or genotype isolates in a subject. Likewise, in other embodiments, pharmaceutical compositions of the invention can include polycistronic mRNAs (or recombinant DNA constructs or viral vectors having cassettes which, when expressed, produce polycistronic mRNAs) that encode multiple engineered meganucleases described herein. In other embodiments, pharmaceutical compositions of the invention can include polycistronic mRNAs (or recombinant DNA constructs or viral vectors having cassettes which, when expressed, produce polycistronic mRNAs) that encode at least two engineered meganucleases, wherein at least a first engineered meganuclease is one described herein that binds and cleaves the HBV 11-12 recognition sequence, and wherein at least a second engineered meganuclease binds and cleaves a second recognition sequence in the HBV genome other than the HBV 11-12 recognition sequence. Such pharmaceutical compositions are also broadly useful for the treatment of a wide array of HBV genotypes and/or genotype isolates in a subject. In either case, such pharmaceutical compositions can be useful as a single treatment when the specific HBV genotype or isolate is known or unknown in the subject.

For example, pharmaceutical compositions comprising multiple different engineered meganucleases (including at least one of the engineered meganucleases described herein) or comprising nucleic molecules encoding multiple different engineered meganucleases (including at least one of the engineered meganucleases described herein) that target recognition sequences within the HBV genome, can be administered to a patient infected with multiple genotypes of HBV, or infected with unknown genotypes of HBV. Accordingly, providing pharmaceutical compositions with multiple different engineered meganucleases or comprising nucleic molecules encoding multiple different engineered meganucleases affords a flexible option for treatment and control of HBV infection where resources do not allow for accurate genotyping HBV and where fast and broad treatment solutions are desired.

The pharmaceutical compositions described herein can include a therapeutically effective amount of any engineered meganuclease described herein, or any polynucleotide described herein encoding any engineered meganuclease described herein. For example, in some embodiments, the pharmaceutical composition can include polynucleotides described herein at any of the doses (e.g., gc/kg of an encoding nucleic acid sequence or mg/kg of mRNA) described herein.

In particular embodiments of the invention, the pharmaceutical composition can comprise one or more polynucleotides (e.g., mRNAs) described herein encapsulated within lipid nanoparticles, which are described elsewhere herein. In particular embodiments, lipid nanoparticles can comprise two or more mRNAs described herein. In other embodiments, lipid nanoparticles can comprise at least two mRNAs, wherein at least a first mRNA is an mRNA described herein that encodes an engineered meganuclease described herein that binds and cleaves the HBV 11-12 recognition sequence, and wherein at least a second mRNA encodes a second engineered meganuclease that binds and cleaves a recognition sequence within an HBV genome other than the HBV 11-12 recognition sequence. In other embodiments, lipid nanoparticles can comprise one or more polycistronic mRNAs described herein, wherein each polycistronic mRNA encodes two or more engineered meganucleases, wherein at least one engineered meganuclease is an engineered meganuclease described herein that binds and cleaves the HBV 11-12 recognition sequence, and wherein at least a second engineered meganuclease binds and cleaves a recognition sequence within a HBV genome other than the HBV 11-12 recognition sequence.

Some lipid nanoparticles contemplated for use in the invention comprise at least one cationic lipid, at least one non-cationic lipid, and at least one conjugated lipid. In more particular examples, lipid nanoparticles can comprise from about 50 mol % to about 85 mol % of a cationic lipid, from about 13 mol % to about 49.5 mol % of a non-cationic lipid, and from about 0.5 mol % to about 10 mol % of a lipid conjugate, and are produced in such a manner as to have a non-lamellar (i.e., non-bilayer) morphology. In other particular examples, lipid nanoparticles can comprise from about 40 mol % to about 85 mol % of a cationic lipid, from about 13 mol % to about 49.5 mol % of a non-cationic lipid, and from about 0.5 mol % to about 10 mol % of a lipid conjugate, and are produced in such a manner as to have a non-lamellar (i.e., non-bilayer) morphology.

Cationic lipids can include, for example, one or more of the following: palmitoyi-oleoyl-nor-arginine (PONA), MPDACA, GUADACA, ((6Z,9Z,28Z,31Z)-heptatriaconta-6,9,28,31-tetraen-19-yl 4-(dimethylamino)butanoate) (MC3), LenMC3, CP-LenMC3, γ-LenMC3, CP-γ-LenMC3, MC3MC, MC2MC, MC3 Ether, MC4 Ether, MC3 Amide, Pan-MC3, Pan-MC4 and Pan MC5,1,2-dilinoleyloxy-N,N-dimethylaminopropane (DLinDMA), 1,2-dilinolenyloxy-N,N-dimethylaminopropane (DLenDMA), 2,2-dilinoleyl-4-(2-dimethylaminoethyl)-[1,3]-dioxolane (DLin-K-C2-DMA; "XTC2"), 2,2-dilinoleyl-4-(3-dimethylaminopropyl)-[1,3]-dioxolane (DLin-K-C3-DMA), 2,2-dilinoleyl-4-(4-dimethylaminobutyl)-[1,3]-dioxolane (DLin-K-C4-DMA), 2,2-dilinoleyl-5-dimethylaminomethyl-[1,3]-dioxane (DLin-K6-DMA), 2,2-dilinoleyl-4-N-methylpepiazino-[1,3]-dioxolane (DLin-K-MPZ), 2,2-dilinoleyl-4-dimethylaminomethyl-[1,3]-dioxolane (DLin-K-DMA), 1,2-dilinoleylcarbamoyloxy-3-dimethylaminopropane (DLin-C-DAP), 1,2-dilinoleyoxy-3-(dimethylamino)acetoxypropane (DLin-DAC), 1,2-dilinoleyoxy-3-morpholinopropane (DLin-MA), 1,2-dilinoleoyl-3-dimethylaminopropane (DLinDAP), 1,2-dilinoleylthio-3-dimethylaminopropane (DLin-S-DMA), 1-linoleoyl-2-linoleyloxy-3-dimethylaminopropane (DLin-2-DMAP), 1,2-dilinoleyloxy-3-trimethylaminopropane chloride salt (DLin-TMA.Cl), 1,2-dilinoleoyl-3-trimethylaminopropane chloride salt (DLin-TAP.Cl), 1,2-dilinoleyloxy-3-(N-methylpiperazino)propane (DLin-MPZ), 3-(N,N-dilinoleylamino)-1,2-propanediol (DLinAP), 3-(N,N-dioleylamino)-1,2-propanedio (DOAP), 1,2-dilinoleyloxo-3-(2-N,N-dimethylamino)ethoxypropane (DLin-EG-DMA), N,N-dioleyl-N,N-dimethylammonium chloride (DODAC), 1,2-dioleyloxy-N,N-dimethylaminopropane (DODMA), 1,2-distearyloxy-N,N-dimethylaminopropane (DSDMA), N-(1-(2,3-dioleyloxy)propyl)-N,N,N-trimethylammonium chloride (DOTMA), N,N-distearyl-N,N-dimethylammonium bromide (DDAB), N-(1-(2,3-dioleoyloxy)propyl)-N,N,N-trimethylammonium chloride (DOTAP), 3-(N—(N',N'-dimethylaminoethane)-carbamoyl)cholesterol (DC-Chol), N-(1,2-dimyristyloxyprop-3-yl)-N,N-dimethyl-N-hydroxyethyl ammonium bromide (DMRIE), 2,3-dioleyloxy-N-[2(spermine-carboxamido)ethyl]-N,N-dimethyl-1-propanaminiumtrifluoroacetate (DOSPA), dioctadecylamidoglycyl spermine (DOGS), 3-dimethylamino-2-(cholest-5-en-3-beta-oxybutan-4-oxy)-1-(cis,cis-9,12-octadecadienoxy)propane (CLinDMA), 2-[5'-(cholest-5-en-3-beta-oxy)-3'-oxapentoxy)-3-dimethy-1-(cis,cis-9',1-2'-octadecadienoxy) propane (CpLinDMA), N,N-dimethyl-3,4-dioleyloxybenzylamine (DMOBA), 1,2-N,N'-dioleylcarbamyl-3-dimethylaminopropane (DOcarbDAP), 1,2-N,N'-dilinoleylcarbamyl-3-dimethylaminopropane (DLincarbDAP), or mixtures thereof. The cationic lipid can also be DLinDMA, DLin-K-C2-DMA ("XTC2"), MC3, LenMC3, CP-LenMC3, γ-LenMC3, CP-γ-LenMC3, MC3MC, MC2MC, MC3 Ether, MC4 Ether, MC3 Amide, Pan-MC3, Pan-MC4, Pan MC5, or mixtures thereof.

In various embodiments, the cationic lipid may comprise from about 50 mol % to about 90 mol %, from about 50 mol % to about 85 mol %, from about 50 mol % to about 80 mol %, from about 50 mol % to about 75 mol %, from about 50 mol % to about 70 mol %, from about 50 mol % to about 65 mol %, or from about 50 mol % to about 60 mol % of the total lipid present in the particle.

In other embodiments, the cationic lipid may comprise from about 40 mol % to about 90 mol %, from about 40 mol % to about 85 mol %, from about 40 mol % to about 80 mol %, from about 40 mol % to about 75 mol %, from about 40 mol % to about 70 mol %, from about 40 mol % to about 65 mol %, or from about 40 mol % to about 60 mol % of the total lipid present in the particle.

The non-cationic lipid may comprise, e.g., one or more anionic lipids and/or neutral lipids. In particular embodiments, the non-cationic lipid comprises one of the following neutral lipid components: (1) cholesterol or a derivative thereof; (2) a phospholipid; or (3) a mixture of a phospholipid and cholesterol or a derivative thereof. Examples of cholesterol derivatives include, but are not limited to, cholestanol, cholestanone, cholestenone, coprostanol, cholesteryl-2'-hydroxyethyl ether, cholesteryl-4'-hydroxybutyl ether, and mixtures thereof. The phospholipid may be a neutral lipid including, but not limited to, dipalmitoylphosphatidylcholine (DPPC), distearoylphosphatidylcholine (DSPC), dioleoylphosphatidylethanolamine (DOPE), palmitoyloleoyl-phosphatidylcholine (POPC), palmitoyloleoyl-phosphatidylethanolamine (POPE), palmitoyloleyol-phosphatidylglycerol (POPG), dipalmitoyl-phosphatidylethanolamine (DPPE), dimyristoyl-phosphatidylethanolamine (DMPE), distearoyl-phosphatidylethanolamine (DSPE), monomethyl-phosphatidylethanolamine, dimethyl-phosphatidylethanolamine, dielaidoyl-phosphatidylethanolamine (DEPE), stearoyloleoyl-phosphatidylethanolamine (SOPE), egg phosphatidylcholine (EPC), and mixtures thereof. In certain embodiments, the phospholipid is DPPC, DSPC, or mixtures thereof.

In some embodiments, the non-cationic lipid (e.g., one or more phospholipids and/or cholesterol) may comprise from about 10 mol % to about 60 mol %, from about 15 mol % to about 60 mol %, from about 20 mol % to about 60 mol %, from about 25 mol % to about 60 mol %, from about 30 mol % to about 60 mol %, from about 10 mol % to about 55 mol %, from about 15 mol % to about 55 mol %, from about 20 mol % to about 55 mol %, from about 25 mol % to about 55 mol %, from about 30 mol % to about 55 mol %, from about 13 mol % to about 50 mol %, from about 15 mol % to about 50 mol % or from about 20 mol % to about 50 mol % of the total lipid present in the particle. When the non-cationic lipid is a mixture of a phospholipid and cholesterol or a cholesterol derivative, the mixture may comprise up to about 40, 50, or 60 mol % of the total lipid present in the particle.

The conjugated lipid that inhibits aggregation of particles may comprise, e.g., one or more of the following: a polyethyleneglycol (PEG)-lipid conjugate, a polyamide (ATTA)-lipid conjugate, a cationic-polymer-lipid conjugates (CPLs), or mixtures thereof. In one particular embodiment, the nucleic acid-lipid particles comprise either a PEG-lipid conjugate or an ATTA-lipid conjugate. In certain embodiments, the PEG-lipid conjugate or ATTA-lipid conjugate is used together with a CPL. The conjugated lipid that inhibits aggregation of particles may comprise a PEG-lipid including, e.g., a PEG-diacylglycerol (DAG), a PEG dialkyloxypropyl (DAA), a PEG-phospholipid, a PEG-ceramide (Cer), or mixtures thereof. The PEG-DAA conjugate may be PEG-di lauryloxypropyl (C12), a PEG-dimyristyloxypropyl (C14), a PEG-dipalmityloxypropyl (C16), a PEG-distearyloxypropyl (C18), or mixtures thereof.

Additional PEG-lipid conjugates suitable for use in the invention include, but are not limited to, mPEG2000-1,2-di-O-alkyl-sn3-carbomoylglyceride (PEG-C-DOMG). The synthesis of PEG-C-DOMG is described in PCT Application No. PCT/US08/88676. Yet additional PEG-lipid conjugates suitable for use in the invention include, without limitation, 1-[8'-(1,2-dimyristoyl-3-propanoxy)-carboxamido-3',6'-dioxaoctanyl]carbamoyl-ω-methyl-poly(ethylene glycol) (2KPEG-DMG). The synthesis of 2KPEG-DMG is described in U.S. Pat. No. 7,404,969.

In some cases, the conjugated lipid that inhibits aggregation of particles (e.g., PEG-lipid conjugate) may comprise from about 0.1 mol % to about 2 mol %, from about 0.5 mol % to about 2 mol %, from about 1 mol % to about 2 mol %, from about 0.6 mol % to about 1.9 mol %, from about 0.7 mol % to about 1.8 mol %, from about 0.8 mol % to about 1.7 mol %, from about 1 mol % to about 1.8 mol %, from about 1.2 mol % to about 1.8 mol %, from about 1.2 mol % to about 1.7 mol %, from about 1.3 mol % to about 1.6 mol %, from about 1.4 mol % to about 1.5 mol %, or about 1, 1.1, 1.2, 1.3, 1.4, 1.5, 1.6, 1.7, 1.8, 1.9, or 2 mol % (or any fraction thereof or range therein) of the total lipid present in the particle. Typically, in such instances, the PEG moiety has an average molecular weight of about 2,000 Daltons. In other cases, the conjugated lipid that inhibits aggregation of particles (e.g., PEG-lipid conjugate) may comprise from about 5.0 mol % to about 10 mol %, from about 5 mol % to about 9 mol %, from about 5 mol % to about 8 mol %, from about 6 mol % to about 9 mol %, from about 6 mol % to about 8 mol %, or about 5 mol %, 6 mol %, 7 mol %, 8 mol %, 9 mol %, or 10 mol % (or any fraction thereof or range therein) of the total lipid present in the particle. Typically, in such instances, the PEG moiety has an average molecular weight of about 750 Daltons.

In other embodiments, the composition may comprise amphoteric liposomes, which contain at least one positive and at least one negative charge carrier, which differs from the positive one, the isoelectric point of the liposomes being between 4 and 8. This objective is accomplished owing to the fact that liposomes are prepared with a pH-dependent, changing charge.

Liposomal structures with the desired properties are formed, for example, when the amount of membrane-forming or membrane-based cationic charge carriers exceeds that of the anionic charge carriers at a low pH and the ratio is reversed at a higher pH. This is always the case when the ionizable components have a pKa value between 4 and 9. As the pH of the medium drops, all cationic charge carriers are charged more and all anionic charge carriers lose their charge.

Cationic compounds useful for amphoteric liposomes include those cationic compounds previously described herein above. Without limitation, strongly cationic compounds can include, for example: DC-Chol 3-β-[N—(N',N'-dimethylmethane) carbamoyl] cholesterol, TC-Chol 3-β-[N—(N', N', N'-trimethylaminoethane) carbamoyl cholesterol, BGSC bisguanidinium-spermidine-cholesterol, BGTC bis-guadinium-tren-cholesterol, DOTAP (1,2-dioleoyloxypropyl)-N,N,N-trimethylammonium chloride, DOSPER (1,3-dioleoyloxy-2-(6-carboxy-spermyl)-propylarnide, DOTMA (1,2-dioleoyloxypropyl)-N,N,N-trimethylamronium chloride) (Lipofectin®), DORIE 1,2-dioleoyloxypropyl)-3-dimethylhydroxyethylammonium bromide, DOSC (1,2-dioleoyl-3-succinyl-sn-glyceryl choline ester), DOGSDSO (1,2-dioleoyl-sn-glycero-3-succinyl-2-hydroxyethyl disulfide omithine), DDAB dimethyldioctadecylammonium bromide, DOGS ((C18)2GlySper3+) N,N-dioctadecylamido-glycol-spermin (Transfectam®) (C18)2Gly+N, N-dioctadecylamido-glycine, CTAB cetyltrimethylarnmonium bromide, CpyC cetylpyridinium chloride, DOEPC 1,2-dioleoly-sn-glycero-3-ethylphosphocholine or other O-alkyl-phosphatidylcholine or ethanolamines, amides from lysine, arginine or ornithine and phosphatidyl ethanolamine.

Examples of weakly cationic compounds include, without limitation: His-Chol (histaminyl-cholesterol hemisuccinate), Mo-Chol (morpholine-N-ethylamino-cholesterol hemisuccinate), or histidinyl-PE.

Examples of neutral compounds include, without limitation: cholesterol, ceramides, phosphatidyl cholines, phosphatidyl ethanolamines, tetraether lipids, or diacyl glycerols.

Anionic compounds useful for amphoteric liposomes include those non-cationic compounds previously described herein. Without limitation, examples of weakly anionic compounds can include: CHEMS (cholesterol hemisuccinate), alkyl carboxylic acids with 8 to 25 carbon atoms, or diacyl glycerol hemisuccinate. Additional weakly anionic compounds can include the amides of aspartic acid, or glutamic acid and PE as well as PS and its amides with glycine, alanine, glutamine, asparagine, serine, cysteine, threonine, tyrosine, glutamic acid, aspartic acid or other amino acids or aminodicarboxylic acids. According to the same principle, the esters of hydroxycarboxylic acids or hydroxydicarboxylic acids and PS are also weakly anionic compounds.

In some embodiments, amphoteric liposomes may contain a conjugated lipid, such as those described herein above. Particular examples of useful conjugated lipids include, without limitation, PEG-modified phosphatidylethanolamine and phosphatidic acid, PEG-ceramide conjugates (e.g., PEG-CerC14 or PEG-CerC20), PEG-modified dialkylamines and PEG-modified 1,2-diacyloxypropan-3-amines. Particular are PEG-modified diacylglycerols and dialkylglycerols.

In some embodiments, the neutral lipids may comprise from about 10 mol % to about 60 mol %, from about 15 mol % to about 60 mol %, from about 20 mol % to about 60 mol %, from about 25 mol % to about 60 mol %, from about 30 mol % to about 60 mol %, from about 10 mol % to about 55 mol %, from about 15 mol % to about 55 mol %, from about 20 mol % to about 55 mol %, from about 25 mol % to about 55 mol %, from about 30 mol % to about 55 mol %, from about 13 mol % to about 50 mol %, from about 15 mol % to about 50 mol % or from about 20 mol % to about 50 mol % of the total lipid present in the particle.

In some cases, the conjugated lipid that inhibits aggregation of particles (e.g., PEG-lipid conjugate) may comprise from about 0.1 mol % to about 2 mol %, from about 0.5 mol % to about 2 mol %, from about 1 mol % to about 2 mol %, from about 0.6 mol % to about 1.9 mol %, from about 0.7 mol % to about 1.8 mol %, from about 0.8 mol % to about 1.7 mol %, from about 1 mol % to about 1.8 mol %, from about 1.2 mol % to about 1.8 mol %, from about 1.2 mol % to about 1.7 mol %, from about 1.3 mol % to about 1.6 mol %, from about 1.4 mol % to about 1.5 mol %, or about 1, 1.1, 1.2, 1.3, 1.4, 1.5, 1.6, 1.7, 1.8, 1.9, or 2 mol % (or any fraction thereof or range therein) of the total lipid present in the particle. Typically, in such instances, the PEG moiety has an average molecular weight of about 2,000 Daltons. In other cases, the conjugated lipid that inhibits aggregation of particles (e.g., PEG-lipid conjugate) may comprise from about 5.0 mol % to about 10 mol %, from about 5 mol % to about 9 mol %, from about 5 mol % to about 8 mol %, from about 6 mol % to about 9 mol %, from about 6 mol % to about 8 mol %, or about 5 mol %, 6 mol %, 7 mol %, 8 mol %, 9 mol %, or 10 mol % (or any fraction thereof or range therein) of the total lipid present in the particle. Typically, in such instances, the PEG moiety has an average molecular weight of about 750 Daltons.

Considering the total amount of neutral and conjugated lipids, the remaining balance of the amphoteric liposome can comprise a mixture of cationic compounds and anionic compounds formulated at various ratios. The ratio of cationic to anionic lipid may selected in order to achieve the desired properties of nucleic acid encapsulation, zeta potential, pKa, or other physicochemical property that is at least in part dependent on the presence of charged lipid components.

In some embodiments, the lipid nanoparticles have a composition which specifically enhances delivery and uptake in the liver, and specifically within hepatocytes.

In some embodiments, pharmaceutical compositions of the invention can further comprise one or more additional agents useful in the treatment of HBV infection or HCC in the subject.

The present disclosure also provides engineered meganucleases described herein (or nucleic acids encoding the same or cells expressing the engineered meganucleases) for use as a medicament. The present disclosure further provides the use of an engineered meganuclease described herein (or a nucleic acid encoding the same or cells expressing an engineered meganuclease) in the manufacture of a medicament for treating HBV, for reducing the level or proliferation of HBV, reducing the symptoms associated with HBV, or treating HCC.

2.5 Methods for Producing Recombinant Viral Vectors

In some embodiments, the invention provides recombinant viruses, such as recombinant AAVs, for use in the methods of the invention. Recombinant AAVs are typically produced in mammalian cell lines such as HEK-293. Because the viral cap and rep genes are removed from the recombinant virus to prevent its self-replication to make room for the therapeutic gene(s) to be delivered (e.g. the meganuclease gene), it is necessary to provide these in trans in the packaging cell line. In addition, it is necessary to provide the "helper" (e.g. adenoviral) components necessary to support replication (Cots D et al., (2013) Curr. Gene Ther. 13(5): 370-81). Frequently, recombinant AAVs are produced using a triple-transfection in which a cell line is transfected with a first plasmid encoding the "helper" components, a second plasmid comprising the cap and rep genes, and a third plasmid comprising the viral ITRs containing the intervening DNA sequence to be packaged into the virus. Viral particles comprising a genome (ITRs and intervening gene(s) of interest) encased in a capsid are then isolated from cells by freeze-thaw cycles, sonication, detergent, or other means known in the art. Particles are then purified using cesium-chloride density gradient centrifugation or affinity chromatography and subsequently delivered to the gene(s) of interest to cells, tissues, or an organism such as a human patient.

Because recombinant AAV particles are typically produced (manufactured) in cells, precautions must be taken in practicing the current invention to ensure that the engineered meganuclease is not expressed in the packaging cells. Because the recombinant viral genomes of the invention may comprise a recognition sequence for the meganuclease, any meganuclease expressed in the packaging cell line may be capable of cleaving the viral genome before it can be packaged into viral particles. This will result in reduced packaging efficiency and/or the packaging of fragmented genomes. Several approaches can be used to prevent meganuclease expression in the packaging cells, including:

The meganuclease can be placed under the control of a tissue-specific promoter that is not active in the packaging cells. For example, if a viral vector is developed for delivery of (a) meganuclease gene(s) to muscle tissue, a muscle-specific promoter can be used. Examples of muscle-specific promoters include C5-12 (Liu, et al. (2004) Hum Gene Ther. 15:783-92), the muscle-specific creatine kinase (MCK) promoter (Yuasa, et al. (2002) Gene Ther. 9:1576-88), or the smooth muscle 22 (SM22) promoter (Haase, et al. (2013) BMC Biotechnol. 13:49-54). Examples of CNS (neuron)-specific promoters include the NSE, Synapsin, and MeCP2 promoters (Lentz, et al. (2012) Neurobiol Dis. 48:179-88). Examples of liver-specific promoters include albumin promoters (such as Palb), human α1-antitrypsin (such as Pa1AT), and hemopexin (such as Phpx) (Kramer et al., (2003) Mol. Therapy 7:375-85), hybrid liver-specific promoter (hepatic locus control region from ApoE gene (ApoE-HCR) and a liver-specific alpha1-antitrypsin promoter), human thyroxine binding globulin (TBG) promoter, and apolipoprotein A-II promoter. Examples of eye-specific promoters include opsin, and corneal epithelium-specific K12 promoters (Martin et al. (2002) Methods (28): 267-75) (Tong et al., (2007) J Gene Med, 9:956-66). These promoters, or other tissue-specific promoters known in the art, are not highly-active in HEK-293 cells and, thus, will not be expected to yield significant levels of meganuclease gene expression in packaging cells when incorporated into viral vectors of the present invention. Similarly, the viral vectors of the present invention contemplate the use of other cell lines with the use of incompatible tissue specific promoters (i.e., the well-known HeLa cell line (human epithelial cell) and using the liver-specific hemopexin promoter). Other examples of tissue specific promoters include: synovial sarcomas PDZD4 (cerebellum), C6 (liver), ASB5 (muscle), PPP1R12B (heart), SLC5A12 (kidney), cholesterol regulation APOM (liver), ADPRHL1 (heart), and monogenic malformation syndromes TP73L (muscle). (Jacox et al., (2010), PLoS One v.5(8):e12274).

The nuclease can be placed under the control of a tissue-specific promoter that is not active in the packaging cells. Any tissue specific promoter described herein for expression of the engineered meganuclease or for a nucleic acid sequence of interest can be used. For example, if a recombinant virus is developed for delivery of genes encoding an engineered meganuclease to liver tissue, a liver-specific promoter can be used. Examples of liver-specific promoters include, without limitation, those liver-specific promoters described elsewhere herein.

Alternatively, the recombinant virus can be packaged in cells from a different species in which the meganuclease is not likely to be expressed. For example, viral particles can be produced in microbial, insect, or plant cells using mammalian promoters, such as the well-known cytomegalovirus—or SV40 virus-early promoters, which are not active in the non-mammalian packaging cells. In a particular embodiment, viral particles are produced in insect cells using the baculovirus system as described by Gao, et al. (Gao et al. (2007), J. Biotechnol. 131(2):138-43). A meganuclease under the control of a mammalian promoter is unlikely to be expressed in these cells (Airenne et al. (2013), Mol. Ther. 21(4):739-49). Moreover, insect cells utilize different mRNA splicing motifs than mammalian cells. Thus, it is possible to incorporate a mammalian intron, such as the human growth hormone (HGH) intron or the SV40 large T antigen intron, into the coding sequence of a meganuclease. Because these introns are not spliced efficiently from pre-mRNA transcripts in insect cells, insect cells will not express a functional meganuclease and will package the full-length genome. In contrast, mammalian cells to which the resulting recombinant AAV particles are delivered will properly splice the pre-mRNA and will express functional meganuclease protein. Haifeng Chen has reported the use of the HGH and SV40 large T antigen introns to attenuate expression of the toxic proteins barnase and diphtheria toxin fragment A in insect packaging cells, enabling the production of recombinant AAV vectors carrying these toxin genes (Chen, H (2012) Mol Ther Nucleic Acids. 1(11): e57).

The engineered meganuclease gene can be operably linked to an inducible promoter such that a small-molecule inducer is required for meganuclease expression. Examples of inducible promoters include the Tet-On system (Clontech; Chen et al. (2015), BMC Biotechnol. 15(1):4)) and the RheoSwitch system (Intrexon; Sowa et al. (2011), Spine, 36(10): E623-8). Both systems, as well as similar systems known in the art, rely on ligand-inducible transcription factors (variants of the Tet Repressor and Ecdysone receptor, respectively) that activate transcription in response to a small-molecule activator (Doxycycline or Ecdysone, respectively). Practicing the current invention using such ligand-inducible transcription activators includes: 1) placing the engineered meganuclease gene under the control of a promoter that responds to the corresponding transcription factor, the meganuclease gene having (a) binding site(s) for the transcription factor; and 2) including the gene encoding the transcription factor in the packaged viral genome The latter step is necessary because the engineered meganuclease will not be expressed in the target cells or tissues following recombinant AAV delivery if the transcription activator is not also provided to the same cells. The transcription activator then induces meganuclease gene expression only in cells or tissues that are treated with the cognate small-molecule activator. This approach is advantageous because it enables meganuclease gene expression to be regulated in a spatio-temporal manner by selecting when and to which tissues the small-molecule inducer is delivered. However, the requirement to include the inducer in the viral genome, which has significantly limited carrying capacity, creates a drawback to this approach.

In another particular embodiment, recombinant AAV particles are produced in a mammalian cell line that expresses a transcription repressor that prevents expression of the meganuclease. Transcription repressors are known in the art and include the Tet-Repressor, the Lac-Repressor, the Cro repressor, and the Lambda-repressor. Many nuclear hormone receptors such as the ecdysone receptor also act as transcription repressors in the absence of their cognate hormone ligand. To practice the current invention, packaging cells are transfected/transduced with a vector encoding a transcription repressor and the meganuclease gene in the viral genome (packaging vector) is operably linked to a promoter that is modified to comprise binding sites for the repressor such that the repressor silences the promoter. The gene encoding the transcription repressor can be placed in a variety of positions. It can be encoded on a separate vector; it can be incorporated into the packaging vector outside of the ITR sequences; it can be incorporated into the cap/rep vector or the adenoviral helper vector; or it can be stably integrated into the genome of the packaging cell such that it is expressed constitutively. Methods to modify common mammalian promoters to incorporate transcription repressor sites are known in the art. For example, Chang and Roninson modified the strong, constitutive CMV and RSV promoters to comprise operators for the Lac repressor and showed that gene expression from the modified promoters was greatly attenuated in cells expressing the repressor (Chang and Roninson (1996), Gene 183:137-42). The use of a non-human transcription repressor ensures that transcription of the meganuclease gene will be repressed only in the packaging cells expressing the repressor and not in target cells or tissues transduced with the resulting recombinant AAV.

2.6 Engineered Meganuclease Variants

Embodiments of the invention encompass the engineered meganucleases described herein, and variants thereof. Further embodiments of the invention encompass polynucleotides comprising a nucleic acid sequence encoding the meganucleases described herein, and variants of such polynucleotides.

As used herein, "variants" is intended to mean substantially similar sequences. A "variant" polypeptide is intended to mean a polypeptide derived from the "native" polypeptide by deletion or addition of one or more amino acids at one or more internal sites in the native protein and/or substitution of one or more amino acids at one or more sites in the native polypeptide. As used herein, a "native" polynucleotide or polypeptide comprises a parental sequence from which variants are derived. Variant polypeptides encompassed by the embodiments are biologically active. That is, they continue to possess the desired biological activity of the native protein; i.e., the ability to recognize and cleave the HBV 11-12 recognition sequence (SEQ ID NO: 10) within the genome of a Hepatitis B virus, and in some embodiments, exhibit at least one improved property over previously described engineered HBV meganucleases (e.g., the HBV 11-12x.26 or HBV 11-12L.363 meganuclease), such as improved (i.e., increased) specificity and enhanced (i.e., increased) efficiency of cleavage and indel formation. Such variants may result, for example, from human manipulation. Biologically active variants of a native polypeptide of the embodiments (e.g., SEQ ID NOs: 12, 13, 14, 15, 16, and 17), or biologically active variants of the recognition half-site binding subunits described herein, will have at least about 40%, about 45%, about 50%, about 55%, about 60%, about 65%, about 70%, about 75%, about 80%, about 85%, about 90%, about 91%, about 92%, about 93%, about 94%, about 95%, about 96%, about 97%, about 98%, or about 99%, sequence identity to the amino acid sequence of the native polypeptide, native subunit, native HVR1 region, and/or native HVR2 region, as determined by sequence alignment programs and parameters described elsewhere herein. A biologically active variant of a polypeptide or subunit of the embodiments may differ from that polypeptide or subunit by as few as about 1-40 amino acid residues, as few as about 1-20, as few as about 1-10, as few as about 5, as few as 4, 3, 2, or even 1 amino acid residue.

The polypeptides of the embodiments may be altered in various ways including amino acid substitutions, deletions, truncations, and insertions. Methods for such manipulations are generally known in the art. For example, amino acid sequence variants can be prepared by mutations in the DNA. Methods for mutagenesis and polynucleotide alterations are well known in the art. See, for example, Kunkel (1985) Proc. Natl. Acad. Sci. USA 82:488-492; Kunkel et al. (1987) Methods in Enzymol. 154:367-382; U.S. Pat. No. 4,873,192; Walker and Gaastra, eds. (1983) Techniques in Molecular Biology (MacMillan Publishing Company, New York) and the references cited therein. Guidance as to appropriate amino acid substitutions that do not affect biological activity of the protein of interest may be found in the model of Dayhoff et al. (1978) Atlas of Protein Sequence and Structure (Natl. Biomed. Res. Found., Washington, D.C.), herein incorporated by reference. Conservative substitutions, such as exchanging one amino acid with another having similar properties, may be optimal.

In some embodiments, engineered meganucleases of the invention can comprise variants of the HVR1 and HVR2 regions described herein. Parental HVR regions can comprise, for example, residues 24-79 or residues 215-270 of the exemplified engineered meganucleases. Thus, variant HVRs can comprise an amino acid sequence having at least 80%, at least 85%, at least 90%, at least 91%, at least 92%, at least 93%, at least 94%, at least 95%, at least 96%, at least 97%, at least 98%, at least 99% or more, sequence identity to an amino acid sequence corresponding to residues 24-79 or residues 215-270 of the engineered meganucleases exemplified herein, such that the variant HVR regions maintain the biological activity of the engineered meganuclease (i.e., binding to and cleaving the recognition sequence). Further, in some embodiments of the invention, a variant HVR1 region or variant HVR2 region can comprise residues corresponding to the amino acid residues found at specific positions within the parental HVR. In this context, "corresponding to" means that an amino acid residue in the variant HVR is the same amino acid residue (i.e., a separate identical residue) present in the parental HVR sequence in the same relative position (i.e., in relation to the remaining amino acids in the parent sequence). By way of example, if a parental HVR sequence comprises a serine residue at position 26, a variant HVR that "comprises a residue corresponding to" residue 26 will also comprise a serine at a position that is relative (i.e., corresponding) to parental position 26.

In particular embodiments, engineered meganucleases of the invention comprise an HVR1 that has at least at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or more sequence identity to an amino acid sequence corresponding to residues 215-270 of SEQ ID NO: 12, 13, 14, 15, 16, or 17.

In certain embodiments, engineered meganucleases of the invention comprise an HVR2 region that has at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to an amino acid sequence corresponding to residues 24-79 of SEQ ID NO: 12, 13, 14, 15, 16, or 17.

In other particular embodiments, engineered meganucleases of the invention comprise an HVR1 region that has at least 92% sequence identity to an amino acid sequence corresponding to residues 215-270 of SEQ ID NO: 12, 13, 14, 15, 16 or 17 and an HVR2 region that has at least 93% sequence identity to an amino acid sequence corresponding to residues 24-79 of SEQ ID NO: 12, 13, 14, 15, 16, or 17.

A substantial number of amino acid modifications to the DNA recognition domain of the wild-type I-CreI meganuclease have previously been identified (e.g., U.S. Pat. No. 8,021,867) which, singly or in combination, result in engineered meganucleases with specificities altered at individual bases within the DNA recognition sequence half-site, such that the resulting rationally-designed meganucleases have half-site specificities different from the wild-type enzyme. Table 3 provides potential substitutions that can be made in an engineered meganuclease monomer or subunit to enhance specificity based on the base present at each half-site position (−1 through −9) of a recognition half-site.

TABLE 3

| Posn. | A | C | G | T | A/T | A/C | A/G | C/T | G/T | A/G/T | A/C/G/T |
|---|---|---|---|---|---|---|---|---|---|---|---|
| −1 | Y75 | R70* | K70 | Q70* | | | | T46* | | | G70 |
| | L75* | H75* | E70* | C70 | | | | | | | A70 |
| | C75* | R75* | E75* | L70 | | | | | | | S70 |
| | Y139* | H46* | E46* | Y75* | | | | | | | G46* |
| | C46* | K46* | D46* | Q75* | | | | | | | |
| | A46* | R46* | | H75* | | | | | | | |
| | | | | H139 | | | | | | | |
| | | | | Q46* | | | | | | | |
| | | | | H46* | | | | | | | |
| −2 | Q70 | E70 | H70 | Q44* | C44* | | | | | | |
| | T44* | D70 | D44* | | | | | | | | |
| | A44* | K44* | E44* | | | | | | | | |
| | V44* | R44* | | | | | | | | | |
| | I44* | | | | | | | | | | |
| | L44* | | | | | | | | | | |
| | N44* | | | | | | | | | | |
| −3 | Q68 | E68 | R68 | M68 | | H68 | | Y68 | K68 | | |
| | C24* | F68 | | C68 | | | | | | | |
| | I24* | K24* | | L68 | | | | | | | |
| | | R24* | | F68 | | | | | | | |
| −4 | A26* | E77 | R77 | | | | | S77 | | | S26* |
| | Q77 | K26* | E26* | | | | | Q26* | | | |
| −5 | | E42 | R42 | | | K28* | C28* | | | | M66 |
| | | | | | | | Q42 | | | | K66 |
| −6 | Q40 | E40 | R40 | C40 | A40 | | | | | | S40 |
| | C28* | R28* | | I40 | A79 | | | | | | S28* |
| | | | | V40 | A28* | | | | | | |
| | | | | C79 | H28* | | | | | | |
| | | | | I79 | | | | | | | |
| | | | | V79 | | | | | | | |
| | | | | Q28* | | | | | | | |
| −7 | N30* | E38 | K38 | I38 | | | C38 | | | | H38 |
| | Q38 | K30* | R38 | L38 | | | | | | | N38 |
| | | R30* | E30* | | | | | | | | Q30* |
| −8 | F33 | E33 | F33 | L33 | | R32* | R33 | | | | |
| | Y33 | D33 | H33 | V33 | | | | | | | |
| | | | | I33 | | | | | | | |
| | | | | F33 | | | | | | | |
| | | | | C33 | | | | | | | |
| −9 | | E32 | R32 | L32 | | | | D32 | | | S32 |
| | | | K32 | V32 | | | | I32 | | | N32 |
| | | | | A32 | | | | | | | H32 |
| | | | | C32 | | | | | | | Q32 |
| | | | | | | | | | | | T32 |

Bold entries are wild-type contact residues and do not constitute "modifications" as used herein. An asterisk indicates that the residue contacts the base on the antisense strand.

Certain modifications can be made in an engineered meganuclease monomer or subunit to modulate DNA-binding affinity and/or activity. For example, an engineered meganuclease monomer or subunit described herein can comprise a G, S, or A at a residue corresponding to position 19 of I-CreI or position 210 of SEQ ID NO: 12, 13, 14, 15, 16, or 17 (WO 2009/001159), a Y, R, K, or D at a residue corresponding to position 66 of I-CreI or position 257 of SEQ ID NO: 12, 13, 14, 15, 16, or 17, and/or an E, Q, or K at a residue corresponding to position 80 of I-CreI or position 271 of SEQ ID NO: 12, 13, 14, 15, 16, or 17 (U.S. Pat. No. 8,021,867).

For polynucleotides, a "variant" comprises a deletion and/or addition of one or more nucleotides at one or more sites within the native polynucleotide. One of skill in the art will recognize that variants of the nucleic acids of the embodiments will be constructed such that the open reading frame is maintained. For polynucleotides, conservative variants include those sequences that, because of the degeneracy of the genetic code, encode the amino acid sequence of one of the polypeptides of the embodiments. Variant polynucleotides include synthetically derived polynucleotides, such as those generated, for example, by using site-directed mutagenesis but which still encode a recombinant nuclease of the embodiments. Generally, variants of a particular polynucleotide of the embodiments will have at least about 40%, about 45%, about 50%, about 55%, about 60%, about 65%, about 70%, about 75%, about 80%, about 85%, about 90%, about 91%, about 92%, about 93%, about 94%, about 95%, about 96%, about 97%, about 98%, about 99% or more sequence identity to that particular polynucleotide as determined by sequence alignment programs and parameters described elsewhere herein. Variants of a particular polynucleotide of the embodiments (i.e., the reference polynucleotide) can also be evaluated by comparison of the percent sequence identity between the polypeptide encoded by a variant polynucleotide and the polypeptide encoded by the reference polynucleotide.

The deletions, insertions, and substitutions of the protein sequences encompassed herein are not expected to produce radical changes in the characteristics of the polypeptide. However, when it is difficult to predict the exact effect of the substitution, deletion, or insertion in advance of doing so, one skilled in the art will appreciate that the effect will be evaluated by screening the polypeptide its intended activity. For example, variants of an engineered meganuclease would be screened for their ability to preferentially bind and cleave the HBV 11-12 recognition sequence within the genome of a Hepatitis B virus.

2.7 Combination Therapy for HBV

In certain embodiments, a method for treating or preventing an HBV infection in a human having or at risk of having the infection is provided, comprising administering to the human a therapeutically effective amount of an engineered meganuclease described herein, or a nucleic acid encoding the same, in combination with a therapeutically effective amount of one or more (e.g., agents are combined or co-administered with one, two, three, four, one or two, one to three, or one to four) additional therapeutic agents. In one embodiment, a method for treating an HBV infection in a human having or at risk of having the infection is provided, comprising administering to the human a therapeutically effective amount of an engineered meganuclease described herein, or a nucleic acid encoding the same, in combination with a therapeutically effective amount of one or more (e.g., one, two, three, four, one or two, one to three, or one to four) additional therapeutic agents.

In certain embodiments, the present disclosure provides a method for treating an HBV infection, comprising administering to a patient in need thereof a therapeutically effective amount of an engineered meganuclease described herein, or a nucleic acid encoding the same, in combination with a therapeutically effective amount of one or more (e.g., one, two, three, four, one or two, one to three, or one to four) additional therapeutic agents which are suitable for treating an HBV infection.

In certain embodiments, an engineered meganuclease described herein, or a nucleic acid encoding the same, is combined with one, two, three, four, or more additional therapeutic agents. In certain embodiments, an engineered meganuclease described herein, or a nucleic acid encoding the same, is combined with two additional therapeutic agents. In other embodiments, an engineered meganuclease described herein, or a nucleic acid encoding the same, is combined with three additional therapeutic agents. In further embodiments, an engineered meganuclease described herein, or a nucleic acid encoding the same, is combined with four additional therapeutic agents. The one, two, three, four, or more additional therapeutic agents can be different therapeutic agents selected from the same class of therapeutic agents, and/or they can be selected from different classes of therapeutic agents.

Administration of HBV Combination Therapy

In certain embodiments, when an engineered meganuclease described herein, or a nucleic acid encoding the same, is combined with one or more additional therapeutic agents as described above, the components of the composition are administered as a simultaneous or sequential regimen. When administered sequentially, the combination may be administered in two or more administrations.

Co-administration of an engineered meganuclease described herein, or a nucleic acid encoding the same, with one or more additional therapeutic agents generally refers to simultaneous or sequential administration of an engineered meganuclease described herein, or a nucleic acid encoding the same, and one or more additional therapeutic agents, such that therapeutically effective amounts of each agent are present in the body of the patient.

Co-administration includes administration of unit dosages of the compounds described herein before or after administration of unit dosages of one or more additional therapeutic agents. The engineered meganuclease described herein, or a nucleic acid encoding the same, may be administered within seconds, minutes, or hours of the administration of one or more additional therapeutic agents. For example, in some embodiments, a unit dose of an engineered meganuclease described herein, or a nucleic acid encoding the same, is administered first, followed within seconds or minutes by administration of a unit dose of one or more additional therapeutic agents. Alternatively, in other embodiments, a unit dose of one or more additional therapeutic agents is administered first, followed by administration of a unit dose of an engineered meganuclease described herein, or a nucleic acid encoding the same, within seconds or minutes. In some embodiments, a unit dose of an engineered meganuclease described herein, or a nucleic acid encoding the same, is administered first, followed, after a period of hours (e.g., 1-12 hours), by administration of a unit dose of one or more additional therapeutic agents. In other embodiments, a unit dose of one or more additional therapeutic agents is administered first, followed, after a period of hours (e.g., 1-12 hours), by administration of a unit dose of an engineered meganuclease described herein, or a nucleic acid encoding the same.

In certain embodiments, an engineered meganuclease described herein, or a nucleic acid encoding the same, is combined with one or more additional therapeutic agents in a unitary dosage form for simultaneous administration to a patient.

HBV Combination Therapy

The engineered meganucleases described herein, or nucleic acids encoding the same, may be combined or co-administered with one, two, three, four or more additional therapeutic agents selected from HBV combination drugs, HBV vaccines, HBV DNA polymerase inhibitors, immunomodulators, toll-like receptor (TLR) modulators, interferon alpha receptor ligands, hyaluronidase inhibitors, HBV antigen inhibitors (e.g., HBV core antigen (HBcAg) inhibitors, HBV surface antigen (HBsAg) inhibitors, HBx inhibitors, HBV E antigen inhibitors), anti-HBV antigen antibodies, inhibitory nucleic acids targeting HBV (e.g., antisense oligonucleotide, short interfering RNA (siRNA), DNA-directed RNA interference (ddRNAi)), HBsAg secretion or assembly inhibitors, HBV viral entry inhibitors, immune checkpoint inhibitor, cytotoxic T-lymphocyte-associated protein 4 (CTLA4) inhibitors, cyclophilin inhibitors, endonuclease modulators, ribonucleotide reductase inhibitors, covalently closed circular DNA (cccDNA) inhibitors, farnesoid X receptor (FXR) agonists, STING agonists, anti-HBV antibodies, CCR2 chemokine antagonists, thymosin agonists, cytokines, nucleoprotein modulators, retinoic acid-inducible gene 1 stimulators, NOD2 stimulators, phosphatidylinositol 3-kinase (PI3K) inhibitors, indoleamine-2, 3-dioxygenase (IDO) pathway inhibitors, PD-1 inhibitors, PD-L1 inhibitors, recombinant thymosin alpha-1, Bruton's tyrosine kinase (BTK) inhibitors, KDM inhibitors, HBV replication inhibitors, arginase inhibitors, gene therapy and cell therapy, gene editors, cellular therapy, TCR-T cell therapy, and other HBV drugs.

In certain embodiments, the engineered meganucleases described herein, or nucleic acids encoding the same, may be used or combined with one or more of a chemotherapeutic agent, an immunomodulator, an immunotherapeutic agent, a therapeutic antibody, a therapeutic vaccine, a bispecific antibody and "antibody-like" therapeutic protein (such as DARPins®, anti-pMHC TCR-like antibodies, DARTs®, Duobodies®, Bites®, XmAbs®, TandAbs®, Fab derivatives), an antibody-drug conjugate (ADC), gene modifiers or gene editors targeting HBV (e.g., CRISPR-Cas (e.g., Cas9, Cas12, Cascade, Cas13), zinc finger nucleases, homing endonucleases (e.g., engineered I-CreI variant meganucleases), synthetic nucleases, TALENs, cell therapies (e.g., T-cells, NK cells, macrophages having a chimeric antigen receptor (CAR)), and TCR-T (an engineered T cell receptor) or any combination thereof.

In some embodiments, an engineered meganuclease described herein is combined with one or more additional engineered nucleases, which bind and cleave a second recognition sequence other than the HBV 11-12 recognition sequence in the HBV genome. For example, one, two, three or more additional engineered nucleases (e.g., one, two, three or more engineered meganucleases) that bind and cleave a recognition sequence other than HBV 11-12 may be combined with the engineered meganucleases according to the invention (e.g., SEQ ID NOs: 12, 13, 14, 15, 16 or 17). The one or more additional engineered nucleases may bind and cleave a recognition sequence found in any location within the HBV genome including one or more HBV gene coding sequences or non-coding sequences. For example, the one or more additional engineered nucleases may bind and cleave a recognition sequence within a HBV genomic sequence including but not limited to, gene S, which encodes the major hepatitis B surface antigen (HBsAg) protein; sequences upstream from gene S, which encode the pre-S domain; gene C, which encodes the hepatitis B core antigen (HBcAg); the P region, which encodes the viral reverse transcriptase; gene X, which encodes the HBx viral protein; and within a pre-core region, which encodes the HBeAg gene. In some embodiments, the one or more additional engineered nucleases bind and cleave a recognition sequence described in PCT/US2017/056638. In some embodiments, the one or more additional nucleases are engineered I-CreI derived meganucleases, such as those described in PCT/US2017/056638 or a variant of the engineered meganucleases described therein, wherein the one or more additional engineered meganucleases bind and cleave a recognition sequence other than HBV 11-12 (SEQ ID NO: 10). Accordingly, in some embodiments, the one or more additional engineered nucleases are engineered I-CreI derived meganucleases, which binds and cleaves a recognition sequence comprising SEQ ID NOs: 30, 41, or 43.

In certain embodiments, an engineered meganuclease described herein, or a nucleic acid encoding the same, are optionally combined or co-administered with one, two, three, four, or more additional therapeutic agents, e.g., 3-dioxygenase (IDO) inhibitors, apolipoprotein A1 modulator, arginase inhibitors, B—and T-lymphocyte attenuator inhibitors, Bruton's tyrosine kinase (BTK) inhibitors, CCR2 chemokine antagonist, CD137 inhibitors, CD160 inhibitors, CD305 inhibitors, CD4 agonist and modulator, compounds targeting hepatitis B core antigen (HBcAg), core protein allosteric modulators, covalently closed circular DNA (cccDNA) inhibitors, cyclophilin inhibitors, cytotoxic T-lymphocyte-associated protein 4 (CTLA4) inhibitors, DNA polymerase inhibitor, endonuclease modulators, epigenetic modifiers, farnesoid X receptor (FXR) agonists, HBV DNA polymerase inhibitors, HBV replication inhibitors, HBV RNAse inhibitors, HBV viral entry inhibitors, HBx inhibitors, Hepatitis B large envelope protein modulator, Hepatitis B large envelope protein stimulator, Hepatitis B structural protein modulator, hepatitis B surface antigen (HBsAg) inhibitors, hepatitis B surface antigen (HBsAg) secretion or assembly inhibitors, hepatitis B virus E antigen inhibitors, hepatitis B virus replication inhibitors, Hepatitis virus structural protein inhibitor, HIV-1 reverse transcriptase inhibitor, Hyaluronidase inhibitor, inhibitor of apoptosis proteins family proteins (IAPs) inhibitors, IL-2 agonist, IL-7 agonist, immunomodulators, indoleamine-2 inhibitors, inhibitors of ribonucleotide reductase, Interleukin-2 ligand, ipi4 inhibitors, lysine demethylase inhibitors, histone demethylase inhibitors, KDM1 inhibitors, KDM5 inhibitors, killer cell lectin-like receptor subfamily G member 1 inhibitors, lymphocyte-activation gene 3 inhibitors, lymphotoxin beta receptor activators, modulators of Axl, modulators of B7-H3, modulators of B7-H4, modulators of CD160, modulators of CD161, modulators of CD27, modulators of CD47, modulators of CD70, modulators of GITR, modulators of HEVEM, modulators of ICOS, modulators of Mer, modulators of NKG2A, modulators of NKG2D, modulators of OX40, modulators of SIRPalpha, modulators of TIGIT, modulators of Tim-4, modulators of Tyro, Na+-taurocholate cotransporting polypeptide (NTCP) inhibitors, natural killer cell receptor 2B4 inhibitors, NOD2 gene stimulator, Nucleoprotein inhibitor, nucleoprotein modulators, OX-40 receptor agonist, PD-1 inhibitors, PD-L1 inhibitors, peptidylprolyl isomerase inhibitor, phosphatidylinositol-3 kinase (PI3K) inhibitors, Retinoic acid-inducible gene 1 stimulator, Reverse transcriptase inhibitor, Ribonuclease inhibitor, RNA DNA polymerase inhibitor, SLC10A1 gene inhibitor, SMAC mimetics, Src tyrosine kinase inhibitor, stimulator of interferon gene (STING) agonists, stimulators of NOD1, T cell surface glycoprotein CD28 inhibitor, T-cell surface glycoprotein CD8 modulator, Thymosin agonist, Thymosin alpha 1 ligand, Tim-3 inhibitors, TLR-3 agonists, TLR-7 agonists, TLR-9 agonists, TLR9 gene stimulator, toll-like receptor (TLR) modulators, viral ribonucleotide reductase inhibitor, and combinations thereof.

HBV Inhibiting Antiviral Drugs

In various embodiments, an engineered meganuclease described herein, or a nucleic acid encoding the same, are combined or co-administered with one or more antiviral agents. In some embodiments, the one or more antiviral agents are selected from the group consisting of lamivudine (LAM), adefovir dipivoxil (ADV), entecavir (ETV), telbivudine (LdT), tenofovir disoproxil fumarate (TDF), tenofovir disoproxil fumarate and emtricitabine (TRUVADA®), tenofovir alafenamide (TAF or VEMLIDY®) and ledipasvir and sofosbuvir (HARVONI®). In certain embodiments, the engineered meganuclease, or nucleic acid encoding the same are combined with long acting forms of anti-HBV drugs. Illustrative long acting forms of anti-HBV drugs that can be combined include entecavir (subcutaneous depot), long acting tenofovir (TFD and TAF) implants (devices) or subcutaneous depot. An example of long acting entecavir is described in Henry, et al., Eur J Pharm Sci. 2019 Aug. 1; 136:104958.

Other HBV Drugs

Examples of other drugs for the treatment of HBV include alpha-hydroxytropolones, amdoxovir, antroquinonol, beta-hydroxycytosine nucleosides, ARB-199, CCC-0975, ccc-R08, elvucitabine, ezetimibe, cyclosporin A, gentiopicrin (gentiopicroside), HH-003, hepalatide, JNJ-56136379, nitazoxanide, birinapant, NJK14047, NOV-205 (molixan, BAM-205), oligotide, mivotilate, feron, GST-HG-131, levamisole, Ka Shu Ning, alloferon, WS-007, Y-101 (Ti Fen Tai), rSIFN-co, PEG-IIFNm, KW-3, BP-Inter-014, oleanolic acid, HepB-nRNA, cTP-5 (rTP-5), HSK-II-2, HEISCO-106-1, HEISCO-106, Hepbarna, IB PB-0061A, Hepuyinfen, DasKloster 0014-01, ISA-204, Jiangantai (Ganxikang), MIV-210, OB-AI-004, PF-06, picroside, DasKloster-0039, hepulantai, IMB-2613, TCM-800B, reduced glutathione, RO-6864018, RG-7834, QL-007, sofosbuvir, ledipasvir, UB-551, and ZH-2N, and the compounds disclosed in US20150210682, (Roche), US 2016/0122344 (Roche), WO2015173164, WO2016023877, US2015252057A (Roche), WO16128335A1 (Roche), WO16120186A1 (Roche), US2016237090A (Roche), WO16107833A1 (Roche), WO16107832A1 (Roche), US2016176899A (Roche), WO16102438A1 (Roche), WO16012470A1 (Roche), US2016220586A (Roche), and US2015031687A (Roche).

HBV Vaccines

HBV vaccines include both prophylactic and therapeutic vaccines. Examples of HBV prophylactic vaccines include Vaxelis, Hexaxim, Heplisav, Mosquirix, DTwP-HBV vaccine, Bio-Hep-B, D/T/P/HBV/M (LBVP-0101; LBVW-0101), DTwP-Hepb-Hib-IPV vaccine, Heberpenta L, DTwP-HepB-Hib, V-419, CVI—HBV-001, Tetrabhay, hepatitis B prophylactic vaccine (Advax Super D), Hepatrol-07, GSK-223192A, ENGERIX B®, recombinant hepatitis B vaccine (intramuscular, Kangtai Biological Products), recombinant hepatitis B vaccine (*Hansenual polymorpha* yeast, intramuscular, Hualan Biological Engineering), recombinant hepatitis B surface antigen vaccine, Bimmugen, CARG-101, Euforavac, Eutravac, anrix-DTaP-IPV-Hep B, HBAI-20, Infanrix-DTaP-IPV-Hep B-Hib, Pentabio Vaksin DTP-HB-Hib, Comvac 4, Twinrix, Euvax-B, Tritanrix HB, Infanrix Hep B, Comvax, DTP-Hib-HBV vaccine, DTP-HBV vaccine, Yi Tai, Heberbiovac HB, Trivac HB, GerVax, DTwP-Hep B-Hib vaccine, Bilive, Hepavax-Gene, SUPERVAX, Comvac5, Shanvac-B, Hebsulin, Recombivax HB, Revac B mcf, Revac B+, Fendrix, DTwP-HepB-Hib, DNA-001, Shan5, Shan6, rhHBsAG vaccine, HBI pentavalent vaccine, LBVD, Infanrix HeXa, YS-HBV-001, and DTaP-rHB-Hib vaccine.

Examples of HBV therapeutic vaccines include HBsAG-HBIG complex, ARB-1598, Bio-Hep-B, NASVAC, abi-HB (intravenous), ABX-203, Tetrabhay, GX-110E, GS-4774, peptide vaccine (epsilonPA-44), Hepatrol-07, NASVAC (NASTERAP), IMP-321, BEVAC, Revac B mcf, Revac B+, MGN-1333, KW-2, CVI—HBV-002, AltraHepB, VGX-6200, FP-02, FP-02.2 (HepTcell), NU-500, HBVax, im/Tri-Grid/antigen vaccine, Mega-CD40L-adjuvanted vaccine, HepB-v, RG7944 (INO-1800), recombinant VLP-based therapeutic vaccine (HBV infection, VLP Biotech), AdTG-17909, AdTG-17910 AdTG-18202, ChronVac-B, TG-1050, VVX-001, GSK-3528869A (ChAd155-hli-HBV+MVA-HBV+Hbc-HBs/AS01B-4), VBI-2601, VTP-300 (ChAdOx1-SIi-HBV-CPmut-TPA-Ssh prime and MVA-SIi-HBV-CPmut-TPA-Ssh boost), MVA-BN, and Lm HBV. HBV arenavirus vaccines are described, e.g., in WO2017076988 and WO2017198726.

HBV DNA Polymerase Inhibitors

Examples of HBV DNA polymerase inhibitors include adefovir (HEPSERA®), emtricitabine (EMTRIVA®), tenofovir disoproxil fumarate (VIREAD®), tenofovir alafenamide, tenofovir, tenofovir disoproxil, tenofovir alafenamide fumarate, tenofovir alafenamide hemifumarate, tenofovir dipivoxil, tenofovir dipivoxil fumarate, tenofovir octadecyloxyethyl ester, CMX-157, tenofovir exalidex, besifovir, entecavir (BARACLUDE®), entecavir maleate, telbivudine (TYZEKA®), filocilovir, pradefovir, clevudine, ribavirin, lamivudine (EPIVIR-HBV®), phosphazide, famciclovir, fusolin, metacavir, SNC-019754, FMCA, AGX-1009, AR-II-04-26, HIP-1302, tenofovir disoproxil aspartate, tenofovir disoproxil orotate, and HS-10234.

Immunomodulators

Examples of immunomodulators include rintatolimod, imidol hydrochloride, ingaron, dermaVir, plaquenil (hydroxychloroquine), proleukin, hydroxyurea, mycophenolate mofetil (MPA) and its ester derivative mycophenolate mofetil (MMF), JNJ-440,WF-10, AB-452, ribavirin, IL-12, INO-9112, polymer polyethyleneimine (PEI), Gepon, VGV-1, MOR-22, CRV-431, JNJ-0535, TG-1050, ABI-H2158, BMS-936559, GS-9688, RO-7011785, RG-7854, RO-6871765, AIC-649, and IR-103.

Toll-Like Receptor (TLR) Agonists

In various embodiments, an engineered meganuclease described herein, or a nucleic acid encoding the same, is combined with an agonist of a toll-like receptor (TLR), e.g., an agonist of TLR1 (NCBI Gene ID: 7096), TLR2 (NCBI Gene ID: 7097), TLR3 (NCBI Gene ID: 7098), TLR4 (NCBI Gene ID: 7099), TLRS (NCBI Gene ID: 7100), TLR6 (NCBI Gene ID: 10333), TLR7 (NCBI Gene ID: 51284), TLR8 (NCBI Gene ID: 51311), TLR9 (NCBI Gene ID: 54106), and/or TLR10 (NCBI Gene ID: 81793), TLR11, TLR12 and TLR13. Examples of TLR3 modulators include rintatolimod, poly-ICLC, RIBOXXON®, Apoxxim, RIBOXXIM®, IPH-33, MCT-465, MCT-475 and ND-1.1.

Example TLR7 agonists that can be co-administered include without limitationAL-034, DSP-0509, GS-9620 (vesatolimod), LHC-165, TMX-101 (imiquimod), GSK-2245035, resiquimod, DSR-6434, DSP-3025, IMO-4200, MCT-465, MEDI-9197, 3M-051, SB-9922, 3M-052, Limtop, TMX-30X, TMX-202, RG-7863, RG-7854, RG-7795, and the compounds disclosed in US20100143301 (Gilead Sciences), US20110098248 (Gilead Sciences), and US20090047249 (Gilead Sciences), US20140045849 (Janssen), US20140073642 (Janssen), WO2014/056953 (Janssen), WO2014/076221 (Janssen), WO2014/128189 (Janssen), US20140350031 (Janssen), WO2014/023813 (Janssen), US20080234251 (Array Biopharma), US20080306050 (Array Biopharma), US20100029585 (Ventirx Pharma), US20110092485 (Ventirx Pharma), US20110118235 (Ventirx Pharma), US20120082658 (Ventirx Pharma), US20120219615 (Ventirx Pharma), US20140066432 (Ventirx Pharma), US20140088085 (Ventirx Pharma), US20140275167 (Novira Therapeutics), and US20130251673 (Novira Therapeutics).

An TLR7/TLR8 agonist that can be co-administered is NKTR-262, telratolimod and BDB-001.

Example TLR8 agonists that can be co-administered include without limitation E-6887, IMO-4200, IMO-8400, IMO-9200, MCT-465, MEDI-9197, motolimod, resiquimod, selgantolimod (GS-9688), VTX-1463, VTX-763, 3M-051, 3M-052, ZG-170607, and the compounds disclosed in US20140045849 (Janssen), US20140073642 (Janssen), WO2014/056953 (Janssen), WO2014/076221 (Janssen), WO2014/128189 (Janssen), US20140350031

(Janssen), WO2014/023813 (Janssen), US20080234251 (Array Biopharma), US20080306050 (Array Biopharma), US20100029585 (Ventirx Pharma), US20110092485 (Ventirx Pharma), US20110118235 (Ventirx Pharma), US20120082658 (Ventirx Pharma), US20120219615 (Ventirx Pharma), US20140066432 (Ventirx Pharma), US20140088085 (Ventirx Pharma), US20140275167 (Novira Therapeutics), and US20130251673 (Novira Therapeutics), U.S. Pat. No. 9,670,205 (Gilead Sciences, Inc.), US20160289229 (Gilead Sciences, Inc.), WO2017/048727 (Gilead Sciences, Inc.), US20180065938 (Gilead Sciences, Inc.), and US20180086755 (Gilead Sciences, Inc.).

Example TLR9 agonists that can be co-administered include without limitation AST-008, cobitolimod, CMP-001, IMO-2055, IMO-2125, IMO-3100, IMO-8400, IR-103, IMO-9200, agatolimod, DIMS-9054, DV-1079, DV-1179, AZD-1419, lefitolimod (MGN-1703), CYT-003, CYT-003-QbG10, tilsotolimod and PUL-042.

Examples of TLR7, TLR8 and TLR9 modulators include the compounds disclosed in WO2017047769 (Teika Seiyaku), WO2015014815 (Janssen), WO2018045150 (Gilead Sciences Inc), WO2018045144 (Gilead Sciences Inc), WO2015162075 (Roche), WO2017034986 (University of Kansas), WO2018095426 (Jiangsu Hengrui Medicine Co Ltd), WO2016091698 (Roche), WO2016075661 (GlaxoSmithKline Biologicals), WO2016180743 (Roche), WO2018089695 (Dynavax Technologies), WO2016055553 (Roche), WO2015168279 (Novartis), WO2016107536 (Medshine Discovery), WO2018086593 (Livo (Shanghai) Pharmaceutical), WO2017106607 (Merck), WO2017061532 (Sumitomo Dainippon Pharma), WO2016023511 (Chia Tai Tianqing Pharmaceutical), WO2017076346 (Chia Tai Tianqing Pharmaceutical), WO2017046112 (Roche), WO2018078149 (Roche), WO2017040233 (3M Co), WO2016141092 (Gilead Sciences), WO2018049089 (BristolMyers Squibb), WO2015057655 (Eisai Co Ltd), WO2017001307 (Roche), WO2018005586 (BristolMyers Squibb), WO201704023 (3M Co), WO2017163264 (Council of Scientific and Industrial Research (India)), WO2018046460 (GlaxoSmithKline Biologicals), WO2018047081 (Novartis), WO2016142250 (Roche), WO2015168269 (Novartis), WO201804163 (Roche), WO2018038877 (3M Co), WO2015057659 (Eisai Co Ltd), WO2017202704 (Roche), WO2018026620 (BristolMyers Squibb), WO2016029077 (Janus Biotherapeutics), WO201803143 (Merck), WO2016096778 (Roche), WO2017190669 (Shanghai De Novo Pharmatech), US09884866 (University of Minnesota), WO2017219931 (Sichuan KelunBiotech Biopharmaceutical), WO2018002319 (Janssen Sciences), WO2017216054 (Roche), WO2017202703 (Roche), WO2017184735 (IFM Therapeutics), WO2017184746 (IFM Therapeutics), WO2015088045 (Takeda Pharmaceutical), WO2017038909 (Takeda Pharmaceutical), WO2015095780 (University of Kansas), and WO2015023958 (University of Kansas).

In certain embodiments, an engineered meganuclease described herein, or a nucleic acid encoding the same, is co-administered with a TLR7, TLR8 or TLR9 agonist.

Interferon Alpha Receptor Ligands

Examples of interferon alpha receptor ligands include interferon alpha-2b (INTRON A®), pegylated interferon alpha-2a (PEGASYS®), PEGylated interferon alpha-lb, interferon alpha 1b (HAPGEN®), Veldona, Infradure, Roferon-A, YPEG-interferon alfa-2a (YPEG-rhIFNalpha-2a), P-1101, Algeron, Alfarona, Ingaron (interferon gamma), rSIFN-co (recombinant super compound interferon), Ypeginterferon alfa-2b (YPEG-rhIFNalpha-2b), MOR-22, peginterferon alfa-2b (PEG-INTRON®), Bioferon, Novaferon, Inmutag (Inferon), MULTIFERON®, interferon alfa-n1 (HUMOFERON®), interferon beta-1a (AVONEX®), Shaferon, interferon alfa-2b (Axxo), Alfaferone, interferon alfa-2b (BioGeneric Pharma), interferon-alpha 2 (CJ), Laferonum, VIPEG, BLAUFERON-A, BLAUFERON-B, Intermax Alpha, Realdiron, Lanstion, Pegaferon, PDferon-B PDferon-B, interferon alfa-2b (IFN, Laboratorios Bioprofarma), alfainterferona 2b, Kalferon, Pegnano, Feronsure, PegiHep, interferon alfa 2b (Zydus-Cadila), interferon alfa 2a, Optipeg A, Realfa 2B, Reliferon, interferon alfa-2b (Amega), interferon alfa-2b (Virchow), ropeginterferon alfa-2b, rHSA-IFN alpha-2a (recombinant human serum albumin intereferon alpha 2a fusion protein), PEG-IFN-alpha, rHSA-IFN alpha 2b, recombinant human interferon alpha-(1b, 2a, 2b), peginterferon alfa-2b (Amega), peginterferon alfa-2a, Reaferon-EC, Proquiferon, Uniferon, Urifron, interferon alfa-2b (Changchun Institute of Biological Products), Anterferon, Shanferon, Layfferon, Shang Sheng Lei Tai, INTEFEN, SINOGEN, Fukangtai, Pegstat, rHSA-IFN alpha-2b, SFR-9216, and Interapo (Interapa).

Hyaluronidase Inhibitors

Examples of hyaluronidase inhibitors include astodrimer.

Hepatitis B Surface Antigen (HBsAg) Inhibitors

Examples of HBsAg inhibitors include AK-074, HBF-0259, PBHBV-001, PBHBV-2-15, PBHBV-2-1, REP-9AC, REP-9C, REP-9, REP-2139, REP-2139-Ca, REP-2055, REP-2163, REP-2165, REP-2053, REP-2031, REP-006, and REP-9AC'.

Examples of HBsAg secretion inhibitors include BM601, GST-HG-131, and AB-452.

Cytotoxic T-Lymphocyte-Associated Protein 4 (ipi4) Inhibitors

Examples of Cytotoxic T-lymphocyte-associated protein 4 (ipi4) inhibitors include AGEN-2041, AGEN-1884, ipilumimab, belatacept, PSI-001, PRS-010, Probody mAbs, tremelimumab, and JHL-1155.

Cyclophilin Inhibitors

Examples of cyclophilin inhibitors include CPI-431-32, EDP-494, OCB-030, SCY-635, NVP-015, NVP-018, NVP-019, STG-175, and the compounds disclosed in U.S. Pat. No. 8,513,184 (Gilead Sciences), US20140030221 (Gilead Sciences), US20130344030 (Gilead Sciences), and US20130344029 (Gilead Sciences).

HBV Viral Entry Inhibitors

Examples of HBV viral entry inhibitors include Myrcludex B.

Antisense Oligonucleotide Targeting Viral mRNA

Examples of antisense oligonucleotide targeting viral mRNA include ISIS-HBVRx, IONIS-HBVRx, IONIS—HBV-LRx, IONIS-GSK6-LRx, GSK-3389404, and RG-6004.

Short Interfering RNAs (siRNA) and ddRNAi

Examples of siRNA include TKM-HBV (TKM-HepB), ALN-HBV, SR-008, HepB-nRNA, ARC-520, ARC-521, ARB-1740, ARB-1467, AB-729, DCR-HBVS, RG-6084 (PD-L1), RG-6217, ALN-HBV-02, JNJ-3989 (ARO-HBV), STSG-0002, ALG-010133, ALG-ASO, LUNAR-HBV and DCR-HBVS (DCR-5219.

Examples of DNA-directed RNA interference (ddRNAi) include BB—HB-331.

Endonuclease Modulators

Examples of endonuclease modulators include PGN-514.

Ribonucleotide Reductase Inhibitors

Examples of inhibitors of ribonucleotide reductase include Trimidox.

Nonnucleoside Reverse Transcriptase Inhibitors

Examples of nonnucleoside reverse transcriptase inhibitors (NNRTIs) include the compounds disclosed in WO2018118826 (Merck), WO2018080903 (Merck), WO2018119013 (Merck), WO2017100108 (Idenix), WO2017027434 (Merck), WO2017007701 (Merck), and WO2008005555 (Gilead).

HBV Replication Inhibitors

Examples of hepatitis B virus replication inhibitors include GP-31502, isothiafludine, IQP-HBV, RM-5038, and Xingantie.

Covalently Closed Circular DNA (cccDNA) Inhibitors

Examples of cccDNA inhibitors include BSBI-25, ccc-R08, and CHR-101.

Farnesoid X Receptor Agonist

Examples of farnesoid x receptor agonists include, e.g., EYP-001, GS-9674, EDP-305, MET-409, Tropifexor, AKN-083, RDX-023, BWD-100, LMB-763, INV-3, NTX-023-1, EP-024297 and GS-8670.

Anti-HBV Antibodies

In various embodiments, an engineered meganuclease described herein, or a nucleic acid encoding the same, is combined or co-administered with one or more antibodies that specifically binds to an HBV antigen, including an HBV peptide presented in a major histocompatibility molecule (MHC) molecule (pMHC). Examples of HBV antibodies targeting the surface antigens of the hepatitis B virus that can be combined or co-administered include lenvervimab (GC-1102), XTL-17, XTL-19, KN-003, IV Hepabulin SN, and fully human monoclonal antibody therapy (hepatitis B virus infection, Humabs BioMed). Antibodies targeting HBV X protein (HBx) that can be combined or co-administered are described, e.g., in Kornyeyev, et al., *J Virol.* 2019 Jul. 30; 93(16). pii: e00248-19.

Examples of HBV antibodies, including monoclonal antibodies and polyclonal antibodies, that can be combined or co-administered include Zutectra, Shang Sheng Gan Di, Uman Big (Hepatitis B Hyperimmune), Omri-Hep-B, Nabi-HB, Hepatect CP, HepaGam B, igantibe, Niuliva, CT-P24, hepatitis B immunoglobulin (intravenous, pH4, HBV infection, Shanghai RAAS Blood Products), and Fovepta (BT-088).

Examples of fully human monoclonal HBV antibodies that can be combined or co-administered include HBC-34.

Antibodies against HBV viral peptide/major histocompatibility complex (MHC) class I (pMHC) complexes that can be combined or co-administered are described, e.g., in Sastry, et al., J Virol. 2011 March; 85(5):1935-42 and in WO2011062562.

CCR2 Chemokine Antagonists

Examples of CCR2 chemokine antagonists include propagermanium.

Thymosin Agonists

Examples of thymosin agonists include Thymalfasin and recombinant thymosin alpha 1 (GeneScience).

Cytokines

Examples of cytokines include recombinant IL-7, CYT-107, interleukin-2 (IL-2, Immunex), recombinant human interleukin-2 (Shenzhen Neptunus), IL-15, IL-21, IL-24, and celmoleukin.

Interleukin Agonists

In certain embodiments, an engineered meganuclease described herein, or a nucleic acid encoding the same, is combined with an interleukin agonist, such as IL-2, IL-7, IL-15, IL-10, IL-12 agonists. Examples of IL-2 agonists include proleukin (aldesleukin, IL-2); pegylated IL-2 (eg NKTR-214), modified variants of IL-2 (eg THOR-707), bempegaldesleukin, AIC-284, ALKS-4230, CUI-101, and Neo-2/15. Examples of IL-15 agonists include ALT-803, NKTR-255, hetIL-15, interleukin-15/Fc fusion protein, AM-0015, NIZ-985, SO—C101, IL-15 Synthorin (pegylated Il-15), P-22339, and a IL-15-PD-1 fusion protein N-809. Examples of IL-7 include CYT-107.

Nucleoprotein Modulators

Nucleoprotein modulators may be either HBV core or capsid protein inhibitors. Examples of nucleoprotein modulators include GS-4882, AB-423, AT-130, ALG-001075, ALG-001024, ALG-000184, EDP-514, GLS4, NVR-1221, NVR-3778, AL-3778, BAY 41-4109, morphothiadine mesilate, ARB-168786, ARB-880, ARB-1820, GST-HG-141, JNJ-379, JNJ-632, RG-7907, GST-HG-141, HEC-72702, KL-060332, AB-506, ABI-H0731, ABI-H3733, JNJ-440, ABI-H2158, CB—HBV-001, and DVR-23.

Examples of capsid inhibitors include the compounds disclosed in US20140275167 (Novira Therapeutics), US20130251673 (Novira Therapeutics), US20140343032 (Roche), WO2014037480 (Roche), US20130267517 (Roche), WO2014131847 (Janssen), WO2014033176 (Janssen), WO2014033170 (Janssen), WO2014033167 (Janssen), WO2015/059212 (Janssen), WO2015118057(Janssen), WO2015011281 (Janssen), WO2014184365 (Janssen), WO2014184350 (Janssen), WO2014161888 (Janssen), WO2013096744 (Novira), US20150225355 (Novira), US20140178337 (Novira), US20150315159 (Novira), US20150197533 (Novira), US20150274652 (Novira), US20150259324, (Novira), US20150132258 (Novira), U.S. Pat. No. 9,181,288 (Novira), WO2014184350 (Janssen), WO2013144129 (Roche), WO2017198744(Roche), US 20170334882(Novira), US 20170334898 (Roche), WO2017202798(Roche), WO2017214395(Enanta), WO2018001944 (Roche), WO2018001952(Roche), WO2018005881(Novira), WO2018005883(Novira), WO2018011100(Roche), WO2018011160(Roche), WO2018011162(Roche), WO2018011163(Roche), WO2018036941(Roche), WO2018043747(Kyoto Univ), US20180065929 (Janssen), WO2016168619 (Indiana University), WO2016195982 (The Penn State Foundation), WO2017001655 (Janssen), WO2017048950 (Assembly Biosciences), WO2017048954 (Assembly Biosciences), WO2017048962 (Assembly Biosciences), US20170121328 (Novira), US20170121329 (Novira).

Examples of transcript inhibitors include the compounds disclosed in WO2017013046 (Roche), WO2017016960 (Roche), WO2017017042 (Roche), WO2017017043 (Roche), WO2017061466 (Toyoma chemicals), WO2016177655 (Roche), WO2016161268 (Enanta). WO2017001853 (Redex Pharma), WO2017211791 (Roche), WO2017216685 (Novartis), WO2017216686 (Novartis), WO2018019297 (Ginkgo Pharma), WO2018022282 (Newave Pharma), US20180030053 (Novartis), WO2018045911 (Zhejiang Pharma).

Innate Immune Activators

In some embodiments, an engineered meganuclease described herein, or a nucleic acid encoding the same, is combined or co-administered with one or more innate immune activators. In various embodiments, the one or more innate immune activators comprises an agonist of a receptor selected from the group consisting of fms related tyrosine kinase 3 (FLT3), stimulator of interferon genes (STING) receptor, DExD/H-box helicase 58 (DDX58; a.k.a., RIG-I), nucleotide binding oligomerization domain containing 2 (NOD2). In some embodiments, the methods entail co-administering GS-3583 and/or GS-9992.

STING Agonists, RIG-I and NOD2 Modulators

In some embodiments, an engineered meganuclease described herein, or a nucleic acid encoding the same, is combined or co-administered with a stimulator of interferon response cGAMP interactor 1 (STING or STING1; NCBI Gene ID: 340061) agonist. In some embodiments, the STING/STING1 agonist or activator is selected from the group consisting of ADU-S100 (MIW-815), SB-11285, MK-1454, SR-8291, AdVCA0848, STINGVAX, GSK-532, SYN-STING, MSA-1, SR-8291, 5,6-dimethylxanthenone-4-acetic acid (DMXAA), cyclic-GAMP (cGAMP) and cyclic-di-AMP. Examples of STING agonists that can be combined or co-administered include the compounds disclosed in WO 2018065360 (Biolog Life Science Institute Forschungslabor and Biochemica-Vertrieb GmbH, Germany), WO 2018009466 (Aduro Biotech), WO 2017186711 (InvivoGen), WO 2017161349 (Immune Sensor), WO 2017106740 (Aduro Biotech), US 20170158724 (Glaxo Smithkline), WO 2017075477 (Aduro Biotech), US 20170044206 (Merck), WO 2014179760 (University of California), WO2018098203 (Janssen), WO2018118665 (Merck), WO2018118664 (Merck), WO2018100558 (Takeda), WO2018067423 (Merck), WO2018060323 (Boehringer).

In some embodiments, an engineered meganuclease described herein, or a nucleic acid sequence encoding the same, is combined or co-administered with a DExD/H-box helicase 58 (DDX58; a.k.a., retinoic acid-inducible gene 1 (RIG-I), RIG1, RIGI, RLR-1, SGMRT2; NCBI Gene ID: 23586). Illustrative RIG-I agonists that can be combined or co-administered include inarigivir soproxil (SB-9200, GS-9992), SB-40, SB-44, ORI-7246, ORI-9350, ORI-7537, ORI-9020, ORI-9198, ORI-7170, and RGT-100.

In some embodiments, an engineered meganuclease described herein, or a nucleic acid sequence encoding the same, is combined or co-administered with a nucleotide binding oligomerization domain containing 2 (NOD2; NCBI Gene ID: 64127) agonist, such as inarigivir soproxil (SB-9200, GS-9992), and IR-103.

Phosphatidylinositol 3-kinase (PI3K) Inhibitors

Examples of PI3K inhibitors include idelalisib, ACP-319, AZD-8186, AZD-8835, buparlisib, CDZ-173, CLR-457, pictilisib, neratinib, rigosertib, rigosertib sodium, EN-3342, TGR-1202, alpelisib, duvelisib, IPI-549, UCB-5857, taselisib, XL-765, gedatolisib, ME-401, VS-5584, copanlisib, CAI orotate, perifosine, RG-7666, GSK-2636771, DS-7423, panulisib, GSK-2269557, GSK-2126458, CUDC-907, PQR-309, INCB-40093, pilaralisib, BAY-1082439, puquitinib mesylate, SAR-245409, AMG-319, RP-6530, ZSTK-474, MLN-1117, SF-1126, RV-1729, sonolisib, LY-3023414, SAR-260301, TAK-117, HMPL-689, tenalisib, voxtalisib, and CLR-1401.

Immune Checkpoint Modulators

In various embodiments, an engineered meganuclease described herein, or a nucleic acid sequence encoding the same, is combined with one or more blockers or inhibitors of inhibitory immune checkpoint proteins or receptors and/or with one or more stimulators, activators or agonists of one or more stimulatory immune checkpoint proteins or receptors. Blockade or inhibition of inhibitory immune checkpoints can positively regulate T-cell or NK cell activation and prevent immune escape of infected cells. Activation or stimulation of stimulatory immune check points can augment the effect of immune checkpoint inhibitors in infective therapeutics. In various embodiments, the immune checkpoint proteins or receptors regulate T cell responses (e.g., reviewed in Xu, et al., *J Exp Clin Cancer Res.* (2018) 37:110). In various embodiments, the immune checkpoint proteins or receptors regulate NK cell responses (e.g., reviewed in Davis, et al., *Semin Immunol.* (2017) 31:64-75 and Chiossone, et al., *Nat Rev Immunol.* (2018) 18(11):671-688).

Examples of immune checkpoint proteins or receptors include without limitation CD27 (NCBI Gene ID: 939); CD70 (NCBI Gene ID: 970); CD40 (NCBI Gene ID: 958); CD40LG (NCBI Gene ID: 959); CD47 (NCBI Gene ID: 961); CD48 (SLAMF2; NCBI Gene ID: 962); transmembrane and immunoglobulin domain containing 2 (TMIGD2, CD28H; NCBI Gene ID: 126259); CD84 (LY9B, SLAMF5; NCBI Gene ID: 8832); CD96 (NCBI Gene ID: 10225); CD160 (NCBI Gene ID: 11126); MS4A1 (CD20; NCBI Gene ID: 931); CD244 (SLAMF4; NCBI Gene ID: 51744); CD276 (B7H3; NCBI Gene ID: 80381); V-set domain containing T cell activation inhibitor 1 (VTCN1, B7H4; NCBI Gene ID: 79679); V-set immunoregulatory receptor (VSIR, B7H5, VISTA; NCBI Gene ID: 64115); immunoglobulin superfamily member 11 (IGSF11, VSIG3; NCBI Gene ID: 152404); natural killer cell cytotoxicity receptor 3 ligand 1 (NCR3LG1, B7H6; NCBI Gene ID: 374383); HERV-H LTR-associating 2 (HHLA2, B7H7; NCBI Gene ID: 11148); inducible T cell co-stimulator (ICOS, CD278; NCBI Gene ID: 29851); inducible T cell co-stimulator ligand (ICOSLG, B7H2; NCBI Gene ID: 23308); TNF receptor superfamily member 4 (TNFRSF4, OX40; NCBI Gene ID: 7293); TNF superfamily member 4 (TNFSF4, OX40L; NCBI Gene ID: 7292); TNFRSF8 (CD30; NCBI Gene ID: 943); TNFSF8 (CD30L; NCBI Gene ID: 944); TNFRSF10A (CD261, DR4, TRAILR1; NCBI Gene ID: 8797); TNFRSF9 (CD137; NCBI Gene ID: 3604); TNFSF9 (CD137L; NCBI Gene ID: 8744); TNFRSF10B (CD262, DR5, TRAILR2; NCBI Gene ID: 8795); TNFRSF10 (TRAIL; NCBI Gene ID: 8743); TNFRSF14 (HVEM, CD270; NCBI Gene ID: 8764); TNFSF14 (HVEML; NCBI Gene ID: 8740); CD272 (B and T lymphocyte associated (BTLA); NCBI Gene ID: 151888); TNFRSF17 (BCMA, CD269; NCBI Gene ID: 608); TNFSF13B (BAFF; NCBI Gene ID: 10673); TNFRSF18 (GITR; NCBI Gene ID: 8784); TNFSF18 (GITRL; NCBI Gene ID: 8995); MHC class I polypeptide-related sequence A (MICA; NCBI Gene ID: 100507436); MHC class I polypeptide-related sequence B (MICB; NCBI Gene ID: 4277); CD274 (CD274, PDL1, PD-L1; NCBI Gene ID: 29126); programmed cell death 1 (PDCD1, PD1, PD-1; NCBI Gene ID: 5133); cytotoxic T-lymphocyte associated protein 4 (CTLA4, CD152; NCBI Gene ID: 1493); CD80 (B7-1; NCBI Gene ID: 941); CD28 (NCBI Gene ID: 940); nectin cell adhesion molecule 2 (NECTIN2, CD112; NCBI Gene ID: 5819); CD226 (DNAM-1; NCBI Gene ID: 10666); Poliovirus receptor (PVR) cell adhesion molecule (PVR, CD155; NCBI Gene ID: 5817); PVR related immunoglobulin domain containing (PVRIG, CD112R; NCBI Gene ID: 79037); T cell immunoreceptor with Ig and ITIM domains (TIGIT; NCBI Gene ID: 201633); T cell immunoglobulin and mucin domain containing 4 (TIMD4; TIM4; NCBI Gene ID: 91937); hepatitis A virus cellular receptor 2 (HAVCR2, TIMD3, TIM3; NCBI Gene ID: 84868); galectin 9 (LGALS9; NCBI Gene ID: 3965); lymphocyte activating 3 (LAG3, CD223; NCBI Gene ID: 3902); signaling lymphocytic activation molecule family member 1 (SLAMF1, SLAM, CD150; NCBI Gene ID: 6504); lymphocyte antigen 9 (LY9, CD229, SLAMF3; NCBI Gene ID: 4063); SLAM family member 6 (SLAMF6, CD352; NCBI Gene ID: 114836); SLAM family member 7 (SLAMF7, CD319; NCBI Gene ID: 57823); UL16 binding protein 1 (ULBP1; NCBI Gene ID: 80329); UL16 binding protein 2 (ULBP2; NCBI Gene ID: 80328); UL16 binding protein 3 (ULBP3; NCBI Gene ID: 79465); retinoic acid early transcript 1E (RAET1E; ULBP4; NCBI Gene ID: 135250); retinoic acid early transcript 1G (RAET1G; ULBPS; NCBI Gene ID: 353091); retinoic acid early transcript 1L (RAET1L; ULBP6; NCBI Gene ID: 154064); killer cell lectin like receptor C1 (KLRC1, NKG2A, CD159A; NCBI Gene ID: 3821); killer cell lectin like receptor K1 (KLRK1, NKG2D, CD314; NCBI Gene ID: 22914); killer cell lectin like receptor C2 (KLRC2, CD159c, NKG2C; NCBI Gene ID: 3822); killer cell lectin like receptor C3 (KLRC3, NKG2E; NCBI Gene ID: 3823); killer cell lectin like receptor C4 (KLRC4, NKG2F; NCBI Gene ID: 8302); killer cell immunoglobulin like receptor, two Ig domains and long cytoplasmic tail 1 (KIR2DL1; NCBI Gene ID: 3802); killer cell immunoglobulin like receptor, two Ig domains and long cytoplasmic tail 2 (KIR2DL2; NCBI Gene ID: 3803); killer cell immunoglobulin like receptor, two Ig domains and long cytoplasmic tail 3 (KIR2DL3; NCBI Gene ID: 3804); killer cell immunoglobulin like receptor, three Ig domains and long cytoplasmic tail 1 (KIR3DL1, KIR, CD158E1; NCBI Gene ID: 3811) (e.g., Lirilumab (IPH2102/BMS-986015), IPH-4102); and killer cell lectin like receptor D1 (KLRD1; NCBI Gene ID: 3824).

In various embodiments, an engineered meganuclease described herein, or a nucleic acid sequence encoding the same, is combined with one or more blockers or inhibitors of one or more T-cell inhibitory immune checkpoint proteins or receptors. Illustrative T-cell inhibitory immune checkpoint proteins or receptors include without limitation CD274 (CD274, PDL1, PD-L1); programmed cell death 1 ligand 2 (PDCD1LG2, PD-L2, CD273); programmed cell death 1 (PDCD1, PD1, PD-1); cytotoxic T-lymphocyte associated protein 4 (CTLA4, CD152); CD276 (B7H3); V-set domain containing T cell activation inhibitor 1 (VTCN1, B7H4); V-set immunoregulatory receptor (VSIR, B7H5, VISTA); immunoglobulin superfamily member 11 (IGSF11, VSIG3); TNFRSF14 (HVEM, CD270), TNFSF14 (HVEML); CD272 (B and T lymphocyte associated (BTLA)); PVR related immunoglobulin domain containing (PVRIG, CD112R); T cell immunoreceptor with Ig and ITIM domains (TIGIT); lymphocyte activating 3 (LAG3, CD223); hepatitis A virus cellular receptor 2 (HAVCR2, TIMD3, TIM3); galectin 9 (LGALS9); killer cell immunoglobulin like receptor, three Ig domains and long cytoplasmic tail 1 (KIR, CD158E1); killer cell immunoglobulin like receptor, two Ig domains and long cytoplasmic tail 1 (KIR2DL1); killer cell immunoglobulin like receptor, two Ig domains and long cytoplasmic tail 2 (KIR2DL2); killer cell immunoglobulin like receptor, two Ig domains and long cytoplasmic tail 3 (KIR2DL3); and killer cell immunoglobulin like receptor, three Ig domains and long cytoplasmic tail 1 (KIR3DL1). In various embodiments, an engineered meganuclease described herein, or a nucleic acid sequence encoding the same, is combined with one or more agonist or activators of one or more T-cell stimulatory immune checkpoint proteins or receptors. Illustrative T-cell stimulatory immune checkpoint proteins or receptors include without limitation CD27, CD70; CD40, CD40LG; inducible T cell costimulator (ICOS, CD278); inducible T cell costimulator ligand (ICOSLG, B7H2); TNF receptor superfamily member 4 (TNFRSF4, OX40); TNF superfamily member 4 (TNFSF4, OX40L); TNFRSF9 (CD137), TNFSF9 (CD137L); TNFRSF18 (GITR), TNFSF18 (GITRL); CD80 (B7-1), CD28; nectin cell adhesion molecule 2 (NECTIN2, CD112); CD226 (DNAM-1); CD244 (2B4, SLAMF4); and Poliovirus receptor (PVR) cell adhesion molecule (PVR, CD155). See, e.g., Xu, et al., *J Exp Clin Cancer Res*. (2018) 37:110.

In various embodiments, an engineered meganuclease described herein, or a nucleic acid sequence encoding the same, is combined with one or more blockers or inhibitors of one or more NK-cell inhibitory immune checkpoint proteins or receptors. Illustrative NK-cell inhibitory immune checkpoint proteins or receptors include without limitation killer cell immunoglobulin like receptor, three Ig domains and long cytoplasmic tail 1 (KIR, CD158E1); killer cell immunoglobulin like receptor, two Ig domains and long cytoplasmic tail 1 (KIR2DL1); killer cell immunoglobulin like receptor, two Ig domains and long cytoplasmic tail 2 (KIR2DL2); killer cell immunoglobulin like receptor, two Ig domains and long cytoplasmic tail 3 (KIR2DL3); killer cell immunoglobulin like receptor, three Ig domains and long cytoplasmic tail 1 (KIR3DL1); killer cell lectin like receptor C1 (KLRC1, NKG2A, CD159A); and killer cell lectin like receptor D1 (KLRD1, CD94). In various embodiments, an engineered meganuclease described herein, or a nucleic acid sequence encoding the same, is combined with one or more agonist or activators of one or more NK-cell stimulatory immune checkpoint proteins or receptors. Illustrative NK-cell stimulatory immune checkpoint proteins or receptors include without limitation CD16, CD226 (DNAM-1); CD244 (2B4, SLAMF4); killer cell lectin like receptor K1 (KLRK1, NKG2D, CD314); and SLAM family member 7 (SLAMF7). See, e.g., Davis, et al., *Semin Immunol.* (2017) 31:64-75; Fang, et al., *Semin Immunol.* (2017) 31:37-54; and Chiossone, et al., *Nat Rev Immunol.* (2018) 18(11):671-688.

In some embodiments, the one or more immune checkpoint inhibitors comprises a proteinaceous (e.g., antibody or fragment thereof, or antibody mimetic) inhibitor of PD-L1 (CD274), PD-1 (PDCD1) or CTLA4. In some embodiments, the one or more immune checkpoint inhibitors comprises a small organic molecule inhibitor of PD-L1 (CD274), PD-1 (PDCD1) or CTLA4. In some embodiments, the small molecule inhibitor of CD274 or PDCD1 is selected from the group consisting of GS-4224, GS-4416, INCB086550 and MAX10181. In some embodiments, the small molecule inhibitor of CTLA4 comprises BPI-002.

Examples of inhibitors of CTLA4 that can be co-administered include without limitation ipilimumab, tremelimumab, BMS-986218, AGEN1181, AGEN1884, BMS-986249, MK-1308, REGN-4659, ADU-1604, CS-1002, BCD-145, APL-509, JS-007, BA-3071, ONC-392, AGEN-2041, JHL-1155, KN-044, CG-0161, ATOR-1144, PBI-5D3H5, BPI-002, as well as multi-specific inhibitors FPT-155 (CTLA4/PD-L1/CD28), PF-06936308 (PD-1/CTLA4), MGD-019 (PD-1/CTLA4), KN-046 (PD-1/CTLA4), MEDI-5752 (CTLA4/PD-1), XmAb-20717 (PD-1/CTLA4), and AK-104 (CTLA4/PD-1).

Examples of inhibitors of PD-L1 (CD274) or PD-1 (PDCD1) that can be co-administered include without limitation pembrolizumab, nivolumab, cemiplimab, pidilizumab, AMP-224, MEDI0680 (AMP-514), spartalizumab, atezolizumab, avelumab, durvalumab, ALN-PDL, BMS-936559, CK-301, PF-06801591, BGB-108, BGB-A317 (tislelizumab), GLS-010 (WBP-3055), AK-103 (HX-008), GB-226, AK-105, CS-1003, HLX-10, MGA-012, BI-754091, PDR-001, AGEN-2034, JS-001 (toripalimab), JNJ-63723283, genolimzumab (CBT-501), LZM-009, BCD-100, LY-3300054, SHR-1201, SHR-1210 (camrelizumab), Sym-021, ABBV-181, PD1-PIK, BAT-1306, RO-6084 (PD-L1 antisense oligonucleotide), STI-1110, GX-P2, RG-7446, mDX-400, (MSB0010718C), CX-072, CBT-502, TSR-042 (dostarlimab), MSB-2311, JTX-4014, BGB-A333, SHR-1316, CS-1001 (WBP-3155), MEDI-0680, envafolimab (KN-035), KD-033, KY-1003, IBI-308 (sintilimab), HLX-20, KL-A167, STI-A1014, STI-A1015 (IMC-001), BCD-135, FAZ-053, TQB-2450, MDX1105-01, MSB-0010718C, GS-4224, GS-4416, INCB086550, MAX10181, as well as multi-specific inhibitors FPT-155 (CTLA4/PD-L1/CD28), PF-06936308 (PD-1/CTLA4), MGD-013 (PD-1/LAG-3), FS-118 (LAG-3/PD-L1) MGD-019 (PD-1/CTLA4), KN-046 (PD-1/CTLA4), MEDI-5752 (CTLA4/PD-1), RO-7121661 (PD-1/TIM-3), XmAb-20717 (PD-1/CTLA4), AK-104 (CTLA4/PD-1), M7824 (PD-L1/TGFβ-EC domain), CA-170 (PD-L1/VISTA), CDX-527 (CD27/PD-L1), LY-3415244 (TIM3/PDL1), GNS-1480 (Epidermal growth factor receptor antagonist; Programmed cell death ligand 1 inhibitor), M-7824 (PD-L1/TGF-β bifunctional fusion protein), and INBRX-105 (4-1BB/PDL1).

Examples of PD-1inhibitors include the compounds disclosed in WO2017112730 (Incyte Corp), WO2017087777 (Incyte Corp), WO2017017624, WO2014151634 (BristolMyers Squibb Co), WO201317322 (BristolMyers Squibb Co), WO2018119286 (Incyte Corp), WO2018119266 (Incyte Corp), WO2018119263(Incyte Corp), WO2018119236 (Incyte Corp), WO2018119221(Incyte Corp), WO2018118848 (BristolMyers Squibb Co), WO20161266460(BristolMyers Squibb Co), WO2017087678 (BristolMyers Squibb Co), WO2016149351 (BristolMyers Squibb Co), WO2015033299 (Aurigene Discovery Technologies Ltd), WO2015179615(Eisai Co Ltd; Eisai Research Institute), WO2017066227(BristolMyers Squibb Co), WO2016142886 (Aurigene Discovery Technologies Ltd), WO2016142852(Aurigene Discovery Technologies Ltd), WO2016142835 (Aurigene Discovery Technologies Ltd; Individual), WO2016142833 (Aurigene Discovery Technologies Ltd), WO2018085750 (BristolMyers Squibb Co), WO2015033303 (Aurigene Discovery Technologies Ltd), WO2017205464 (Incyte Corp), WO2016019232 (3M Co; Individual; Texas A&M University System), WO2015160641 (BristolMyers Squibb Co), WO2017079669 (Incyte Corp), WO2015033301 (Aurigene Discovery Technologies Ltd), WO2015034820 (BristolMyers Squibb Co), WO2018073754 (Aurigene Discovery Technologies Ltd), WO2016077518 (BristolMyers Squibb Co), WO2016057624 (BristolMyers Squibb Co), WO2018044783 (Incyte Corp), WO2016100608 (BristolMyers Squibb Co), WO2016100285 (BristolMyers Squibb Co), WO2016039749 (BristolMyers Squibb Co), WO2015019284 (Cambridge Enterprise Ltd), WO2016142894 (Aurigene Discovery Technologies Ltd), WO2015134605 (BristolMyers Squibb Co), WO2018051255 (Aurigene Discovery Technologies Ltd), WO2018051254 (Aurigene Discovery Technologies Ltd), WO2017222976 (Incyte Corp), WO2017070089 (Incyte orp), WO2018044963 (BristolMyers Squibb Co), WO2013144704 (Aurigene Discovery Technologies Ltd), WO2018013789 (Incyte Corp), WO2017176608 (BristolMyers Squibb Co), WO2018009505 (BristolMyers Squibb Co), WO2011161699 (Aurigene Discovery Technologies Ltd), WO2015119944 (Incyte Corp; Merck Sharp & Dohme Corp), WO2017192961 (Incyte Corp), WO2017106634 (Incyte Corp), WO2013132317 (Aurigene Discovery Technologies Ltd), WO2012168944 (Aurigene Discovery Technologies Ltd), WO2015036927 (Aurigene Discovery Technologies Ltd), WO2015044900 (Aurigene Discovery Technologies Ltd), WO2018026971 (Arising International).

In various embodiments, an engineered meganuclease described herein, or a nucleic acid sequence encoding the same, is combined with anti-TIGIT antibodies, such as BMS-986207, RG-6058, and AGEN-1307.

TNF Receptor Superfamily (TNFRSF) Member Agonists or Activators

In various embodiments, an engineered meganuclease described herein, or a nucleic acid sequence encoding the same, is combined with an agonist of one or more TNF receptor superfamily (TNFRSF) members, e.g., an agonist of one or more of TNFRSF1A (NCBI Gene ID: 7132), TNFRSF1B (NCBI Gene ID: 7133), TNFRSF4 (OX40, CD134; NCBI Gene ID: 7293), TNFRSF5 (CD40; NCBI Gene ID: 958), TNFRSF6 (FAS, NCBI Gene ID: 355), TNFRSF7 (CD27, NCBI Gene ID: 939), TNFRSF8 (CD30, NCBI Gene ID: 943), TNFRSF9 (4-1BB, CD137, NCBI Gene ID: 3604), TNFRSF10A (CD261, DR4, TRAILR1, NCBI Gene ID: 8797), TNFRSF10B (CD262, DR5, TRAILR2, NCBI Gene ID: 8795), TNFRSF10C (CD263, TRAILR3, NCBI Gene ID: 8794), TNFRSF10D (CD264, TRAILR4, NCBI Gene ID: 8793), TNFRSF11A (CD265, RANK, NCBI Gene ID: 8792), TNFRSF11B (NCBI Gene ID: 4982), TNFRSF12A (CD266, NCBI Gene ID: 51330), TNFRSF13B (CD267, NCBI Gene ID: 23495), TNFRSF13C (CD268, NCBI Gene ID: 115650), TNFRSF16 (NGFR, CD271, NCBI Gene ID: 4804), TNFRSF17 (BCMA, CD269, NCBI Gene ID: 608), TNFRSF18 (GITR, CD357, NCBI Gene ID: 8784), TNFRSF19 (NCBI Gene ID: 55504), TNFRSF21 (CD358, DR6, NCBI Gene ID: 27242), and TNFRSF25 (DR3, NCBI Gene ID: 8718).

Example anti-TNFRSF4 (OX40) antibodies that can be co-administered include without limitation, MEDI6469, MEDI6383, MEDI0562 (tavolixizumab), MOXR0916, PF-04518600, RG-7888, GSK-3174998, INCAGN1949, BMS-986178, GBR-8383, ABBV-368, IBI-101 and those described in WO2016179517, WO2017096179, WO2017096182, WO2017096281, and WO2018089628.

Example anti-TNFRSF5 (CD40) antibodies that can be co-administered include without limitation RG7876, SEA-CD40, APX-005M and ABBV-428.

In some embodiments, the anti-TNFRSF7 (CD27) antibody varlilumab (CDX-1127) is co-administered.

Example anti-TNFRSF9 (4-1BB, CD137) antibodies that can be co-administered include without limitation urelumab, utomilumab (PF-05082566), AGEN2373 and ADG-106.

Example anti-TNFRSF18 (GITR) antibodies that can be co-administered include without limitation, MEDI1873, FPA-154, INCAGN-1876, TRX-518, BMS-986156, MK-1248, GWN-323, and those described in WO2017096179, WO2017096276, WO2017096189, and WO2018089628. In some embodiments, an antibody, or fragment thereof, co-targeting TNFRSF4 (OX40) and TNFRSF18 (GITR) is co-administered. Such antibodies are described, e.g., in WO2017096179 and WO2018089628.

Indoleamine-pyrrole-2,3-dioxygenase (IDO1) Inhibitors

In various embodiments, an engineered meganuclease described herein, or a nucleic acid sequence encoding the same, is combined with an inhibitor of indoleamine 2,3-dioxygenase 1 (IDO1; NCBI Gene ID: 3620). Examples of IDO1 inhibitors include without limitation, BLV-0801, epacadostat, resminostat, F-001287, GBV-1012, GBV-1028, GDC-0919, indoximod, NKTR-218, NLG-919-based vaccine, PF-06840003, pyranonaphthoquinone derivatives (SN-35837), SBLK-200802, BMS-986205, and shIDO-ST, EOS-200271, KHK-2455, LY-3381916, and the compounds disclosed in US20100015178 (Incyte), US2016137652 (Flexus Biosciences, Inc.), WO2014073738 (Flexus Biosciences, Inc.), and WO2015188085(Flexus Biosciences, Inc.).

LAG-3 and TIM-3 Inhibitors

In certain embodiments, an engineered meganuclease described herein, or a nucleic acid sequence encoding the same, is combined with an anti-TIM-3 antibody, such as TSR-022, LY-3321367, MBG-453, INCAGN-2390.

In certain embodiments, an engineered meganuclease described herein, or a nucleic acid sequence encoding the same, is combined with an anti LAG-3 (Lymphocyte-activation) antibody, such as relatlimab (ONO-4482), LAG-525, MK-4280, REGN-3767, INCAGN2385.

Inhibitor of Apoptosis Proteins Family Proteins (IAPs)

Examples of IAP inhibitors include APG-1387.

Recombinant Thymosin Alpha-1

Examples of recombinant thymosin alpha-1 include NL-004 and PEGylated thymo sin alpha-1.

Bruton's Tyrosine Kinase (BTK) Inhibitors

Examples of BTK inhibitors include ABBV-105, acalabrutinib (ACP-196), ARQ-531, BMS-986142, dasatinib, ibrutinib, GDC-0853, PRN-1008, SNS-062, ONO-4059, BGB-3111, ML-319, MSC-2364447, RDX-022, X-022, AC-058, RG-7845, spebrutinib, TAS-5315, TP-0158, TP-4207, HM-71224, KBP-7536, M-2951, TAK-020, AC-0025, and the compounds disclosed in US20140330015 (Ono Pharmaceutical), US20130079327 (Ono Pharmaceutical), and US20130217880 (Ono Pharmaceutical).

KDM Inhibitors

Examples of KDMS inhibitors include the compounds disclosed in WO2016057924 (Genentech/Constellation Pharmaceuticals), US20140275092 (Genentech/Constellation Pharmaceuticals), US20140371195 (Epitherapeutics) and US20140371214 (Epitherapeutics), US20160102096 (Epitherapeutics), US20140194469 (Quanticel), US20140171432, US20140213591 (Quanticel), US20160039808 (Quanticel), US20140275084 (Quanticel), and WO2014164708 (Quanticel).

Examples of KDM1 inhibitors include the compounds disclosed in U.S. Pat. No. 9,186,337 B2 (Oryzon Genomics), GSK-2879552, RG-6016, and ORY-2001.

Arginase Inhibitors

Examples of Arginase inhibitors include CB-1158, C-201, and resminostat.

Bi—and Tri-Specific Natural Killer (NK)-Cell Engagers

In various embodiments, an engineered meganuclease described herein, or a nucleic acid sequence encoding the same, is combined with a bi-specific NK-cell engager (BiKE) or a tri-specific NK-cell engager (TriKE) (e.g., not having an Fc) or bi-specific antibody (e.g., having an Fc) against an NK cell activating receptor, e.g., CD16A, C-type lectin receptors (CD94/NKG2C, NKG2D, NKG2E/H and NKG2F), natural cytotoxicity receptors (NKp30, NKp44 and NKp46), killer cell C-type lectin-like receptor (NKp65, NKp80), Fc receptor FcγR (which mediates antibody-dependent cell cytotoxicity), SLAM family receptors (e.g., 2B4, SLAM6 and SLAM7), killer cell immunoglobulin-like receptors (KIR) (KIR-2DS and KIR-3DS), DNAM-1 and CD137 (4-1BB). As appropriate, the anti-CD16 binding bi-specific molecules may or may not have an Fc. Illustrative bi-specific NK-cell engagers that can be co-administered target CD16 and one or more HBV-associated antigens as described herein. BiKEs and TriKEs are described, e.g., in Felices, et al., *Methods Mol Biol.* (2016) 1441:333-346; Fang, et al., *Semin Immunol.* (2017) 31:37-54.

Gene Therapy and Cell Therapy

In certain embodiments, an engineered meganuclease described herein, or a nucleic acid sequence encoding the same, is combined with a gene or cell therapy regimen. Gene therapy and cell therapy include without limitation the genetic modification to silence a gene; genetic approaches to directly kill the infected cells; the infusion of immune cells designed to replace most of the patient's own immune system to enhance the immune response to infected cells, or activate the patient's own immune system to kill infected cells, or find and kill the infected cells; and/or genetic approaches to modify cellular activity to further alter endogenous immune responsiveness against the infection.

CAR-T Cell Therapy

CAR-T cell therapy includes a population of immune effector cells engineered to express a chimeric antigen receptor (CAR), wherein the CAR includes an HBV antigen-binding domain. In certain embodiments, the antigen-binding domain is a domain described herein. In certain embodiments, the antigen-binding domain is other than a domain described herein. In certain embodiments, the antigen is HBsAg (i.e., HbsAg-CART). The immune effector cell is a T-cell or an NK cell. In certain embodiments, the T-cell is a CD4+ T-cell, a CD8+ T-cell, a NK cell, or a combination thereof. Cells can be autologous or allogeneic. An example of a CART directed to HBV is described in Cytotherapy. 2018 May; 20(5):697-705 doi: 10.1016/j.jcyt.2018.02.

TCR-T Cell Therapy

TCR-T cell therapy includes T cells expressing HBV-specific T cell receptors. TCR-T cells are engineered to target HBV derived peptides presented on the surface of virus-infected cells. An example of a TCR directed to HBV is described in Wisskirchen, K. et al. *J Clin Invest.* 2019; 129(7):2932-2945.

TCR-T cell therapy includes T-Cells expressing HBV surface antigen (HBsAg)-specific TCR.

TCR-T cell therapy includes TCR-T therapy directed to treatment of HBV, such as LTCR-H2-1.

In another specific embodiment, an engineered meganuclease described herein, or a nucleic acid encoding the same, is combined with an HBV DNA polymerase inhibitor, one or two additional therapeutic agents selected from the group consisting of immunomodulators, TLR modulators, HBsAg inhibitors, HBsAg secretion or assembly inhibitors, HBV therapeutic vaccines, HBV antibodies including HBV antibodies targeting the surface antigens of the hepatitis B virus and bispecific antibodies and "antibody-like" therapeutic proteins (such as DARTs®, DUOBODIES®, BITES®, XmAbs®, TandAbs®, Fab derivatives, or TCR-like antibodies), cyclophilin inhibitors, stimulators of retinoic acid-inducible gene 1, stimulators of RIG-I like receptors, PD-1 inhibitors, PD-L1 inhibitors, Arginase inhibitors, PI3K inhibitors, IDO inhibitors, and stimulators of NOD2, and one or two additional therapeutic agents selected from the group consisting of HBV viral entry inhibitors, NTCP inhibitors, HBx inhibitors, cccDNA inhibitors, HBV antibodies targeting the surface antigens of the hepatitis B virus, siRNA, miRNA gene therapy agents, sshRNAs, KDM5 inhibitors, and nucleoprotein modulators (HBV core or capsid protein modulators).

In another specific embodiment, an engineered meganuclease described herein, or a nucleic acid encoding the same, is combined with at least a second additional therapeutic agent selected from the group consisting of: HBV DNA polymerase inhibitors, immunomodulators, TLR modulators, HBsAg inhibitors, HBV therapeutic vaccines, HBV antibodies including HBV antibodies targeting the surface antigens of the hepatitis B virus and bispecific antibodies and "antibody-like" therapeutic proteins (such as DARPins®, anti-pMHC TCR-like antibodies, DARTs®, DUOBODIES®, BITES®, XmAbs®, TandAbs®, Fab derivatives, or TCR-like antibodies), cyclophilin inhibitors, stimulators of retinoic acid-inducible gene 1, stimulators of RIG-I like receptors, PD-1 inhibitors, PD-L1 inhibitors, Arginase inhibitors, PI3K inhibitors, IDO inhibitors, and stimulators of NOD2.

In another specific embodiment, an engineered meganuclease described herein, or a nucleic acid encoding the same, is combined with at least a second additional therapeutic agent selected from the group consisting of: HBV DNA polymerase inhibitors, HBV viral entry inhibitors, NTCP inhibitors, HBx inhibitors, cccDNA inhibitors, HBV antibodies targeting the surface antigens of the hepatitis B virus, siRNA, miRNA gene therapy agents, sshRNAs, KDM5 inhibitors, and nucleoprotein modulators (HBV core or capsid protein inhibitors).

In a particular embodiment, an engineered meganuclease described herein, or a nucleic acid encoding the same, is combined with compounds such as those disclosed in U.S. Publication No. 2010/0143301 (Gilead Sciences), U.S. Publication No. 2011/0098248 (Gilead Sciences), U.S. Publication No. 2009/0047249 (Gilead Sciences), U.S. Pat. No. 8,722,054 (Gilead Sciences), U.S. Publication No. 2014/0045849 (Janssen), U.S. Publication No. 2014/0073642 (Janssen), WO2014/056953 (Janssen), WO2014/076221 (Janssen), WO2014/128189 (Janssen), U.S. Publication No. 2014/0350031 (Janssen), WO2014/023813 (Janssen), U.S. Publication No. 2008/0234251 (Array Biopharma), U.S. Publication No. 2008/0306050 (Array Biopharma), U.S. Publication No. 2010/0029585 (Ventirx Pharma), U.S. Publication No. 2011/0092485 (Ventirx Pharma), US2011/0118235 (Ventirx Pharma), U.S. Publication No. 2012/0082658 (Ventirx Pharma), U.S. Publication No. 2012/0219615 (Ventirx Pharma), U.S. Publication No. 2014/0066432 (Ventirx Pharma), U.S. Publication No. 2014/0088085 (Ventirx Pharma), U.S. Publication No. 2014/0275167 (Novira Therapeutics), U.S. Publication No. 2013/0251673 (Novira Therapeutics), U.S. Pat. No. 8,513,184 (Gilead Sciences), U.S. Publication No. 2014/0030221 (Gilead Sciences), U.S. Publication No. 2013/0344030 (Gilead Sciences), U.S. Publication No. 2013/0344029 (Gilead Sciences), US20140275167 (Novira Therapeutics), US20130251673 (Novira Therapeutics), U.S. Publication No. 2014/0343032 (Roche), WO2014037480 (Roche), U.S. Publication No. 2013/0267517 (Roche), WO2014131847 (Janssen), WO2014033176 (Janssen), WO2014033170 (Janssen), WO2014033167 (Janssen), WO2015/059212 (Janssen), WO2015118057(Janssen), WO2015011281 (Janssen), WO2014184365 (Janssen), WO2014184350 (Janssen), WO2014161888 (Janssen), WO2013096744 (Novira), US20150225355 (Novira), US20140178337 (Novira), US20150315159 (Novira), US20150197533 (Novira), US20150274652 (Novira), US20150259324, (Novira), US20150132258 (Novira), U.S. Pat. No. 9,181,288 (Novira), WO2014184350 (Janssen), WO2013144129 (Roche), US20100015178 (Incyte), US2016137652 (Flexus Biosciences, Inc.), WO2014073738 (Flexus Biosciences, Inc.), WO2015188085(Flexus Biosciences, Inc.), U.S. Publication No. 2014/0330015 (Ono Pharmaceutical), U.S. Publication No. 2013/0079327 (Ono Pharmaceutical), U.S. Publication No. 2013/0217880 (Ono pharmaceutical), WO2016057924 (Genentech/Constellation Pharmaceuticals), US20140275092 (Genentech/Constellation Pharmaceuticals), US20140371195 (Epitherapeutics) and US20140371214 (Epitherapeutics)., US20160102096 (Epitherapeutics), US20140194469 (Quanticel), US20140171432, US20140213591 (Quanticel), US20160039808 (Quanticel), US20140275084 (Quanticel), WO2014164708 (Quanticel), U.S. Pat. No. 9,186,337B2 (Oryzon Genomics), and other drugs for treating HBV, and combinations thereof.

In certain embodiments, an engineered meganuclease described herein, or a nucleic acid encoding the same, is combined with 5-30 mg tenofovir alafenamide fumarate, tenofovir alafenamide hemifumarate, or tenofovir alafenamide. In certain embodiments, an engineered meganuclease described herein, or a nucleic acid encoding the same, is combined with 5-10; 5-15; 5-20; 5-25; 25-30; 20-30; 15-30; or 10-30 mg tenofovir alafenamide fumarate, tenofovir alafenamide hemifumarate, or tenofovir alafenamide. In certain embodiments, an engineered meganuclease described herein, or a nucleic acid encoding the same, is combined with 10 mg tenofovir alafenamide fumarate, tenofovir alafenamide hemifumarate, or tenofovir alafenamide. In certain embodiments, an engineered meganuclease described herein, or a nucleic acid encoding the same, is combined with 25 mg tenofovir alafenamide fumarate, tenofovir alafenamide hemifumarate, or tenofovir alafenamide. An engineered meganuclease described herein, or a nucleic acid encoding the same, may be combined with the agents provided herein in any dosage amount of the compound (e.g., from 50 mg to 500 mg of compound) the same as if each combination of dosages were specifically and individually listed.

In certain embodiments, an engineered meganuclease described herein, or a nucleic acid encoding the same, is combined with 100-400 mg tenofovir disoproxil fumarate, tenofovir disoproxil hemifumarate, or tenofovir disoproxil. In certain embodiments, an engineered meganuclease described herein, or a nucleic acid encoding the same, is combined with 100-150; 100-200, 100-250; 100-300; 100-350; 150-200; 150-250; 150-300; 150-350; 150-400; 200-250; 200-300; 200-350; 200-400; 250-350; 250-400; 350-400 or 300-400 mg tenofovir disoproxil fumarate, tenofovir disoproxil hemifumarate, or tenofovir disoproxil. In certain embodiments, an engineered meganuclease described herein, or a nucleic acid encoding the same, is combined with 300 mg tenofovir disoproxil fumarate, tenofovir disoproxil hemifumarate, or tenofovir disoproxil. In certain embodiments, an engineered meganuclease described herein, or a nucleic acid encoding the same, is combined with 250 mg tenofovir disoproxil fumarate, tenofovir disoproxil hemifumarate, or tenofovir disoproxil. In certain embodiments, an engineered meganuclease described herein, or a nucleic acid encoding the same, is combined with 150 mg tenofovir disoproxil fumarate, tenofovir disoproxil hemifumarate, or tenofovir disoproxil. An engineered meganuclease described herein, or a nucleic acid encoding the same, may be combined with the agents provided herein in any dosage amount of the compound (e.g., from 50 mg to 500 mg of compound) the same as if each combination of dosages were specifically and individually listed.

In one embodiment, kits comprising an engineered meganuclease described herein, or a nucleic acid encoding the same, in combination with one or more (e.g., one, two, three, four, one or two, or one to three, or one to four) additional therapeutic agents are provided.

EXAMPLES

This invention is further illustrated by the following examples, which should not be construed as limiting. Those skilled in the art will recognize, or be able to ascertain, using no more than routine experimentation, numerous equivalents to the specific substances and procedures described herein. Such equivalents are intended to be encompassed in the scope of the claims that follow the examples below.

Example 1

Generation of Indels at the HBV 11-12 Recognition Sequence by HBV 11-12 Meganucleases in Hep3B Cells After Electroporation with HBV 11-12 mRNA HBV 11-12 meganucleases were generated to have better on-target activity and improved specificity compared to previously described HBV meganucleases. Studies were conducted to evaluate the efficacy of these HBV 11-12 meganucleases for causing insertions and/or deletions ("indels") at their intended recognition sequence (i.e., the HBV 11-12 recognition sequence). Indel formation was detected in these experiments by digital PCR analysis.

To evaluate editing efficiency of HBV 11-12 meganucleases to an integrated hepatitis B sequence, we utilized the Hep3B cell line, an HCC cell line with multiple hepatitis B integrations. 1e6 Hep3B cells were electroporated using the Lonza Amaxa 4D system with 100 ng or 10 ng of mRNA encoding the HBV 11-12L.638, HBV 11-12L.699, HBV 11-12L.638S19, or HBV 11-12L.520S19 engineered meganucleases or GFP. In addition, previously described meganucleases HBV 11-12x.26 and HBV 11-12L.363 were transfected. Cells were collected at two days post transfection, for genomic DNA extraction and evaluated for transfection efficiency using a Beckman Coulter CytoFlex S cytometer. Transfection efficiency exceeded 90%. Genomic DNA was prepared using the Macherey Nagel NucleoSpin Blood QuickPure kit.

Digital droplet PCR was utilized to determine the frequency of target insertions and deletions (indel %) at the HBV 11-12 binding site using primers P1, F1, and R1 to generate an amplicon surrounding the binding site, as well as primers P2, F2, R2 to generate a reference amplicon. Amplifications were multiplexed in a 20 µL reaction containing 1× ddPCR Supermix for Probes (no dUTP, BioRad), 250 nM of each probe, 900 nM of each primer, 5U of HindIII-HF, and ~50 ng cellular gDNA. Droplets were generated using a QX100 droplet generator (BioRad). Cycling conditions were as follows: 1 cycle of 95° C. (2° C./s ramp) for 10 minutes, 45 cycles of 94° C. (2° C./s ramp) for 10 seconds, 61° C. (2° C./s ramp) for 30 seconds, 72C (2° C./s ramp) for 2 minutes, 1 cycle of 98° C. for 10 minutes, 4° C. hold. Droplets were analyzed using a QX200 droplet reader (BioRad) and QuantaSoft analysis software (BioRad) was used to acquire and analyze data. Indel frequencies were calculated by dividing the number of positive droplets for the binding site probe by the number of positive droplets for the reference probe. The sequences for the primers and probes used in this study are provided below.

```
P1:
                                      (SEQ ID NO: 32)
[5'TGCCGATCCATACTGCGGAACT t-3']

F1:
                                      (SEQ ID NO: 33)
[5'-GGTCTGTGCCAAGTGTTTG-3']
```

-continued

R1:
(SEQ ID NO: 34)
[5'-GTATATTTCCGCGAGAGGAC-3']

P2:
(SEQ ID NO: 35)
[5'-CTTGGCCCCCAATACCACATCATC-3']

F2:
(SEQ ID NO: 36)
[5'-GGATGGAAATTGCACCTGTATTC-3']

R2:
(SEQ ID NO: 37)
[5'-GGGTTTAAATGTATACCCAGAGAC-3']

Figure 5:
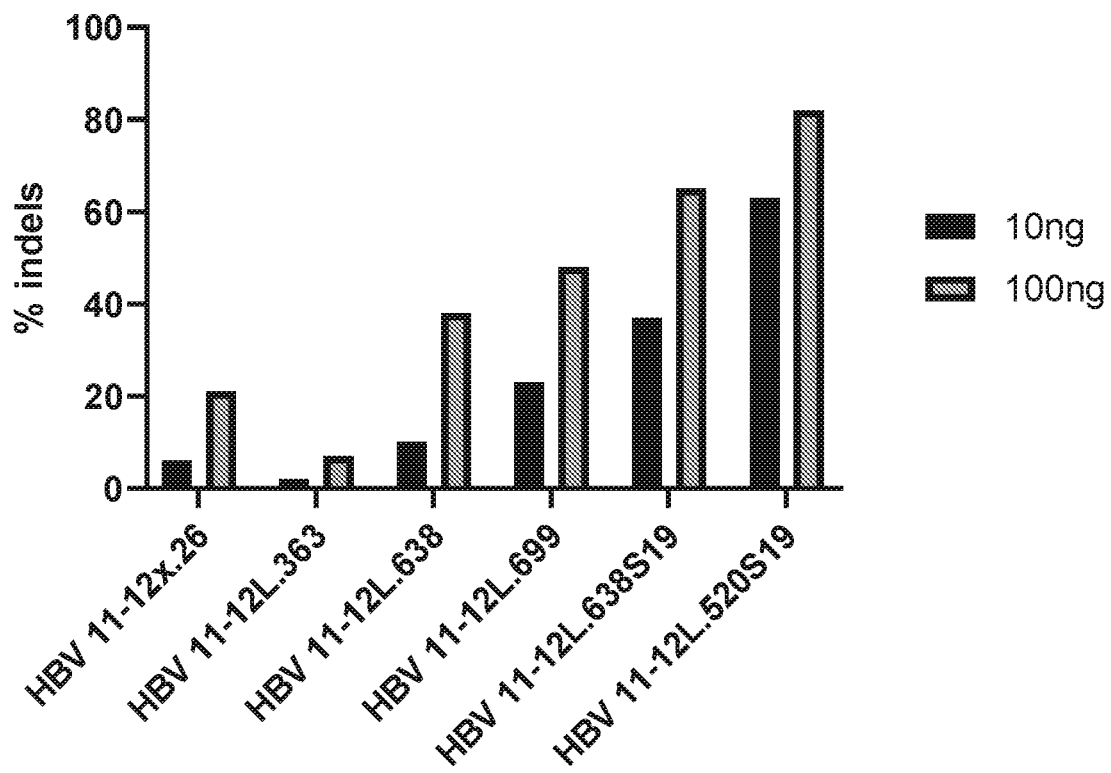
FIG. 5. Bar graph showing on target indel frequency assessed by digital droplet PCR (ddPCR) in Hep3B cells after transfection with the HBV 11-12x.26, HBV 11-12L.363, HBV 11-12L.638, HBV 11-12L.699, HBV 11-12L.638S19, and HBV 11-12L.520S19 meganucleases.

Meganucleases designed against the HBV 11-12 target sequence were evaluated for on-target activity in Hep3B cells. All meganucleases tested showed dose-dependent editing of the target site (FIG. 5). HBV 11-12L.520S19 showed the highest on-target activity, yielding 82% indels at the 100 ng dose. Each of the HBV 11-12L.638, HBV 11-12L.699, HBV 11-12L.638S19, and HBV 11-12L.520S19 meganucleases demonstrated significantly higher percent indels at each tested dose.

These data demonstrate that the HBV 11-12 meganucleases according to the invention give rise to higher editing rates of integrated hepatitis B sequence compared to the previously described engineered meganucleases HBV 11-12x.26 and HBV 11-12L.363.

Example 2

Off-Targeting Analysis of HBV 11-12 Meganucleases

In these studies, an oligo capture assay was used to identify off target cutting induced by the HBV 11-12L.520S19, HBV 11-12L638, HBV 11-12L638S19, and HBV 11-12L699 meganucleases. Off target cutting was assessed in a lentivirus-modified HepG2 cell line that comprises in its genome a partial HBV genome comprising the HBV 11-12 recognition sequence.

Similar to GUIDE-seq, the oligo capture assay identifies potential off-target sites produced by the HBV 11-12 meganucleases by capturing an oligonucleotide at break sites within the cell's genomic DNA. GUIDE-seq was developed for CRISPR-Cas9 generated DNA breaks and there are a few key modifications to the chemistry and analysis in order to apply this technique to the present nucleases. Unlike CRISPR-cas9, the engineered meganucleases of the invention generate a four base pair 3' overhang. To accommodate for this difference, the oligonucleotides used in oligo capture have randomized four base pair overhangs that could be compatible with the overhangs generated with the HBV 11-12 meganuclease. A higher frequency of insertion is observed due to the greater efficiency of ligating sticky ends rather than blunt ends. Cells were transfected with mRNA encoding the nuclease and the double stranded DNA oligonucleotides. After two days, the genomic DNA from these cells was isolated and sonicated to shear the DNA to smaller sizes. An oligonucleotide adapter was ligated to the sheared DNA and PCR was used to amplify any DNA pieces that contain an adapter at one end and the captured oligonucleotide at the other end. The amplified DNA was purified and sequencing libraries were prepared using standard commercial kits.

Sequencing libraries were run on an Illumina MiSeq using V2 2×150 kits. The data was filtered and analyzed for valid sites that captured an oligonucleotide and a potential off-target site is predicted. Here again, the protocol needed to be adjusted from the PAM search used for CRISPR-cas9 to the HBV 11-12 meganuclease search. The software developed checks each sequence to make sure there is adapter and captured oligo flanking the sequence to verify that it is a valid read. The software also checks for PCR duplicates and removes reads that are identical to help reduce PCR bias. The sequence reads are aligned to a reference genome and grouped sequences within thousand base pair windows are scanned for a potential HBV 11-12 meganuclease site.

Each HBV 11-12 meganuclease is a linked dimer. Each monomer recognizes a nine base pair half site with a four base pair spacer in the center between the two half sites. The software looks for the closest sequence match for each half site with no allowed gaps. The middle four base pairs are not considered in the off-target selection because the HBV 11-12 meganucleases can generally tolerate a higher amount of degeneracy at these positions in the target site. The software outputs a list of potential off-target sites with the number of base mismatches in the combined half sites but not counting the middle four base pair mismatches. The software does not eliminate any off-targets based on an arbitrary mismatch filter, unlike CRISPR-Cas9 which eliminates any off-target identified with more than six base pairs mismatched. Instead, background noise generated from random capture of the oligo at fragile spots or hot spots within the genome can be reduced in two ways. First, an untreated mock sample is also run though oligo capture and windows of integration sites without the nuclease present can be subtracted from the nuclease containing samples. We have also found that running the assay in triplicate and eliminating any sites that do not repeat in at least two of the three repeats is a good way to empirically remove random integration noise.

Figure 6:
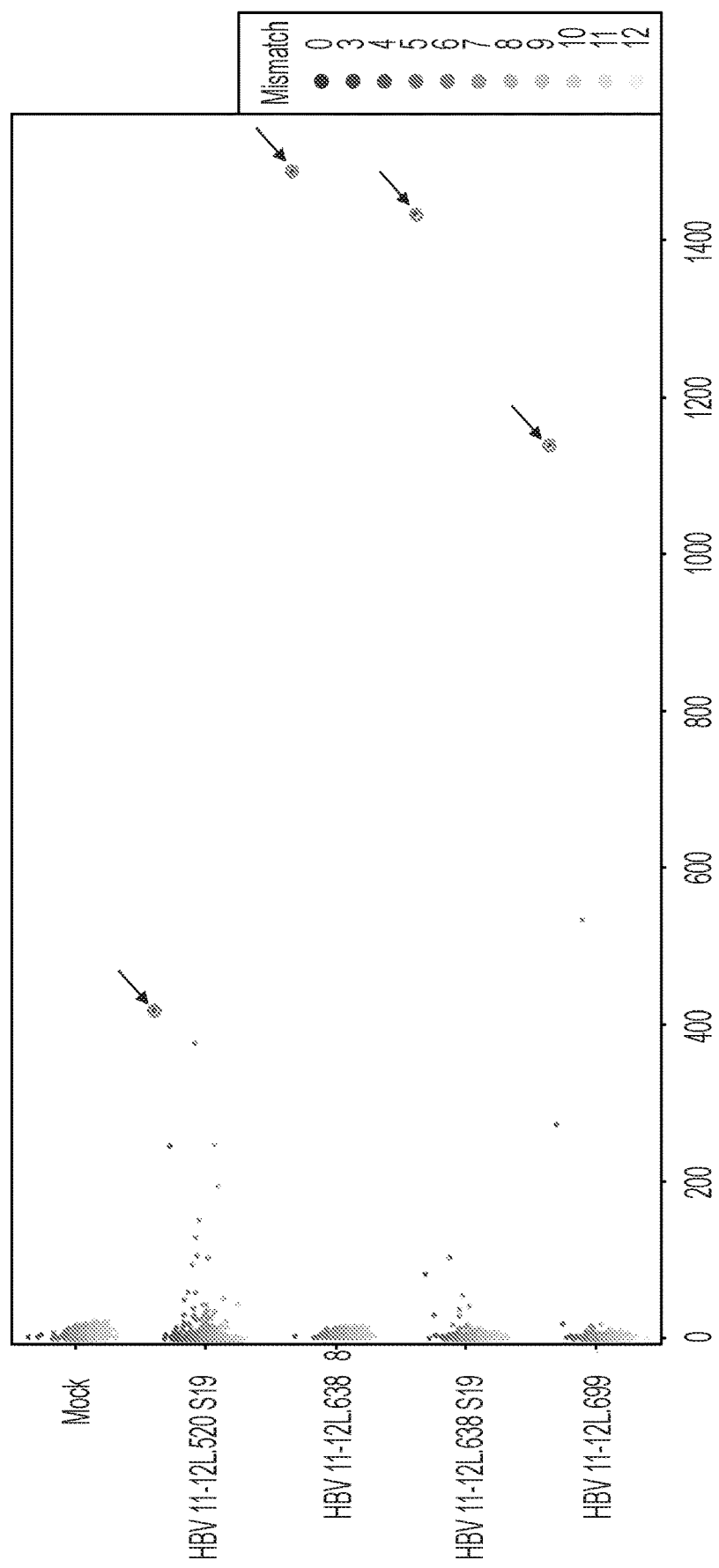
FIG. 6. Graph depicting results from an oligo capture assay to identify off target cutting induced by the HBV 11-12L.520S19, HBV 11-12L638, HBV 11-12L638S19, and HBV 11-12L699 meganucleases transfected in HepG2 Hep3B1 cells. The dots indicated as circled represent the on-target site.

Although read count does not directly correlate with cutting frequency at a particular site, it can generally highlight off-targets that are potentially more concerning or more valid because they occur more often. One way to graphically visualize the oligo capture data as a measure of number of potentially valid off-target sites is shown in FIG. 6. Each off-target generated by a particular nuclease is plotted based on the number of unique sequence reads aligned at that site. The number of base pair mismatches between the putative off-target site and the intended site are indicated by color scale with darker colors indicating sites that are more similar to the intended target site (circled). For a nuclease with high-specificity, the intended site should have the highest read count. Better nucleases remove both the higher count sites (to the right of the graph) and the sites with high similarity (darker colored points).

In FIG. 6, HBV 11-12L.520S19, HBV 11-12L638, HBV 11-12L638S19, and HBV 11-12L.699 were compared in the HepG2 HepB1 cell line, which comprises a partial HBV genome including the HBV 11-12 recognition sequence (see PCT/US2019/27203). While the number of reads aligned at the intended site cannot be compared between samples as a measure of total activity at the intended site, the distance between the points indicating the intended site (circled) and the points indicating off-target sites can be compared. The far larger distance between the intended site and the off-target sites for HBV 11-12L.638, HBV 11-12L.638S19 and HBV 11-12L.699 than that of HBV 11-12L.520S19 indicates a large increase in the specificity of the enzyme and a large decrease in cleavage of off-target sites both in number of sites and percentage cleaved.

In summary, the presently disclosed engineered HBV 11-12 meganucleases displayed a range of off-target profiles. In all cases, the intended target site was the most frequently recovered. HBV 11-12L.638 showed no off-targeted above the mock background and HBV 11-12L.520S19 showed the most off-targeting of the four nucleases.

Example 3

Evaluation of HBV 11-12 Meganucleases in HepAD38 Cells

The primary purpose of this experiment was to evaluate whether meganucleases described herein were capable of inactivating and/or eliminating HBV genomes and reduce viral antigen in mammalian cells. In this study, meganuclease effectiveness was evaluated in the HepAD38 cell line. The HepAD38 cell line is a hepatocellular carcinoma cell line engineered to contain a single promoter-inducible 1.1mer integrant copy of HBV capable of producing all the HBV products (Ladner et al., *Antimicrob Agents Chemother.* 1997; 41(8):1715-20). This cell line was used to assess HBV 11-12L.520S19, HBV 11-12L.638, HBV 11-12L.638S19, and HBV 11-12L.699 efficacy against integrated HBV genomes by INDEL and HBsAg reduction analysis.

HepAd38 cells were transfected with 4 different mRNA encoding meganuclease HBV 11-12L.520S19, HBV 11-12L.638, HBV 11-12L.638S19, and HBV 11-12L.699 respectively. All engineered meganucleases target a sequence specific to the HBV P gene (polymerase gene) in the HBV genome. As a control, HepAd38 cells were transfected with mRNA coding for the non-targeting meganuclease PCS 7-8L.197 and mRNA encoding for mCherry. Transfection was conducted 24 hours after seeding, using a lipofectamin-based mRNA transfection protocol. Cells were washed at 24 hours post-transfection to remove remaining transfection complexes. On day 3 and day 6 post-transfection, culture supernatant was harvested to determine HBsAg levels by chemiluminescence (CLIA). Cellular DNA was extracted on day 3 post-transfection and INDEL formation at the HBV 11-12 target site was measured using digital droplet PCR (ddPCR).

Figure 7:
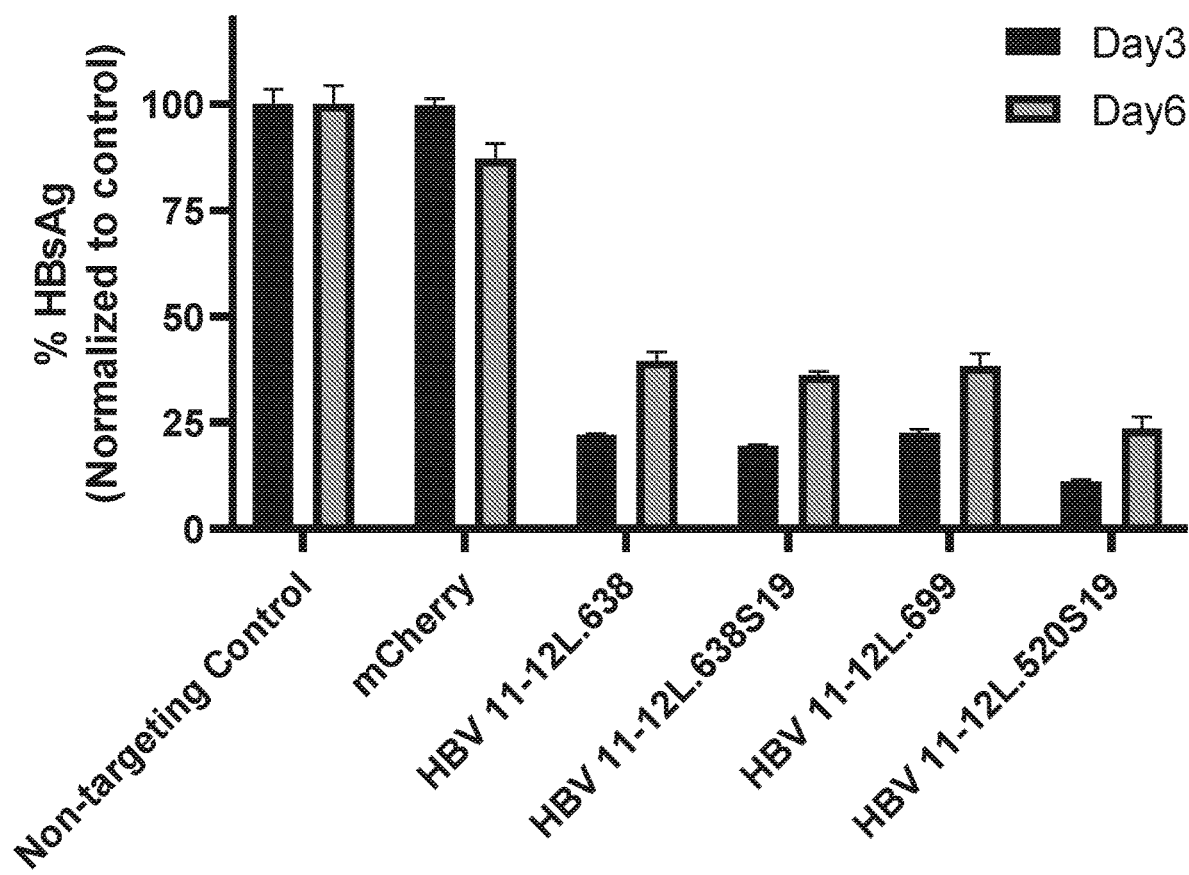
FIG. 7. Bar graph showing the effectiveness of the HBV 11-12L.520S19, HBV 11-12L.638, HBV 11-12L.638S19, HBV 11-12L.699, or a non-targeting control meganuclease in reducing the percent HBsAg in HepAD38 cells.

CLIA data were normalized to the amount of HBsAg in the supernatant of non-targeting meganuclease transfected HepAD38 cells. As shown in FIG. 7, on day 3 post-transfection, cells transfected with HBV 11-12L.520S19 mRNA showed 90% HBsAg reduction in the supernatant compared to non-targeting control. Cells transfected with mRNA expressing meganucleases HBV 11-12L.638S19, HBV 11-12L.638 or HBV 11-12L.699 showed HBsAg reduction of 80.6%, 78% and 77.5% respectively (FIG. 7). Non-targeting control meganuclease and mCherry transfected cells revealed similar HBsAg level on day 3 and 6 post transfection (FIG. 7). HBsAg levels rebounded on day 6 post-transfection to 76.5%, 63.9%, 60.4% and 61.7% HbsAg reduction for meganucleases HBV 11-12L.520S19, HBV 11-12L.638S19, HBV 11-12L.638 and HBV 11-12L.699, respectively (FIG. 7).

Figure 8:
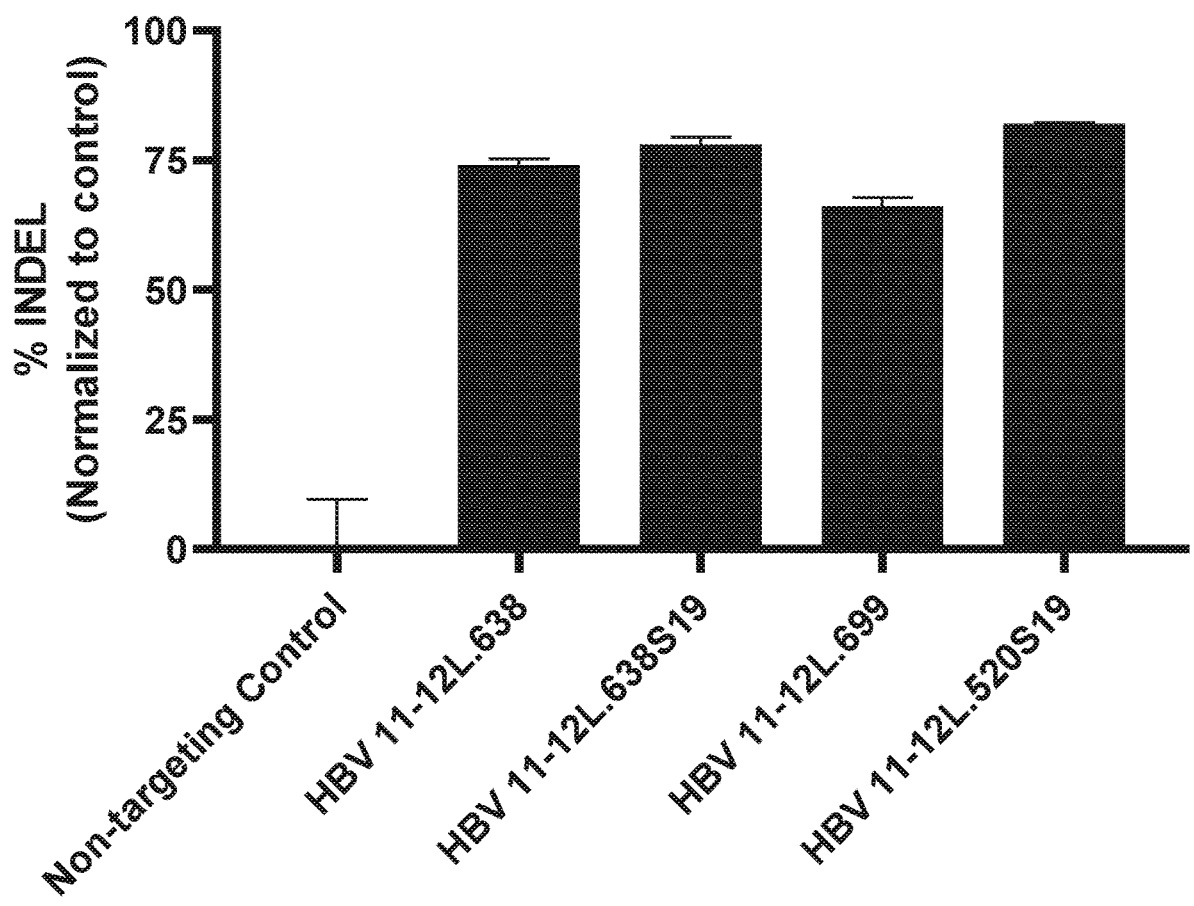
FIG. 8. Bar graph showing on target indel frequency assessed by ddPCR in HepAD38 cells after transfection with the HBV 11-12L.638, HBV 11-12L.699, HBV 11-12L.638S19, HBV 11-12L.520S19, or a non-targeting control meganuclease.

DNA editing efficiency was measured by ddPCR and revealed high levels of on-target editing with all meganucleases in comparison to the non-targeting control. Transfection of meganuclease HBV 11-12L.520S19, HBV 11-12L.638S19, HBV 11-12L.638 and HBV 11-12L.699 resulted in INDEL frequencies of 82%, 78%, 74% and 66% on day 3 post transfection, respectively (FIG. 8). A high correlation of on-target editing on day 3 post transfection with HBsAg reduction was observed, suggesting that the reduction in supernatant HBsAg levels was due to meganuclease activity.

These data demonstrate that transfection of mRNA encoding meganucleases HBV 11-12L.520S19, HBV 11-12L.638, HBV 11-12L.638S19, and HBV 11-12L.699 into HepAD38 cells resulted in high levels of HBsAg reduction between 77% and 90%. High levels of on-targeting editing between 66% and 82% suggest HBsAg reduction is due to the meganuclease activity against HBV genome in AD38 cells.

Example 4

Evaluation of HBV 11-12 Meganucleases in HBV-Infected Primary Human Hepatocytes

The primary purpose of this experiment is to evaluate the meganuclease cutting and degradation efficiency of cccDNA and subsequent reduction of viral antigen in primary human hepatocytes (PHH). PHH represent the only in vitro culture system that supports the entire replication cycle of HBV, including cccDNA formation and HBV DNA replication. PHH were used to assess HBV 11-12L.520S19, HBV 11-12L.638, HBV 11-12L.638S19, and HBV 11-12L.699 efficacy.

De novo infected PHH were transfected with four different mRNA encoding engineered meganucleases HBV 11-12L.520S19, HBV 11-12L.638, HBV 11-12L.638S19, and HBV 11-12L.699 at both 3 and 6 days post infection following cccDNA establishment. Briefly, PHH were seeded 24 hours prior to infection with HBV. The following day, the cells were washed and transfected with TransIT-mRNA (Mirus) according to the manufacturer's protocol both on day 3 (single delivery) and 6 (dual delivery) post infection. A non-targeting engineered meganuclease PCS 7-8L.197 was used as control. Viral DNA was isolated from cells to monitor on-target indel frequency and cccDNA reduction by Southern Blot 3 days post transfection. Cell culture supernatant was collected 3 days post each transfection monitoring secreted HBsAg by chemiluminescence (CLIA) and albumin by ELISA.

Figure 9:
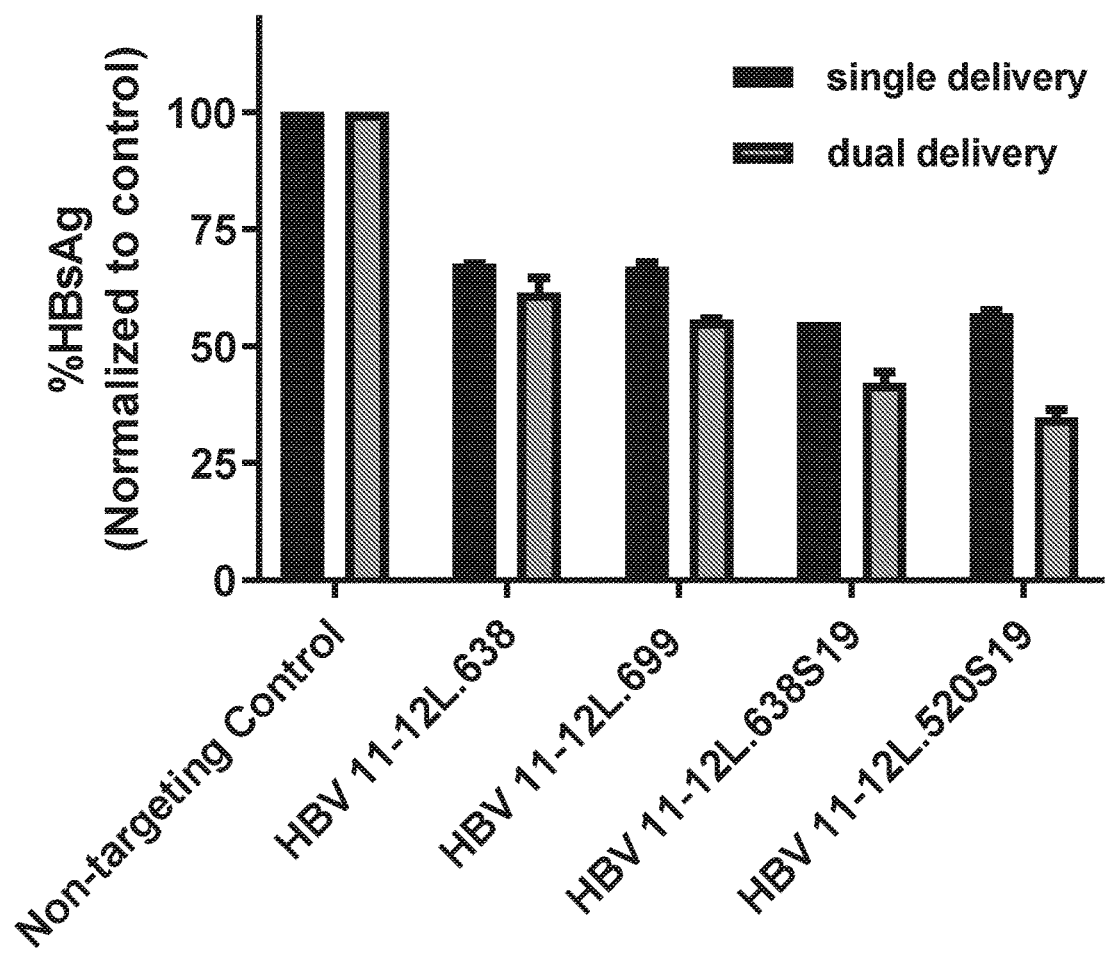
FIG. 9. Bar graph showing the effectiveness of the HBV 11-12L.520S19, HBV 11-12L.638, HBV 11-12L.638S19, HBV 11-12L.699, or a non-targeting control meganuclease in reducing the percent HBsAg in HBV infected primary human hepatocytes (PHH). The meganucleases were transfected once (single delivery) or transfected twice (dual delivery).
Figure 10:
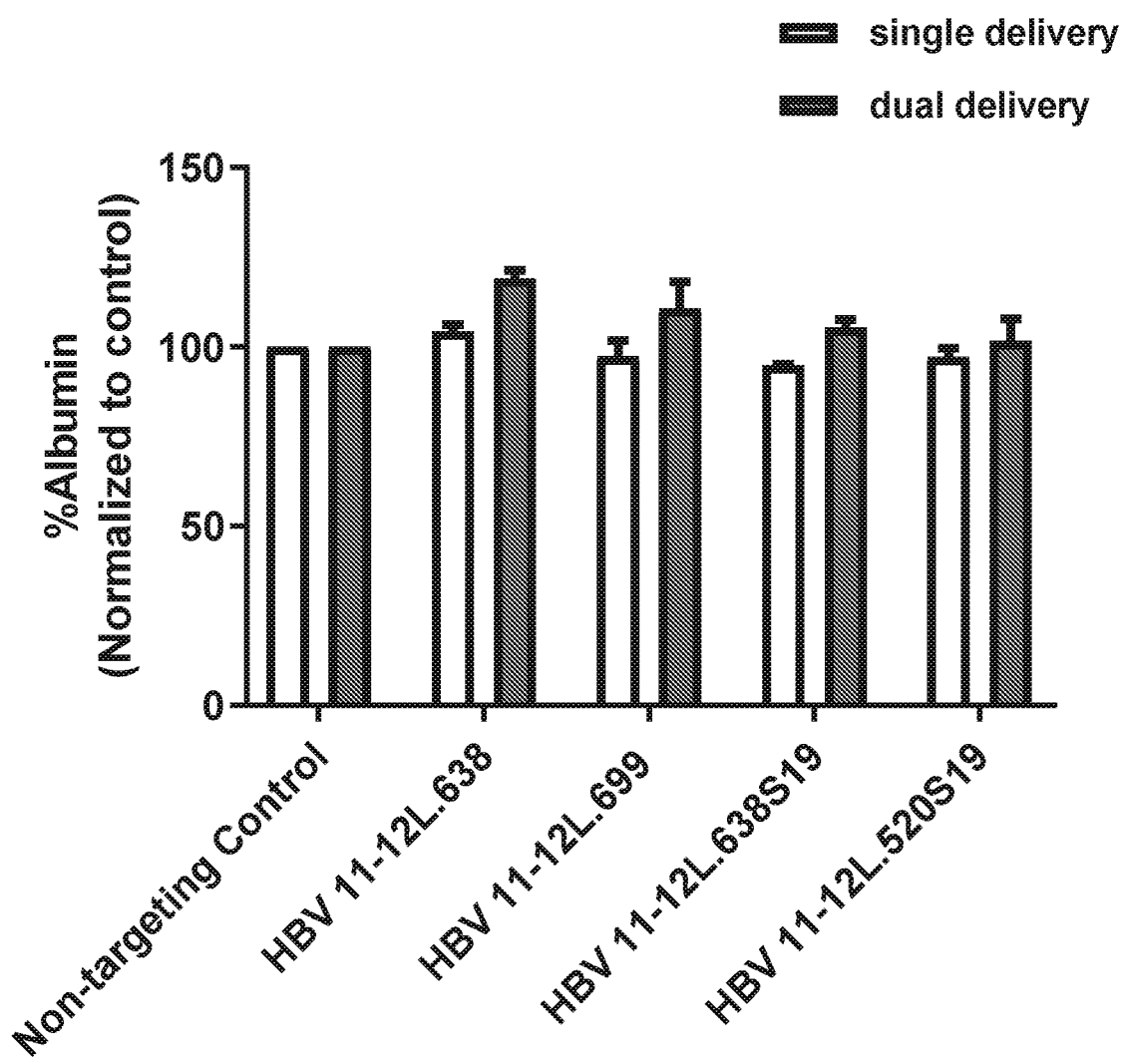
FIG. 10. Bar graph showing albumin levels in PHHs transfected with the HBV 11-12L.520S19, HBV 11-12L.638, HBV 11-12L.638S19, HBV 11-12L.699, or a non-targeting control meganuclease. The meganucleases were transfected once (single delivery) or transfected twice (dual delivery).
Figure 11:
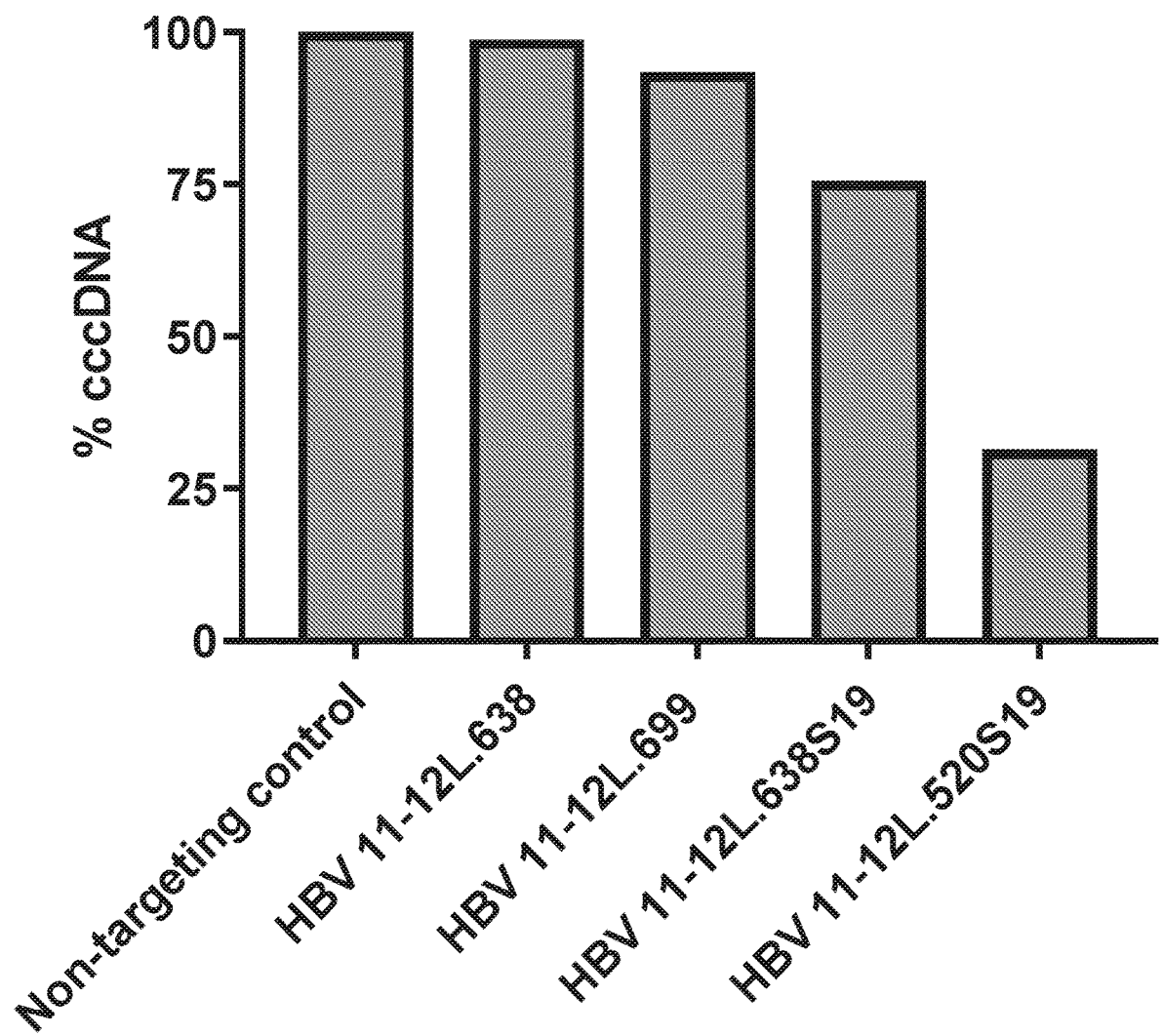
FIG. 11. Bar graph showing the effectiveness of the HBV 11-12L.520S19, HBV 11-12L.638, HBV 11-12L.638S19, HBV 11-12L.699, or a non-targeting control meganuclease in reducing the percent cccDNA in HBV infected PHHs. The levels of cccDNA shown were measured 3 days following the second transfection of the respective meganucleases.
Figure 12:
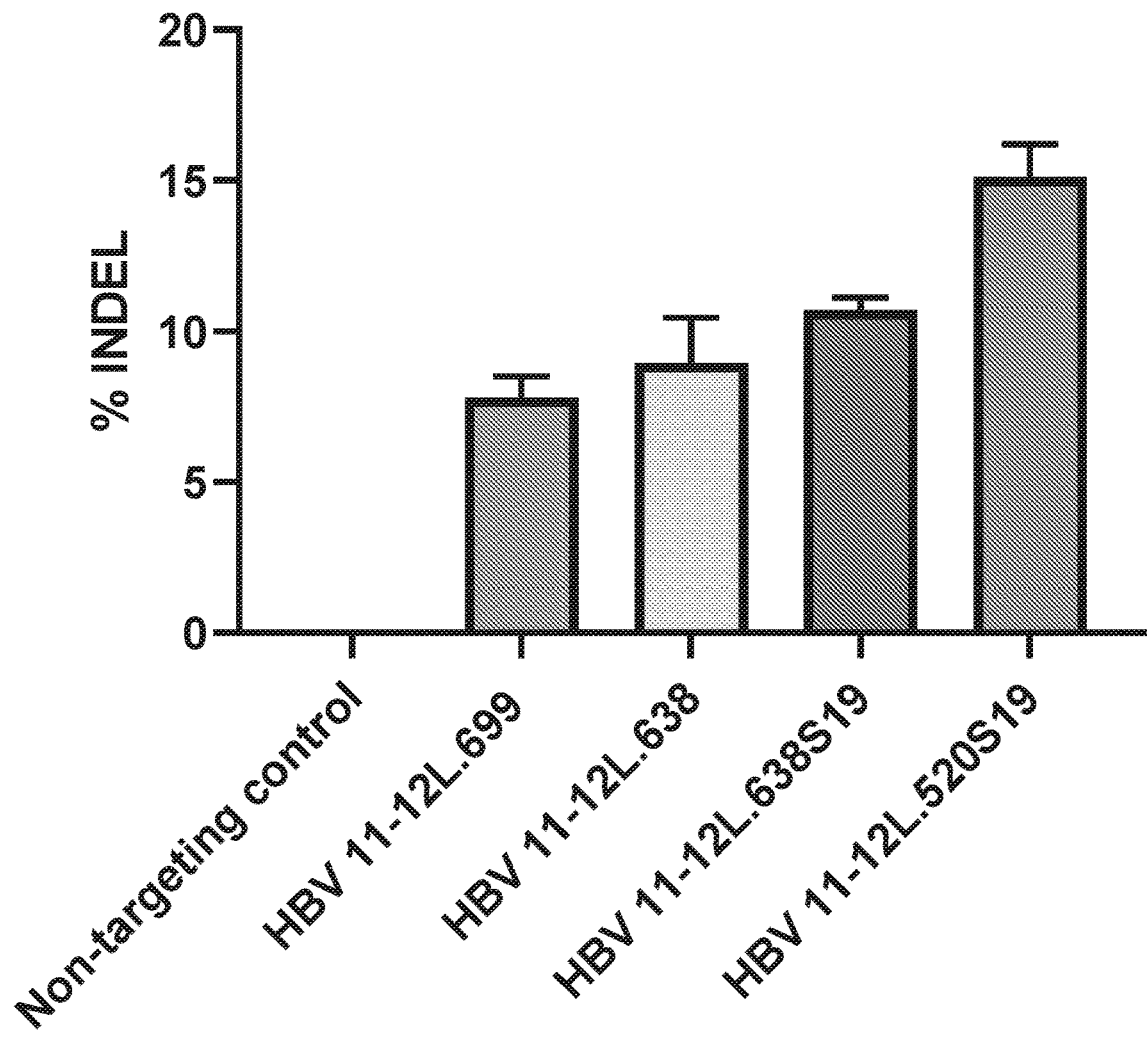
FIG. 12. Bar graph showing on target indel frequency assessed by ddPCR in HBV infected PHHs after transfection with the HBV 11-12L.638, HBV 11-12L.699, HBV 11-12L.638S19, HBV 11-12L.520S19, or a non-targeting control meganuclease. The levels of indels shown were measured 3 days following the second transfection of the respective meganucleases.

As shown in FIG. 9, the non-targeting engineered meganuclease PCS 7-8L.197 showed no effect on HBsAg levels in the supernatant of PHH and all subsequent HBsAg data from targeting engineered meganucleases were normalized to engineered meganuclease PCS 7-8L.197. A single mRNA transfection (single delivery) of engineered meganuclease HBV 11-12L.520S19, HBV 11-12L.638, HBV 11-12L.638S19, or HBV 11-12L.699, demonstrated reductions in extracellular HBsAg levels by 43%, 33%, 45% and 34%, respectively (FIG. 9). Following a second round of mRNA engineered meganuclease transfections (dual delivery) of HBV 11-12L.520S19, HBV 11-12L.638, HBV 11-12L.638S19, or HBV 11-12L.699, HBsAg levels were reduced by 64%, 37%, 57% and 45% respectively (FIG. 9). No toxicity was observed with any evaluated engineered meganuclease, as determined by albumin secretion (FIG. 10). Southern Blot analysis 3 days post the second mRNA delivery demonstrated a significant reduction of cccDNA for engineered meganuclease HBV 11-12L.520S19 and HBV 11-12L.638S19 by 69% and 25%, respectively (FIG. 11). The remaining engineered meganucleases HBV 11-12L.638 and HBV 11-12L.699 reduced cccDNA by 2% and 7%, respectively (FIG. 11). On-target editing of the remaining viral cccDNA showed 15%, 9%, 11%, and 8% indels for HBV 11-12L.520S19, HBV 11-12L.638, HBV 11-12L.638S19, and HBV 11-12L.699, respectively as determined by NGS (FIG. 12).

These data demonstrate mRNA transfection of HBV-infected primary human hepatocytes with engineered meganuclease HBV 11-12L.520S19, HBV 11-12L.638, HBV 11-12L.638S19, or HBV 11-12L.699 show varying levels of reduction in HBsAg and cccDNA without any signs of toxicity. The HBsAg and cccDNA reduction in engineered meganuclease mRNA transfected infected cells strongly suggest on-target activity mediated by the meganuclease activity.

Example 5

Generation of Indels at Recognition Sequence by Engineered HBV 11-12 Meganucleases in Hep3B Cells After Electroporation with HBV 11-12 mRNA Additional HBV 11-12 meganucleases were generated to improve on-target activity and reduce off-target cutting, yielding two additional HBV nucleases—HBV 11-12L.1036 and HBV 11-12L.1090. Studies were conducted to evaluate the efficacy of these optimized HBV 11-12 meganucleases for causing indels at their intended recognition sequence (i.e., the HBV 11-12 recognition sequence). Indel formation was detected in these experiments by digital PCR analysis as described in Example 1.

Figure 13:
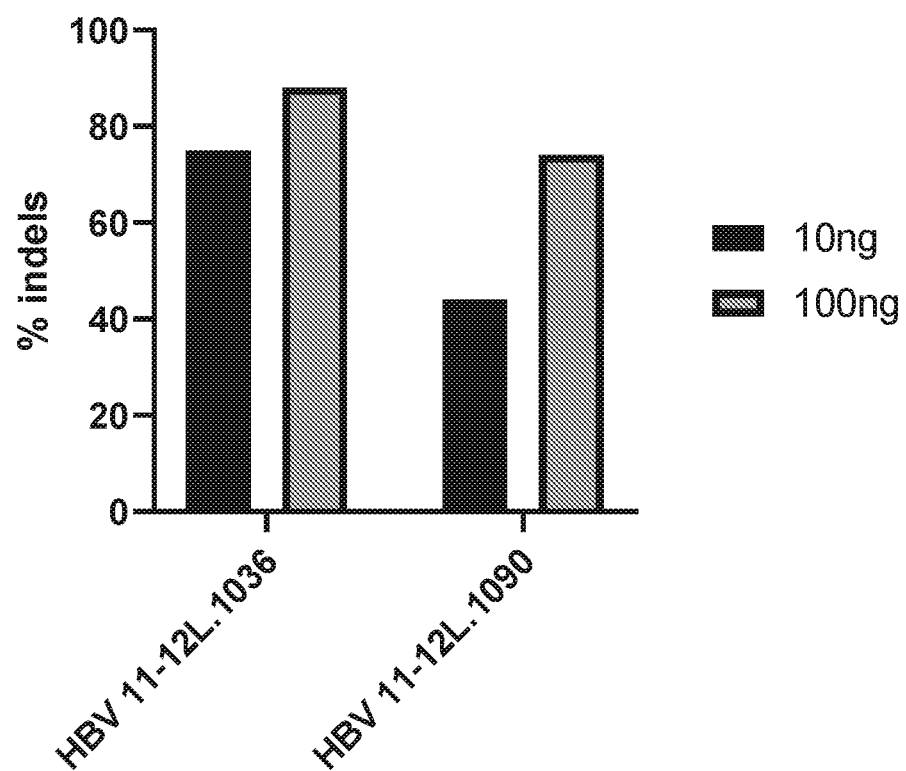
FIG. 13. Bar graph showing on target indel frequency assessed by ddPCR in Hep3B cells after transfection with the HBV 11-12L.1036 or HBV 11-12L.1090 meganucleases.

Both HBV 11-12L.1036 and HBV 11-12L.1090 show high levels of on-target editing (FIG. 13). HBV 11-12L.1036 showed higher editing efficiency than HBV 11-12L.1090, with 88% indels at the 100 ng dose. Both nucleases resulted in dose-dependent indels in Hep3B cells.

These data demonstrate that both nucleases tested show comparable or better on-target editing than previously described HBV 11-12 meganucleases.

Example 6

Off-Targeting Analysis of HBV 11-12 Meganucleases

In these studies, an oligo capture assay as described in example 2 was used to identify off target cutting induced by the HBV 11-12L.1036 and HBV 11-12L.1090 meganucleases. Off target cutting was assessed in a lentivirus-modified HepG2 cell line that comprises in its genome a partial HBV genome comprising the HBV 11-12 recognition sequence.

Figure 14:
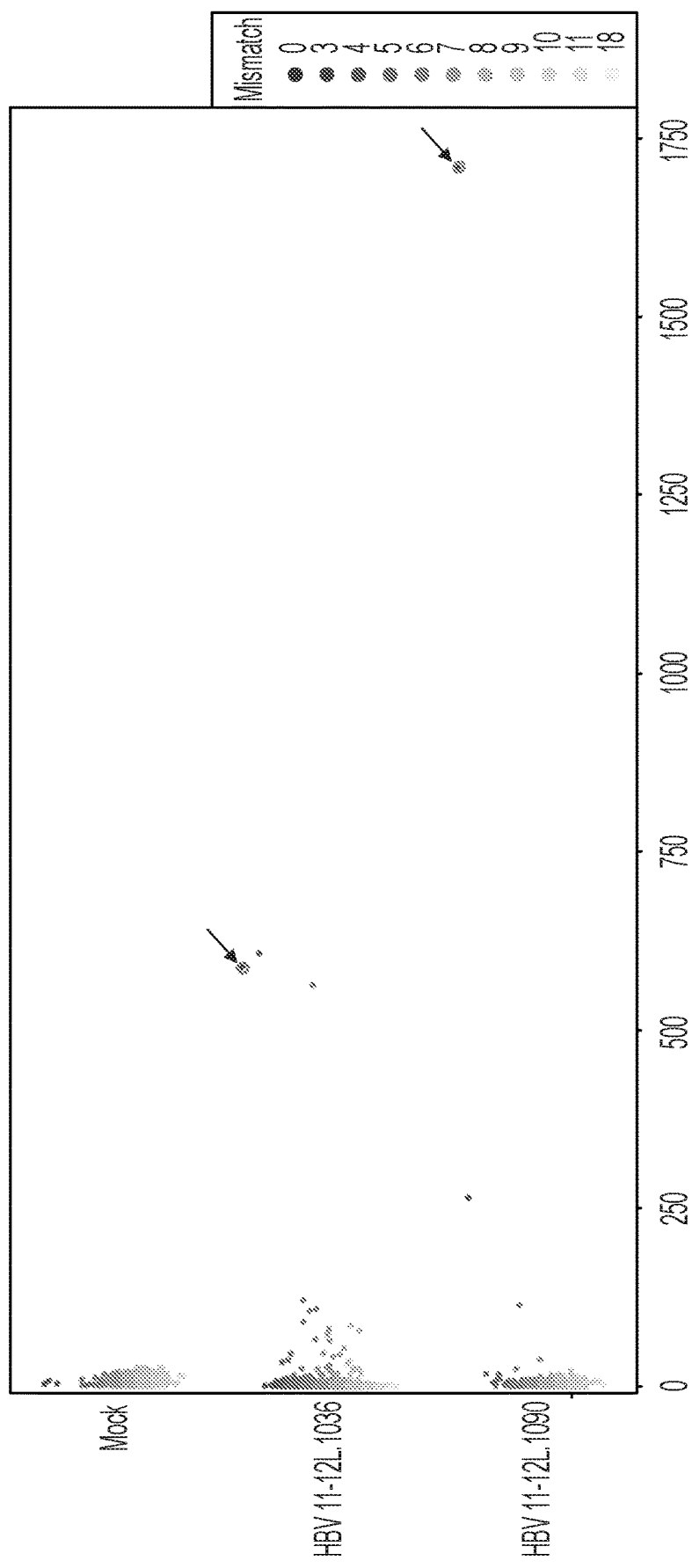
FIG. 14. Graph depicting results from an oligo capture assay to identify off target cutting induced by the HBV 11-12L.1036 and HBV L.1090 meganucleases transfected in HepG2 HepB1 cells. The dots indicated as circled represent the on-target site.

As shown in FIG. 14, HBV 11-12L.1036 and HBV 11-12L.1090 were compared in the HepG2 HepB1 cell line, which comprises a partial HBV genome including the HBV 11-12 recognition sequence. While the number of reads aligned at the intended site cannot be compared between samples as a measure of total activity at the intended site, the distance between the points indicating the intended site (circled) and the points indicating off-target sites can be compared. The far larger distance between the intended site and the off-target sites for HBV 11-12L.1090 than that of HBV 11-12L.1036 indicates a large increase in the specificity of the enzyme and a large decrease in cleavage of off-target sites both in number of sites and percentage cleaved.

In summary, HBV 11-12L.1090 showed only two off-target sites significantly above the mock background. Those same two sites were recovered much more frequently in the HBV 11-12L.1036 sample along with an additional ~20 off-target sites.

Example 7

Evaluation of HBV 11-12 Meganucleases in HBV-Infected Primary Human Hepatocytes

The primary purpose of this experiment is to evaluate the meganuclease cutting and degradation efficiency of cccDNA and subsequent reduction of viral antigen in PHH. The PHH were used to assess HBV 11-12L.520S19, HBV 11-12L.1036, and HBV 11-12L.1090 efficacy.

De novo infected PHH were transfected with 4 different mRNA encoding engineered meganucleases, PCS 7-8 L.197, HBV 11-12L.520S19, HBV 11-12L.1036, and HBV 11-12L.1090 at both 3 and 6 days post infection following cccDNA establishment. Briefly, PHH were seeded 24 hours prior to infection with HBV. The following day, the cells were washed and transfected with Transit-mRNA (Mires) according to the manufacturer's protocol both on day 3 (first transfection and 6 (second transfection) post infection. A non-targeting engineered meganuclease PCS 7-8 L.197 that targets the PCSK9 gene was used as control. Viral DNA was isolated from cells to monitor cccDNA reduction by Southern Blot 3, 6, 9, 12, and 17 days post transfection. Cell culture supernatant was also collected 3, 6, 9, 12, and 17 days post each transfection monitoring secreted HBsAg by chemiluminescence (CLIA).

Figure 15:
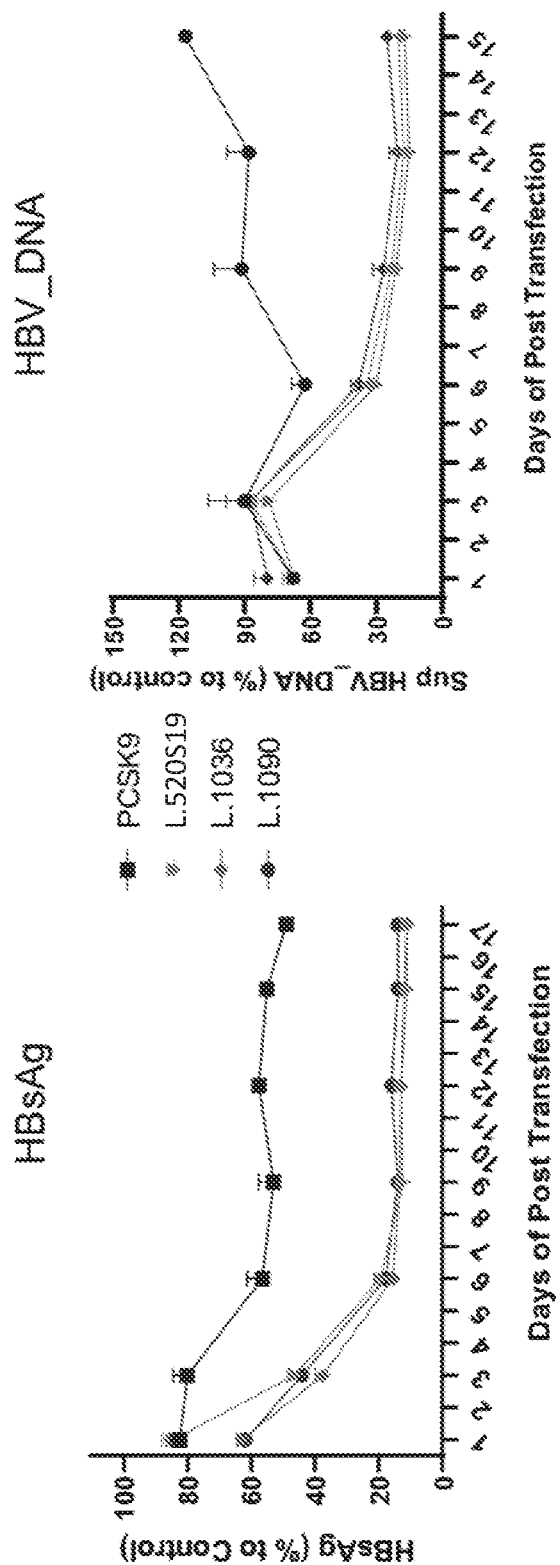
FIG. 15. Line graph showing the effectiveness of the HBV 11-12L.520S19, HBV 11-12L.1036, HBV 11-12L.1090, or a non-targeting PCSK9 control meganuclease PCS 7-8 L.197 in reducing the percent HBsAg (left panel) or HBV DNA (right panel) in HBV infected PHH.
Figure 16A:
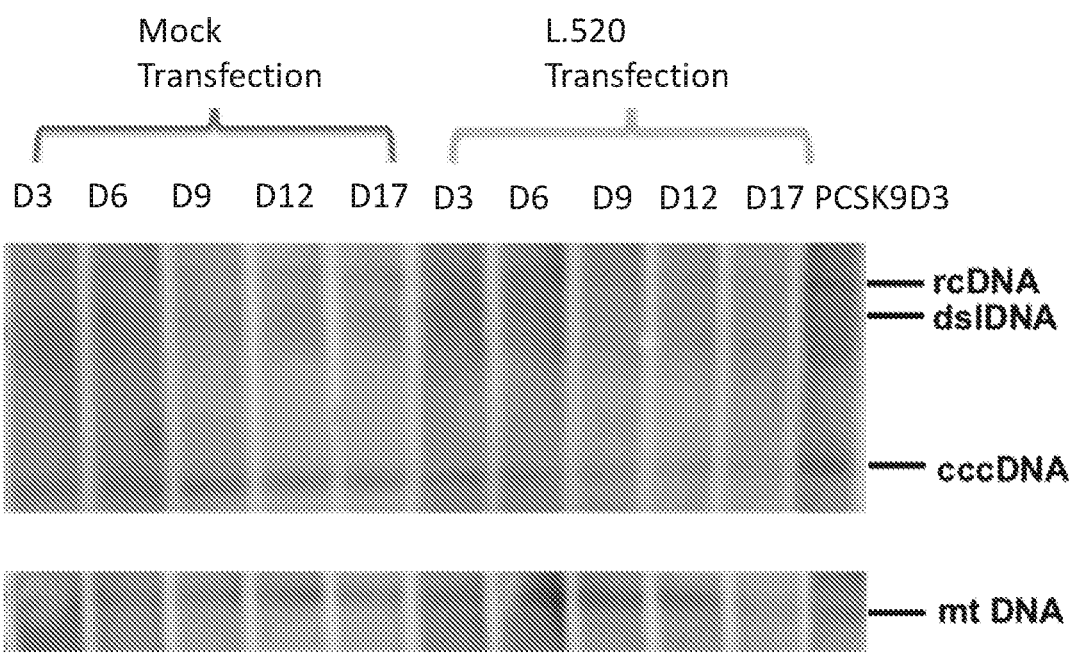
FIGS. 16A-16B.
Figure 16B:
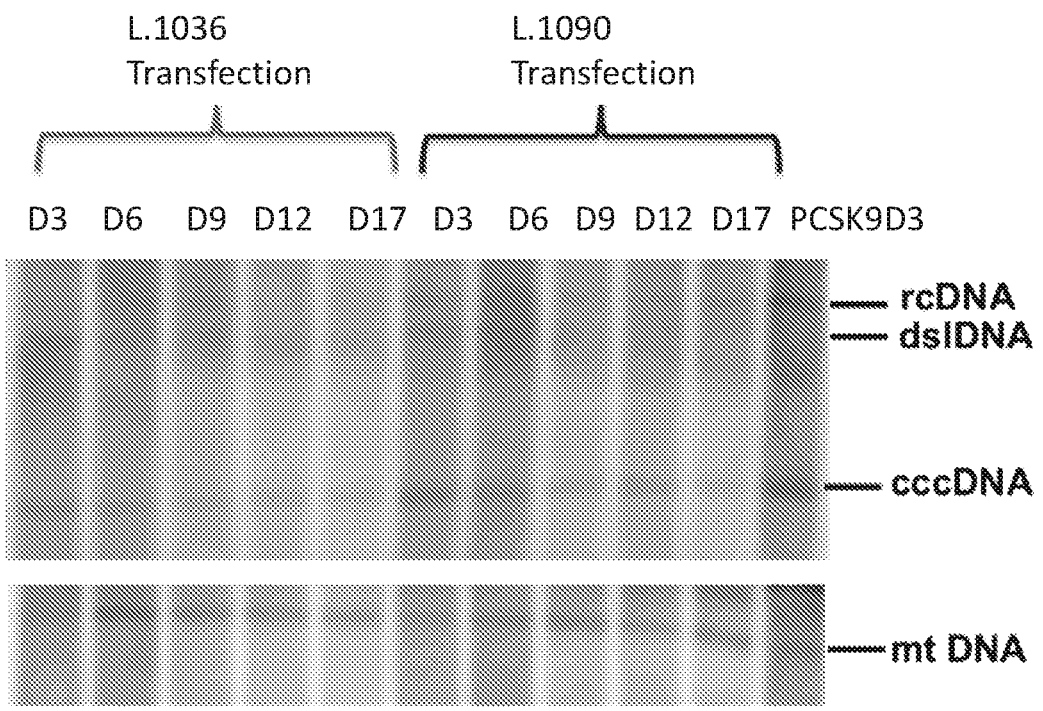
Figure 17A:
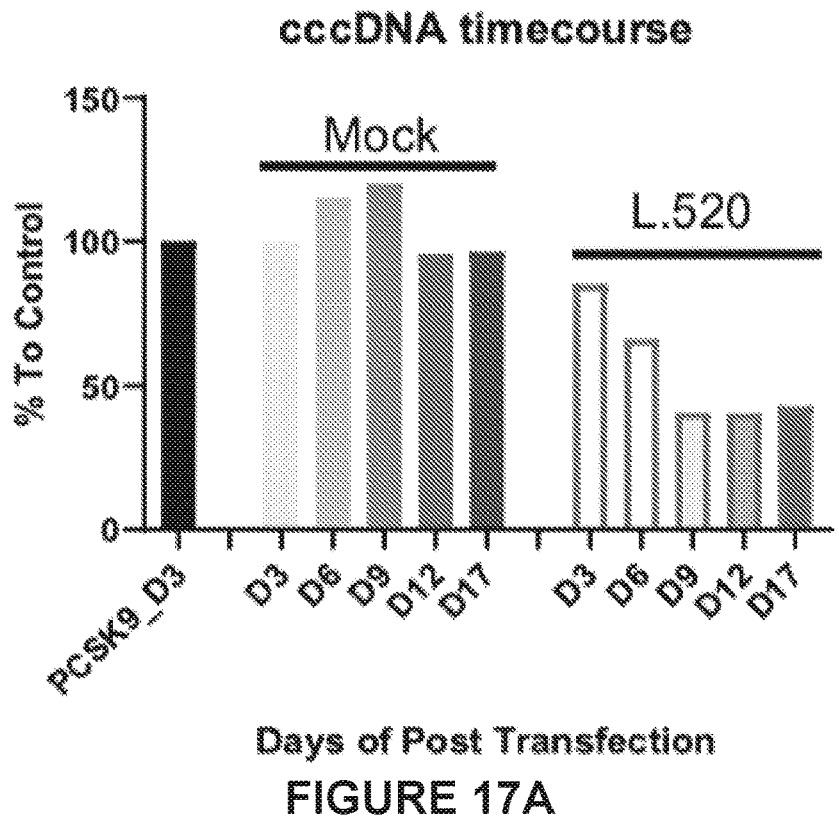
FIGS. 17A-17B.
Figure 17B:
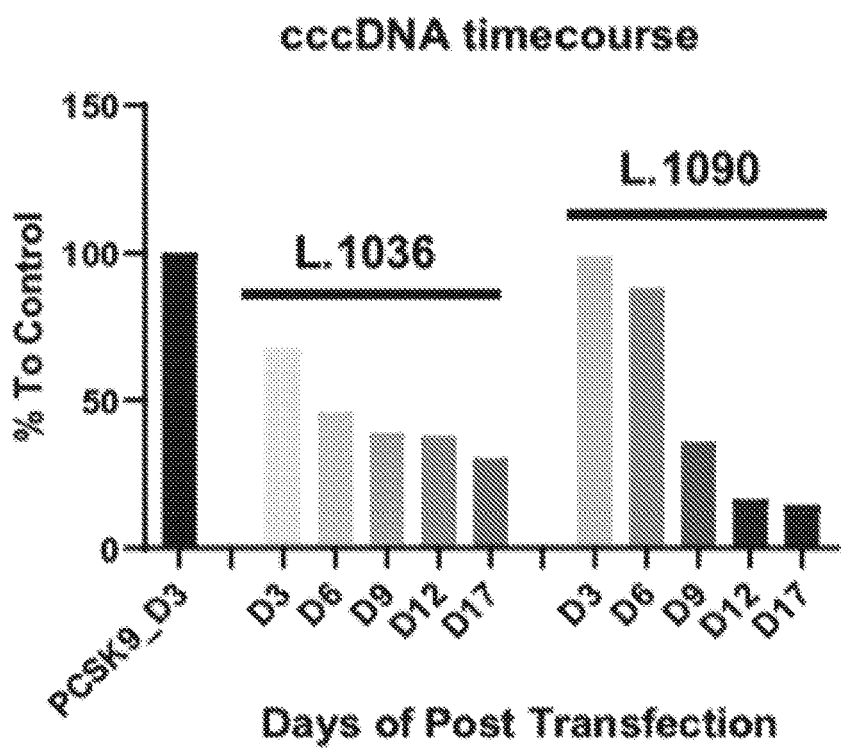

As shown in FIG. 15, the non-targeting engineered meganuclease PCS 7-8 L.197 showed little effect on HBsAg levels in the supernatant of PHH and all subsequent HBsAg data from targeting engineered meganucleases were normalized to PHH transfected with a mock cherry vector. Similarly, there was no effect in the supernatant levels of HBV DNA for the control PCS 7-8 L.197. Two mRNA transfections of engineered meganucleases HBV 11-12L.520S19, HBV 11-12L.1036, and HBV 11-12L.1090, demonstrated reductions in extracellular HBsAg levels by approximately 85% after 6 days post the first transfection maintained out to 17 days (FIG. 15). Southern Blot analysis at 3, 6, 9, 12, and 17 days post the first mRNA delivery demonstrated a significant reduction of cccDNA for engineered meganuclease HBV 11-12L.520S19, HBV 11-12L.1036, and HBV 11-12L.1090 compared to untreated cells (FIG. 16A and FIG. 16B). A double stranded linear DNA (dslDNA) species was detectable 3 days after transfection in the engineered meganuclease-treated samples, but disappeared by day 17. The time course quantification of reduction in cccDNA following transfection is shown in FIG. 17A and FIG. 17B. For the HBV 11-12L.520S19 and HBV 11-12L.1036 meganucleases there was a reduction in cccDNA of up to 60%, which was maintained until day 17 (FIGS. 17A and 17B). The engineered meganuclease, HBV 11-12L.1090 reduced cccDNA by up to 80% (FIG. 17B).

These data demonstrate mRNA transfection of HBV-infected primary human hepatocytes with engineered meganuclease HBV 11-12L.520S19, HBV 11-12L.1036, and HBV 11-12L.1090 reduce HBsAg and cccDNA with the HBV 11-12L.1036 and HBV 11-12L.1090 meganucleases showing the greatest reduction. The HBsAg and cccDNA reduction in engineered meganuclease mRNA transfected infected cells strongly suggest on-target activity mediated by the meganuclease activity consistent with the results obtained in Example 4.

Example 8

Evaluation of HBV Integration and Translocation Events in HBV-Infected Primary Human Hepatocytes Following Treatment with HBV 11-12 Meganucleases The primary purpose of this experiment was to evaluate the number and position of HBV integration and translocation events following transfection of the HBV 11-12L.520S19, HBV 11-12L.1036, and HBV 11-12L.1090 meganucleases in PHH infected with HBV. De novo HBV infected PHH were transfected with different mRNA encoding engineered meganucleases HBV 11-12L.520S19, HBV 11-12L.1036, and HBV 11-12L.1090 or a mock transfection as described in Example 7.

This integration/translocation assay is accomplished using HBV DNA target enrichment from PHH genomic DNA followed by PacBio long read sequencing to identify chimeric HBV/human DNA junctions. Briefly, PHH genomic DNA was isolated and sheared to a size that is slightly less than 10 kb. DNA libraries were prepared by ligating DNA adapters to the sheared DNA and the DNA library was purified from the ligation reaction mixture using AMpure PB magnetic beads (Beckman Coulter, Indianapolis, IN) and PCR amplified. The HBV target genome was enriched by incubating the sheared and amplified PHH genomic library with 120 bp biotinylated probes (Integrated DNA Technologies, Coralville, IA) complementary to various regions of the HBV genome. In addition, an internal normalization control was established from the host genome using similar probes that were specific for a limited number of genes of the host genome. Next magnetic streptavidin dynabeads (ThermoFisher Scientific, Waltham, MA) were used to pull down the hybridized biotinylated probe/HBV or host genomic DNA. These isolated genomic DNA fragments were then PCR amplified and purified with AMpure PB magnetic beads. The samples were then indexed, pooled, and DNA sequenced using long range next generation DNA sequencing with sequenced read lengths of between 5 kb and 10 kb. From the sequencing data, the number of HBV integrations and translocation events were determined. The chimeric junction between PHH host cell genomic DNA and HBV genomic sequence indicates an integration event. When two different chromosomal host cell DNA fragments flanking the HBV genomic sequence are detected, this indicates a chromosomal translocation event.

Figure 18A:
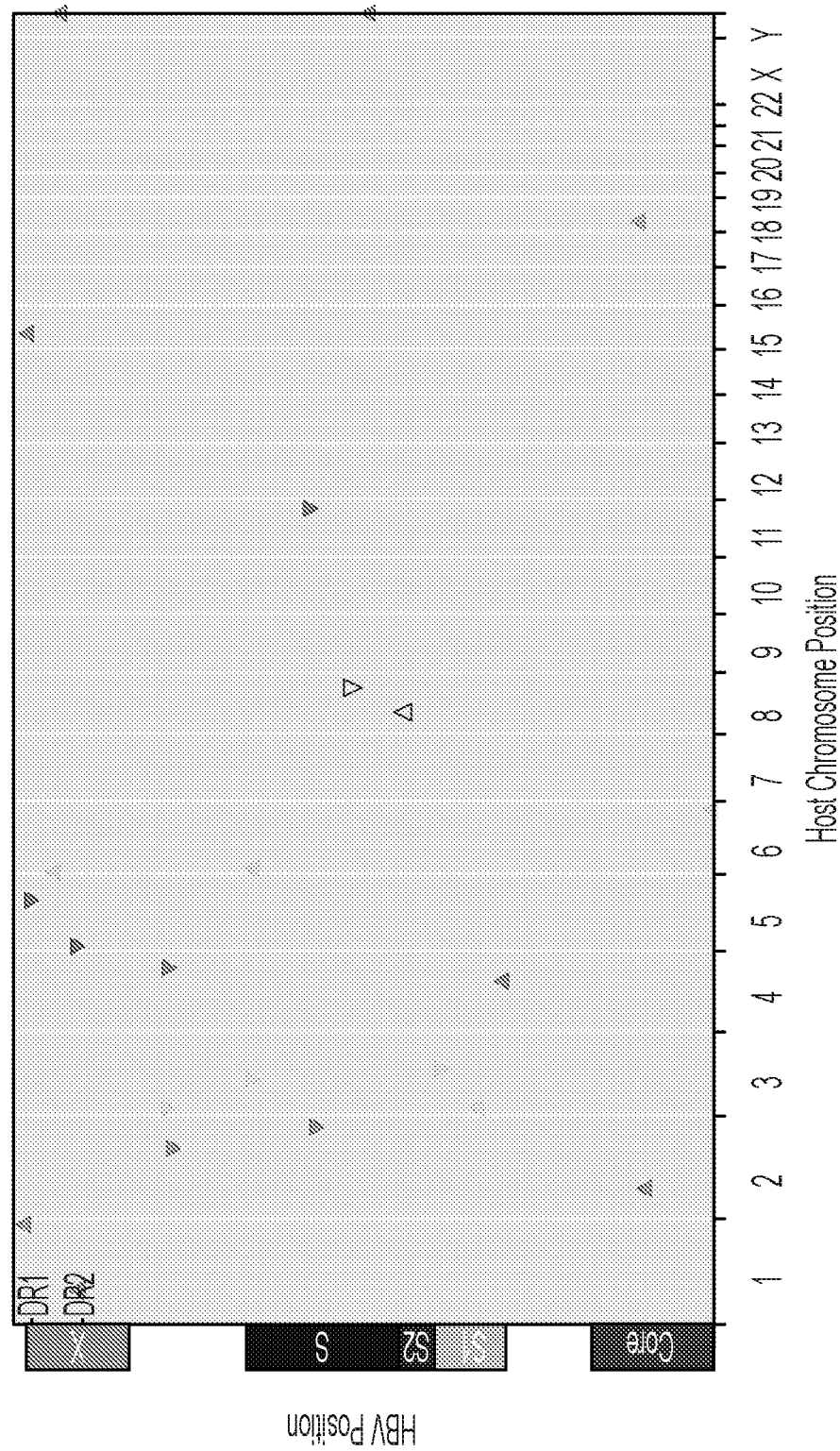
Figure 18B:
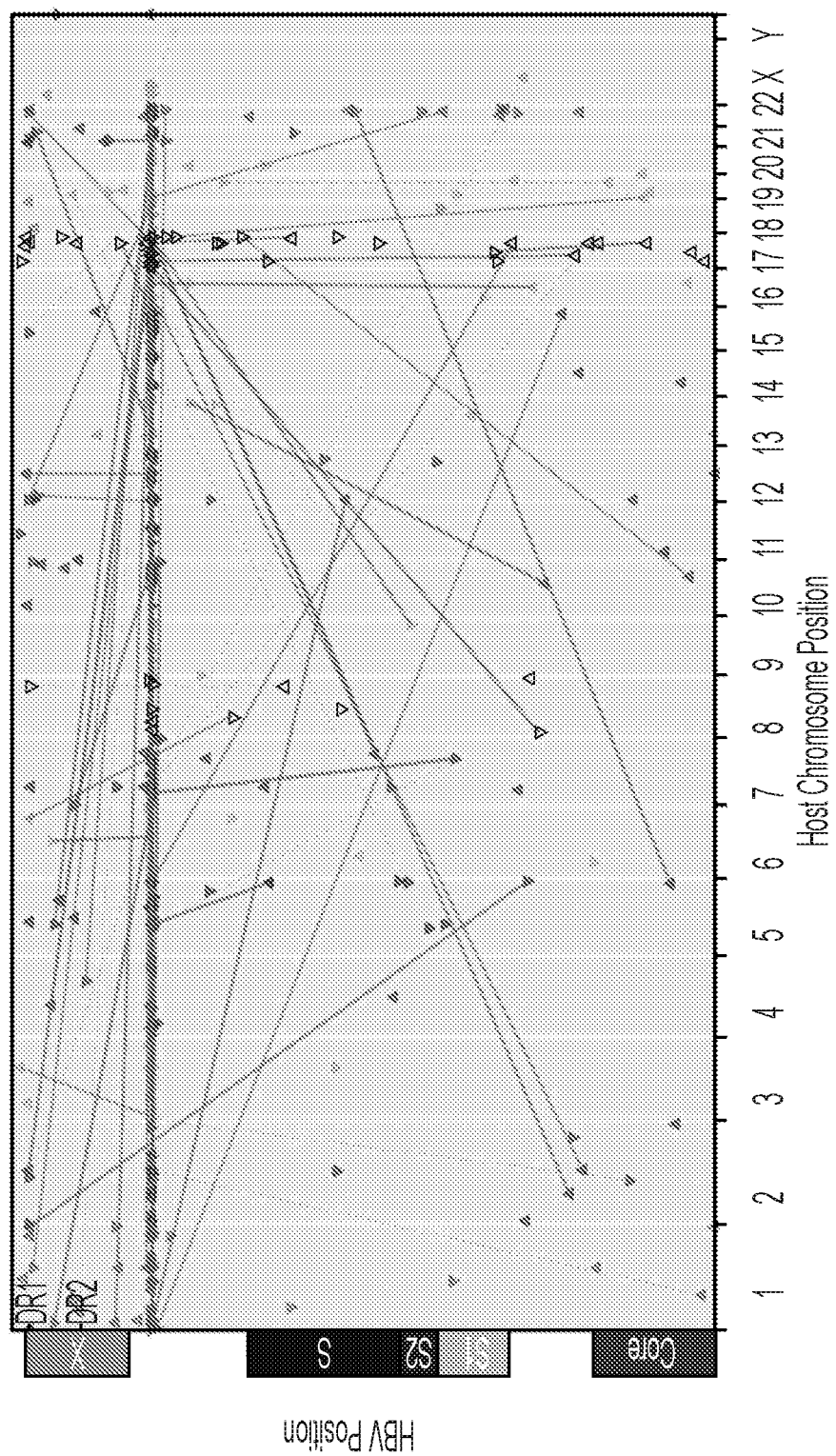
Figure 18C:
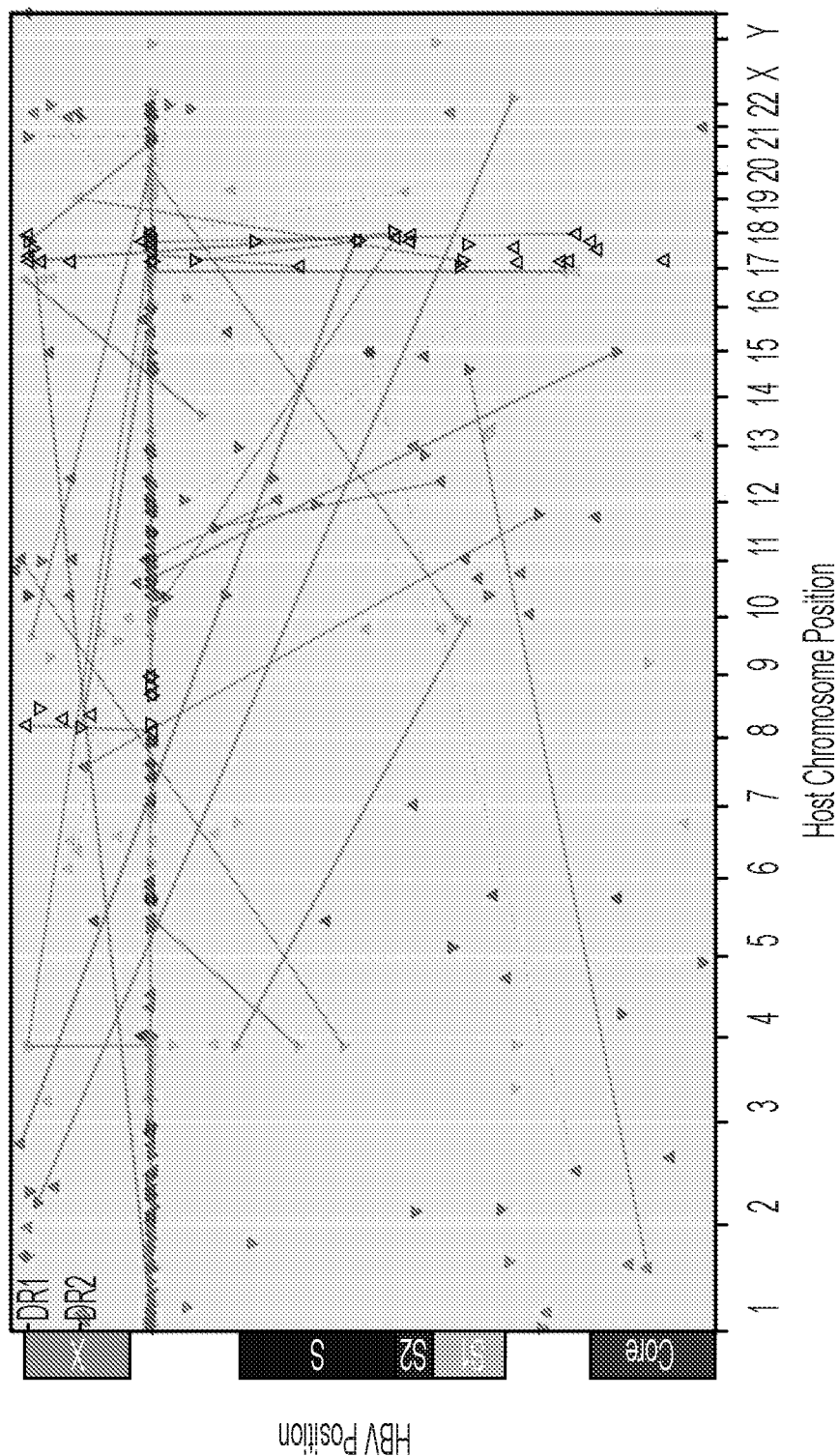

FIG. 18A-18D provides diagrams showing HBV integration events (i.e., chimeric sequence reads between a host genomic fragment and HBV genomic fragment) shown with triangles. FIG. 18A represents integration and translocation information from infected PHH that were mock transfected. FIG. 18B, 18C, and 18D shows the integration and translocation events of infected PHH that were transfected with the HBV 11-12L.520S19, HBV 11-12L.1036, and HBV 11-12L.1090 meganucleases, respectively.

The infected PHH transfected with the HBV 11-12L.520S19 and HBV 11-12L.1036 meganucleases had similarly elevated levels of HBV integrations, whereas the mock control and HBV 11-12L.1090 transfected PHH had lower levels of HBV integrations. As shown in FIG. 18, the HBV 11-12L.520S19 nuclease had substantially more translocation events compared to the HBV 11-12L.1036 meganuclease. The HBV 11-12L.1090 meganuclease showed no translocation events identical to the mock control.

A summary of the depicted data in FIG. 18 is provided in table 4 below. The data shown in this table was normalized in two ways. The first HBV normalization was the number of HBV genomic reads divided by the total number of host reads. The second chimeric normalization was the number of chimeric reads (i.e., the number of reads where both an HBV genomic segment and a host cell genomic segment were in a contiguous sequence) divided by the total number of host reads. This normalization procedure takes into account any differences in sample preparation, bead pull down efficiency, or library preparation and amplification between individual samples. The data of table 4 quantifies that the HBV 11-12L.1036 and HBV 11-12L.1090 meganucleases had less total translocation events than the HBV 11-12L.520S19 meganuclease with the HBV 11-12L.1090 meganuclease having no detectable translocation events. In addition, the chimeric normalization column indicates that the HBV 11-12L.1036 and HBV 11-12L.1090 meganucleases had approximately 1.4 and 9.2 fold less HBV integration or integration and translocation events, respectively than the HBV 11-12L.520S19 meganuclease.

TABLE 4

HBV Integration and Translocation Event Summary

| Sample | HBV Reads | Chimeric Reads | Host Reads | Transloc. | HBV Norm. | Chim. Norm. |
|---|---|---|---|---|---|---|
| Mock | 2836 | 21 | 97817 | 0 | 0.029 | 0.00021 |
| HBV 11-12L.520S19 | 14776 | 10223 | 122892 | 82 | 0.12 | 0.083 |
| HBV 11-12L.1036 | 6080 | 4088 | 69173 | 56 | 0.088 | 0.059 |
| HBV 11-12L.1090 | 5886 | 1010 | 111814 | 0 | 0.053 | 0.0090 |

Overall, these data demonstrate that it is possible to quantify HBV integration and translocation events in PHH. Following this procedure, it was determined that each meganuclease results in differing levels of HBV integrations or HBV integration and translocation events. Coupled with data provided in FIG. 17, the HBV 11-12L.1090 meganuclease demonstrated the largest reduction in cccDNA and the lowest number of HBV integrations and translocation events.

---

Sequence Listing

SEQ ID NO: 1
MNTKYNKEFLLYLAGFVDGDGSIIAQIKPNQSYKFKHQLSLAFQVTQKTQRRWFLD
KLVDEIGVGYVRDRGSVSDYILSEIKPLHNFLTQLQPFLKLKQKQANLVLKIIWRLPS
AKESPDKFLEVCTWVDQIAALNDSKTRKTTSETVRAVLDSLSEKKKSSP

SEQ ID NO: 2
LAGLIDADG

SEQ ID NO: 3
TTCCACTGCCTTCCACCAAGCTCTGCAGGATCCCAGAGTCAGGGGTCTGTATTTT
CCTGCTGGTGGCTCCAGTTCAGGAACAGTAAACCCTGCTCCGAATATTGCCTCTC
ACATCTCGTCAATCTCCGCGAGGACTGGGGACCCTGTGGCGAACATGGAGAACA

```
TCACATCAGGATTCCTAGGACCCCTGCTCGTGTTACAGGCGGGGTTTTCTTGTTG
ACAAGAATCCTCACAATACCGCAGAGTCTAGACTCGTGGTGGACTTCTCTCAATT
TTCTAGGGGGATCACCCGTGTGTCTTGGCCAAAATTCGCAGTCCCCAACCTCCAA
TCACTCACCAACCTCCTGTCCTCCAATTTGTCCTGGTTATCGCTGGATGTGTCTGC
GGCGTTTTATCATATTCCTCTTCATCCTGCTGCTATGCCTCATCTTCTTATTGGTTC
TTCTGGATTATCAAGGTATGTTGCCCGTTTGTCCTCTAATTCCAGGATCAACAAC
AACCAGTACGGGACCATGCAAAACCTGCACGACTCCTGCTCAAGGCAACTCTAT
GTTTCCCTCATGTTGCTGTACAAAACCTACGGATGGAAATTGCACCTGTATTCCC
ATCCCATCGTCCTGGGCTTTCGCAAAATACCTATGGGAGTGGGCCTCAGTCCGTT
TCTCTTGGCTCAGTTTACTAGTGCCATTTGTTCAGTGGTTCGTAGGGCTTTCCCCC
ACTGTTTGGCTTTCAGCTATATGGATGATGTGGTATTGGGGGCCAAGTCTGTACA
GCATCGTGAGTCCCTTTATACCGCTGTTACCAATTTTCTTTTGTCTCTGGGTATAC
ATTTAAACCCTAACAAAACAAAAAGATGGGGTTATTCCCTAAACTTCATGGGTTA
CATAATTGGAAGTTGGGGAACTTTGCCACAGGATCATATTGTACAAAAGATCAA
ACACTGTTTTAGAAAACTTCCTGTTAACAGGCCTATTGATTGGAAAGTATGTCAA
AGAATTGTGGGTCTTTTGGGCTTTGCTGCTCCATTTACACAATGTGGATATCCTGC
CTTAATGCCTTTGTATGCATGTATACAAGCTAAACAGGCTTTCACTTTCTCGCCAA
CTTACAAGGCCTTTCTAAGTAAACAGTACATGAACCTTTACCCCGTTGCTCGGCA
ACGGCCTGGTCTGTGCCAAGTGTTTGCTGACGCAACCCCCACTGGCTGGGGCTTG
GCCATAGGCCATCAGCGCATGCGTGGAACCTTTGTGGCTCCTCTGCCGATCCATA
CTGCGGAACTCCTAGCCGCTTGTTTTGCTCGCAGCCGGTCTGGAGCAAAGCTCAT
CGGAACTGACAATTCTGTCGTCCTCTCGCGGAAATATACATCGTTTCCATGGCTG
CTAGGCTGTGCTGCCAACTGGATCCTTCGCGGAACGTCCTTTGTCTACGTCCCGT
CGGCGCTGAATCCCGCGGACGACCCCTCTCGGGGCCGCTTGGGACTCTCTCGTCC
CCTTCTCCGTCTGCCGTTCCAGCCGACCACGGGGCGCACCTCTCTTTACGCGGTCT
CCCCGTCTGTGCCTTCTCATCTGCCGGTCCGTGTGCACTTCGCTTCACCTCTGCAC
GTTGCATGGAGACCACCGTGAACGCCCATCAGATCCTGCCCAAGGTCTTACATAA
GAGGACTCTTGGACTCCCAGCAATGTCAACGACCGACCTTGAGGCCTACTTCAAA
GACTGTGTGTTTAAGGACTGGGAGGAGCTGGGGGAGGAGATTAGGTTAAAGGTC
TTTGTATTAGGAGGCTGTAGGCATAAATTGGTCTGCGCACCAGCACCATGCAACT
TTTTCACCTCTGCCTAATCATCTCTTGTACATGTCCCACTGTTCAAGCCTCCAAGC
TGTGCCTTGGGTGGCTTTGGGGCATGGACATTGACCCTTATAAAGAATTTGGAGC
TACTGTGGAGTTACTCTCGTTTTTGCCTTCTGACTTCTTTCCTTCCGTCAGAGATCT
CCTAGACACCGCCTCAGCTCTGTATCGAGAAGCCTTAGAGTCTCCTGAGCATTGC
TCACCTCACCATACTGCACTCAGGCAAGCCATTCTCTGCTGGGGGGAATTGATGA
CTCTAGCTACCTGGGTGGGTAATAATTTGGAAGATCCAGCATCCAGGGATCTAGT
AGTCAATTATGTTAATACTAACATGGGTTTAAAGATCAGGCAACTATTGTGGTTT
CATATATCTTGCCTTACTTTTGGAAGAGAGACTGTACTTGAATATTTGGTCTCTTT
CGGAGTGTGGATTCGCACTCCTCCAGCCTATAGACCACCAAATGCCCCTATCTTA
TCAACAATTCCGGAAACTACTGTTGTTAGACGACGGGACCGAGGCAGGTCCCCT
AGAAGAAGAACTCCCTCGCCTCGCAGACGCAGATCTCAATCGCCGCGTCGCAGA
AGATCTCAATCTCGGGAATCTCAATGTTAGTATTCCTTGGACTCATAAGGTGGGA
AACTTTACGGGGCTTTATTCCTCTACAGTACCTATCTTTAATCCTGAATGGCAAAC
TCCTTCCTTTCCTAAGATTCATTTACAAGAGGACATTATTAATAGGTGTCAACAAT
TTGTGGGCCCTCTCACTGTAAATGAAAAGAGAAGATTGAAATTAATTATGCCTGC
TAGATTCTATCCTACCCACACTAAATATTTGCCCTTAGACAAAGGAATTAAACCT
TATTATCCAGATCAGGTAGTTAATCATTACTTCCAAACCAGACATTATTTACATA
CTCTTTGGAAGGCTGGTATTCTATATAAGAGGGAAACCACACGTAGCGCATCATT
TTGCGGGTCACCATATTCTTGGGAACAAGAGCTACAGCATGGGAGGTTGGTCATC
AAAACCTCGCAAAGGCATGGGGACGAATCTTTCTGTTCCCAACCCTCTGGGATTC
TTTCCCGATCATCAGTTGGACCCTGCATTCGGAGCCAACTCAAACAATCCAGATT
GGGACTTCAACCCCATCAAGGACCACTGGCCAACAGCCAACCAGGTAGGAGTGG
GAGCATTCGGGCCAGGGCTCACCCCTCCACACGGCGGTATTTTGGGGGGGAGCC
CTCAGGCTCAGGGCATATTGACCACAGTGTCAACAATTCCTCCTCCTGCCTCCAC
CAATCGGCAGTCAGGAAGGCAGCCTACTCCCATCTCTCCACCTCTAAGAGACAGT
CATCCTCAGGCCATGCAGTGGAA

SEQ ID NO: 4
TCCACCACTTTCCACCAAACTCTTCAAGATCCCAGAGTCAGGGCCCTGTACTTTC
CTGCTGGTGGCTCCAGTTCAGGAACAGTGAGCCCTGCTCAGACTACTGTCTCTGC
CATATCGTCAATCTTATCGAAGACTGGGGACCCTGTACCGAACATGGAGAACAT
CGCATCAGGACTCCTAGGACCCCTGCTCGTGTTACAGGCGGGGTTTTCTTGTTG
ACAAAAATCCTCACAATACCACAGAGTCTAGACTCGTGGTGGACTTCTCTCAATT
TTCTAGGGGGAAMACCCGTGTGTCTTGGCCAAAATTCGCAGTCCCAAATCTCCA
GTCACTCACYAACCTGTTGTCCTCCAATTTGTCCTGGTTATCGCTGGATGTGTCTG
CGGCGTTTTATCATCTTCCTYTGCATCCTGCTGCTATGCCTCATCTTCTTGTTGGTT
CTTCTGGACTATCRAGGTATGTTGCCCGTTTGTCCTCWAMTTCCAGGATCAWCA
ACAACCAGCACCGGACCATGCAAAACCTGCACGACTCCTGCTCAAGGAACCTCT
ATRYKTCCCTCATGTTGCTGTACAAAACCTACGGACGGAAACTGCACCTGTATTC
CCATCCCATCATCTTGGGCTTTCGCAAATACCTATGGGAGTGGCCTCAGYCCG
TTTCTCTTGGCTCAGTTTACTAGCGCCATTTGTTCAGTGGTTCGTAGGGCTTTCCC
CCACTGTCTGGCTTTCAGTTATATGGATGATGTGGTATTGGGGGCCAAGTCTGTA
CAACATCTTGAGTCCCTTTATGCCGCTGTTACCAATTTYCTTTTGTCTTTGGGTAT
ACAYTTGAACCCTCACAAAACAAAAAGATGGGGTATTCCCTTAACTTCATGGG
ATATGTAATTGGGTGTTGGGCACATTGCCACAGGAACATATTGTACAAAAAATC
AAAATGTGTTTTMGGAAACTTCCTGTAAACAGACCTATTGATTGGAAAGTATGTC
AACGAATTGTGGGTCTTTTGGGGTTTGCCGCCCCTTTCACGCAATGTGGATATCC
```

Sequence Listing

TGCTTTRATGCCTTTATATGCATGTATACAAGCAAAACAGGCTTTTACTTTCTCGC
CAACTTACAAGGCCTTTCTAAGTAAACAGTATCTGAACCTTTACCCCGTTACTCG
GCAACGGTCTGGTCTGTGCCAAGTGTTTGCTGACGCAACCCCCACTGGTTGGGGC
TTGGCCATAGGCCWTCAGCGCATGCGTGGAACCTTTGTGTCTCCTCTGCCGATCC
ATACTGCGGAACTCCTAGCCGCTTGTTTTGCTCGCAGCAGGTCTGGGGCAAAACT
CATCGGGACTGACAATTCTGTCGTGCTCTCCCGCAAGTATACATCGTTCCCATGG
CTGCTAGGCTGTGCTGCCAACTGGATCCTGCGCGGGACGTCCTTTGTTTACGTCC
CGTCGGCGCTGAATCCCGCGGACGACCCCTCCCGGGGCCGCTTGGGGCTCTACCG
CCCGCTTCTCCGCCTGTTGTACCGTCCGACCACGGGGCGCACCTCTCTTTACGCG
GACTCCCCGTCTGTGCCTTCTCATCTRCCGGACCGTGTGCACTTCGCTTCACCTCT
GCACGTCGCATGGAGACCACCGTGAACGCCCACCGGAACCTGCCCAAGGTCTTG
CATAAGAGGACTCTTGGACTTTCCGCAATGTCAACGACCGACCTTGAGGCATACT
TCAAAGACTGTGTGTTTAMTGAGTGGGAGGAGTTGGGGGAGGAGAKTAGGTTAA
AGGTCTTTGTACTAGGAGGCTGTAGGCATAAATTGGTGTGTTCACCAGCACCATG
CAACTTTTTCACCTCTGCCTAATCATCTCWTGTTCATGTCCTACTGTTCAAGCCTC
CAAGCTGTGCCTTGGGTGGCTTTAGGGCATGGACATTGACCCGTATAAAGAATTT
GGAGCTTCTGTGGAGTTACTCTCTTTTTTGCCTMMTGACTTCTTTCCTTCTATTCG
AGATCTCCTCGACACCGCCTCTGCTTTGTATCGGGAGGCCTTAGAGTCTCCGGAA
CATTGTTCACCTCACCATACGGCACTCAGGCAAGCTATTCTGTGTTGGGGTGAGT
TGATGAATCTAGCCACCTGGGTGGGAAGTAATTTGGAAGATCCAGCATCCAGGG
AATTAGTMGTTAGCTATGTCAACGTTAATATGGGCMTAAAAATCAGACAACTAT
TGTGGTTTCACATTTCCTGTCTTACTTTTGGGARAGAMACTGTTCTTGAATATTTG
GTGTCTTTTGGAGTGTGGATTCGCACTCCTCCTGCATATAGACCAYCAAATGCCC
CTATCTTATCAACACTTCCGGAAACTACTGTTGTTAGACGAAGAGGCAGGTCCCC
TAGAAGAAGAACTCCCTCGCCTCGCAGACGAAGGTCTCAATCGCCGCGTCGCAG
AAGATCTCAATCTCGGGAATCTCAATGTTAGTATTCCTTGGACACATAAGGTGGG
AAACTTTACGGGGCTTTATTCTTCTACGGTACCTTGCTTTAATCCTAAWTGGCAA
ACTCCTTCTTTTCCTGACATTCATTTGCAGGAGGACATTGTTGATAGATGTAAGCA
MTTTGTGGGGCCCCTTACAGTAAATGAAAACAGGAGACTAAAATTAATTATGCC
TGCTAGGTTTTATCCCAATGTTACCAAATATTTGCCCTTAGATAAAGGGATCAAA
CCTTATTATCCAGAGCATGTAGTTAATCATTACTTCCAGACGAGACATTATTTAC
AYACTCTTTGGAAGGCGGGTATCYTATATAAAAGAGAGTCCACACGTAGCGCCT
CATTTTGCGGATCACCATATTCTTGGGAACAAGATCTACAGCATGGGAGGTTGGT
CTTCCAAACCTCGAAAAGGCATGGGGACAAATCTTTCTGTCCCCAATCCCCTGGG
ATTCTTCCCMGATCATCAGTTGGACCCTGCATTCAAAGCCAACTCASAAAATCCA
GATTGGGACCTCAACCCGCACAAGGACAACTGGCCGGACGCCAACAAGGTGGGA
GTGGGAGCATTCGGGCCAGGGTTCATCCCTCCCCATGGGGGACTGTTGGGGTGG
ARCCCTCAGGCTCAGGGCATACTCACAACTGTGCCAGCAGCTCCTCCTCCTGCCT
CCACCAATCGGCAGTCAGGAAGGCAGCCTACTCCCTTATCTCCACCTCTAAGGGA
CACTCATCCTCAGGCCATGCAGTGGAA

SEQ ID NO: 5
TCCACAACATTCCACCAAGCTCTGCTAGATCCCAGAGTGAGGGGCCTATATTTTC
CTGCTGGTGGCTCCAGTTCCGAACAGTAAACCCTGTTCCGACTACTGCCTCACC
CATATCGTCAATCTTCTCGAGGACTGGGGACCCTGCACCGAACATGGAGAGCAC
AACATCAGGATTCCTAGGACCCCTGCTCGTGTTACAGGCGGGGTTTTTCTTGTTG
ACAAGAATCCTCACAATACCACAGAGTCTAGACTCGTGGTGGACTTCTCTCAATT
TTCTAGGGGAGCACCCACGTGTCCTGGCCAAAATTCGCAGTCCCCAACCTCCAA
TCACTCACCAACCTCTTGTCCTCCAATTTGTCCTGGCTATCGTCTGGATGTGTCTGC
GGCGTTTTATCATATTCCTCTTCATCCTGCTGCTATGCCTCATCTTCTTGTTGGTTC
TTCTGGACTACCAAGGTATGTTGCCCGTTTGTCCTCTACTTCCAGGAACATCAACT
ACCAGCACGGGACCATGCAAGACCTGCACGATTCCTGCTCAAGGAACCTCTATG
TTTCCCTCTTGTTGCTGTACAAAACCTTCGGACGGAAACTGCACTTGTATTCCCAT
CCCATCATCCTGGGCTTTCGCAAGATTCCTATGGGAGTGGGCCTTAGTCCGTTTCT
CCTGGCTCAGTTTACTAGTGCCATTGTTCAGTGGTTCGCAGGGCTTTCCCCCACT
GTTTGGCTTTCAGTTATATGGATGATGTGGTATTGGGGGCCAAGTCTGTACAACA
TCTTGAGTCCCTTTTTACCTCTATTACCAATTTTCTTTTGTCGTTGGGTATACATTT
GAACCCTAATAAAACCAAACGTTGGGGCTACTCCCTTAACTTCATGGGATATGTA
ATTGGAAGTTGGGGGACTTTACCACAGGAACATATTGTATTAAAAATCAAGCAA
TGTTTTCGGAAACTGCCTGTAAATAGACCTATTGATTGGAAAGTATGTCAAAGAA
TTGTGGGTCTTTTGGGCTTTGCTGCCCCTTTTACACAATGTGGCTATCCTGCCTTG
ATGCCTTTATATGCATGTATACAATCTAAGCAGGCTTTCACTTTCTCGCCAACTTA
CAAGGCCTTTCTGTGTCAACAATACCTGCACCTTTACCCCGTTGCCCGGCAACGG
TCAGGTCTCTGCCAAGTGTTTGCTGACGCAACCCCCACTGGATGGGCTTGGCCA
TAGGCCATCGGCGCATGCGTGGAACCTTTGTGGCTCCTCTGCCGATCCCATACTGC
GGAACTCCTAGCAGCTTGTTTTGCTCGCAGCCGGTCTGGAGCAAAACTTATCGGG
ACTGACAACTCTGTTGTCCTCTCTCGGAAATACACCTCCTTCCCATGGCTGCTCGG
GTGTGCTGCCAACTGGATCCTGCGCGGGACGTCCTTTGTCTACGTCCCGTCGGCG
CTGAATCCCGCGGACGACCCGTCTCGGGGCCGTTGGGCCTCTACCGTCCCCTTC
TTCATCTGCTGTTCCAGCCGACTACGGGGCGCACCTCTCTTTACGCGGTCTCCCCG
TCTGTGCCTTCTCATCTGCCGGACCGTGTGCACTTCGCTTCACCTCTGCACGTCGC
ATGGAGACCACCGTGAATGCCCACCAGGTCTTGCCCAAGCTCTTACATAAGAGG
ACTCTTGGACTCTCAGCAATGTCAACGACCGACCTTGAGGCATACTTCAAAGACT
GTTTGTTAAGGACTGGGAGGAGTTGGGGGAGGAGATTAGGTTAAAGGTCTTTGT
ACTAGGAGGCTGTAGGCATAAATTGGTCTGTTCACCAGCACCATGCAACTTTTTC
ACCTCTGCCTAATCATCTCATGTTCATGTCCTACTGTTCAAGCCTCCAAGCTGTGC
CTTGGGTGGCTTTGGGGCATGGACATTGACCCGTATAAAGAATTTGGAGCTTCTG

```
TGGAGTTACTCTCTTTTTTGCCTTCTGACTTCTTTCCTTCTATTCGAGATCTCCTCG
ACACCGCCTCTGCTCTGTATCGGGAGGCCTTAGAGTCTCCGGAACATTGTTCACC
TCACCATACAGCACTCAGGCAAGCTATTCTCTGTTGGGGTGAGTTGATGAATCTG
GCCACCTGGGTGGGAAGTAATTTGGAAGACCCAGCATCCAGGGAATTAGTAGTC
AGCTATGTCAATGTTAATATGGGCCTAAAAATCAGACAACTATTGTGGTTTCACA
TTTCCTGTCTTACTTTTGGAAGAGAAACTGTTCTTGAGTATTTGGTGTCTTTTGGA
GTGTGGATTCGCACTCCTCCAGCTTACAGACCACCAAATGCCCCTATCTTATCAA
CACTTCCGGAAACTACTGTTGTTAGACGACGAGGCAGGTCCCCTAGAAGAAGAA
CTCCCTCGCCTCGCAGACGAAGGTCTCAATCGCCGCGTCGCAGAAGATCTCAATC
TCGGGAATCTCAATGTTAGTATCCCTTGGACTCATAAGGTGGGAAACTTTACTGG
GCTTTATTCTTCTACTGTTCCTGTCTTTAATCCTGAGTGGCAAACTCCCTCCTTTCC
TAACATTCATTTACAGGAAGACATTATTAATAGATGTCAACAATATGTGGGCCCT
CTTACAGTTAATGAAAAAAGGAGATTAAAATTAATTATGCCTGCTAGGTTCTATC
CTAACCTTACCAAATATTTGCCCTTGGATAAAGGCATTAAACCTTATTATCCTGA
ACATGCAGTTAATCATTACTTCAAAACTAGGCATTATTTACATACTCTGTGGAAG
GCTGGCATTCTATATAAAAGAGAAACTACACGCAGCGCTTCATTTTGTGGGTCAC
CATATTCTTGGGAACAAGAGCTACAGCATGGGAGGTTGGTCTTCCAAACCTCGAC
AAGGCATGGGGACGAATCTTTCTGTTCCCAATCCTCTGGGATTCTTTCCCGATCA
CCAGTTGGACCCTGCGTTCGGAGCCAACTCAAACAATCCAGATTGGGACTTCAAC
CCCAACAAGGATCACTGGCCAGAGGCAAATCAGGTAGGAGCGGGAGCATTCGG
GCCAGGGTTCACCCCACCACACGGCGGTCTTTTGGGGTGGAGCCCTCAGGCTCAG
GGCATATTGACAACAGTGCCAGCAGCGCCTCCTCCTGCCTCCACCAATCGGCAGT
CAGGAAGACAGCCTACTCCCATCTCTCCACCTCTAAGAGACAGTCATCCTCAGGC
CATGCAGTGGAA

SEQ ID NO: 6
TTCCACAACCTTTCACCAAACTCTGCAAGATCCCAGAGTGAGAGGCCTGTATTTC
CCTGCTGGTGGCTCCAGTTCAGGAGCAGTAAACCCTGTTCCGACTACTGCCTCTC
CCTTATCGTCAATCTTCTCGAGGATTGGGGACCCTGCGCTGAACATGGAGAACAT
CACATCAGGATTCCTAGGACCCCTTCTCGTGTTACAGGCGGGGTTTTTCTTGTTGA
CAAGAATCCTCACAATACCGCAGAGTCTAGACTCGTGGTGGACTTCTCTCAATTT
TCTAGGGGGAACTACCGTGTGTCTTGGCCAAAATTCGCAGTCCCCAACCTCCAAT
CACTCACCAACCTCCTGTCCTCCAACTTGTCCTGGTTATCGCTGGATGTGTCTGCG
GCGTTTTATCATCTTCCTCTTCATCCTGCTGCTATGCCTCATCTTCTTGTTGGTTCT
TCTGGACTATCAAGGTATGTTGCCCGTTTGTCCTCTAATTCCAGGATCCTCAACCA
CCAGCACGGGACCATGCCGAACCTGCATGACTACTGCTCAAGGAACCTCTATGT
ATCCCTCCTGTTGCTGTACCAAACCTTCGGACGGAAATTGCACCTGTATTCCCAT
CCCATCATCCTGGGCTTTCGGAAAATTCCTATGGGAGTGGGCCTCAGCCCGTTTC
TCCTGGCTCAGTTTACTAGTGCCATTTGTTCAGTGGTTCGTAGGGCTTTCCCCCAC
TGTTTGGCTTTCAGTTATATGATGATGTGGTATTGGGGGCCAAGTCTGTACAGC
ATCTTGAGTCCCTTTTTACCGCTGTTACCAATTTCTTTTGTCTTTGGGTATACATT
TAAACCCTAACAAAACAAAGAGATGGGGTTACTCTCTGAATTTTATGGGTTATGT
CATTGGAAGTTATGGGTCCTTGCCACAAGAACACATCATACAAAAAATCAAAGA
ATGTTTTAGAAAACTTCCTATTAACAGGCCTATTGATTGGAAAGTATGTCAACGA
ATTGTGGGTCTTTTGGGTTTTGCTGCCCCATTTACACAATGTGGTTATCCTGCGTT
AATGCCCTTGTATGCATGTATTCAATCTAAGCAGGCTTTCACTTTCTCGCCAACTT
ACAAGGCCTTTCTGTGTAAACAATACCTGAACCTTTACCCCGTTGCCCGGCAACG
GCCAGGTCTGTGCCAAGTGTTTGCTGACGCAACCCCCACTGGCTGGGGCTTGGTC
ATGGGCCATCAGCGCGTGCGTGGAACCTTTTCGGCTCCTCTGCCGATCCATACTG
CGGAACTCCTAGCCGCTTGTTTTGCTCGCAGCAGGTCTGGAGCAAACATTATCGG
GACTGATAACTCTGTTGTCCTCTCCCGCAAATATACATCGTATCCATGGCTGCTA
GGCTGTGCTGCCAACTGGATCCTGCGCGGGACGTCCTTTGTTTACGTCCCGTCGG
CGCTGAATCCTGCGGACGACCCTTCTCGGGGTCGCTTGAGACTCTCTCGTCCCCT
TCTCCGTCTGCCGTTCCGACCGACCACGGGGCGCACCTCTCTTTACGCGGACTCC
CCGTCTGTGCCTTCTCATCTGCCGGACCGTGTGCACTTCGCTTCACCTCTGCACGT
CGCATGGAGACCACCGTGAACGCCCACCGAATGTTGCCCAAGGTCTTACATAAG
AGGACTCTTGGACTCTCTGCAATGTCAACGACCGACCTTGAGGCATACTTCAAAG
ACTGTTTGTTTAAAGACTGGGAGGAGTTGGGGGAGGAGATTAGATTAAAGGTCT
TTGTACTAGGAGGCTGTAGGCATAAATTGGTCTGCGCACCGGCGCCATGCACCTT
TTTCACCTCTGCCTAATCATCTCTTGTTCATGTCCTACTGTTCAAGCCTCCAAGCT
GTGCCTTGGGTGGCTTTGGGGCATGGACATCGACCCTTATAAAGAATTTGGAGCT
ACTGTGGAGTTACTCTCGTTTTTGCCTTCTGACTTCTTTCCTTCAGTACGAGATCTT
CTAGATACCGCCTCAGCTCTGTATCGGGAAGCCTTAGAGTCTCCTGAGCATTGTT
CACCTCACCATACTGCACTCAGGCAAGCAATTCTTTGCTGGGGGGAACTAATGAC
TCTAGCTACCTGGGTGGGTGTTAATTTGGAAGATCCAGCATCTAGAGACCTAGTA
GTCAGTTATGTCAACACTAATATGGGCTAAAGTTCAGGCAACTCTTGTGGTTTC
ACATTTCTTGTCTCACTTTTGGAAGAGAAACCGTTATAGAGTATTTGGTGTCTTTC
GGAGTGTGGATTCGCACTCCTCCAGCTTATAGACCACCAAATGCCCCTATCCTAT
CAACACTTCCGGAAACTACTGTTGTTAGACGACGAGGCAGGTCCCCTAGAAGAA
GAACTCCCTCGCCTCGCAGACGAAGGTCTCAATCGCCGCGTCGCAGAAGATCTC
AATCTCGGGAACCTCAATGTTAGTATTCCTTGGACTCATAAGGTGGGAACTTTA
CTGGTCTTTATTCTTCTACTGTACCTGTCTTTAATCCTCATTGGAAAACACCATCT
TTTCCTAATATACATTTACACCAAGACATTATCAAAAAATGTGAACAGTTTGTAG
GCCCACTTACAGTTAATGAGAAAGAAGATTGCAATTGATTATGCCTGCTAGGTT
TTATCCAAAGGTTACCAAATATTTACCATTGGATAAGGGTATTAAACCTTATTAT
CCAGAACATCTAGTTAATCATTACTTCCAAACTAGACACTATTTACACACTCTAT
GGAAGGCGGGTATATTATATAAGAGAGAAACAACACATAGCGCCTCATTTTGTG
```

| Sequence Listing |
|---|
| GGTCACCATATTCTTGGGAACAAGATCTACAGCATGGGCAGAATCTTTCCACCA |
| GCAATCCTCTGGGATTCTTTCCCGACCACCAGTTGGATCCAGCCTTCAGAGCAAA |
| CACAGCAAATCCAGATTGGGACTTCAATCCCAACAAGGACACCTGGCCAGCAGC |
| CAACAAGGTAGGAGCTGGAGCATTCGGGCTGGGTTTCACTCCACCGCACGGAGG |
| CCTTTTGGGGTGGAGCTCTCAGGCTCAGGGCATACTACAAACTTTGCCAGCAAAT |
| CCGCCTCCTGCCTCCACCAATCGCCAGACAGGAAGGCAGCCTACCCCGCTGTCTC |
| CACCTTTGAGAAACACTCATCCTCAGGCCATGCAGTGGAA |
| |
| SEQ ID NO: 7 |
| TTCCACAACATTCCACCAAGCTCASCAGGATCCCAGAGTAAGRGGCCTGTATYTT |
| CCTGCTGGTGGCTCCAGTTCCGGAACAGTGAACCCTGTTCCGACTACTGCCTCAC |
| TCATCTCGTCAATCTTCTCGAGGATTGGGGACCCTGCACCGAACATGGAAGGCAT |
| CACATCAGGATTCCTAGGACCCCTGCTCGTGTTACAGGCGGGGTTTTCTTGTTG |
| ACAAAAATCCTCACAATACCGCAGAGTCTAGACTCGTGGTGGACTTCTCTCAATT |
| TTCYAGGGGAAGCTCCCGTGTGTCGTGGCCAAAATTCGCAGTYCCCAACCTCCAA |
| TCACTCACCAACCTCTTGTCCTCCAATTTGTCCTGGCTATCGCTGGATGTGTCTGC |
| GGCGTTTTATCATCTTCCTCTTCATCCTGCTGCTATGCCTCATCTTCTTGTTGGTTC |
| TTCTGGACTATCAAGGTATGTTGCCCGTTTGTCCTCTAATTCCAGGATCATCAACC |
| ACCAGTACGGGACCCTGCCGAACCTGCACGACTCTTGCTCAAGGAACCTCTATGT |
| TTCCCTCATGTTGCTGTTCAAAACCTTCGGACGGAAATTGCACTTGTATTCCCATC |
| CCATCATCATGGGCTTTCGGAAAATTCCTATGGGAGTGGGCCTCAGCCCGTTTCT |
| CCTGGCTCAGTTTACTAGTGCCATTTGTTCAGTGGTTCGCCGGGCTTTCCCCCACT |
| GTCTGGCTTTCAGTTATATGGATGATGTGGTATTGGGGGCCAAGTCTGTACAACA |
| TCTTGAGTCCCTTTATACCTCTGTTACCAATTTTCTTTTGTCTTTGGGTATACATTT |
| AAATCCTAACAAAACAAAAAGATGGGGATATTCCCTAAATTTCATGGGTTATGTT |
| ATTGGTAGTTGGGGGTCATTACCACAGGAACACATCAGAATGAAAATCAAAGAC |
| TGTTTTAGAAAACTCCCTGTTAACCGGCCTATTGATTGGAAAGTATGTCAAAGAA |
| TTGTGGGTCTCTTGGGCTTTGCTGCCCCTTTTACACAATGTGGATATCCTGCTTTA |
| ATGCCTCTGTATGCGTGTATTCAATCTAAGCAGGCTTTCACTTTCTCGCCAACTTA |
| CAAGGCCTTTCTGTGTAAACAATACCTGAACCTTTACCCCGTTGCCCGGCAACGG |
| CCAGGTCTGTGCCAAGTGTTTGCTGATGCAACCCCCACTGGTTGGGGCTTGGCCA |
| TAGGCCATCAGCGCATGCGTGGAACCTTTGYGGCTCCTCTGCCGATCCATACTGC |
| GGAACTCCTGGCCGCTTGTTTTGCTCGCAGCAGGTCTGGAGCGAAACTTATTGGA |
| ACGGATAATTCTGTCGTTCTCTCCCGGAAATATACATCATTTCCATGGCTGCTAG |
| GCTGTGCTGCCAACTGGATCCTGCGAGGGACGTCCTTTGTCTACGTCCCGTCAGC |
| GCTGAATCCTGCGGACGACCCGTCTCGGGGTCGCTTGGGGATCTATCGTCCCCTT |
| CTCCGTCTGCCGTTCCGGCCGACCACGGGGCGCACCTCTCTTTACGCGGTCTCCC |
| CGTCTGTGCCTTCTCATCTGCCGGACCGTGTGCACTTCGCTTCACCTCTGCACGTC |
| GCATGGAAACCACCGTGAACGCCCACCAAATCTTGCCCAAGGTCTTATATAAGA |
| GGACTCTTGGACTCTCTGCAATGTCAACGACCGACCTTGAGGCATACTTCAAAGA |
| CTGCTTGTTTAAAGACTGGGAGGAGTTGGGGGAGGAGATTAGATTAATGATCTTT |
| GTACTAGGAGGCGTATAGGCATAAATTGGTCTGCGCACCAGCACCATGCAACTTTT |
| TCACCTCTGCCTAATCATCTCTTGTTCATGTCCTACTGTTCAAGCCTCCAAGCTGT |
| GCCTTGGGTGGCTTTAGGACATGGACATTGACCCTTATAAAGAATTTGGAGCTWC |
| TGTGGAGTTACTCTCKTTTTTGCCTCATGACTTCTTTCCTTCAATAAGAGATCTTC |
| TAGATACCGCCACAGCTCTGTATCGGGATGCCTTAGAATCTCCTGAGCATTGTTC |
| ACCTCACCACACGGCACTCAGGCAAGCCATTCTTTGCTGGGGGGATGTAATGAAT |
| CTAGCTACCTGGGTGGGTGTAAATTTGGAAGATCCAGCATCCAGGGACCTGGTA |
| GTCGGTTATGTCAATACTAATATGGGCCTAAAGTTCAGACAATTATTGTGGTTTC |
| ACACTTCCTGTCTCACTTTTGGAAGAGAAACCGTCTTAGAGTATTTGGTGTCTTTT |
| GGGAGTGTGGATTCGCACTCCTCCACCTTATAGACCACCAAATGCCCCTATCTTAT |
| CAACACTTCCGGAGACTACTGTTGTTAGACGAAGAGGCAGGTCCCCTAGAAGAA |
| GAACTCCCTCRCCTCGCAGACGTAGATCTCAATCGCCGCGTCGCAGAAGATCTCA |
| ATCTCCAGCTTCCCGATGTTAGTATTCCTTGGACTCACAAGGTGGGAAATTTTAC |
| GGGGCTTTACTCTTCTACTATACCTGTCTTTAATCCTAACTGGAAAACTCCATCTT |
| TTCCTGATATTCATTTGCACCAGGACATTATTAACAAATGTGAACAATTTGTAGG |
| TCCCCTAACAGTAAATGAAAAACGAAGATTAACTTAGTCATGCCTGCTAGATT |
| TTTTCCCATCTCTACGAAATATTTGCCTCTAGAGAAAGGTATAAAACCCTATTAT |
| CCAGATAATGTAGTTAATCATTACTTCCAAACCAGACACTATTTACATACCCTAT |
| GGAAGGCGGGTATCTTATATAAAAGAGAAACTGCACGTAGCGCCTCATTTTGTG |
| GGTCACCATATTCTTGGGAACAAGAGCTACATCATGGGTCTTTCTTGGACGGTCC |
| CTCTCGAATGGGGAAGAATCATTCCACCACCAATCCTCTGGGATTTTTTCCCGA |
| CCACCAGTTGGATCCAGCATTCAGAGCAAACACCAGAAATCCAGATTGGGACCA |
| CAATCCCAACAAAGACCACTGGACAGAAGCCAACAAGGTAGGAGTGGGAGCAT |
| TCGGGCCGGGGTTCACTCCCCCACACGGAGGCCTTTGGGGTGGAGCCCTCAGGC |
| TCAAGGCATGCTAAAAACATTGCCAGCAGATCCGCCTCCTGCCTCCACCAATCGG |
| CAGTCAGGAAGGCAGCCTACCCCAATCACTCCACCTTTGAGAGACACTCATCCTC |
| AGGCCATRCAGTGGAA |
| |
| SEQ ID NO: 8 |
| TTCCATCAGGCTCTGTTGGATCCCAGGGTAAGGGCTCTGTATCTTCCTGCTGGTG |
| GCTCCAGTTCAGGAACACAAAACCCTGCTCCGACTATTGCCTCTCTCACATCCTC |
| AATCTTCTCGACGACTGGGGGCCCTGCTATGAACATGGACAACATTACATCAGG |
| ACTCCTAGGACCCCTGCTCGTGTTACAGGCGGTGTGTTTCTTGTTGACAAAAATC |
| CTCACAATACCACAGAGTCTAGACTCGTGGTGGACTTCTCTCAATTTTCTAGGGG |
| GACTACCCGGGTGTCCTGGCCAAAATTCGCAGTCCCCAACCTCCAATCACTTACC |
| AACCTCCTGTCCTCCAACTTGTCCTGGCTATCGTTGGATGTGTCTGCGGCGTTTTA |

```
TCATCTTCCTCTTCATCCTGCTGCTATGCCTCATCTTCTTGTTGGTTCTTCTGGACT
ACCAGGGTATGTTGCCCGTTTGTCCTCTACTTCCAGGATCCACGACCACCAGCAC
GGGACCCTGCAAAACCTGCACAACTCTTGCACAAGGAACCTCTATGTTTCCCTCC
TGTTGCTGTTCAAAACCCTCGGACGGAAACTGCACTTGTATTCCCATCCCATCAT
CCTGGGCTTTAGGAAAATACCTATGGGAGTGGGCCTCAGCCCGTTTCTCATGGCT
CAGTTTACTAGTGCAATTTGTTCAGTGGTGCGTAGGGCTTTCCCCCACTGTCTGGC
TTTTAGTTATATTGATGATCTGGTATTGGGGGCCAAATCTGTGCAGCACCTTGAG
TCCCTTTATACCGCTGTTACCAATTTTCTGTTATCTGTGGGTATCCATTTAAATAC
TTCTAAAACTAAGAGATGGGGTTACACCCTACATTTTATGGGTTATGTCATTGGT
AGTTGGGGATCATTACCTCAAGATCATATTGTACACAAAATCAAAGAATGTTTTC
GGAAACTGCCTGTAAATCGTCCAATTGATTGGAAAGTCTGTCAACGCATTGTGGG
TCTTTTGGGCTTTGCTGCCCCTTTCACACAATGTGGTTATCCTGCTCTCATGCCTC
TGTATGCTTGTATTACTGCTAAACAGGCTTTTGTTTTTTCGCCAACTTACAAGGCC
TTTCTCTGTAAACAATACATGAACCTTTACCCCGTTGCCAGGCAACGGCCGGGCC
TGTGCCAAGTGTTTGCTGACGCAACCCCCACTGGTTGGGGCTTGGCCATTGGCCA
TCAGCGCATGCGTGGAACCTTTGTGGCTCCTCTGCCGATCCATACTGCGGAACTC
CTTGCAGCTTGTTTCGCTCGCAGCAGGTCTGGAGCGACTCTCATCGGCACGGACA
ACTCTGTTGTCCTCTCTAGGAAGTACACCTCCTTCCCATGGCTGCTCGGGTGTGCT
GCAAACTGGATCCTGCGCGGGACGTCCTTTGTTTACGTCCCGTCGGCGCTGAATC
CCGCGGACGACCCCTCCCGGGGCCGCTTGGGGCTGTACCGCCCTCTTCTCCGTCT
GCCGTTCCAGCCGACAACGGGTCGCACCTCTCTTTACGCGGACTCCCCGTCTGTT
CCTTCTCATCTGCCGGACCGTGTGCACTTCGCTTCACCTCTGCACGTCGCATGGA
GACCACCGTGAACGCCCCTTGGAGTTTGCCAACAGTCTTACATAAGAGGACTCTT
GGACTTTCAGGAGGGTCAATGACCCGGATTGCAGAATACATCAAAGACTGTGTA
TTTAAGGACTGGGAGGAGTTGGGGGAGGAGACTAGGTTAATGATCTTTGTACTA
GGAGGCTGTAGGCATAAATTGGTCTGTTCACCAGCACCATGCAACTTTTTCACCT
CTGCCTAATCATCTTTTGTTCATGTCCTACTGTTCAAGCCTCCAAGCTGTGCCTTG
GGTGGCTTTGGGACATGGACATTGACCCTTATAAAGAATTTGGCGCTTCTGTGGA
GTTACTCTCTTTTTTGCCTTCTGATTTCTTTCCATCGGTTCGGGACCTACTCGACAC
CGCTTCAGCCCTTTACCGGGATGCTTTAGAGTCACCTGAACATTGCACTCCCCAT
CACACTGCCCTCAGGCAAGTTATTTTGTGCTGGGGTGAGTTAATGACTTTGGCTT
CCTGGGTGGCAATAACTTGGAAGACCCTGCTGCCAGGGATTTAGTAGTTAACTA
TGTTAACACTAACATGGGCCTAAAAATTAGACAACTACTGTGGTTTCACATTTCC
TGCCTTACTTTTGGAAGAGATATAGTTCTTGAGTATTTGGTGTCCTTTGGAGTGTG
GATTCGCACTCCTCCTGCTTACAGACCACAAAATGCCCCTATCCTATCCACACTT
CCGGAAACTACTGTTGTTAGACGACGAGGCAGGTCCCCTAGAAGAAGAACTCCC
TCGCCTCGCAGACGAAGATCTCAATCGCGCGTCGCCGAAGATCTCAATCTCCAG
CTTCCCAATGTTAGTATTCCTTGGACTCATAAGGTGGGAAATTTTACGGGGCTTT
ACTCTTCTACTGTGCCTGCTTTTAATCCTGACTGGTTAACTCCTTCTTTTCCTAATA
TTCATTTACATCAAGACCTAATTTCTAAATGTGAACAATTTGTAGGCCCACTCAC
TAAAAATGAATTAAGGAGGTTAAAATTGGTTATGCCAGCTAGATTTTATCCTAAG
GTTACCAAATATTTTCCTATGGAGAAAGGAATCAAGCCTTATTATCCTGAGCATG
CAGTTAATCATTACTTTAAAACAAGACATTATTTGCATACTTTATGGAAGGCGGG
AATTTTATATAAGAGAGAATCCACACGTAGCGCATCATTTTGTGGGTCACCTATAT
TCCTGGGAACAAGAGCTACAGCATGGGAGCACCTCTCTCAACGACAAGAAGAGG
CATGGGACAGAATCTTTCTGTGCCCAATCCTCTGGGATTCTTTCCAGACCATCAG
CTGGATCCGCTATTCAAAGCAAATTCCAGCAGTCCCGACTGGGACTTCAACACAA
ACAAGGACAGTTGGCCAATGGCAAACAAGGTAGGAGTGGGAGCATACGGTCCA
GGGTTCACACCCCCACACGGTGGCCTGCTGGGGTGGAGCCCTCAGGCACAAGGT
ATGTTAACAACCTTGCCAGCAGATCCGCCTCCTGCTTCCACCAATCGGCGGTCCG
GGAGAAAGCCAACCCCAGTCTCTCCACCTCTAAGAGACACTCATCCACAGGCAA
TGCAGTGGAA

SEQ ID NO: 9
TCTACAGCATTCCACCAAGCTCTACAAAATCCCAAAGTCAGGGGCCTGTATTTTC
CTGCTGGTGGCTCCAGTTCAGGGATAGTGAACCCTGTTCCGACTATTGCCTCTCA
CATCTCGTCAATCTTCTCCAGGATTGGGGACCCTGCACCGAACATGGAGAACATC
ACATCAGGATTCCTAGGACCCCTGCTCGTGTTACAGGCGGGGTTTTTCTTGTTGA
CAAGAATCCTCACAATACCGCAGAATCTAGACTCGTGGTGGACTTCTCTCAATTT
TCTAGGGGGAGTGCCCGTGTGTCCTGGCCTAAATTCGCAGTCCCCAACCTCCAAT
CACTCACCAATCTCCTGTCCTCCAACTTGTCCTGGCTATCGCTGGATGTGTCTGCG
GCGTTTTATCATATTCCTCTTCATCCTGCTGCTATGCCTCATCTTCTTGTTGGTTCT
TCTGGACTATCAAGGTATGTTGCCCGTTTGTCCTCTGATTCCAGGATCCTGACCA
CCAGTACGGGACCCTGCAAAACCTGCACGACTCCTGCTCAAGGCAACTCTATGTA
TCCCTCATGTTGCTGTACAAAACCTTCGGACGGAAATTGCACCTGTATTCCCATC
CCATCATCTTGGGCTTTCGCAAAATACCTATGGGAGTGGGCCTCAGTCCGTTTCT
CTTGGCTCAGTTTACTAGTGCCATTTGTTCAGTGGTTCGTAGGGCTTTCCCCCACT
GTCTGGCTTTCAGCTATATGGATGATGTGGTATTGGGGGCCAAATCTGTACAACA
TCTTGAGTCCCTTTATACCGCTGTTACCAATTTTCTTTTGTCTTTGGGTATACATCT
AAACCCTAACAAAACAAAAGATGGGGTTATTCCTTAAATTTTATGGGATATGTA
ATTGGAAGTTGGGGTACTTTGCCACAAGAACACATCACACAGAAAATTAAGCAA
TGTTTTCGGAAACTCCCTGTTAACAGGCCAATTGATTGGAAAGTCTGTCAACGAA
TAACTGGTCTGTTGGGTTTCGCTGCTCCTTTTACCCAATGTGGTTACCCTGCCTTA
ATGCCTTTATATGCATGTATACAAGCTAAGCAGGCTTTTACTTTCTCGCCAACTTA
TAAGGCCTTTCTCTGTAAACAATACATGAACCTTTACCCCGTTGCTAGGCAACGG
CCCGGTCTGTGCCAAGTGTTTGCTGACGCAACCCCCACTGGTTGGGGCTTGGCCA
TCGGCCATCAGCGCATGCGTGGAACCTTTGTGGCTCCTCTGCCGATCCATACTGC
```

| Sequence Listing |
|---|
| GGAACTCCTAGCTGCTTGTTTTGCTCGCAGCCGGTCTGGAGCAAAACTCATTGGG
ACTGACAATTCTGTCGTCCTTTCTCGGAAATATACATCCTTTCCATGGCTGCTAGG
CTGTGCTGCCAACTGGATCCTTCGCGGGACGTCCTTTGTTTACGTCCCGTCAGCG
CTGAATCCAGCGGACGACCCCTCCCGGGGCCGTTTGGGGCTCTGTCGCCCCCTTC
TCCGTCTGCCGTTCCTGCCGACCACGGGGCGCACCTCTCTTTACGCGGTCTCCCC
GTCTGTTCCTTCTCATCTGCCGGACCGTGTGCACTTCGCTTCACCTCTGCACGTTA
CATGGAAACCGCCATGAACACCTCTCATCATCTGCCAAGGCAGTTATATAAGAG
GACTCTTGGACTGTTTGTTATGTCAACAACCGGGGTGGAGAAATACTTCAAGGAC
TGTGTTTTGCTGAGTGGGAAGAATTAGGCAATGAGTCCAGGTTAATGACCTTTG
TATTAGGAGGCTGTAGGCATAAATTGGTCTGCGCACCAGCACCATGTAACTTTTT
CACCTCTGCCTAATCATCTCTTGTTCATGTCCTACTGTTCAAGCCTCCAAGCTGTG
CCTTGGGTGGCTTTAGGGCATGGATAGAACAACTTTGCCATATGGCCTTTTTGGC
TTAGACATTGACCCTTATAAAGAATTTGGAGCTACTGTGGAGTTGCTCTCGTTTTT
GCCTTCTGACTTTTTCCCGTCTGTTCGTGATCTTCTCGACACCGCTTCAGCTTTGT
ACCGGGAATCCTTAGAGTCCTCTGATCATTGTTCGCCTCACCATACAGCACTCAG
GCAAGCAATCCTGTGCTGGGGTGAGTTGATGACTCTAGCCACCTGGGTGGGTAAT
AATTTGGAAGATCCAGCATCCAGAGATTTGGTGGTCAATTATGTTAATACTAATA
TGGGTTTAAAAATCAGGCAACTATTGTGGTTTCACATTTCCTGTCTTACTTTTGGG
AGAGAAACCGTTCTTGAGTATTTGGTGTCTTTTGGAGTGTGGATTCGCACTCCTCC
TGCTTATAGACCACCAAATGCCCCTATCCTATCAACACTTCCGGAGACTACTGTT
GTTAGACGAAGAGGCAGGTCCCCTCGAAGAAGAACTCCCTCGCCTCGCAGACGA
AGATCTCAATCGCCGCGTCGCAGAAGATCTGCATCTCCAGCTTCCCAATGTTAGT
ATTCCTTGGACTCACAAGGTGGGAAACTTTACGGGCTGTATTCTTCTACTATAC
CTGTCTTTAATCCTGATTGGCAAACTCCTTCTTTTCCAAATATCCATTTGCATCAA
GACATTATAACTAAATGTGAACAATTTGTGGGCCCTCTCACAGTAAATGAGAAA
CGAAGATTAAAACTAGTTATGCCTGCCAGATTTTTCCCAAACTCTACTAAATATT
TACCATTAGACAAAGGTATCAAACCGTATTATCCAGAAAATGTAGTTAATCATTA
CTTCCAGACCAGACATTATTTACATACCCTTTGGAAGGCGGGTATTCTATATAAG
AGAGAAACATCCCGTAGCGCTTCATTTTGTGGGTCACCATATACTTGGGAACAAG
ATCTACAGCATGGGCTTTCTTGGACGGTCCCTCTCGAGTGGGAAAGAACCTTT
CCACCAGCAATCCTCTAGGATTCCTTCCCGATCACCAGTTGGACCCAGCATTCAG
AGCAAATACCAACAATCCAGATTGGGACTTCAATCCCAAAAAGGACCCTTGGCC
AGAGGCCAACAAGGTAGGAGTTGGAGCCTATGGACCCGGGTTCACCCCTCCACA
CGGAGGCCTTTTGGGGTGGAGCCCTCAGTCTCAGGGCACACTAACAACTTTGCCA
GCAGATCCGCCTCCTGCCTCCACCAATCGTCAGTCAGGGAGGCAGCCGACTCCCA
TCTCTCCACCACTAAGAGACAGTCATCCTCAGGCCATGCAGTGGAA |

SEQ ID NO: 10
TGCCGATCCATACTGCGGAACT

SEQ ID NO: 11
ACGGCTAGGTATGACGCCTTGA

SEQ ID NO: 12
MNTKYNKEFLLYLAGFVDSDGSINASISPRQSFKFKHGLKLRFEVGQKTQHRWFLDK
LVDEIGVGYVYDNGSVSVYSLSQIKPLHNFLTQLQPFLKLKQKQANLVLKIIEQLPSA
KESPDKFLEVCTWVDQIAALNDSKTRKTTSETVRAVLDSLPGSVGGLSPSQASSAAS
SASSSPGSGISEALRAGAGSGTGYNKEFLLYLAGFVDGDGSIFASIRPRQHAKFKHDL
ELCFNVRQKTQRRWFLDKLVDEIGVGYVIDWRGASTYKLSQIKPLHNFLTQLQPFLK
LKQKQANLVLKIIEQLPSAKESPDKFLEVCTWVDQIAALNDSKTRKTTSETVRAVLD
SLSEKKKSSP

SEQ ID NO: 13
MNTKYNKEFLLYLAGFVDADGSINASIQPRQSFKFKHSLKLRFEVGQKTQRRWFLD
KLVDEIGVGYVYDNGSVSVYSLSQIKPLHNFLTQLQPFLKLKQKQANLVLKIIEQLPS
AKESPDKFLEVCTWVDQIAALNDSKTRKTTSETVRAVLDSLPGSVGGLSPSQASSAA
SSASSSPGSGISEALRAGAGSGTGYNKEFLLYLAGFVDGDGSIFASIRPRQHAKFKHD
LELCFNVRQKTQRRWFLDKLVDEIGVGYVLDWRGASTYKLSEIKPLHNFLTQLQPFL
KLKQKQANLVLKIIEQLPSAKESPDKFLEVCTWVDQIAALNDSRTRKTTSETVRAVL
DSLSEKKKSSP

SEQ ID NO: 14
MNTKYNKEFLLYLAGFVDGDGSINASIAPRQSFKFKHGLKLRFEVGQKTQRRWFLD
KLVDEIGVGYVYDNGSVSVYSLSQIKPLHNFLTQLQPFLKLKQKQANLVLKIIEQLPS
AKESPDKFLEVCTWVDQIAALNDSKTRKTTSETVRAVLDSLPGSVGGLSPSQASSAA
SSASSSPGSGISEALRAGAGSGTGYNKEFLLYLAGFVDSDGSIFASIRPRQMAKFKHD
LELCFNVRQKTQRRWFLDKLVDEIGVGYVHDWGSVSTYKLSEIKPLHNFLTQLQPFL
KLKQKQANLVLKIIEQLPSAKESPDKFLEVCTWVDQIAALNDSKTRKTTSETVRAVL
DSLSEKKKSSP

SEQ ID NO: 15
MNTKYNKEFLLYLAGFVDGDGSINATIAPRQSFKFKHGLKLRFEVGQKTQRRWFLD
KLVDEIGVGYVYDNGSVSVYCLSQIKPLHNFLTQLQPFLKLKQKQANLVLKIIEQLPS
AKESPDKFLEVCTWVDQIAALNDSKTRKTTSETVRAVLDSLPGSVGGLSPSQASSAA
SSASSSPGSGISEALRAGAGSGTGYNKEFLLYLAGFVDGDGSIYASIRPRQHAKFKHD

```
LELIFNVRQLTSRRWFLDKLVDEIGVGYVIDWRGASTYKLSEIKPLHNFLTQLQPFLK
LKQKQANLVLKIIEQLPSAKESPDKFLEVCTWVDQIAALNDSKTRKTTSETVRAVLD
SLSEKKKSSP

SEQ ID NO: 16
MNTKYNKEFLLYLAGFVDGDGSINATIAPRQSFKFKHGLKLRFEVGQKTQRRWFLD
KLVDEIGVGYVYDNGSVSVYCLSQIKPLHNFLTQLQPFLKLKQKQANLVLKIIEQLPS
AKESPDKFLEVCTWVDQIAALNDSKTRKTTSETVRAVLDSLPGSVGGLSPSQASSAA
SSASSSPGSGISEALRAGAGSGTGYNKEFLLYLAGFVDSDGSIYASIRPRQHAKFKHD
LELIFNVRQLTSRRWFLDKLVDEIGVGYVIDWRGASTYKLSEIKPLHNFLTQLQPFLK
LKQKQANLVLKIIEQLPSAKESPDKFLEVCTWVDQIAALNDSKTRKTTSETVRAVLD
SLSEKKKSSP

SEQ ID NO: 17
MNTKYNKEFLLYLAGFVDGDGSINAAIAPRQSFKFKHGLKLRFEVGQKTQRRWFLD
KLVDEIGVGYVYDNGSVSVYCLSQIKPLHNFLTQLQPFLKLKQKQANLVLKIIEQLPS
AKESPDKFLEVCTWVDQIAALNDSKTRKTTSETVRAVLDSLPGSVGGLSPSQASSAA
SSASSSPGSGISEALRAGAGSGTGYNKEFLLYLAGFVDGDGSIYASIRPRQQSKFKHD
LELYFNVRQKTRRRWFLDKLVDEIGVGYVNDWRGTSTYKLSEIKPLHNFLTQLQPFL
KLKQKQANLVLKIIEQLPSAKESPDKFLEVCTWVDQIAALNDSKTRKTTSETVRAVL
DSLSEKKKSSP

SEQ ID NO: 18
KEFLLYLAGFVDGDGSIFASIRPRQHAKFKHDLELCFNVRQKTQRRWFLDKLVDEIG
VGYVIDWRGASTYKLSQIKPLHNFLTQLQPFLKLKQKQANLVLKIIEQLPSAKESPDK
FLEVCTWVDQIAALNDSKTRKTTSETVRAVLD

SEQ ID NO: 19
KEFLLYLAGFVDGDGSIFASIRPRQHAKFKHDLELCFNVRQKTQRRWFLDKLVDEIG
VGYVLDWRGASTYKLSEIKPLHNFLTQLQPFLKLKQKQANLVLKIIEQLPSAKESPDK
FLEVCTWVDQIAALNDSRTRKTTSETVRAVLD

SEQ ID NO: 20
KEFLLYLAGFVDSDGSIFASIRPRQMAKFKHDLELCFNVRQKTQRRWFLDKLVDEIG
VGYVHDWGSVSTYKLSEIKPLHNFLTQLQPFLKLKQKQANLVLKIIEQLPSAKESPDK
FLEVCTWVDQIAALNDSKTRKTTSETVRAVLD

SEQ ID NO: 21
KEFLLYLAGFVDGDGSIYASIRPRQHAKFKHDLELIFNVRQLTSRRWFLDKLVDEIGV
GYVIDWRGASTYKLSEIKPLHNFLTQLQPFLKLKQKQANLVLKIIEQLPSAKESPDKF
LEVCTWVDQIAALNDSKTRKTTSETVRAVLD

SEQ ID NO: 22
KEFLLYLAGFVDSDGSIYASIRPRQHAKFKHDLELIFNVRQLTSRRWFLDKLVDEIGV
GYVIDWRGASTYKLSEIKPLHNFLTQLQPFLKLKQKQANLVLKIIEQLPSAKESPDKF
LEVCTWVDQIAALNDSKTRKTTSETVRAVLD

SEQ ID NO: 23
KEFLLYLAGFVDGDGSIYASIRPRQQSKFKHDLELYFNVRQKTRRRWFLDKLVDEIG
VGYVNDWRGTSTYKLSEIKPLHNFLTQLQPFLKLKQKQANLVLKIIEQLPSAKESPDK
FLEVCTWVDQIAALNDSKTRKTTSETVRAVLD

SEQ ID NO: 24
KEFLLYLAGFVDSDGSINASISPRQSFKFKHGLKLRFEVGQKTQHRWFLDKLVDEIGV
GYVYDNGSVSVYSLSQIKPLHNFLTQLQPFLKLKQKQANLVLKIIEQLPSAKESPDKF
LEVCTWVDQIAALNDSKTRKTTSETVRAVLD

SEQ ID NO: 25
KEFLLYLAGFVDADGSINASIQPRQSFKFKHSLKLRFEVGQKTQRRWFLDKLVDEIG
VGYVYDNGSVSVYSLSQIKPLHNFLTQLQPFLKLKQKQANLVLKIIEQLPSAKESPDK
FLEVCTWVDQIAALNDSKTRKTTSETVRAVLD

SEQ ID NO: 26
KEFLLYLAGFVDGDGSINASIAPRQSFKFKHGLKLRFEVGQKTQRRWFLDKLVDEIG
VGYVYDNGSVSVYSLSQIKPLHNFLTQLQPFLKLKQKQANLVLKIIEQLPSAKESPDK
FLEVCTWVDQIAALNDSKTRKTTSETVRAVLD

SEQ ID NO: 27
KEFLLYLAGFVDGDGSINATIAPRQSFKFKHGLKLRFEVGQKTQRRWFLDKLVDEIG
VGYVYDNGSVSVYCLSQIKPLHNFLTQLQPFLKLKQKQANLVLKIIEQLPSAKESPDK
FLEVCTWVDQIAALNDSKTRKTTSETVRAVLD

SEQ ID NO: 28
KEFLLYLAGFVDGDGSINATIAPRQSFKFKHGLKLRFEVGQKTQRRWFLDKLVDEIG
VGYVYDNGSVSVYCLSQIKPLHNFLTQLQPFLKLKQKQANLVLKIIEQLPSAKESPDK
FLEVCTWVDQIAALNDSKTRKTTSETVRAVLD
```

| Sequence Listing |
|---|

SEQ ID NO: 29
KEFLLYLAGFVDGDGSINAAIAPRQSFKFKHGLKLRFEVGQKTQRRWFLDKLVDEIG
VGYVYDNGSVSVYCLSQIKPLHNFLTQLQPFLKLKQKQANLVLKIIEQLPSAKESPDK
FLEVCTWVDQIAALNDSKTRKTTSETVRAVLD

SEQ ID NO: 30
GATGATGTGGTATTGGGGGCCA

SEQ ID NO: 31
CTACTACACCATAACCCCCGGT

SEQ ID NO: 32
TGCCGATCCATACTGCGGAACT

SEQ ID NO: 33
GGTCTGTGCCAAGTGTTTG

SEQ ID NO: 34
GTATATTTCCGCGAGAGGAC

SEQ ID NO: 35
CTTGGCCCCCAATACCACATCATC

SEQ ID NO: 36
GGATGGAAATTGCACCTGTATTC

SEQ ID NO: 37
GGGTTTAAATGTATACCCAGAGAC

SEQ ID NO: 38
SLPGSVGGLSPSQASSAASSASSSPGSGISEALRAGAGSGTG

SEQ ID NO: 39
MNTKYNKEFLLYLAGFVDGDGSINASIAPRQSFKFKHGLKLRFEVGQKTQRRWFLD
KLVDEIGVGYVYDNGSVSVYSLSQIKPLHNFLTQLQPFLKLKQKQANLVLKIIEQLPS
AKESPDKFLEVCTWVDQIAALNDSKTRKTTSETVRAVLDSLPGSVGGLSPSQASSAA
SSASSSPGSGISEALRAGAGSGTGYNKEFLLYLAGFVDGDGSIYASIRPRQYAKFKHD
LELRFNVRQKTQRRWFLDKLVDEIGVGYVVDWGSVSTYQLSQIKPLHNFLTQLQPFL
KLKQKQANLVLKIIEQLPSAKESPDKFLEVCTWVDQIAALNDSKTRKTTSETVRAVL
DSLSEKKKSSP

SEQ ID NO: 40
MNTKYNKEFLLYLAGFVDGDGSINAAIAPRQSFKFKHGLKLRFEVGQKTQRRWFLD
KLVDEIGVGYVYDNGSVSVYCLSQIKPLHNFLTQLQPFLKLKQKQANLVLKIIEQLPS
AKESPDKFLEVCTWVDQIAALNDSKTRKTTSETVRAVLDSLPGSVGGLSPSQASSAA
SSASSSPGSGISEALRAGAGSGTGYNKEFLLYLAGFVDGDGSIYASIRPRQHAKFKHD
LELIFNVRQLTSRRWFLDKLVDEIGVGYVIDWGGASTYKLSEIKPLHNFLTQLQPFLK
LKQKQANLVLKIIEQLPSAKESPDKFLEVCTWVDQIAALNDSKTRKTTSETVRAVLD
SLSEKKKSSP

SEQ ID NO: 41
CCCCTGCTCGTGTTACAGGCGG

SEQ ID NO: 42
GGGGACGAGCACAATGTCCGCC

SEQ ID NO: 43
TTTGCTGACGCAACCCCCACTG

SEQ ID NO: 44
AAACGACTGCGTTGGGGTGAC

SEQ ID NO: 45
ATGAATACAAAATATAATAAAGAGTTCTTACTCTACTTAGCAGGGTTTGTAGACT
CTGACGGTTCCATCAACGCCAGCATCTCGCCGCGGCAGTCGTTCAAGTTCAAGCA
CGGGCTGAAGCTCCGGTTCGAGGTCGGTCAGAAGACACAGCACCGTTGGTTCCT
CGACAAGCTGGTCGACGAGATCGGTGTGGGTTACGTGTATGACAATGGCAGCGT
CTCCGTTTACTCTCTGTCCCAGATCAAGCCTTTGCATAATTTTTTAACACAACTAC
AACCTTTTCTAAAACTAAAACAAAAACAAGCAAATTTAGTTTTAAAAATTATTGA
CAACTTCCGTCAGCAAAAGAATCCCCGGACAAATTCTTAGAGGTTTGTACATGG
GTGGATCAAATTGCAGCTCTGAATGATTCGAAGACGCGTAAAACAACTTCTGAA
ACCGTTCGTGCTGTGCTAGACAGTTTACCAGGATCCGTGGGAGGTCTATCGCCAT
CTCAGGCATCCAGCGCCGCATCCTCGGCTTCCTCAAGCCCGGGTTCAGGGATCTC
CGAAGCACTCAGAGCTGGAGCAGGTTCCGGCACTGGATACAACAAGGAATTCCT
GCTCTACCTGGCGGGCTTCGTCGACGGGGACGGCTCCATCTTTGCATCGATCCGG
CCTCGTCAACATGCTAAGTTCAAGCACGATCTGGAGCTCGTTTCAATGTCAGGC
AGAAGACACAGCGCCGTTGGTTCCTCGACAAGCTGGTGGACGAGATCGGTGTGG

```
GTTACGTGATTGACTGGCGTGGCGCCTCCACTTACAAGCTGTCCCAGATCAAGCC
TCTGCACAACTTCCTGACCCAGCTCCAGCCCTTCCTGAAGCTCAAGCAGAAGCAG
GCCAACCTCGTGCTGAAGATCATCGAGCAGCTGCCCTCCGCCAAGGAATCCCCG
GACAAGTTCCTGGAGGTGTGCACCTGGGTGGACCAGATCGCCGCTCTGAACGAC
TCCAAGACCCGCAAGACCACTTCCGAAACCGTCCGCGCCGTTCTAGACAGTCTCT
CCGAGAAGAAGAAGTCGTCCCCCTAA

SEQ ID NO: 46
ATGAATACAAAATATAATAAAGAGTTCTTACTCTACTTAGCAGGGTTTGTAGACG
CTGACGGTTCCATCAACGCCAGCATCCAGCCGCGGCAGTCGTTCAAGTTCAAGCA
CTCTCTGAAGCTCCGGTTCGAGGTCGGTCAGAAGACACAGCGCCGTTGGTTCCTC
GACAAGCTGGTGGACGAGATCGGTGTGGGTTACGTGTATGACAATGGCAGCGTC
TCCGTTTACTCTCTGTCCCAGATCAAGCCTTTGCATAATTTTTTAACACAACTACA
ACCTTTTCTAAAACTAAAACAAAAACAAGCAAATTTAGTTTTAAAAATTATTGAA
CAACTTCCGTCAGCAAAAGAATCCCCGGACAAATTCTTAGAAGTTTGTACATGGG
TGGATCAAATTGCAGCTCTGAATGATTCGAAGACGCGTAAAACAACTTCTGAAA
CCGTTCGTGCTGTGCTAGACAGTTTACCAGGATCCGTGGGAGGTCTATCGCCATC
TCAGGCATCCAGCGCCGCATCCTCGGCTTCCTCAAGCCCGGGTTCAGGGATCTCC
GAAGCACTCAGAGCTGGAGCAGGTTCCGGCACTGGATACAACAAGGAATTCCTG
CTCTACCTGGCGGGCTTCGTCGACGGGGACGGCTCCATCTTTGCATCGATCCGGC
CTCGTCAACATGCTAAGTTCAAGCACGATCTGGAGCTCTGTTTCAATGTCAGGCA
GAAGACACAGCGCCGTTGGTTCCTCGACAAGCTGGTGGACGAGATCGGTGTGGG
TTACGTGCTTGACTGGCGTGGCGCCTCCACTTACAAGCTGTCCGAGATCAAGCCT
CTGCACAACTTCCTGACCCAGCTCCAGCCCTTCCTGAAGCTCAAGCAGAAGCAGG
CCAACCTCGTGCTGAAGATCATCGAGCAGCTGCCCTCCGCCAAGGAATCCCCGG
ACAAGTTCCTGGAGGTGTGCACCTGGGTGGACCAGATCGCCGCTCTGAACGACT
CCAGGACCCGCAAGACCACTTCCGAAACCGTCCGCGCCGTTCTAGACAGTCTCTC
CGAGAAGAAGAAGTCGTCCCCCTAA

SEQ ID NO: 47
ATGAATACAAAATATAATAAAGAGTTCTTACTCTACTTAGCAGGGTTTGTAGACG
GTGACGGTTCCATCAATGCCAGTATCGCTCCGCGGCAGTCGTTTAAGTTCAAGCA
CGGTCTGAAGCTCCGGTTCGAGGTCGGTCAGAAGACACAGCGCCGTTGGTTCCTC
GACAAGCTGGTGGACGAGATCGGTGTGGGTTACGTGTATGACAATGGCAGCGTC
TCCGTTTACTCTCTGTCCCAGATCAAGCCTTTGCATAATTTTTTAACACAACTACA
ACCTTTTCTAAAACTAAAACAAAAACAAGCAAATTTAGTTTTAAAAATTATTGAA
CAACTTCCGTCAGCAAAAGAATCCCCGGACAAATTCTTAGAAGTTTGTACATGGG
TGGATCAAATTGCAGCTCTGAATGATTCGAAGACGCGTAAAACAACTTCTGAAA
CCGTTCGTGCTGTGCTAGACAGTTTACCAGGATCCGTGGGAGGTCTATCGCCATC
TCAGGCATCCAGCGCCGCATCCTCGGCTTCCTCAAGCCCGGGTTCAGGGATCTCC
GAAGCACTCAGAGCTGGAGCAGGTTCCGGCACTGGATACAACAAGGAATTCCTG
CTCTACCTGGCGGGCTTCGTCGACTCCGACGGCTCCATCTTTGCATCGATCCGGC
CTCGTCAAATGGCTAAGTTCAAGCACGATCTGGAGCTCTGTTTCAATGTCAGGCA
GAAGACACAGCGCCGTTGGTTCCTCGACAAGCTGGTGGACGAGATCGGTGTGGG
TTACGTGCATGACTGGGGCAGCGTCTCCACTTACAAGCTGTCCGAGATCAAGCCT
CTGCACAACTTCCTGACCCAGCTCCAGCCCTTCCTGAAGCTCAAGCAGAAGCAGG
CCAACCTCGTGCTGAAGATCATCGAGCAGCTGCCCTCCGCCAAGGAATCCCCGG
ACAAGTTCCTGGAGGTGTGCACCTGGGTGGACCAGATCGCCGCTCTGAACGACT
CCAAGACCCGCAAGACCACTTCCGAAACCGTCCGCGCCGTTCTAGACAGTCTCTC
CGAGAAGAAGAAGTCGTCCCCCTAA

SEQ ID NO: 48
ATGAATACAAAATATAATAAAGAGTTCTTACTCTACTTAGCAGGGTTTGTAGACG
GTGACGGTTCCATCAATGCCACTATCGCTCCGCGGCAGTCGTTTAAGTTCAAGCA
CGGTCTGAAGCTCCGGTTCGAGGTCGGTCAGAAGACACAGCGCCGTTGGTTCCTC
GACAAGCTGGTGGACGAGATCGGTGTGGGTTACGTGTATGACAATGGCAGCGTC
TCCGTTTACTGTCTGTCCCAGATCAAGCCTTTGCATAATTTTTTAACACAACTACA
ACCTTTTCTAAAACTAAAACAAAAACAAGCAAATTTAGTTTTAAAAATTATTGAA
CAACTTCCGTCAGCAAAAGAATCCCCGGACAAATTCTTAGAAGTTTGTACATGGG
TGGATCAAATTGCAGCTCTGAATGATTCGAAGACGCGTAAAACAACTTCTGAAA
CCGTTCGTGCTGTGCTAGACAGTTTACCAGGATCCGTGGGAGGTCTATCGCCATC
TCAGGCATCCAGCGCCGCATCCTCGGCTTCCTCAAGCCCGGGTTCAGGGATCTCC
GAAGCACTCAGAGCTGGAGCAGGTTCCGGCACTGGATACAACAAGGAATTCCTG
CTCTACCTGGCGGGCTTCGTCGACGGGGACGGCTCCATCTATGCATCTATCAGGC
CTCGTCAACATGCTAAGTTCAAGCACGATCTGGAGCTCATTTTCAATGTCAGGCA
GCTGACAAGCCGCCGTTGGTTCCTCGACAAGCTGGTGGACGAGATCGGTGTGGG
TTACGTGATTGACTGGCGTGGCGCCTCCACTTACAAGCTGTCCGAGATCAAGCCT
CTGCACAACTTCCTGACCCAGCTCCAGCCCTTCCTGAAGCTCAAGCAGAAGCAGG
CCAACCTCGTGCTGAAGATCATCGAGCAGCTGCCCTCCGCCAAGGAATCCCCGG
ACAAGTTCCTGGAGGTGTGCACCTGGGTGGACCAGATCGCCGCTCTGAACGACT
CCAAGACCCGCAAGACCACTTCCGAAACCGTCCGCGCCGTTCTAGACAGTCTCTC
CGAGAAGAAGAAGTCGTCCCCCTAA

SEQ ID NO: 49
ATGAATACAAAATATAATAAAGAGTTCTTACTCTACTTAGCAGGGTTTGTAGACG
GTGACGGTTCCATCAATGCCACTATCGCTCCGCGGCAGTCGTTTAAGTTCAAGCA
CGGTCTGAAGCTCCGGTTCGAGGTCGGTCAGAAGACACAGCGCCGTTGGTTCCTC
```

-continued

```
GACAAGCTGGTGGACGAGATCGGTGTGGGTTACGTGTATGACAATGGCAGCGTC
TCCGTTTACTGTCTGTCCCAGATCAAGCCTTTGCATAATTTTTTAACACAACTACA
ACCTTTTCTAAAACTAAAACAAAAACAAGCAAATTTAGTTTTAAAAATTATTGAA
CAACTTCCGTCAGCAAAAGAATCCCCGGACAAATTCTTAGAAGTTTGTACATGGG
TGGATCAAATTGCAGCTCTGAATGATTCGAAGACGCGTAAAACAACTTCTGAAA
CCGTTCGTGCTGTGCTAGACAGTTTACCAGGATCCGTGGGAGGTCTATCGCCATC
TCAGGCATCCAGCGCCGCATCCTCGGCTTCCTCAAGCCCGGGTTCAGGGATCTCC
GAAGCACTCAGAGCTGGAGCAGGTTCCGGCACTGGATACAACAAGGAATTCCTG
CTCTACCTGGCGGGCTTCGTCGACTCCGACGGCTCCATCTATGCATCTATCAGGC
CTCGTCAACATGCTAAGTTCAAGCACGATCTGGAGCTCATTTTCAATGTCAGGCA
GCTGACAAGCCGCGTTGGTTCCTCGACAAGCTGGTGGACGAGATCGGTGTGGG
TTACGTGATTGACTGGCGTGGCGCCTCCACTTACAAGCTGTCCGAGATCAAGCCT
CTGCACAACTTCCTGACCCAGCTCCAGCCCTTCCTGAAGCTCAAGCAGAAGCAGG
CCAACCTCGTGCTGAAGATCATCGAGCAGCTGCCCTCCGCCAAGGAATCCCCGG
ACAAGTTCCTGGAGGTGTGCACCTGGGTGGACCAGATCGCCGCTCTGAACGACT
CCAAGACCCGCAAGACCACTTCCGAAACCGTCCGCGCCGTTCTAGACAGTCTCTC
CGAGAAGAAGAAGTCGTCCCCCTAA

SEQ ID NO: 50
ATGAATACAAATATAATAAAGAGTTCTTACTCTACTTAGCAGGGTTTGTAGACG
GTGACGGTTCCATCAATGCCGCGATCGCTCCGCGGCAGTCGTTTAAGTTCAAGCA
CGGTCTGAAGCTCCGGTTCGAGGTCGGTCAGAAGACACAGCGCCGTTGGTTCCTC
GACAAGCTGGTGGACGAGATCGGTGTGGGTTACGTGTATGACAATGGCAGCGTC
TCCGTTTACTGTCTGTCCCAGATCAAGCCTTTGCATAATTTTTTAACACAACTACA
ACCTTTTCTAAAACTAAAACAAAAACAAGCAAATTTAGTTTTAAAAATTATTGAA
CAACTTCCGTCAGCAAAAGAATCCCCGGACAAATTCTTAGAAGTTTGTACATGGG
TGGATCAAATTGCAGCTCTGAATGATTCGAAGACGCGTAAAACAACTTCTGAAA
CCGTTCGTGCTGTGCTAGACAGTTTACCAGGATCCGTGGGAGGTCTATCGCCATC
TCAGGCATCCAGCGCCGCATCCTCGGCTTCCTCAAGCCCGGGTTCAGGGATCTCC
GAAGCACTCAGAGCTGGAGCAGGTTCCGGCACTGGATACAACAAGGAATTCCTG
CTCTACCTGGCGGGCTTCGTCGACGGGACGGCTCCATCTATGCAAGTATCAGGC
CTCGTCAACAGTCGAAGTTCAAGCACGATCTGGAGCTCTATTTCAATGTCAGGCA
GAAGACAAGGCGCCGTTGGTTCCTCGACAAGCTGGTGGACGAGATCGGTGTGGG
TTACGTGAATGACTGGCGTGGCACCTCCACTTACAAGCTGTCCGAGATCAAGCCT
CTGCACAACTTCCTGACCCAGCTCCAGCCCTTCCTGAAGCTCAAGCAGAAGCAGG
CCAACCTCGTGCTGAAGATCATCGAGCAGCTGCCCTCCGCCAAGGAATCCCCGG
ACAAGTTCCTGGAGGTGTGCACCTGGGTGGACCAGATCGCCGCTCTGAACGACT
CCAAGACCCGCAAGACCACTTCCGAAACCGTCCGCGCCGTTCTAGACAGTCTCTC
CGAGAAGAAGAAGTCGTCCCCCTAA

SEQ ID NO: 51
MAPKKKRKVH
```

The invention claimed is:

1. An engineered meganuclease that binds and cleaves a recognition sequence consisting of SEQ ID NO: 10 within a Hepatitis B virus genome, wherein said engineered meganuclease comprises a first subunit, a second subunit, and a linker that covalently joins said first subunit and said second subunit, wherein said first subunit binds to a first recognition half-site of said recognition sequence and comprises a first hypervariable (HVR1) region, wherein said HVR1 region comprises residues corresponding to residues 215, 217, 219, 221, 223, 224, 229, 231, 233, 235, 237, 259, 261, 262, 263, 264, 266, and 268 of SEQ ID NO: 12, and wherein said second subunit binds to a second recognition half-site of said recognition sequence and comprises a second hypervariable (HVR2) region, wherein said HVR2 region comprises residues corresponding to residues 24, 26, 28, 30, 32, 33, 38, 40, 42, 44, 46, 51, 68, 70, 75, and 77 of SEQ ID NO: 12,
    wherein said first subunit has at least 97% sequence identity to residues 198-344 of SEQ ID NO: 12, and
    wherein said second subunit has at least 97% sequence identity to residues 7-153 of SEQ ID NO: 12.

2. The engineered meganuclease of claim 1, wherein said HVR1 region comprises residues 215-270 of SEQ ID NO: 12.

3. The engineered meganuclease of claim 1, wherein said first subunit comprises a residue corresponding to residue 271 of SEQ ID NO: 12.

4. The engineered meganuclease of claim 1, wherein said second subunit comprises a residue corresponding to residue 19 of SEQ ID NO: 12.

5. The engineered meganuclease of claim 1, wherein said engineered meganuclease comprises the amino acid sequence of SEQ ID NO: 12.

6. The engineered meganuclease of claim 1, wherein said HVR2 region comprises residues 24-79 of SEQ ID NO: 12.

7. The engineered meganuclease of claim 1, wherein said HVR1 region comprises residues 215-270 of SEQ ID NO: 12, and wherein said HVR2 region comprises residues 24-79 of SEQ ID NO: 12.

8. The engineered meganuclease of claim 1, wherein said first subunit comprises residues 198-344 of SEQ ID NO: 12.

9. The engineered meganuclease of claim 1, wherein said second subunit comprises a residue corresponding to residue 80 of SEQ ID NO: 12.

10. The engineered meganuclease of claim 1, wherein said second subunit comprises residues 7-153 of SEQ ID NO: 12.

11. The engineered meganuclease of claim 1, wherein said first subunit comprises a residue corresponding to residue 271 of SEQ ID NO: 12, and wherein said second subunit comprises residues corresponding to residues 19 and 80 of SEQ ID NO: 12.

12. A pharmaceutical composition comprising a pharmaceutically acceptable carrier and said engineered meganuclease of claim 1.

\* \* \* \* \*

SEQUENCE LISTING

<160> NUMBER OF SEQ ID NOS: 51

<210> SEQ ID NO 1
<211> LENGTH: 163
<212> TYPE: PRT
<213> ORGANISM: Chlamydomonas reinhardtii

<400> SEQUENCE: 1

Met Asn Thr Lys Tyr Asn Lys Glu Phe Leu Leu Tyr Leu Ala Gly Phe
1               5                   10                  15

Val Asp Gly Asp Gly Ser Ile Ile Ala Gln Ile Lys Pro Asn Gln Ser
            20                  25                  30

Tyr Lys Phe Lys His Gln Leu Ser Leu Ala Phe Gln Val Thr Gln Lys
        35                  40                  45

Thr Gln Arg Arg Trp Phe Leu Asp Lys Leu Val Asp Glu Ile Gly Val
    50                  55                  60

Gly Tyr Val Arg Asp Arg Gly Ser Val Ser Asp Tyr Ile Leu Ser Glu
65                  70                  75                  80

Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Trp Arg Leu

```
              100                 105                 110
Pro Ser Ala Lys Glu Ser Pro Asp Lys Phe Leu Glu Val Cys Thr Trp
        115                 120                 125

Val Asp Gln Ile Ala Ala Leu Asn Asp Ser Lys Thr Arg Lys Thr Thr
        130                 135                 140

Ser Glu Thr Val Arg Ala Val Leu Asp Ser Leu Ser Glu Lys Lys Lys
145                 150                 155                 160

Ser Ser Pro

<210> SEQ ID NO 2
<211> LENGTH: 9
<212> TYPE: PRT
<213> ORGANISM: Chlamydomonas reinhardtii

<400> SEQUENCE: 2

Leu Ala Gly Leu Ile Asp Ala Asp Gly
1               5

<210> SEQ ID NO 3
<211> LENGTH: 3221
<212> TYPE: DNA
<213> ORGANISM: Hepatitis B virus

<400> SEQUENCE: 3
```

| | | | | | |
|---|---|---|---|---|---|
| ttccactgcc | ttccaccaag | ctctgcagga | tcccagagtc | aggggtctgt | attttcctgc | 60 |
| tggtggctcc | agttcaggaa | cagtaaaccc | tgctccgaat | attgcctctc | acatctcgtc | 120 |
| aatctccgcg | aggactgggg | accctgtggc | gaacatggag | aacatcacat | caggattcct | 180 |
| aggacccctg | ctcgtgttac | aggcggggtt | tttcttgttg | acaagaatcc | tcacaatacc | 240 |
| gcagagtcta | gactcgtggt | ggacttctct | caattttcta | ggggatcac | ccgtgtgtct | 300 |
| tggccaaaat | tcgcagtccc | caacctccaa | tcactcacca | acctcctgtc | ctccaatttg | 360 |
| tcctggttat | cgctggatgt | gtctgcggcg | ttttatcata | ttcctcttca | tcctgctgct | 420 |
| atgcctcatc | ttcttattgg | ttcttctgga | ttatcaaggt | atgttgcccg | tttgtcctct | 480 |
| aattccagga | tcaacaacaa | ccagtacggg | accatgcaaa | acctgcacga | ctcctgctca | 540 |
| aggcaactct | atgtttccct | catgttgctg | tacaaaacct | acggatggaa | attgcacctg | 600 |
| tattcccatc | ccatcgtcct | gggctttcgc | aaaataccta | tgggagtggg | cctcagtccg | 660 |
| tttctcttgg | ctcagtttac | tagtgccatt | tgttcagtgg | ttcgtagggc | tttcccccac | 720 |
| tgtttggctt | tcagctatat | ggatgatgtg | gtattggggg | ccaagtctgt | acagcatcgt | 780 |
| gagtcccttt | ataccgctgt | taccaatttt | cttttgtctc | tgggtataca | tttaaaccct | 840 |
| aacaaaacaa | aaagatgggg | ttattcccta | aacttcatgg | gttacataat | ggaagttgg | 900 |
| ggaactttgc | cacaggatca | tattgtacaa | aagatcaaac | actgttttag | aaaacttcct | 960 |
| gttaacaggc | ctattgattg | gaaagtatgt | caaagaattg | tgggtctttt | gggctttgct | 1020 |
| gctccatta | cacaatgtgg | atatcctgcc | ttaatgcctt | tgtatgcatg | tatacaagct | 1080 |
| aaacaggctt | tcactttctc | gccaacttac | aaggcctttc | taagtaaaca | gtacatgaac | 1140 |
| ctttaccccg | ttgctcggca | acggcctggt | ctgtgccaag | tgtttgctga | cgcaaccccc | 1200 |
| actggctggg | gcttggccat | aggccatcag | cgcatgcgtg | gaacctttgt | ggctcctctg | 1260 |
| ccgatccata | ctgcggaact | cctagccgct | tgttttgctc | gcagccggtc | tggagcaaag | 1320 |
| ctcatcggaa | ctgacaattc | tgtcgtcctc | tcgcggaaat | atacatcgtt | tccatggctg | 1380 |
| ctaggctgtg | ctgccaactg | gatccttcgc | ggaacgtcct | ttgtctacgt | cccgtcggcg | 1440 |

-continued

```
ctgaatcccg cggacgaccc ctctcggggc cgcttgggac tctctcgtcc ccttctccgt    1500
ctgccgttcc agccgaccac ggggcgcacc tctctttacg cggtctcccc gtctgtgcct    1560
tctcatctgc cggtccgtgt gcacttcgct tcacctctgc acgttgcatg gagaccaccg    1620
tgaacgccca tcagatcctg cccaaggtct tacataagag gactcttgga ctcccagcaa    1680
tgtcaacgac cgaccttgag gcctacttca aagactgtgt gtttaaggac tgggaggagc    1740 tggggggagga gattaggtta aaggtctttg tattaggagg ctgtaggcat aaattggtct    1800
gcgcaccagc accatgcaac tttttcacct ctgcctaatc atctcttgta catgtcccac    1860
tgttcaagcc tccaagctgt gccttgggtg gctttggggc atggacattg acccttataa    1920
agaatttgga gctactgtgg agttactctc gttttttgcct tctgacttct ttccttccgt    1980
cagagatctc ctagacaccg cctcagctct gtatcgagaa gccttagagt ctcctgagca    2040
ttgctcacct caccatactg cactcaggca agccattctc tgctgggggg aattgatgac    2100
tctagctacc tgggtgggta ataatttgga agatccagca tccagggatc tagtagtcaa    2160
ttatgttaat actaacatgg gtttaaagat caggcaacta ttgtggtttc atatatcttg    2220
ccttactttt ggaagagaga ctgtacttga atatttggtc tctttcggag tgtggattcg    2280
cactcctcca gcctatagac caccaaatgc ccctatctta tcaacaattc cggaaactac    2340
tgttgttaga cgacgggacc gaggcaggtc cctagaaga gaactccct cgcctcgcag    2400 acgcagatct caatcgccgc gtcgcagaag atctcaatct cgggaatctc aatgttagta    2460
ttccttggac tcataaggtg ggaaacttta cggggcttta ttcctctaca gtacctatct    2520
ttaatcctga atggcaaact ccttcctttc ctaagattca tttacaagag gacattatta    2580
ataggtgtca acaatttgtg ggccctctca ctgtaaatga aagagaaga ttgaaattaa    2640 ttatgcctgc tagattctat cctacccaca ctaaatattt gcccttagac aaaggaatta    2700
aaccttatta tccagatcag gtagttaatc attacttcca aaccagacat tatttacata    2760
ctctttggaa ggctggtatt ctatataaga gggaaaccac acgtagcgca tcattttgcg    2820
ggtcaccata ttcttgggaa caagagctac agcatgggag gttggtcatc aaaacctcgc    2880
aaaggcatgg ggacgaatct ttctgttccc aaccctctgg gattctttcc cgatcatcag    2940
ttggaccctg cattcggagc caactcaaac aatccagatt gggacttcaa ccccatcaag    3000
gaccactggc caacagccaa ccaggtagga gtgggagcat cgggccagg gctcacccct    3060 ccacacggcg gtattttggg ggggagcct caggctcagg gcatattgac cacagtgtca    3120
acaattcctc ctcctgcctc caccaatcgg cagtcaggaa ggcagcctac tcccatctct    3180
ccacctctaa gagacagtca tcctcaggcc atgcagtgga a                        3221
```

<210> SEQ ID NO 4
<211> LENGTH: 3214
<212> TYPE: DNA
<213> ORGANISM: Hepatitis B virus

<400> SEQUENCE: 4

```
tccaccactt tccaccaaac tcttcaagat cccagagtca gggccctgta ctttcctgct      60
ggtggctcca gttcaggaac agtgagccct gctcagacta ctgtctctgc catatcgtca     120
atcttatcga agactgggga ccctgtaccg aacatggaga acatcgcatc aggactccta     180 ggaccccctgc tcgtgttaca ggcggggttt tcttgttga caaaaatcct cacaatacca     240
cagagtctag actcgtggtg gacttctctc aattttctag ggggaamacc cgtgtgtctt     300
```

```
ggccaaaatt cgcagtccca aatctccagt cactcacyaa cctgttgtcc tccaatttgt      360
cctggttatc gctggatgtg tctgcggcgt tttatcatct tcctytgcat cctgctgcta      420
tgcctcatct tcttgttggt tcttctggac tatcraggta tgttgcccgt ttgtcctcwa      480
mttccaggat cawcaacaac cagcaccgga ccatgcaaaa cctgcacgac tcctgctcaa      540
ggaacctcta tryktccctc atgttgctgt acaaaaccta cggacggaaa ctgcacctgt      600
attcccatcc catcatcttg gctttcgca aataccatat gggagtsggc ctcagyccgt      660
ttctcttggc tcagtttact agcgccattt gttcagtggt tcgtagggct ttccccact      720 gtctggcttt cagttatatg gatgatgtgg tattgggggc caagtctgta caacatcttg      780 agtccctta tgccgctgtt accaattttyc ttttgtcttt gggtatacay ttgaaccctc      840
acaaaacaaa aagatgggga tattcccta cttcatggg atatgtaatt gggtgttggg      900
gcacattgcc acaggaacat attgtacaaa aaatcaaat gtgttttmgg aaacttcctg       960
taaacagacc tattgattgg aaagtatgtc acgaattgt gggtcttttg gggtttgccg     1020
cccctttcac gcaatgtgga tatcctgctt tratgccttt atatgcatgt atacaagcaa     1080
aacaggcttt tactttctcg ccaacttaca aggcctttct aagtaaacag tatctgaacc     1140 tttacccgt tactcggcaa cggtctgtc tgtgccaagt gtttgctgac gcaacccca       1200 ctggttgggg cttggccata ggccwtcagc gcatgcgtgg aacctttgtg tctcctctgc     1260
cgatccatac tgcggaactc ctagccgctt gttttgctcg cagcaggtct ggggcaaaac     1320
tcatcgggac tgacaattct gtcgtgctct cccgcaagta tacatcgttc ccatggctgc     1380
taggctgtgc tgccaactgg atcctgcgcg gacgtccttc tgtttacgtc ccgtcggcgc     1440
tgaatcccgc ggacgacccc tcccggggcc gcttggggct ctaccgcccg cttctccgcc     1500
tgttgtaccg tccgaccacg gggcgcacct ctctttacgc ggactcccg tctgtgcctt      1560 ctcatctrcc ggaccgtgtg cacttcgctt cacctctgca cgtcgcatgg agaccaccgt     1620
gaacgcccac cggaacctgc caaggtcttt gcataagagg actcttggac tttccgcaat     1680
gtcaacgacc gaccttgagg catacttcaa agactgtgtg tttamtgagt gggaggagtt     1740
gggggaggag aktaggttaa aggtctttgt actaggaggc tgtaggcata aattggtgtg     1800
ttcaccagca ccatgcaact ttttcacctc tgcctaatca tctcwtgttc atgtcctact     1860
gttcaagcct ccaagctgtg ccttgggtgg ctttagggca tggacattga cccgtataaa     1920
gaatttggag cttctgtgga gttactctct tttttgcctm mtgacttctt tccttctatt     1980
cgagatctcc tcgacaccgc ctctgctttg tatcggagg ccttagagtc tccggaacat      2040
tgttcacctc accatacggc actcaggcaa gctattctgt gttggggtga gttgatgaat     2100
ctagccacct gggtgggaag taatttggaa gatccagcat ccagggaatt agtmgttagc     2160
tatgtcaacg ttaatatggg cmtaaaaatc agacaactat tgtggttca catttcctgt      2220 cttacttttg ggaragamac tgttcttgaa tatttggtgt cttttggagt gtggattcgc     2280
actcctcctg catatagacc aycaaatgcc cctatcttat caacacttcc ggaaactact     2340
gttgttagac gaagaggcag gtcccctaga agaagaactc cctcgcctcg cagacgaagg     2400
tctcaatcgc cgcgtcgcag aagatctcaa tctcgggaat ctcaatgtta gtattccttg     2460
gacacataag gtgggaaact ttacgggggct ttattcttct acggtaccttt gctttaatcc    2520 taawtggcaa actccttctt ttcctgacat tcatttgcag gaggacattg ttgatagatg     2580
taagcamttt gtgggccccc ttacagtaaa tgaaaacagg agactaaaat taattatgcc     2640
tgctaggttt tatcccaatg ttaccaaata tttgccctta gataaaggga tcaaaccta      2700
```

| | |
|---|---|
| ttatccagag catgtagtta atcattactt ccagacgaga cattatttac ayactctttg | 2760 |
| gaaggcgggt atcytatata aaagagagtc cacacgtagc gcctcatttt gcggatcacc | 2820 |
| atattcttgg gaacaagatc tacagcatgg gaggttggtc ttccaaacct cgaaaaggca | 2880 |
| tggggacaaa tctttctgtc cccaatcccc tgggattctt cccmgatcat cagttggacc | 2940 |
| ctgcattcaa agccaactca saaaatccag attgggacct caacccgcac aaggacaact | 3000 |
| ggccggacgc caacaaggtg ggagtgggag cattcgggcc agggttcatc cctccccatg | 3060 |
| ggggactgtt ggggtggarc cctcaggctc agggcatact cacaactgtg ccagcagctc | 3120 |
| ctcctcctgc ctccaccaat cggcagtcag gaaggcagcc tactccctta tctccacctc | 3180 |
| taagggacac tcatcctcag gccatgcagt ggaa | 3214 |

<210> SEQ ID NO 5
<211> LENGTH: 3214
<212> TYPE: DNA
<213> ORGANISM: Hepatitis B virus

<400> SEQUENCE: 5

| | |
|---|---|
| tccacaacat tccaccaagc tctgctagat cccagagtga ggggcctata ttttcctgct | 60 |
| ggtggctcca gttccggaac agtaaaccct gttccgacta ctgcctcacc catatcgtca | 120 |
| atcttctcga ggactgggga ccctgcaccg aacatggaga gcacaacatc aggattccta | 180 |
| ggacccctgc tcgtgttaca gcggggtttt tcttgttga caagaatcct cacaatacca | 240 |
| cagagtctag actcgtggtg gacttctctc aattttctag ggggagcacc cacgtgtcct | 300 |
| ggccaaaatt cgcagtcccc aacctccaat cactcaccaa cctcttgtcc tccaatttgt | 360 |
| cctggctatc gctggatgtg tctgcggcgt tttatcatat tcctcttcat cctgctgcta | 420 |
| tgcctcatct tcttgttggt tcttctggac taccaaggta tgttgcccgt ttgtcctcta | 480 |
| cttccaggaa catcaactac cagcacggga ccatgcaaga cctgcacgat tcctgctcaa | 540 |
| ggaacctcta tgtttccctc ttgttgctgt acaaaacctt cggacggaaa ctgcacttgt | 600 |
| attcccatcc catcatcctg ggctttcgca agattcctat gggagtgggc cttagtccgt | 660 |
| ttctcctggc tcagtttact agtgccattt gttcagtggt tcgcagggct ttcccccact | 720 |
| gtttggcttt cagttatatg gatgatgtgt tattgggggc caagtctgta acacatcttg | 780 |
| agtccctttt tacctctatt accaattttc ttttgtcgtt gggtatacat ttgaacccta | 840 |
| ataaaaccaa acgttgggggc tactcccctta acttcatggg atatgtaatt ggaagttggg | 900 |
| ggactttacc acaggaacat attgtattaa aaatcaagca atgttttcgg aaactgcctg | 960 |
| taaatagacc tattgattgg aaagtatgtc aaagaattgt gggtcttttg gctttgctg | 1020 |
| cccttttac acaatgtggc tatcctgcct tgatgccttt atatgcatgt atacaatcta | 1080 |
| agcaggcttt cactttctcg ccaacttaca aggcctttct gtgtcaacaa tacctgcacc | 1140 |
| tttacccccgt tgcccggcaa cggtcaggtc tctgccaagt gtttgctgac gcaacccca | 1200 |
| ctggatgggg cttggccata ggccatcggc gcatgcgtgg aacctttgtg gctcctctgc | 1260 |
| cgatccatac tgcggaactc ctagcagctt gttttgctcg cagccggtct ggagcaaaac | 1320 |
| ttatcgggac tgacaactct gttgtcctct ctcggaaata cacctccttc ccatggctgc | 1380 |
| tcgggtgtgc tgccaactgg atcctgcgcg ggacgtcctt tgtctacgtc ccgtcggcgc | 1440 |
| tgaatcccgc ggacgacccg tctcggggcc gtttgggcct ctaccgtccc cttcttcatc | 1500 |
| tgctgttcca gccgactacg gggcgcacct ctctttacgc ggtctccccg tctgtgcctt | 1560 |

| | | | |
|---|---|---|---|
| ctcatctgcc | ggaccgtgtg | cacttcgctt | cacctctgca cgtcgcatgg agaccaccgt | 1620 |
| gaatgcccac | caggtcttgc | ccaagctctt | acataagagg actcttggac tctcagcaat | 1680 |
| gtcaacgacc | gaccttgaag | catacttcaa | agactgtttg tttaaggact gggaggagtt | 1740 |
| gggggaggag | attaggttaa | aggtctttgt | actaggaggc tgtaggcata aattggtctg | 1800 |
| ttcaccagca | ccatgcaact | ttttcacctc | tgcctaatca tctcatgttc atgtcctact | 1860 |
| gttcaagcct | ccaagctgtg | ccttgggtgg | ctttggggca tggacattga cccgtataaa | 1920 |
| gaatttggag | cttctgtgga | gttactctct | tttttgcctt ctgacttctt tccttctatt | 1980 |
| cgagatctcc | tcgacaccgc | ctctgctctg | tatcgggagg ccttagagtc tccgaacat | 2040 |
| tgttcacctc | accatacagc | actcaggcaa | gctattctct gttggggtga gttgatgaat | 2100 |
| ctggccacct | gggtgggaag | taatttggaa | gacccagcat ccaggaatt agtagtcagc | 2160 |
| tatgtcaatg | ttaatatggg | cctaaaaatc | agacaactat tgtggtttca catttcctgt | 2220 |
| cttactttg | gaagagaaac | tgttcttgag | tatttggtgt cttttggagt gtggattcgc | 2280 |
| actcctccag | cttacagacc | accaaatgcc | cctatcttat caacacttcc ggaaactact | 2340 |
| gttgttagac | gacgaggcag | gtcccctaga | agaagaactc cctcgcctcg cagacgaagg | 2400 |
| tctcaatcgc | cgcgtcgcag | aagatctcaa | tctcgggaat ctcaatgtta gtatcccttg | 2460 |
| gactcataag | gtgggaaact | ttactgggct | ttattcttct actgttcctg tctttaatcc | 2520 |
| tgagtggcaa | actccctcct | tcctaacat | tcatttacag aagacatta ttaatagatg | 2580 |
| tcaacaatat | gtgggccctc | ttacagttaa | tgaaaaagg agattaaaat taattatgcc | 2640 |
| tgctaggttc | tatcctaacc | ttaccaaata | tttgcccttg gataaaggca ttaaacctta | 2700 |
| ttatcctgaa | catgcagtta | atcattactt | caaaactagg cattatttac atactctgtg | 2760 |
| gaaggctggc | attctatata | aaagagaaac | tacacgcagc gcttcatttt gtgggtcacc | 2820 |
| atattcttgg | gaacaagagc | tacagcatgg | gaggttggtc ttccaaacct cgacaaggca | 2880 |
| tggggacgaa | tctttctgtt | cccaatcctc | tgggattctt tccgatcac cagttggacc | 2940 |
| ctgcgttcgg | agccaactca | aacaatccag | attgggactt caaccccaac aaggatcact | 3000 |
| ggccagaggc | aaaatcaggta | ggagcgggag | cattcgggcc agggttcacc ccaccacacg | 3060 |
| gcggtctttt | ggggtggagc | cctcaggctc | agggcatatt gacaacagtg ccagcagcgc | 3120 |
| ctcctcctgc | ctccaccaat | cggcagtcag | gaagacagcc tactcccatc tctccacctc | 3180 |
| taagagacag | tcatcctcag | gccatgcagt | ggaa | 3214 |

<210> SEQ ID NO 6
<211> LENGTH: 3182
<212> TYPE: DNA
<213> ORGANISM: Hepatitis B virus

<400> SEQUENCE: 6

| | | | |
|---|---|---|---|
| ttccacaacc | tttcaccaaa | ctctgcaaga | tcccagagtg agaggcctgt atttccctgc | 60 |
| tggtggctcc | agttcaggag | cagtaaaccc | tgttccgact actgcctctc ccttatcgtc | 120 |
| aatcttctcg | aggattgggg | accctgcgct | gaacatggag aacatcacat caggattcct | 180 |
| aggacccctt | ctcgtgttac | aggcggggtt | tttcttgttg acaagaatcc tcacaatacc | 240 |
| gcagagtcta | gactcgtggt | ggacttctct | caattttcta gggggaacta ccgtgtgtct | 300 |
| tggccaaaat | tcgcagtccc | caacctccaa | tcactcacca acctcctgtc ctccaacttg | 360 |
| tcctggttat | cgctggatgt | gtctgcggcg | ttttatcatc ttcctcttca tcctgctgct | 420 |
| atgcctcatc | ttcttgttgg | ttcttctgga | ctatcaaggt atgttgcccg tttgtcctct | 480 |

```
aattccagga tcctcaacca ccagcacggg accatgccga acctgcatga ctactgctca    540
aggaacctct atgtatccct cctgttgctg taccaaacct tcggacggaa attgcacctg    600
tattcccatc ccatcatcct gggctttcgg aaaattccta tgggagtggg cctcagcccg    660
tttctcctgg ctcagtttac tagtgccatt tgttcagtgg ttcgtagggc tttcccccac    720
tgtttggctt tcagttatat ggatgatgtg gtattggggg ccaagtctgt acagcatctt    780
gagtcccttt ttaccgctgt taccaattttt cttttgtctt tgggtataca tttaaaccct    840
aacaaaacaa agagatgggg ttactctctg aattttatgg gttatgtcat tggaagttat    900
gggtccttgc cacaagaaca catcatacaa aaatcaaag aatgttttag aaaacttcct    960
attaacaggc ctattgattg gaaagtatgt caacgaattg tgggtctttt gggttttgct   1020
gccccattta cacaatgtgg ttatcctgcg ttaatgccct tgtatgcatg tattcaatct   1080
aagcaggctt tcactttctc gccaacttac aaggcctttc tgtgtaaaca atacctgaac   1140
ctttaccccg ttgcccggca acggccaggt ctgtgccaag tgtttgctga cgcaaccccc   1200
actggctggg gcttggtcat gggccatcag cgcgtgcgtg gaaccttttc ggctcctctg   1260
ccgatccata ctgcggaact cctagccgct tgttttgctc gcagcaggtc tggagcaaac   1320
attatcggga ctgataactc tgttgtcctc tcccgcaaat atacatcgta tccatggctg   1380
ctaggctgtg ctgccaactg gatcctgcgc gggacgtcct ttgtttacgt cccgtcggcg   1440
ctgaatcctg cggacgaccc ttctcggggt cgcttgagac tctctcgtcc ccttctccgt   1500
ctgccgttcc gaccgaccac ggggcgcacc tctctttacg cggactcccc gtctgtgcct   1560
tctcatctgc cggaccgtgt gcacttcgct tcacctctgc acgtcgcatg gagaccaccg   1620
tgaacgccca ccgaatgttg cccaaggtct tacataagag gactcttgga ctctctgcaa   1680
tgtcaacgac cgaccttgag gcatacttca aagactgttt gtttaaagac tgggaggagt   1740
tgggggagga gattagatta aaggtctttg tactaggagg ctgtaggcat aaattggtct   1800
gcgcaccggc gccatgcacc ttttcacct ctgcctaatc atctcttgtt catgtcctac   1860
tgttcaagcc tccaagctgt gccttgggtg gctttgggc atggacatcg acccttataa   1920
agaatttgga gctactgtgg agttactctc gttttgcct tctgacttct ttccttcagt   1980
acgagatctt ctagataccg cctcagctct gtatcgggaa gccttagagt ctcctgagca   2040
ttgttcacct caccatactg cactcaggca agcaattctt tgctgggggg aactaatgac   2100
tctagctacc tgggtgggtg ttaatttgga agatccagca tctagagacc tagtagtcag   2160
ttatgtcaac actaatatgg gcctaaagtt caggcaactc ttgtggtttc acatttcttg   2220
tctcactttt ggaagagaaa ccgttataga gtatttggtg tctttcggag tgtggattcg   2280
cactcctcca gcttatagac caccaaatgc ccctatccta tcaacacttc cggaaactac   2340
tgttgttaga cgacgaggca ggtcccctag aagaagaact ccctcgcctc gcagacgaag   2400
gtctcaatcg ccgcgtcgca gaagatctca atctcgggaa cctcaatgtt agtattcctt   2460
ggactcataa ggtggggaac tttactggtc tttattcttc tactgtacct gtctttaatc   2520
ctcattggaa acaccatct tttcctaata tacatttaca ccaagacatt atcaaaaaat   2580
gtgaacagtt tgtaggccca cttacagtta atgagaaaag aagattgcaa ttgattatgc   2640
ctgctaggtt ttatccaaag gttaccaaat atttaccatt ggataagggt attaaacctt   2700
attatccaga acatctagtt aatcattact tccaaactag acactattta cacactctat   2760
ggaaggcggg tatattatat aagagagaaa caacacatag cgcctcattt tgtgggtcac   2820
```

| | |
|---|---:|
| catattcttg ggaacaagat ctacagcatg ggcagaatc tttccaccag caatcctctg | 2880 |
| ggattctttc ccgaccacca gttggatcca gccttcagag caaacacagc aaatccagat | 2940 |
| tgggacttca atcccaacaa ggacacctgg ccagacgcca acaaggtagg agctggagca | 3000 |
| ttcgggctgg gtttcactcc accgcacgga ggccttttgg ggtggagctc tcaggctcag | 3060 |
| ggcatactac aaactttgcc agcaaatccg cctcctgcct ccaccaatcg ccagacagga | 3120 |
| aggcagccta ccccgctgtc tccacctttg agaaacactc atcctcaggc catgcagtgg | 3180 |
| aa | 3182 |

<210> SEQ ID NO 7
<211> LENGTH: 3212
<212> TYPE: DNA
<213> ORGANISM: Hepatitis B virus

<400> SEQUENCE: 7

| | |
|---|---:|
| ttccacaaca ttccaccaag ctcascagga tcccagagta agrggcctgt atyttcctgc | 60 |
| tggtggctcc agttccggaa cagtgaaccc tgttccgact actgcctcac tcatctcgtc | 120 |
| aatcttctcg aggattgggg accctgcacc gaacatggaa ggcatacat caggattcct | 180 |
| aggaccctg ctcgtgttac aggcgggtt tttcttgttg acaaaaatcc tcacaatacc | 240 |
| gcagagtcta gactcgtggt ggacttctct caattttcya ggggaagctc ccgtgtgtcg | 300 |
| tggccaaaat tcgcagtycc caacctccaa tcactcacca acctcttgtc ctccaatttg | 360 |
| tcctggctat cgctggatgt gtctgcggcg ttttatcatc ttcctcttca tcctgctgct | 420 |
| atgcctcatc ttcttgttgg ttcttctgga ctatcaaggt atgttgcccg tttgtcctct | 480 |
| aattccagga tcatcaacca ccagtacggg accctgccga acctgcacga ctcttgctca | 540 |
| aggaacctct atgtttccct catgttgctg ttcaaaacct tcggacggaa attgcacttg | 600 |
| tattcccatc ccatcatcat gggctttcg aaaattccta tgggagtggg cctcagcccg | 660 |
| tttctcctgg ctcagtttac tagtgccatt tgttcagtgg ttcgccgggc tttcccccac | 720 |
| tgtctggctt tcagttatat ggatgatgtg gtattggggg ccaagtctgt acaacatctt | 780 |
| gagtcccttt atacctctgt taccaatttt cttttgtctt tgggtataca tttaaatcct | 840 |
| aacaaaacaa aaagatgggg atattcccta aatttcatgg gttatgttat tggtagttgg | 900 |
| gggtcattac cacaggaaca catcagaatg aaaatcaaag actgttttag aaaactccct | 960 |
| gttaaccggc ctattgattg gaaagtatgt caaagaattg tgggtctctt gggctttgct | 1020 |
| gccccttta cacaatgtgg atatcctgct ttaatgcctc tgtatgcgtg tattcaatct | 1080 |
| aagcaggctt tcactttctc gccaacttac aaggcctttc tgtgtaaaca atacctgaac | 1140 |
| ctttaccccg ttgcccggca acggccaggt ctgtgccaag tgtttgctga tgcaaccccc | 1200 |
| actggttggg gcttggccat aggccatcag cgcatgcgtg gaacctttgy ggctcctctg | 1260 |
| ccgatccata ctgcggaact cctggccgct tgttttgctc gcagcaggtc tggagcgaaa | 1320 |
| cttattggaa cggataattc tgtcgttctc tcccggaaat atacatcatt tccatggctg | 1380 |
| ctaggctgtg ctgccaactg gatcctgcga gggacgtcct ttgtctacgt cccgtcagcg | 1440 |
| ctgaatcctg cggacgaccc gtctcggggt cgcttgggga tctatcgtcc ccttctccgt | 1500 |
| ctgccgttcc ggccgaccac ggggcgcacc tctctttacg cggtctcccc gtctgtgcct | 1560 |
| tctcatctgc cggaccgtgt gcacttcgct tcacctctgc acgtcgcatg gaaaccaccg | 1620 |
| tgaacgccca ccaaatcttg cccaaggtct tatataagag gactcttgga ctctctgcaa | 1680 |
| tgtcaacgac cgaccttgag gcatacttca aagactgctt gtttaaagac tgggaggagt | 1740 |

```
tggggagga gattagatta atgatctttg tactaggagg ctgtaggcat aaattggtct    1800
gcgcaccagc accatgcaac tttttcacct ctgcctaatc atctcttgtt catgtcctac    1860
tgttcaagcc tccaagctgt gccttgggtg gctttaggac atggacattg acccttataa    1920
agaatttgga gctwctgtgg agttactctc kttttgcct catgacttct ttccttcaat    1980
aagagatctt ctagataccg ccacagctct gtatcgggat gccttagaat ctcctgagca    2040
ttgttcacct caccacacgg cactcaggca agccattctt tgctgggggg atgtaatgaa    2100
tctagctacc tgggtgggtg taaatttgga agatccagca tccagggacc tggtagtcgg    2160
ttatgtcaat actaatatgg gcctaaagtt cagacaatta ttgtggtttc acacttcctg    2220
tctcactttt ggaagagaaa ccgtcttaga gtatttggtg tcttttggag tgtggattcg    2280
cactcctcca ccttatagac caccaaatgc ccctatctta tcaacacttc cggagactac    2340
tgttgttaga cgaagaggca ggtcccctag aagaagaact ccctcrcctc gcagacgtag    2400
atctcaatcg ccgcgtcgca gaagatctca atctccagct tcccgatgtt agtattcctt    2460
ggactcacaa ggtgggaaat ttacggggc tttactcttc tactatacct gtctttaatc    2520
ctaactggaa aactccatct tttcctgata ttcatttgca ccaggacatt attaacaaat    2580
gtgaacaatt tgtaggtccc ctaacagtaa atgaaaaacg aagattmaac ttagtcatgc    2640
ctgctagatt ttttcccatc tctacgaaat atttgcctct agagaaaggt ataaaaccct    2700
attatccaga taatgtagtt aatcattact ccaaaccag acactattta catacctat    2760
ggaaggcggg tatcttatat aaaagagaaa ctgcacgtag cgcctcattt tgtgggtcac    2820
catattcttg ggaacaagag ctacatcatg ggtctttctt ggacggtccc tctcgaatgg    2880
gggaagaatc attccaccac caatcctctg ggattttttc ccgaccacca gttggatcca    2940
gcattcagag caaacaccag aaatccagat tgggaccaca atcccaacaa agaccactgg    3000
acagaagcca acaaggtagg agtgggagca ttcgggccgg ggttcactcc cccacacgga    3060
ggccttttgg ggtggagccc tcaggctcaa ggcatgctaa aaacattgcc agcagatccg    3120
cctcctgcct ccaccaatcg gcagtcagga aggcagccta ccccaatcac tccacctttg    3180
agagacactc atcctcaggc catrcagtgg aa                                  3212

<210> SEQ ID NO 8
<211> LENGTH: 3205
<212> TYPE: DNA
<213> ORGANISM: Hepatitis B virus

<400> SEQUENCE: 8
ttccatcagg ctctgttgga tcccagggta agggctctgt atcttcctgc tggtggctcc     60
agttcaggaa cacaaaaccc tgctccgact attgcctctc tcacatcctc aatcttctcg    120
acgactgggg gccctgctat gaacatggac aacattacat caggactcct aggacccctg    180
ctcgtgttac aggcggtgtg tttcttgttg acaaaaatcc tcacaatacc acagagtcta    240
gactcgtggt ggacttctct caattttcta ggggactac ccgggtgtcc tggccaaaat    300
tcgcagtccc caacctccaa tcacttacca acctcctgtc ctccaacttg tcctggctat    360
cgttggatgt gtctgcggcg ttttatcatc ttcctcttca tcctgctgct atgcctcatc    420
ttcttgttgg ttcttctgga ctaccagggt atgttgcccg tttgtcctct acttccagga    480
tccacgacca ccagcacggg accctgcaaa acctgcacaa ctcttgcaca aggaacctct    540
atgtttccct cctgttgctg ttcaaaaccc tcggacggaa actgcacttg tattcccatc    600
```

```
ccatcatcct gggctttagg aaaataccta tgggagtggg cctcagcccg tttctcatgg    660
ctcagtttac tagtgcaatt tgttcagtgg tgcgtagggc tttcccccac tgtctggctt    720
ttagttatat tgatgatctg gtattggggg ccaaatctgt gcagcacctt gagtcccttt    780
ataccgctgt taccaatttt ctgttatctg tgggtatcca tttaaatact tctaaaacta    840
agagatgggg ttacacccta catttatgg gttatgtcat tggtagttgg ggatcattac     900
ctcaagatca tattgtacac aaaatcaaag aatgttttcg gaaactgcct gtaaatcgtc    960
caattgattg gaaagtctgt caacgcattg tgggtctttt gggctttgct gccccttca   1020 cacaatgtgg ttatcctgct ctcatgcctc tgtatgcttg tattactgct aaacaggctt   1080
ttgttttttc gccaacttac aaggcctttc tctgtaaaca atacatgaac ctttaccccg   1140
ttgccaggca acggccgggc ctgtgccaag tgtttgctga cgcaacccc actggttggg    1200 gcttggccat tggccatcag cgcatgcgtg aacctttgt ggctcctctg ccgatccata    1260
ctgcggaact ccttgcagct tgtttcgctc gcagcaggtc tggagcgact ctcatcggca   1320
cggacaactc tgttgtcctc tctaggaagt acacctcctt cccatggctg ctcgggtgtg   1380
ctgcaaactg gatcctgcgc gggacgtcct ttgtttacgt cccgtcggcg ctgaatcccg   1440
cggacgaccc ctcccggggc cgcttggggc tgtaccgccc tcttctccgt ctgccgttcc   1500
agccgacaac gggtcgcacc tctctttacg cggactcccc gtctgttcct tctcatctgc   1560
cggaccgtgt gcacttcgct tcacctctgc acgtcgcatg gagaccaccg tgaacgcccc   1620
ttggagtttg ccaacagtct tacataagag gactcttgga ctttcaggag ggtcaatgac   1680
ccggattgca gaatacatca aagactgtgt atttaaggac tgggaggagt tggggaggag   1740
gactaggtta atgatctttg tactaggagg ctgtaggcat aaattggtct gttcaccagc   1800
accatgcaac tttttcacct ctgcctaatc atcttttgtt catgtcctac tgttcaagcc   1860
tccaagctgt gccttgggtg gctttgggac atggacattg accccttataa agaatttggc   1920 gcttctgtgg agttactctc ttttttgcct tctgatttct ttccatcggt tcgggaccta   1980
ctcgacaccg cttcagccct ttaccgggat gctttagagt cacctgaaca ttgcactccc   2040
catcacactg ccctcaggca agttattttg tgctggggtg agttaatgac tttggcttcc   2100
tgggtgggca ataacttgga agaccctgct gccagggatt tagtagttaa ctatgttaac   2160
actaacatgg gcctaaaaat tagacaacta ctgtggtttc acatttcctg ccttactttt   2220
ggaagagata tagttcttga gtatttggtg tcctttggag tgtggattcg cactcctcct   2280
gcttacagac cacaaaatgc ccctatccta tccacacttc cggaaactac tgttgttaga   2340
cgacgaggca ggtcccctag aagaagaact ccctcgcctc gcagacgaag atctcaatcg   2400
ccgcgtcgcc gaagatctca atctccagct tcccaatgtt agtattcctt ggactcataa   2460
ggtgggaaat tttacggggc tttactcttc tactgtgcct gcttttaatc ctgactggtt   2520
aactccttct tttcctaata ttcatttaca tcaagaccta atttctaaat gtgaacaatt   2580
tgtaggccca ctcactaaaa atgaattaag gaggttaaaa ttggttatgc cagctagatt   2640
ttatcctaag gttaccaaat attttcctat ggagaaagga atcaagcctt attatcctga   2700
gcatgcagtt aatcattact ttaaaacaag acattatttg catactttat ggaaggcggg   2760
aattttatat aagagagaat ccacacgtag cgcatcattt tgtgggtcac catattcctg   2820
ggaacaagag ctacagcatg ggagcacctc tctcaacgac aagaagaggc atgggacaga   2880
atctttctgt gcccaatcct ctgggattct ttccagacca tcagctggat ccgctattca   2940
aagcaaattc cagcagtccc gactgggact tcaacacaaa caaggacagt tggccaatgg   3000
```

| | |
|---|---|
| caaacaaggt aggagtggga gcatacggtc cagggttcac accccacac ggtggcctgc | 3060 |
| tggggtggag ccctcaggca caaggtatgt taacaacctt gccagcagat ccgcctcctg | 3120 |
| cttccaccaa tcggcggtcc gggagaaagc caaccccagt ctctccacct ctaagagaca | 3180 |
| ctcatccaca ggcaatgcag tggaa | 3205 |

<210> SEQ ID NO 9
<211> LENGTH: 3247
<212> TYPE: DNA
<213> ORGANISM: Hepatitis B virus

<400> SEQUENCE: 9

| | |
|---|---|
| tctacagcat tccaccaagc tctacaaaat cccaaagtca ggggcctgta ttttcctgct | 60 |
| ggtggctcca gttcagggat agtgaaccct gttccgacta ttgcctctca catctcgtca | 120 |
| atcttctcca ggattgggga ccctgcaccg aacatggaga acatcacatc aggattccta | 180 |
| ggacccctgc tcgtgttaca ggcggggttt tcttgttga caagaatcct cacaataccg | 240 |
| cagaatctag actcgtggtg gacttctctc aattttctag ggggagtgcc cgtgtgtcct | 300 |
| ggcctaaatt cgcagtcccc aacctccaat cactcaccaa tctcctgtcc tccaacttgt | 360 |
| cctggctatc gctggatgtg tctgcggcgt tttatcatat tcctcttcat cctgctgcta | 420 |
| tgcctcatct tcttgttggt tcttctggac atcaaggta tgttgcccgt ttgtcctctg | 480 |
| attccaggat cctcgaccac cagtacggga ccctgcaaaa cctgcacgac tcctgctcaa | 540 |
| ggcaactcta tgtatccctc atgttgctgt acaaaacctt cggacggaaa ttgcacctgt | 600 |
| attcccatcc catcatcttg gctttcgca aaataccttt gggagtgggc ctcagtccgt | 660 |
| ttctcttggc tcagtttact agtgccattt gttcagtggt tcgtagggct ttcccccact | 720 |
| gtctggcttt cagctatatg gatgatgtgg tattgggggc caaatctgta caacatcttg | 780 |
| agtccctta taccgctgtt accaattttc ttttgtcttt gggtatacat ctaaacccta | 840 |
| acaaaacaaa aagatggggt tattccttaa attttatggg atatgtaatt ggaagttggg | 900 |
| gtactttgcc acaagaacac atcacacaga aaattaagca atgttttcgg aaactccctg | 960 |
| ttaacaggcc aattgattgg aaagtctgtc aacgaataac tggtctgttg ggtttcgctg | 1020 |
| ctccttttac ccaatgtggt taccctgcct taatgccttt atatgcatgt atacaagcta | 1080 |
| agcaggcttt tactttctcg ccaacttata aggcctttct ctgtaaacaa tacatgaacc | 1140 |
| tttaccccgt tgctaggcaa cggcccggtc tgtgccaagt gtttgctgac gcaaccccca | 1200 |
| ctggttgggg cttggccatc ggccatcagc gcatgcgtgg aacctttgtg gctcctctgc | 1260 |
| cgatccatac tgcggaactc ctagctgctt gttttgctcg cagccggtct ggagcaaaac | 1320 |
| tcattgggac tgacaattct gtcgtccttt ctcggaaata cacatccttt ccatggctgc | 1380 |
| taggctgtgc tgccaactgg atccttcgcg ggacgtcctt tgtttacgtc ccgtcagcgc | 1440 |
| tgaatccagc ggacgacccc tcccggggcc gtttgggct ctgtcgcccc cttctccgtc | 1500 |
| tgccgttcct gccgaccacg gggcgcacct ctctttacgc ggtctccccg tctgttcctt | 1560 |
| ctcatctgcc ggaccgtgtg cacttcgctt cacctctgca cgttacatgg aaaccgccat | 1620 |
| gaacacctct catcatctgc caaggcagtt atataagagg actcttggac tgtttgttat | 1680 |
| gtcaacaacc ggggtggaga atacttcaa ggactgtgtt tttgctgagt gggaagaatt | 1740 |
| aggcaatgag tccaggttaa tgacctttgt attaggaggc tgtaggcata aattggtctg | 1800 |
| cgcaccagca ccatgtaact ttttcacctc tgcctaatca tctcttgttc atgtcctact | 1860 |

```
gttcaagcct ccaagctgtg ccttgggtgg ctttagggca tggatagaac aactttgcca    1920
tatggccttt ttggcttaga cattgaccct tataaagaat ttggagctac tgtggagttg    1980
ctctcgtttt tgccttctga cttttttccg tctgttcgtg atcttctcga caccgcttca    2040
gctttgtacc gggaatcctt agagtcctct gatcattgtt cgcctcacca tacagcactc    2100
aggcaagcaa tcctgtgctg gggtgagttg atgactctag ccacctgggt gggtaataat    2160
ttggaagatc cagcatccag agatttggtg gtcaattatg ttaatactaa tatgggttta    2220
aaaatcaggc aactattgtg gtttcacatt tcctgtctta cttttgggag agaaaccgtt    2280
cttgagtatt tggtgtcttt tggagtgtgg attcgcactc ctcctgctta tagaccacca    2340 aatgcccta tcctatcaac acttccggag actactgttg ttagacgaag aggcaggtcc    2400
cctcgaagaa gaactccctc gcctcgcaga cgaagatctc aatcgccgcg tcgcagaaga    2460
tctgcatctc cagcttccca atgttagtat tccttggact cacaaggtgg gaaactttac    2520
ggggctgtat tcttctacta tacctgtctt taatcctgat tggcaaactc cttcttttcc    2580
aaatatccat ttgcatcaag acattataac taaatgtgaa caatttgtgg gccctctcac    2640
agtaaatgag aaacgaagat taaaactagt tatgcctgcc agattttttcc caaactctac    2700 taaatattta ccattagaca aaggtatcaa accgtattat ccagaaaatg tagttaatca    2760
ttacttccag accagacatt atttacatac ccttttggaag gcgggtattc tatataagag    2820
agaaacatcc cgtagcgctt cattttgtgg gtcaccatat acttgggaac aagatctaca    2880
gcatggggct ttcttggacg gtccctctcg agtggggaaa gaacctttcc accagcaatc    2940
ctctaggatt ccttcccgat caccagttgg acccagcatt cagagcaaat accaacaatc    3000
cagattggga cttcaatccc aaaaaggacc cttggccaga ggccaacaag gtaggagttg    3060
gagcctatgg acccgggttc acccctccac acggaggcct tttggggtgg agccctcagt    3120
ctcagggcac actaacaact ttgccagcag atccgcctcc tgcctccacc aatcgtcagt    3180
cagggaggca gccgactccc atctctccac cactaagaga cagtcatcct caggccatgc    3240
agtggaa                                                              3247

<210> SEQ ID NO 10
<211> LENGTH: 22
<212> TYPE: DNA
<213> ORGANISM: Hepatitis B virus

<400> SEQUENCE: 10
tgccgatcca tactgcggaa ct                                              22

<210> SEQ ID NO 11
<211> LENGTH: 22
<212> TYPE: DNA
<213> ORGANISM: Hepatitis B virus

<400> SEQUENCE: 11
acggctaggt atgacgcctt ga                                              22

<210> SEQ ID NO 12
<211> LENGTH: 354
<212> TYPE: PRT
<213> ORGANISM: Artificial sequence
<220> FEATURE:
<223> OTHER INFORMATION: Synthesized

<400> SEQUENCE: 12

Met Asn Thr Lys Tyr Asn Lys Glu Phe Leu Leu Tyr Leu Ala Gly Phe
```

```
  1               5                  10                 15
Val Asp Ser Asp Gly Ser Ile Asn Ala Ser Ile Ser Pro Arg Gln Ser
            20                 25                 30
Phe Lys Phe Lys His Gly Leu Lys Leu Arg Phe Glu Val Gly Gln Lys
            35                 40                 45
Thr Gln His Arg Trp Phe Leu Asp Lys Leu Val Asp Glu Ile Gly Val
            50                 55                 60
Gly Tyr Val Tyr Asp Asn Gly Ser Val Ser Val Tyr Ser Leu Ser Gln
 65                 70                 75                 80
Ile Lys Pro Leu His Asn Phe Leu Thr Gln Leu Gln Pro Phe Leu Lys
                85                 90                 95
Leu Lys Gln Lys Gln Ala Asn Leu Val Leu Lys Ile Ile Glu Gln Leu
            100                105                110
Pro Ser Ala Lys Glu Ser Pro Asp Lys Phe Leu Glu Val Cys Thr Trp
            115                120                125
Val Asp Gln Ile Ala Ala Leu Asn Asp Ser Lys Thr Arg Lys Thr Thr
            130                135                140
Ser Glu Thr Val Arg Ala Val Leu Asp Ser Leu Pro Gly Ser Val Gly
145                150                155                160
Gly Leu Ser Pro Ser Gln Ala Ser Ser Ala Ala Ser Ser Ala Ser Ser
                165                170                175
Ser Pro Gly Ser Gly Ile Ser Glu Ala Leu Arg Ala Gly Ala Gly Ser
            180                185                190
Gly Thr Gly Tyr Asn Lys Glu Phe Leu Leu Tyr Leu Ala Gly Phe Val
            195                200                205
Asp Gly Asp Gly Ser Ile Phe Ala Ser Ile Arg Pro Arg Gln His Ala
            210                215                220
Lys Phe Lys His Asp Leu Glu Leu Cys Phe Asn Val Arg Gln Lys Thr
225                230                235                240
Gln Arg Arg Trp Phe Leu Asp Lys Leu Val Asp Glu Ile Gly Val Gly
            245                250                255
Tyr Val Ile Asp Trp Arg Gly Ala Ser Thr Tyr Lys Leu Ser Gln Ile
            260                265                270
Lys Pro Leu His Asn Phe Leu Thr Gln Leu Gln Pro Phe Leu Lys Leu
            275                280                285
Lys Gln Lys Gln Ala Asn Leu Val Leu Lys Ile Ile Glu Gln Leu Pro
            290                295                300
Ser Ala Lys Glu Ser Pro Asp Lys Phe Leu Glu Val Cys Thr Trp Val
305                310                315                320
Asp Gln Ile Ala Ala Leu Asn Asp Ser Lys Thr Arg Lys Thr Thr Ser
                325                330                335
Glu Thr Val Arg Ala Val Leu Asp Ser Leu Ser Glu Lys Lys Lys Ser
            340                345                350
Ser Pro

<210> SEQ ID NO 13
<211> LENGTH: 354
<212> TYPE: PRT
<213> ORGANISM: Artificial sequence
<220> FEATURE:
<223> OTHER INFORMATION: Synthesized

<400> SEQUENCE: 13

Met Asn Thr Lys Tyr Asn Lys Glu Phe Leu Leu Tyr Leu Ala Gly Phe
 1               5                  10                 15
```

Val Asp Ala Asp Gly Ser Ile Asn Ala Ser Ile Gln Pro Arg Gln Ser
            20                  25                  30

Phe Lys Phe Lys His Ser Leu Lys Leu Arg Phe Glu Val Gly Gln Lys
        35                  40                  45

Thr Gln Arg Arg Trp Phe Leu Asp Lys Leu Val Asp Glu Ile Gly Val
    50                  55                  60

Gly Tyr Val Tyr Asp Asn Gly Ser Val Ser Val Tyr Ser Leu Ser Gln
65                  70                  75                  80

Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Glu Gln Leu
            100                 105                 110

Pro Ser Ala Lys Glu Ser Pro Asp Lys Phe Leu Glu Val Cys Thr Trp
        115                 120                 125

Val Asp Gln Ile Ala Ala Leu Asn Asp Ser Lys Thr Arg Lys Thr Thr
    130                 135                 140

Ser Glu Thr Val Arg Ala Val Leu Asp Ser Leu Pro Gly Ser Val Gly
145                 150                 155                 160

Gly Leu Ser Pro Ser Gln Ala Ser Ser Ala Ser Ser Ala Ser Ser
                165                 170                 175

Ser Pro Gly Ser Gly Ile Ser Glu Ala Leu Arg Ala Gly Ala Gly Ser
            180                 185                 190

Gly Thr Gly Tyr Asn Lys Glu Phe Leu Leu Tyr Leu Ala Gly Phe Val
        195                 200                 205

Asp Gly Asp Gly Ser Ile Phe Ala Ser Ile Arg Pro Arg Gln His Ala
    210                 215                 220

Lys Phe Lys His Asp Leu Glu Leu Cys Phe Asn Val Arg Gln Lys Thr
225                 230                 235                 240

Gln Arg Arg Trp Phe Leu Asp Lys Leu Val Asp Glu Ile Gly Val Gly
                245                 250                 255

Tyr Val Leu Asp Trp Arg Gly Ala Ser Thr Tyr Lys Leu Ser Glu Ile
            260                 265                 270

Lys Pro Leu His Asn Phe Leu Thr Gln Leu Gln Pro Phe Leu Lys Leu
        275                 280                 285

Lys Gln Lys Gln Ala Asn Leu Val Leu Lys Ile Ile Glu Gln Leu Pro
    290                 295                 300

Ser Ala Lys Glu Ser Pro Asp Lys Phe Leu Glu Val Cys Thr Trp Val
305                 310                 315                 320

Asp Gln Ile Ala Ala Leu Asn Asp Ser Arg Thr Arg Lys Thr Thr Ser
                325                 330                 335

Glu Thr Val Arg Ala Val Leu Asp Ser Leu Ser Glu Lys Lys Lys Ser
            340                 345                 350

Ser Pro

<210> SEQ ID NO 14
<211> LENGTH: 354
<212> TYPE: PRT
<213> ORGANISM: Artificial sequence
<220> FEATURE:
<223> OTHER INFORMATION: Synthesized

<400> SEQUENCE: 14

Met Asn Thr Lys Tyr Asn Lys Glu Phe Leu Leu Tyr Leu Ala Gly Phe
1               5                   10                  15

Val Asp Gly Asp Gly Ser Ile Asn Ala Ser Ile Ala Pro Arg Gln Ser
            20                  25                  30

Phe Lys Phe Lys His Gly Leu Lys Leu Arg Phe Glu Val Gly Gln Lys
        35                  40                  45

Thr Gln Arg Arg Trp Phe Leu Asp Lys Leu Val Asp Glu Ile Gly Val
    50                  55                  60

Gly Tyr Val Tyr Asp Asn Gly Ser Val Ser Val Tyr Ser Leu Ser Gln
65                  70                  75                  80

Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Glu Gln Leu
            100                 105                 110

Pro Ser Ala Lys Glu Ser Pro Asp Lys Phe Leu Glu Val Cys Thr Trp
        115                 120                 125

Val Asp Gln Ile Ala Ala Leu Asn Asp Ser Lys Thr Arg Lys Thr Thr
    130                 135                 140

Ser Glu Thr Val Arg Ala Val Leu Asp Ser Leu Pro Gly Ser Val Gly
145                 150                 155                 160

Gly Leu Ser Pro Ser Gln Ala Ser Ser Ala Ser Ser Ala Ser Ser
                165                 170                 175

Ser Pro Gly Ser Gly Ile Ser Glu Ala Leu Arg Ala Gly Ala Gly Ser
            180                 185                 190

Gly Thr Gly Tyr Asn Lys Glu Phe Leu Leu Tyr Leu Ala Gly Phe Val
        195                 200                 205

Asp Ser Asp Gly Ser Ile Phe Ala Ser Ile Arg Pro Arg Gln Met Ala
    210                 215                 220

Lys Phe Lys His Asp Leu Glu Leu Cys Phe Asn Val Arg Gln Lys Thr
225                 230                 235                 240

Gln Arg Arg Trp Phe Leu Asp Lys Leu Val Asp Glu Ile Gly Val Gly
                245                 250                 255

Tyr Val His Asp Trp Gly Ser Val Ser Thr Tyr Lys Leu Ser Glu Ile
            260                 265                 270

Lys Pro Leu His Asn Phe Leu Thr Gln Leu Gln Pro Phe Leu Lys Leu
        275                 280                 285

Lys Gln Lys Gln Ala Asn Leu Val Leu Lys Ile Ile Glu Gln Leu Pro
    290                 295                 300

Ser Ala Lys Glu Ser Pro Asp Lys Phe Leu Glu Val Cys Thr Trp Val
305                 310                 315                 320

Asp Gln Ile Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
            340                 345                 350

Ser Pro

<210> SEQ ID NO 15
<211> LENGTH: 354
<212> TYPE: PRT
<213> ORGANISM: Artificial sequence
<220> FEATURE:
<223> OTHER INFORMATION: Synthesized

<400> SEQUENCE: 15

Met Asn Thr Lys Tyr Asn Lys Glu Phe Leu Leu Tyr Leu Ala Gly Phe
1               5                   10                  15

Val Asp Gly Asp Gly Ser Ile Asn Ala Thr Ile Ala Pro Arg Gln Ser

```
            20                  25                  30
Phe Lys Phe Lys His Gly Leu Lys Leu Arg Phe Glu Val Gly Gln Lys
            35                  40                  45
Thr Gln Arg Arg Trp Phe Leu Asp Lys Leu Val Asp Glu Ile Gly Val
        50                  55                  60
Gly Tyr Val Tyr Asp Asn Gly Ser Val Ser Val Tyr Cys Leu Ser Gln
65                  70                  75                  80
Ile Lys Pro Leu His Asn Phe Leu Thr Gln Leu Gln Pro Phe Leu Lys
                85                  90                  95
Leu Lys Gln Lys Gln Ala Asn Leu Val Leu Lys Ile Ile Glu Gln Leu
            100                 105                 110
Pro Ser Ala Lys Glu Ser Pro Asp Lys Phe Leu Glu Val Cys Thr Trp
            115                 120                 125
Val Asp Gln Ile Ala Ala Leu Asn Asp Ser Lys Thr Arg Lys Thr Thr
            130                 135                 140
Ser Glu Thr Val Arg Ala Val Leu Asp Ser Leu Pro Gly Ser Val Gly
145                 150                 155                 160
Gly Leu Ser Pro Ser Gln Ala Ser Ser Ala Ser Ser Ala Ser Ser
                165                 170                 175
Ser Pro Gly Ser Gly Ile Ser Glu Ala Leu Arg Ala Gly Ala Gly Ser
            180                 185                 190
Gly Thr Gly Tyr Asn Lys Glu Phe Leu Leu Tyr Leu Ala Gly Phe Val
            195                 200                 205
Asp Gly Asp Gly Ser Ile Tyr Ala Ser Ile Arg Pro Arg Gln His Ala
            210                 215                 220
Lys Phe Lys His Asp Leu Glu Leu Ile Phe Asn Val Arg Gln Leu Thr
225                 230                 235                 240
Ser Arg Arg Trp Phe Leu Asp Lys Leu Val Asp Glu Ile Gly Val Gly
                245                 250                 255
Tyr Val Ile Asp Trp Arg Gly Ala Ser Thr Tyr Lys Leu Ser Glu Ile
            260                 265                 270
Lys Pro Leu His Asn Phe Leu Thr Gln Leu Gln Pro Phe Leu Lys Leu
            275                 280                 285
Lys Gln Lys Gln Ala Asn Leu Val Leu Lys Ile Ile Glu Gln Leu Pro
            290                 295                 300
Ser Ala Lys Glu Ser Pro Asp Lys Phe Leu Glu Val Cys Thr Trp Val
305                 310                 315                 320
Asp Gln Ile Ala Ala Leu Asn Asp Ser Lys Thr Arg Lys Thr Thr Ser
                325                 330                 335
Glu Thr Val Arg Ala Val Leu Asp Ser Leu Ser Glu Lys Lys Lys Ser
            340                 345                 350
Ser Pro

<210> SEQ ID NO 16
<211> LENGTH: 354
<212> TYPE: PRT
<213> ORGANISM: Artificial sequence
<220> FEATURE:
<223> OTHER INFORMATION: Synthesized

<400> SEQUENCE: 16

Met Asn Thr Lys Tyr Asn Lys Glu Phe Leu Leu Tyr Leu Ala Gly Phe
1               5                   10                  15
Val Asp Gly Asp Gly Ser Ile Asn Ala Thr Ile Ala Pro Arg Gln Ser
            20                  25                  30
```

Phe Lys Phe Lys His Gly Leu Lys Leu Arg Phe Glu Val Gly Gln Lys
            35                  40                  45

Thr Gln Arg Arg Trp Phe Leu Asp Lys Leu Val Asp Glu Ile Gly Val
 50                  55                  60

Gly Tyr Val Tyr Asp Asn Gly Ser Val Ser Val Tyr Cys Leu Ser Gln
 65                  70                  75                  80

Ile Lys Pro Leu His Asn Phe Leu Thr Gln Leu Gln Pro Phe Leu Lys
                 85                  90                  95

Leu Lys Gln Lys Gln Ala Asn Leu Val Leu Lys Ile Ile Glu Gln Leu
            100                 105                 110

Pro Ser Ala Lys Glu Ser Pro Asp Lys Phe Leu Glu Val Cys Thr Trp
            115                 120                 125

Val Asp Gln Ile Ala Ala Leu Asn Asp Ser Lys Thr Arg Lys Thr Thr
130                 135                 140

Ser Glu Thr Val Arg Ala Val Leu Asp Ser Leu Pro Gly Ser Val Gly
145                 150                 155                 160

Gly Leu Ser Pro Ser Gln Ala Ser Ser Ala Ala Ser Ala Ser Ser
            165                 170                 175

Ser Pro Gly Ser Gly Ile Ser Glu Ala Leu Arg Ala Gly Ala Gly Ser
            180                 185                 190

Gly Thr Gly Tyr Asn Lys Glu Phe Leu Leu Tyr Leu Ala Gly Phe Val
            195                 200                 205

Asp Ser Asp Gly Ser Ile Tyr Ala Ser Ile Arg Pro Arg Gln His Ala
            210                 215                 220

Lys Phe Lys His Asp Leu Glu Leu Ile Phe Asn Val Arg Gln Leu Thr
225                 230                 235                 240

Ser Arg Arg Trp Phe Leu Asp Lys Leu Val Asp Glu Ile Gly Val Gly
            245                 250                 255

Tyr Val Ile Asp Trp Arg Gly Ala Ser Thr Tyr Lys Leu Ser Glu Ile
            260                 265                 270

Lys Pro Leu His Asn Phe Leu Thr Gln Leu Gln Pro Phe Leu Lys Leu
            275                 280                 285

Lys Gln Lys Gln Ala Asn Leu Val Leu Lys Ile Ile Glu Gln Leu Pro
            290                 295                 300

Ser Ala Lys Glu Ser Pro Asp Lys Phe Leu Glu Val Cys Thr Trp Val
305                 310                 315                 320

Asp Gln Ile Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
            340                 345                 350

Ser Pro

<210> SEQ ID NO 17
<211> LENGTH: 354
<212> TYPE: PRT
<213> ORGANISM: Artificial sequence
<220> FEATURE:
<223> OTHER INFORMATION: Synthesized

<400> SEQUENCE: 17

Met Asn Thr Lys Tyr Asn Lys Glu Phe Leu Leu Tyr Leu Ala Gly Phe
1               5                   10                  15

Val Asp Gly Asp Gly Ser Ile Asn Ala Ala Ile Ala Pro Arg Gln Ser
            20                  25                  30

```
Phe Lys Phe Lys His Gly Leu Lys Leu Arg Phe Glu Val Gly Gln Lys
            35                  40                  45
Thr Gln Arg Arg Trp Phe Leu Asp Lys Leu Val Asp Glu Ile Gly Val
 50                  55                  60
Gly Tyr Val Tyr Asp Asn Gly Ser Val Ser Val Tyr Cys Leu Ser Gln
 65                  70                  75                  80
Ile Lys Pro Leu His Asn Phe Leu Thr Gln Leu Gln Pro Phe Leu Lys
                 85                  90                  95
Leu Lys Gln Lys Gln Ala Asn Leu Val Leu Lys Ile Ile Glu Gln Leu
            100                 105                 110
Pro Ser Ala Lys Glu Ser Pro Asp Lys Phe Leu Glu Val Cys Thr Trp
            115                 120                 125
Val Asp Gln Ile Ala Ala Leu Asn Asp Ser Lys Thr Arg Lys Thr Thr
130                 135                 140
Ser Glu Thr Val Arg Ala Val Leu Asp Ser Leu Pro Gly Ser Val Gly
145                 150                 155                 160
Gly Leu Ser Pro Ser Gln Ala Ser Ser Ala Ser Ser Ala Ser Ser Ser
                165                 170                 175
Ser Pro Gly Ser Gly Ile Ser Glu Ala Leu Arg Ala Gly Ala Gly Ser
            180                 185                 190
Gly Thr Gly Tyr Asn Lys Glu Phe Leu Leu Tyr Leu Ala Gly Phe Val
            195                 200                 205
Asp Gly Asp Gly Ser Ile Tyr Ala Ser Ile Arg Pro Arg Gln Gln Ser
            210                 215                 220
Lys Phe Lys His Asp Leu Glu Leu Tyr Phe Asn Val Arg Gln Lys Thr
225                 230                 235                 240
Arg Arg Arg Trp Phe Leu Asp Lys Leu Val Asp Glu Ile Gly Val Gly
            245                 250                 255
Tyr Val Asn Asp Trp Arg Gly Thr Ser Thr Tyr Lys Leu Ser Glu Ile
            260                 265                 270
Lys Pro Leu His Asn Phe Leu Thr Gln Leu Gln Pro Phe Leu Lys Leu
            275                 280                 285
Lys Gln Lys Gln Ala Asn Leu Val Leu Lys Ile Ile Glu Gln Leu Pro
290                 295                 300
Ser Ala Lys Glu Ser Pro Asp Lys Phe Leu Glu Val Cys Thr Trp Val
305                 310                 315                 320
Asp Gln Ile Ala Ala Leu Asn Asp Ser Lys Thr Arg Lys Thr Thr Ser
                325                 330                 335
Glu Thr Val Arg Ala Val Leu Asp Ser Leu Ser Glu Lys Lys Lys Ser
            340                 345                 350
Ser Pro

<210> SEQ ID NO 18
<211> LENGTH: 147
<212> TYPE: PRT
<213> ORGANISM: Artificial sequence
<220> FEATURE:
<223> OTHER INFORMATION: Synthesized

<400> SEQUENCE: 18

Lys Glu Phe Leu Leu Tyr Leu Ala Gly Phe Val Asp Gly Asp Gly Ser
 1               5                  10                  15
Ile Phe Ala Ser Ile Arg Pro Arg Gln His Ala Lys Phe Lys His Asp
                 20                  25                  30
Leu Glu Leu Cys Phe Asn Val Arg Gln Lys Thr Gln Arg Arg Trp Phe
```

```
                35                  40                  45
Leu Asp Lys Leu Val Asp Glu Ile Gly Val Gly Tyr Val Ile Asp Trp
     50                  55                  60
Arg Gly Ala Ser Thr Tyr Lys Leu Ser Gln Ile Lys Pro Leu His Asn
 65                  70                  75                  80
Phe Leu Thr Gln Leu Gln Pro Phe Leu Lys Leu Lys Gln Lys Gln Ala
                 85                  90                  95
Asn Leu Val Leu Lys Ile Ile Glu Gln Leu Pro Ser Ala Lys Glu Ser
            100                 105                 110
Pro Asp Lys Phe Leu Glu Val Cys Thr Trp Val Asp Gln Ile Ala Ala
        115                 120                 125
Leu Asn Asp Ser Lys Thr Arg Lys Thr Thr Ser Glu Thr Val Arg Ala
    130                 135                 140
Val Leu Asp
145

<210> SEQ ID NO 19
<211> LENGTH: 147
<212> TYPE: PRT
<213> ORGANISM: Artificial sequence
<220> FEATURE:
<223> OTHER INFORMATION: Synthesized

<400> SEQUENCE: 19

Lys Glu Phe Leu Leu Tyr Leu Ala Gly Phe Val Asp Gly Asp Gly Ser
  1               5                  10                  15
Ile Phe Ala Ser Ile Arg Pro Arg Gln His Ala Lys Phe Lys His Asp
                 20                  25                  30
Leu Glu Leu Cys Phe Asn Val Arg Gln Lys Thr Gln Arg Arg Trp Phe
             35                  40                  45
Leu Asp Lys Leu Val Asp Glu Ile Gly Val Gly Tyr Val Leu Asp Trp
     50                  55                  60
Arg Gly Ala Ser Thr Tyr Lys Leu Ser Glu Ile Lys Pro Leu His Asn
 65                  70                  75                  80
Phe Leu Thr Gln Leu Gln Pro Phe Leu Lys Leu Lys Gln Lys Gln Ala
                 85                  90                  95
Asn Leu Val Leu Lys Ile Ile Glu Gln Leu Pro Ser Ala Lys Glu Ser
            100                 105                 110
Pro Asp Lys Phe Leu Glu Val Cys Thr Trp Val Asp Gln Ile Ala Ala
        115                 120                 125
Leu Asn Asp Ser Arg Thr Arg Lys Thr Thr Ser Glu Thr Val Arg Ala
    130                 135                 140
Val Leu Asp
145

<210> SEQ ID NO 20
<211> LENGTH: 147
<212> TYPE: PRT
<213> ORGANISM: Artificial sequence
<220> FEATURE:
<223> OTHER INFORMATION: Synthesized

<400> SEQUENCE: 20

Lys Glu Phe Leu Leu Tyr Leu Ala Gly Phe Val Asp Ser Asp Gly Ser
  1               5                  10                  15
Ile Phe Ala Ser Ile Arg Pro Arg Gln Met Ala Lys Phe Lys His Asp
                 20                  25                  30
```

```
Leu Glu Leu Cys Phe Asn Val Arg Gln Lys Thr Gln Arg Arg Trp Phe
            35                  40                  45

Leu Asp Lys Leu Val Asp Glu Ile Gly Val Gly Tyr Val His Asp Trp
 50                  55                  60

Gly Ser Val Ser Thr Tyr Lys Leu Ser Glu Ile Lys Pro Leu His Asn
 65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
               100                 105                 110

Pro Asp Lys Phe Leu Glu Val Cys Thr Trp Val Asp Gln Ile Ala Ala
               115                 120                 125

Leu Asn Asp Ser Lys Thr Arg Lys Thr Thr Ser Glu Thr Val Arg Ala
   130                 135                 140

Val Leu Asp
145

<210> SEQ ID NO 21
<211> LENGTH: 147
<212> TYPE: PRT
<213> ORGANISM: Artificial sequence
<220> FEATURE:
<223> OTHER INFORMATION: Synthesized

<400> SEQUENCE: 21

Lys Glu Phe Leu Leu Tyr Leu Ala Gly Phe Val Asp Gly Asp Gly Ser
 1               5                  10                  15

Ile Tyr Ala Ser Ile Arg Pro Arg Gln His Ala Lys Phe Lys His Asp
                20                  25                  30

Leu Glu Leu Ile Phe Asn Val Arg Gln Leu Thr Ser Arg Arg Trp Phe
            35                  40                  45

Leu Asp Lys Leu Val Asp Glu Ile Gly Val Gly Tyr Val Ile Asp Trp
 50                  55                  60

Arg Gly Ala Ser Thr Tyr Lys Leu Ser Glu Ile Lys Pro Leu His Asn
 65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
               100                 105                 110

Pro Asp Lys Phe Leu Glu Val Cys Thr Trp Val Asp Gln Ile Ala Ala
               115                 120                 125

Leu Asn Asp Ser Lys Thr Arg Lys Thr Thr Ser Glu Thr Val Arg Ala
   130                 135                 140

Val Leu Asp
145

<210> SEQ ID NO 22
<211> LENGTH: 147
<212> TYPE: PRT
<213> ORGANISM: Artificial sequence
<220> FEATURE:
<223> OTHER INFORMATION: Synthesized

<400> SEQUENCE: 22

Lys Glu Phe Leu Leu Tyr Leu Ala Gly Phe Val Asp Ser Asp Gly Ser
 1               5                  10                  15

Ile Tyr Ala Ser Ile Arg Pro Arg Gln His Ala Lys Phe Lys His Asp
                20                  25                  30
```

```
Leu Glu Leu Ile Phe Asn Val Arg Gln Leu Thr Ser Arg Arg Trp Phe
            35                  40                  45

Leu Asp Lys Leu Val Asp Glu Ile Gly Val Gly Tyr Val Ile Asp Trp
 50                  55                  60

Arg Gly Ala Ser Thr Tyr Lys Leu Ser Glu Ile Lys Pro Leu His Asn
 65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
                100                 105                 110

Pro Asp Lys Phe Leu Glu Val Cys Thr Trp Val Asp Gln Ile Ala Ala
                115                 120                 125

Leu Asn Asp Ser Lys Thr Arg Lys Thr Thr Ser Glu Thr Val Arg Ala
     130                 135                 140

Val Leu Asp
145

<210> SEQ ID NO 23
<211> LENGTH: 147
<212> TYPE: PRT
<213> ORGANISM: Artificial sequence
<220> FEATURE:
<223> OTHER INFORMATION: Synthesized

<400> SEQUENCE: 23

Lys Glu Phe Leu Leu Tyr Leu Ala Gly Phe Val Asp Gly Asp Gly Ser
 1               5                  10                  15

Ile Tyr Ala Ser Ile Arg Pro Arg Gln Gln Ser Lys Phe Lys His Asp
                20                  25                  30

Leu Glu Leu Tyr Phe Asn Val Arg Gln Lys Thr Arg Arg Arg Trp Phe
            35                  40                  45

Leu Asp Lys Leu Val Asp Glu Ile Gly Val Gly Tyr Val Asn Asp Trp
 50                  55                  60

Arg Gly Thr Ser Thr Tyr Lys Leu Ser Glu Ile Lys Pro Leu His Asn
 65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
                100                 105                 110

Pro Asp Lys Phe Leu Glu Val Cys Thr Trp Val Asp Gln Ile Ala Ala
                115                 120                 125

Leu Asn Asp Ser Lys Thr Arg Lys Thr Thr Ser Glu Thr Val Arg Ala
     130                 135                 140

Val Leu Asp
145

<210> SEQ ID NO 24
<211> LENGTH: 147
<212> TYPE: PRT
<213> ORGANISM: Artificial sequence
<220> FEATURE:
<223> OTHER INFORMATION: Synthesized

<400> SEQUENCE: 24

Lys Glu Phe Leu Leu Tyr Leu Ala Gly Phe Val Asp Ser Asp Gly Ser
 1               5                  10                  15

Ile Asn Ala Ser Ile Ser Pro Arg Gln Ser Phe Lys Phe Lys His Gly
```

```
              20                  25                  30
Leu Lys Leu Arg Phe Glu Val Gly Gln Lys Thr Gln His Arg Trp Phe
            35                  40                  45

Leu Asp Lys Leu Val Asp Glu Ile Gly Val Gly Tyr Val Tyr Asp Asn
        50                  55                  60

Gly Ser Val Ser Val Tyr Ser Leu Ser Gln Ile Lys Pro Leu His Asn
 65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
            130                 135                 140

Val Leu Asp
145

<210> SEQ ID NO 25
<211> LENGTH: 147
<212> TYPE: PRT
<213> ORGANISM: Artificial sequence
<220> FEATURE:
<223> OTHER INFORMATION: Synthesized

<400> SEQUENCE: 25

Lys Glu Phe Leu Leu Tyr Leu Ala Gly Phe Val Asp Ala Asp Gly Ser
 1               5                  10                  15

Ile Asn Ala Ser Ile Gln Pro Arg Gln Ser Phe Lys Phe Lys His Ser
            20                  25                  30

Leu Lys Leu Arg Phe Glu Val Gly Gln Lys Thr Gln Arg Arg Trp Phe
            35                  40                  45

Leu Asp Lys Leu Val Asp Glu Ile Gly Val Gly Tyr Val Tyr Asp Asn
        50                  55                  60

Gly Ser Val Ser Val Tyr Ser Leu Ser Gln Ile Lys Pro Leu His Asn
 65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
            130                 135                 140

Val Leu Asp
145

<210> SEQ ID NO 26
<211> LENGTH: 147
<212> TYPE: PRT
<213> ORGANISM: Artificial sequence
<220> FEATURE:
<223> OTHER INFORMATION: Synthesized

<400> SEQUENCE: 26

Lys Glu Phe Leu Leu Tyr Leu Ala Gly Phe Val Asp Gly Asp Gly Ser
 1               5                  10                  15
```

Ile Asn Ala Ser Ile Ala Pro Arg Gln Ser Phe Lys Phe Lys His Gly
            20                  25                  30

Leu Lys Leu Arg Phe Glu Val Gly Gln Lys Thr Gln Arg Arg Trp Phe
        35                  40                  45

Leu Asp Lys Leu Val Asp Glu Ile Gly Val Gly Tyr Val Tyr Asp Asn
    50                  55                  60

Gly Ser Val Ser Val Tyr Ser Leu Ser Gln Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145

<210> SEQ ID NO 27
<211> LENGTH: 147
<212> TYPE: PRT
<213> ORGANISM: Artificial sequence
<220> FEATURE:
<223> OTHER INFORMATION: Synthesized

<400> SEQUENCE: 27

Lys Glu Phe Leu Leu Tyr Leu Ala Gly Phe Val Asp Gly Asp Gly Ser
1               5                   10                  15

Ile Asn Ala Thr Ile Ala Pro Arg Gln Ser Phe Lys Phe Lys His Gly
            20                  25                  30

Leu Lys Leu Arg Phe Glu Val Gly Gln Lys Thr Gln Arg Arg Trp Phe
        35                  40                  45

Leu Asp Lys Leu Val Asp Glu Ile Gly Val Gly Tyr Val Tyr Asp Asn
    50                  55                  60

Gly Ser Val Ser Val Tyr Cys Leu Ser Gln Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145

<210> SEQ ID NO 28
<211> LENGTH: 147
<212> TYPE: PRT
<213> ORGANISM: Artificial sequence
<220> FEATURE:
<223> OTHER INFORMATION: Synthesized

<400> SEQUENCE: 28

Lys Glu Phe Leu Leu Tyr Leu Ala Gly Phe Val Asp Gly Asp Gly Ser
1               5                   10                  15

Ile Asn Ala Thr Ile Ala Pro Arg Gln Ser Phe Lys Phe Lys His Gly
            20                  25                  30

Leu Lys Leu Arg Phe Glu Val Gly Gln Lys Thr Gln Arg Arg Trp Phe
        35                  40                  45

Leu Asp Lys Leu Val Asp Glu Ile Gly Val Gly Tyr Val Tyr Asp Asn
    50                  55                  60

Gly Ser Val Ser Val Tyr Cys Leu Ser Gln Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145

<210> SEQ ID NO 29
<211> LENGTH: 147
<212> TYPE: PRT
<213> ORGANISM: Artificial sequence
<220> FEATURE:
<223> OTHER INFORMATION: Synthesized

<400> SEQUENCE: 29

Lys Glu Phe Leu Leu Tyr Leu Ala Gly Phe Val Asp Gly Asp Gly Ser
1               5                   10                  15

Ile Asn Ala Ala Ile Ala Pro Arg Gln Ser Phe Lys Phe Lys His Gly
            20                  25                  30

Leu Lys Leu Arg Phe Glu Val Gly Gln Lys Thr Gln Arg Arg Trp Phe
        35                  40                  45

Leu Asp Lys Leu Val Asp Glu Ile Gly Val Gly Tyr Val Tyr Asp Asn
    50                  55                  60

Gly Ser Val Ser Val Tyr Cys Leu Ser Gln Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145

<210> SEQ ID NO 30
<211> LENGTH: 22
<212> TYPE: DNA
<213> ORGANISM: Hepatitis B virus

<400> SEQUENCE: 30
gatgatgtgg tattgggggc ca                                    22

```
<210> SEQ ID NO 31
<211> LENGTH: 22
<212> TYPE: DNA
<213> ORGANISM: Hepatitis B virus

<400> SEQUENCE: 31
ctactacacc ataaccccccg gt                                            22

<210> SEQ ID NO 32
<211> LENGTH: 22
<212> TYPE: DNA
<213> ORGANISM: Artificial sequence
<220> FEATURE:
<223> OTHER INFORMATION: Synthesized

<400> SEQUENCE: 32
tgccgatcca tactgcggaa ct                                             22

<210> SEQ ID NO 33
<211> LENGTH: 19
<212> TYPE: DNA
<213> ORGANISM: Artificial sequence
<220> FEATURE:
<223> OTHER INFORMATION: Synthesized

<400> SEQUENCE: 33
ggtctgtgcc aagtgtttg                                                 19

<210> SEQ ID NO 34
<211> LENGTH: 20
<212> TYPE: DNA
<213> ORGANISM: Artificial sequence
<220> FEATURE:
<223> OTHER INFORMATION: Synthesized

<400> SEQUENCE: 34
gtatatttcc gcgagaggac                                                20

<210> SEQ ID NO 35
<211> LENGTH: 24
<212> TYPE: DNA
<213> ORGANISM: Artificial sequence
<220> FEATURE:
<223> OTHER INFORMATION: Synthesized

<400> SEQUENCE: 35
cttggccccc aataccacat catc                                           24

<210> SEQ ID NO 36
<211> LENGTH: 23
<212> TYPE: DNA
<213> ORGANISM: Artificial sequence
<220> FEATURE:
<223> OTHER INFORMATION: Synthesized

<400> SEQUENCE: 36
ggatggaaat tgcacctgta ttc                                            23

<210> SEQ ID NO 37
<211> LENGTH: 24
<212> TYPE: DNA
<213> ORGANISM: Artificial sequence
<220> FEATURE:
<223> OTHER INFORMATION: Synthesized

<400> SEQUENCE: 37
```
gggtttaaat gtataccag agac                                                    24

<210> SEQ ID NO 38
<211> LENGTH: 42
<212> TYPE: PRT
<213> ORGANISM: Artificial Sequence
<220> FEATURE:
<223> OTHER INFORMATION: Synthesized

<400> SEQUENCE: 38

Ser Leu Pro Gly Ser Val Gly Gly Leu Ser Pro Ser Gln Ala Ser Ser
1               5                   10                  15

Ala Ala Ser Ser Ala Ser Ser Ser Pro Gly Ser Gly Ile Ser Glu Ala
            20                  25                  30

Leu Arg Ala Gly Ala Gly Ser Gly Thr Gly
        35                  40

<210> SEQ ID NO 39
<211> LENGTH: 354
<212> TYPE: PRT
<213> ORGANISM: Artificial Sequence
<220> FEATURE:
<223> OTHER INFORMATION: Synthesized

<400> SEQUENCE: 39

Met Asn Thr Lys Tyr Asn Lys Glu Phe Leu Leu Tyr Leu Ala Gly Phe
1               5                   10                  15

Val Asp Gly Asp Gly Ser Ile Asn Ala Ser Ile Ala Pro Arg Gln Ser
            20                  25                  30

Phe Lys Phe Lys His Gly Leu Lys Leu Arg Phe Glu Val Gly Gln Lys
        35                  40                  45

Thr Gln Arg Arg Trp Phe Leu Asp Lys Leu Val Asp Glu Ile Gly Val
    50                  55                  60

Gly Tyr Val Tyr Asp Asn Gly Ser Val Ser Val Tyr Ser Leu Ser Gln
65              70                  75                  80

Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Glu Gln Leu
            100                 105                 110

Pro Ser Ala Lys Glu Ser Pro Asp Lys Phe Leu Glu Val Cys Thr Trp
        115                 120                 125

Val Asp Gln Ile Ala Ala Leu Asn Asp Ser Lys Thr Arg Lys Thr Thr
    130                 135                 140

Ser Glu Thr Val Arg Ala Val Leu Asp Ser Leu Pro Gly Ser Val Gly
145                 150                 155                 160

Gly Leu Ser Pro Ser Gln Ala Ser Ser Ala Ala Ser Ser Ala Ser Ser
                165                 170                 175

Ser Pro Gly Ser Gly Ile Ser Glu Ala Leu Arg Ala Gly Ala Gly Ser
            180                 185                 190

Gly Thr Gly Tyr Asn Lys Glu Phe Leu Leu Tyr Leu Ala Gly Phe Val
        195                 200                 205

Asp Gly Asp Gly Ser Ile Tyr Ala Ser Ile Arg Pro Arg Gln Tyr Ala
    210                 215                 220

Lys Phe Lys His Asp Leu Glu Leu Arg Phe Asn Val Arg Gln Lys Thr
225                 230                 235                 240

Gln Arg Arg Trp Phe Leu Asp Lys Leu Val Asp Glu Ile Gly Val Gly
                245                 250                 255

```
Tyr Val Val Asp Trp Gly Ser Val Ser Thr Tyr Gln Leu Ser Gln Ile
                260                 265                 270

Lys Pro Leu His Asn Phe Leu Thr Gln Leu Gln Pro Phe Leu Lys Leu
            275                 280                 285

Lys Gln Lys Gln Ala Asn Leu Val Leu Lys Ile Ile Glu Gln Leu Pro
        290                 295                 300

Ser Ala Lys Glu Ser Pro Asp Lys Phe Leu Glu Val Cys Thr Trp Val
305                 310                 315                 320

Asp Gln Ile Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
            340                 345                 350

Ser Pro

<210> SEQ ID NO 40
<211> LENGTH: 354
<212> TYPE: PRT
<213> ORGANISM: Artificial Sequence
<220> FEATURE:
<223> OTHER INFORMATION: Synthesized

<400> SEQUENCE: 40

Met Asn Thr Lys Tyr Asn Lys Glu Phe Leu Leu Tyr Leu Ala Gly Phe
1               5                   10                  15

Val Asp Gly Asp Gly Ser Ile Asn Ala Ile Ala Pro Arg Gln Ser
            20                  25                  30

Phe Lys Phe Lys His Gly Leu Lys Leu Arg Phe Glu Val Gly Gln Lys
        35                  40                  45

Thr Gln Arg Arg Trp Phe Leu Asp Lys Leu Val Asp Glu Ile Gly Val
    50                  55                  60

Gly Tyr Val Tyr Asp Asn Gly Ser Val Ser Val Tyr Cys Leu Ser Gln
65                  70                  75                  80

Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Glu Gln Leu
            100                 105                 110

Pro Ser Ala Lys Glu Ser Pro Asp Lys Phe Leu Glu Val Cys Thr Trp
        115                 120                 125

Val Asp Gln Ile Ala Ala Leu Asn Asp Ser Lys Thr Arg Lys Thr Thr
    130                 135                 140

Ser Glu Thr Val Arg Ala Val Leu Asp Ser Leu Pro Gly Ser Val Gly
145                 150                 155                 160

Gly Leu Ser Pro Ser Gln Ala Ser Ser Ala Ala Ser Ser Ala Ser Ser
                165                 170                 175

Ser Pro Gly Ser Gly Ile Ser Glu Ala Leu Arg Ala Gly Ala Gly Ser
            180                 185                 190

Gly Thr Gly Tyr Asn Lys Glu Phe Leu Leu Tyr Leu Ala Gly Phe Val
        195                 200                 205

Asp Gly Asp Gly Ser Ile Tyr Ala Ser Ile Arg Pro Arg Gln His Ala
    210                 215                 220

Lys Phe Lys His Asp Leu Glu Leu Ile Phe Asn Val Arg Gln Leu Thr
225                 230                 235                 240

Ser Arg Arg Trp Phe Leu Asp Lys Leu Val Asp Glu Ile Gly Val Gly
                245                 250                 255

Tyr Val Ile Asp Trp Gly Gly Ala Ser Thr Tyr Lys Leu Ser Glu Ile
```

```
                260                 265                 270
Lys Pro Leu His Asn Phe Leu Thr Gln Leu Gln Pro Phe Leu Lys Leu
                275                 280                 285
Lys Gln Lys Gln Ala Asn Leu Val Leu Lys Ile Ile Glu Gln Leu Pro
                290                 295                 300
Ser Ala Lys Glu Ser Pro Asp Lys Phe Leu Glu Val Cys Thr Trp Val
305                 310                 315                 320
Asp Gln Ile Ala Ala Leu Asn Asp Ser Lys Thr Arg Lys Thr Thr Ser
                325                 330                 335
Glu Thr Val Arg Ala Val Leu Asp Ser Leu Ser Glu Lys Lys Lys Ser
                340                 345                 350
Ser Pro

<210> SEQ ID NO 41
<211> LENGTH: 22
<212> TYPE: DNA
<213> ORGANISM: Hepatitis B virus

<400> SEQUENCE: 41 ccctgctcg tgttacaggc gg                                            22

<210> SEQ ID NO 42
<211> LENGTH: 22
<212> TYPE: DNA
<213> ORGANISM: Hepatitis B virus

<400> SEQUENCE: 42
ggggacgagc acaatgtccg cc                                           22

<210> SEQ ID NO 43
<211> LENGTH: 22
<212> TYPE: DNA
<213> ORGANISM: Hepatitis B virus

<400> SEQUENCE: 43
tttgctgacg caaccccac tg                                            22

<210> SEQ ID NO 44
<211> LENGTH: 22
<212> TYPE: DNA
<213> ORGANISM: Hepatitis B virus

<400> SEQUENCE: 44
aaacgactgc gttggggtg ac                                            22

<210> SEQ ID NO 45
<211> LENGTH: 1065
<212> TYPE: DNA
<213> ORGANISM: Artificial sequence
<220> FEATURE:
<223> OTHER INFORMATION: Synthesized

<400> SEQUENCE: 45
atgaatacaa atataataa agagttctta ctctacttag cagggtttgt agactctgac     60
ggttccatca acgccagcat ctcgccgcgg cagtcgttca gttcaagca cgggctgaag    120 ctccggttcg aggtcggtca aagacacag caccgttggt tcctcgacaa gctggtggac    180
gagatcggtg tgggttacgt gtatgacaat ggcagcgtct ccgtttactc tctgtcccag    240
atcaagcctt tgcataattt tttaacacaa ctacaacctt ttctaaaact aaaacaaaaa    300
```

```
caagcaaatt tagttttaaa aattattgaa caacttccgt cagcaaaaga atccccggac    360
aaattcttag aggtttgtac atgggtggat caaattgcag ctctgaatga ttcgaagacg    420
cgtaaaacaa cttctgaaac cgttcgtgct gtgctagaca gtttaccagg atccgtggga    480
ggtctatcgc catctcaggc atccagcgcc gcatcctcgg cttcctcaag cccgggttca    540
gggatctccg aagcactcag agctggagca ggttccggca ctggatacaa caaggaattc    600
ctgctctacc tggcgggctt cgtcgacggg acggctcca tctttgcatc gatccggcct     660
cgtcaacatg ctaagttcaa gcacgatctg gagctctgtt tcaatgtcag gcagaagaca    720
cagcgccgtt ggttcctcga caagctggtg gacgagatcg tgtgggtta cgtgattgac     780 tggcgtggcg cctccactta aagctgtcc cagatcaagc ctctgcacaa cttcctgacc     840
cagctccagc ccttcctgaa gctcaagcag aagcaggcca acctcgtgct gaagatcatc    900
gagcagctgc cctccgccaa ggaatccccg acaagttcc tggaggtgtg cacctgggtg     960
gaccagatcg ccgctctgaa cgactccaag acccgcaaga ccacttccga aaccgtccgc   1020
gccgttctag acagtctctc cgagaagaag aagtcgtccc cctaa                   1065

<210> SEQ ID NO 46
<211> LENGTH: 1065
<212> TYPE: DNA
<213> ORGANISM: Artificial sequence
<220> FEATURE:
<223> OTHER INFORMATION: Synthesized

<400> SEQUENCE: 46
atgaatacaa atataataa agagttctta ctctacttag cagggtttgt agacgctgac      60
ggttccatca acgccagcat ccagccgcgg cagtcgttca agttcaagca ctctctgaag    120
ctccggttcg aggtcggtca gaagacacag cgccgttggt tcctcgacaa gctggtggac    180
gagatcggtg tgggttacgt gtatgacaat ggcagcgtct ccgtttactc tctgtcccag    240
atcaagcctt tgcataattt tttaacacaa ctacaacctt ttctaaaact aaaacaaaaa    300
caagcaaatt tagttttaaa aattattgaa caacttccgt cagcaaaaga atccccggac    360
aaattcttag aggtttgtac atgggtggat caaattgcag ctctgaatga ttcgaagacg    420
cgtaaaacaa cttctgaaac cgttcgtgct gtgctagaca gtttaccagg atccgtggga    480
ggtctatcgc catctcaggc atccagcgcc gcatcctcgg cttcctcaag cccgggttca    540
gggatctccg aagcactcag agctggagca ggttccggca ctggatacaa caaggaattc    600
ctgctctacc tggcgggctt cgtcgacggg acggctcca tctttgcatc gatccggcct     660
cgtcaacatg ctaagttcaa gcacgatctg gagctctgtt tcaatgtcag gcagaagaca    720
cagcgccgtt ggttcctcga caagctggtg gacgagatcg tgtgggtta cgtgcttgac     780 tggcgtggcg cctccactta aagctgtcc gagatcaagc ctctgcacaa cttcctgacc     840
cagctccagc ccttcctgaa gctcaagcag aagcaggcca acctcgtgct gaagatcatc    900
gagcagctgc cctccgccaa ggaatccccg acaagttcc tggaggtgtg cacctgggtg     960
gaccagatcg ccgctctgaa cgactccagg acccgcaaga ccacttccga aaccgtccgc   1020
gccgttctag acagtctctc cgagaagaag aagtcgtccc cctaa                   1065

<210> SEQ ID NO 47
<211> LENGTH: 1065
<212> TYPE: DNA
<213> ORGANISM: Artificial sequence
<220> FEATURE:
<223> OTHER INFORMATION: Synthesized
```

<400> SEQUENCE: 47

```
atgaatacaa aatataataa agagttctta ctctacttag cagggtttgt agacggtgac        60
ggttccatca atgccagtat cgctccgcgg cagtcgttta agttcaagca cggtctgaag       120
ctccggttcg aggtcggtca gaagacacag cgccgttggt tcctcgacaa gctggtggac       180
gagatcggtg tgggttacgt gtatgacaat ggcagcgtct ccgtttactc tctgtcccag       240
atcaagcctt tgcataattt tttaacacaa ctacaacctt ttctaaaact aaaacaaaaa       300
caagcaaatt tagttttaaa aattattgaa caacttccgt cagcaaaaga atccccggac       360
aaattcttag aagtttgtac atgggtggat caaattgcag ctctgaatga ttcgaagacg       420
cgtaaaacaa cttctgaaac cgttcgtgct gtgctagaca gtttaccagg atccgtggga       480
ggtctatcgc catctcaggc atccagcgcc gcatcctcgg cttcctcaag cccgggttca       540
gggatctccg aagcactcag agctggagca ggttccggca ctggatacaa caaggaattc       600
ctgctctacc tggcgggctt cgtcgactcc gacggctcca tctttgcatc gatccggcct       660
cgtcaaatgg ctaagttcaa gcacgatctg gagctctgtt tcaatgtcag gcagaagaca       720
cagcgccgtt ggttcctcga caagctggtg gacgagatcg gtgtgggtta cgtgcatgac       780
tggggcagcg tctccactta caagctgtcc gagatcaagc ctctgcacaa cttcctgacc       840
cagctccagc ccttcctgaa gctcaagcag aagcaggcca acctcgtgct gaagatcatc       900
gagcagctgc cctccgccaa ggaatcccccg acaagttcc tggaggtgtg cacctgggtg       960
gaccagatcg ccgctctgaa cgactccaag acccgcaaga ccacttccga accgtccgc      1020
gccgttctag acagtctctc cgagaagaag aagtcgtccc cctaa                     1065
```

<210> SEQ ID NO 48
<211> LENGTH: 1065
<212> TYPE: DNA
<213> ORGANISM: Artificial sequence
<220> FEATURE:
<223> OTHER INFORMATION: Synthesized

<400> SEQUENCE: 48

```
atgaatacaa aatataataa agagttctta ctctacttag cagggtttgt agacggtgac        60
ggttccatca atgccactat cgctccgcgg cagtcgttta agttcaagca cggtctgaag       120
ctccggttcg aggtcggtca gaagacacag cgccgttggt tcctcgacaa gctggtggac       180
gagatcggtg tgggttacgt gtatgacaat ggcagcgtct ccgtttactg tctgtcccag       240
atcaagcctt tgcataattt tttaacacaa ctacaacctt ttctaaaact aaaacaaaaa       300
caagcaaatt tagttttaaa aattattgaa caacttccgt cagcaaaaga atccccggac       360
aaattcttag aagtttgtac atgggtggat caaattgcag ctctgaatga ttcgaagacg       420
cgtaaaacaa cttctgaaac cgttcgtgct gtgctagaca gtttaccagg atccgtggga       480
ggtctatcgc catctcaggc atccagcgcc gcatcctcgg cttcctcaag cccgggttca       540
gggatctccg aagcactcag agctggagca ggttccggca ctggatacaa caaggaattc       600
ctgctctacc tggcgggctt cgtcgacggg gacggctcca tctatgcatc tatcaggcct       660
cgtcaacatg ctaagttcaa gcacgatctg gagctcattt tcaatgtcag gcagctgaca       720
agccgccgtt ggttcctcga caagctggtg gacgagatcg gtgtgggtta cgtgattgac       780
tggcgtggcg cctccactta caagctgtcc gagatcaagc ctctgcacaa cttcctgacc       840
cagctccagc ccttcctgaa gctcaagcag aagcaggcca acctcgtgct gaagatcatc       900
```

| | |
|---|---|
| gagcagctgc cctccgccaa ggaatccccg acaagttcc tggaggtgtg cacctgggtg | 960 |
| gaccagatcg ccgctctgaa cgactccaag acccgcaaga ccacttccga aaccgtccgc | 1020 |
| gccgttctag acagtctctc cgagaagaag aagtcgtccc cctaa | 1065 |

<210> SEQ ID NO 49
<211> LENGTH: 1065
<212> TYPE: DNA
<213> ORGANISM: Artificial sequence
<220> FEATURE:
<223> OTHER INFORMATION: Synthesized

<400> SEQUENCE: 49

| | |
|---|---|
| atgaatacaa atataataa agagttctta ctctacttag cagggtttgt agacggtgac | 60 |
| ggttccatca atgccactat cgctccgcgg cagtcgttta agttcaagca cggtctgaag | 120 |
| ctccggttcg aggtcggtca gaagacacag cgccgttggt tcctcgacaa gctggtggac | 180 |
| gagatcggtg tgggttacgt gtatgacaat ggcagcgtct ccgtttactg tctgtcccag | 240 |
| atcaagcctt tgcataattt tttaacacaa ctacaacctt ttctaaaact aaaacaaaaa | 300 |
| caagcaaatt tagttttaaa aattattgaa caacttccgt cagcaaaaga tccccggac | 360 |
| aaattcttag aagtttgtac atgggtggat caaattgcag ctctgaatga ttcgaagacg | 420 |
| cgtaaaacaa cttctgaaac cgttcgtgct gtgctagaca gtttaccagg atccgtggga | 480 |
| ggtctatcgc catctcaggc atccagcgcc gcatcctcgg cttcctcaag cccgggttca | 540 |
| gggatctccg aagcactcag agctggagca ggttccggca ctggatacaa caaggaattc | 600 |
| ctgctctacc tggcgggctt cgtcgactcc gacggctcca tctatgcatc tatcaggcct | 660 |
| cgtcaacatg ctaagttcaa gcacgatctg gagctcattt tcaatgtcag gcagctgaca | 720 |
| agccgccgtt ggtccctcga caagctggtg gacgagatcg gtgtgggtta cgtgattgac | 780 |
| tggcgtggcg cctccactta caagctgtcc gagatcaagc ctctgcacaa cttcctgacc | 840 |
| cagctccagc cctttcctgaa gctcaagcag aagcaggcca acctcgtgct gaagatcatc | 900 |
| gagcagctgc cctccgccaa ggaatccccg acaagttcc tggaggtgtg cacctgggtg | 960 |
| gaccagatcg ccgctctgaa cgactccaag acccgcaaga ccacttccga aaccgtccgc | 1020 |
| gccgttctag acagtctctc cgagaagaag aagtcgtccc cctaa | 1065 |

<210> SEQ ID NO 50
<211> LENGTH: 1065
<212> TYPE: DNA
<213> ORGANISM: Artificial sequence
<220> FEATURE:
<223> OTHER INFORMATION: Synthesized

<400> SEQUENCE: 50

| | |
|---|---|
| atgaatacaa atataataa agagttctta ctctacttag cagggtttgt agacggtgac | 60 |
| ggttccatca atgccgcgat cgctccgcgg cagtcgttta agttcaagca cggtctgaag | 120 |
| ctccggttcg aggtcggtca gaagacacag cgccgttggt tcctcgacaa gctggtggac | 180 |
| gagatcggtg tgggttacgt gtatgacaat ggcagcgtct ccgtttactg tctgtcccag | 240 |
| atcaagcctt tgcataattt tttaacacaa ctacaacctt ttctaaaact aaaacaaaaa | 300 |
| caagcaaatt tagttttaaa aattattgaa caacttccgt cagcaaaaga tccccggac | 360 |
| aaattcttag aagtttgtac atgggtggat caaattgcag ctctgaatga ttcgaagacg | 420 |
| cgtaaaacaa cttctgaaac cgttcgtgct gtgctagaca gtttaccagg atccgtggga | 480 |
| ggtctatcgc catctcaggc atccagcgcc gcatcctcgg cttcctcaag cccgggttca | 540 |

```
gggatctccg aagcactcag agctggagca ggttccggca ctggatacaa caaggaattc      600
ctgctctacc tggcgggctt cgtcgacggg gacggctcca tctatgcaag tatcaggcct      660
cgtcaacagt cgaagttcaa gcacgatctg gagctctatt tcaatgtcag gcagaagaca      720
aggcgccgtt ggttcctcga caagctggtg gacgagatcg gtgtgggtta cgtgaatgac      780
tggcgtggca cctccactta caagctgtcc gagatcaagc ctctgcacaa cttcctgacc      840
cagctccagc ccttcctgaa gctcaagcag aagcaggcca acctcgtgct gaagatcatc      900
gagcagctgc cctccgccaa ggaatccccg gacaagttcc tggaggtgtg cacctgggtg      960
gaccagatcg ccgctctgaa cgactccaag acccgcaaga ccacttccga aaccgtccgc     1020
gccgttctag acagtctctc cgagaagaag aagtcgtccc cctaa                    1065

<210> SEQ ID NO 51
<211> LENGTH: 10
<212> TYPE: PRT
<213> ORGANISM: Artificial Sequence
<220> FEATURE:
<223> OTHER INFORMATION: Synthesized

<400> SEQUENCE: 51

Met Ala Pro Lys Lys Lys Arg Lys Val His
1               5                   10
```